US010849875B2

(12) United States Patent
Udugamasooriya et al.

(10) Patent No.: US 10,849,875 B2
(45) Date of Patent: Dec. 1, 2020

(54) CANCER SPECIFIC LIPID TARGETED PEPTIDOMIMETICS

(71) Applicants: University of Houston System, Houston, TX (US); University of Texas Southwestern Medical Center, Dallas, TX (US)

(72) Inventors: Damith Gomika Udugamasooriya, Katy, TX (US); Rolf A. Brekken, Dallas, TX (US)

(73) Assignees: University of Houston System, Houston, TX (US); Board of Regents of The University of Texas System, Austin, TX (US)

(*) Notice: Subject to any disclaimer, the term of this patent is extended or adjusted under 35 U.S.C. 154(b) by 107 days.

(21) Appl. No.: 15/747,071

(22) PCT Filed: Jul. 23, 2016

(86) PCT No.: PCT/US2016/043776
§ 371 (c)(1),
(2) Date: Jan. 23, 2018

(87) PCT Pub. No.: WO2017/015644
PCT Pub. Date: Jan. 26, 2017

(65) Prior Publication Data
US 2018/0369189 A1 Dec. 27, 2018

Related U.S. Application Data

(60) Provisional application No. 62/196,144, filed on Jul. 23, 2015, provisional application No. 62/199,107, filed on Jul. 30, 2015.

(51) Int. Cl.
| | | |
|---|---|---|
| *A61K 31/343* | (2006.01) | |
| *A61K 38/00* | (2006.01) | |
| *A61K 31/337* | (2006.01) | |
| *A61K 49/00* | (2006.01) | |
| *A61K 47/55* | (2017.01) | |
| *A61P 35/00* | (2006.01) | |
| *G01N 33/50* | (2006.01) | |
| *G01N 33/53* | (2006.01) | |
| *G01N 33/543* | (2006.01) | |
| *G01N 33/574* | (2006.01) | |

(52) U.S. Cl.
CPC .......... *A61K 31/343* (2013.01); *A61K 31/337* (2013.01); *A61K 38/00* (2013.01); *A61K 47/55* (2017.08); *A61K 49/0056* (2013.01); *A61P 35/00* (2018.01); *G01N 33/5044* (2013.01); *G01N 33/5306* (2013.01); *G01N 33/54393* (2013.01); *G01N 33/574* (2013.01)

(58) Field of Classification Search
None
See application file for complete search history.

(56) References Cited

FOREIGN PATENT DOCUMENTS

WO  2012129457 A2  9/2012

OTHER PUBLICATIONS

Udagamoasooriya ("Phosphatidylserine Targeting Tumor Cell Lytic Peptoids" Grantome, 2014).*
Raghunathan et al. ("Validating Cancer specific Homo- and Hetero-Multimeric peptidomimetics" P15, Poster).*
Lee et al. ("Crosslinked Peptide-Based Dimerization Inhibitors of HIV-1 Protease" Chembiochem, 2010, 11(11): 1513-1516).*
Desai, T.J. et al., Identification of lipid-phosphatidylserine (PS) as the target of unbiasedly selected cancer specific peptide-peptoid hybrid PPS1, Oncotarget, vol. 7, No. 21, Apr. 22, 2016, pp. 30678-30690.
Hooks, J.C. et al., Development of Homomultimers and Heteromultimers of Lung Cancer-Specific Peptoids, PeptideScience vol. 96 / No. 5 / 2011 / pp. 567-577.
Udugamasooria, D.G. et al., On-Bead Two-Color (OBTC) Cell Screen for Direct Identification of Highly Selective Cell Surface Receptor Ligands, Current Protocols in Chemical Biology 4: 35-48, Mar. 2012.
Udugamasooria, D.G. et al., Symposium Title: (POLY004a) Poly(2-oxazoline)s and polypeptoids, 248th ACS National Meeting, San Francisco, CA, Mar. 22, 2014.
Lee, S. et al., Crosslinked Peptide-Based Dimerization Inhibitors of HIV-1 Protease, Chembiochem. Jul. 26, 2010; 11(11): 1513-1516. doi: 10.1002/cbic.201000248.
Raghunathan, S. et al., Validating Peptidomimetics, 42nd Annual Medicinal Chemistry & Pharmacognosy Meeting-in-Miniature, May 17-19, 2015, The University of Mississippi, Dept. of BioMolecular Sciences, p. 58.
Udugamasooria, D.G. et al., Phosphatidylserine Targeted Tumor Cell Lytic Peptoids, Abstract, National Institutes of Health, Jun. 25, 2019.
Matharage, JM, Minna JD, Brekken RA, Udugamasooriya DG. Unbiased Selection of Peptide-Peptoid Hybrids Specific for Lung Cancer Compared to Normal Lung Epithelial Cells. ACS Chem Biol. 2015; 10:2891-2899.
Desai, T.J. et al., A comprehensive lipid binding and activity validation of a cancer-specific peptide-peptoid hybrid PPS1, Biochemical and Biophysical Research Communications 486 (2017) 545-550.
Shukla, S. et al., A unique mid-sequence linker used to multimerize the lipid-phosphatidylserine (PS) binding peptide-peptoid hybrid PPS1, European Journal of Medicinal Chemistry 137 (2017) 1-10.
Singh, J. et al., Identification of the minimum pharmacophore of lipid-phosphatidylserine (PS) binding peptide-peptoid hybrid PPS1D1, Bioorganic & Medicinal Chemistry 24 (2016) 4470-4477.

(Continued)

*Primary Examiner* — James H Alstrum-Acevedo
*Assistant Examiner* — Tara L Martinez
(74) *Attorney, Agent, or Firm* — Winstead PC

(57) ABSTRACT

A phosphatidylserine targeted peptoid has been identified with the ability to bind to cancer cells globally and specifically. A dimer of the peptoid decreases cancer cell viability. Use of the dimerized peptoid enhances the efficacy of docetaxel. The peptoid can be used for including but not limited to diagnosing and treating cancer, diagnosing and treating a viral condition, and diagnosing and treating diabetes.

11 Claims, 105 Drawing Sheets

(56) References Cited

OTHER PUBLICATIONS

Riedl, S., Zweytick, D., and Lohner, K. (2011) Membrane-active host defense peptides—challenges and perspectives for the development of novel anticancer drugs, Chemistry and physics of lipids 164, 766-781.
Stafford JH, Thorpe PE. Increased exposure of phosphatidylethanolamine on the surface of tumor vascular endothelium. Neoplasia. 2011; 13:299-308.
Thapa, N., Kim, S., So, I. S., Lee, B. H., Kwon, I. C., Choi, K., and Kim, I. S. (2008) Discovery of a phosphatidylserine-recognizing peptide and its utility in molecular imaging of tumour apoptosis, J Cell Mol Med 12, 1649-1660.
Utsugi, T, Schroit AJ, Connor J, Bucana CD, Fidler IJ. Elevated expression of phosphatidylserine in the outer membrane leaflet of human tumor cells and recognition by activated human blood monocytes. Cancer Res. 1991; 51:3062-3066.
Xiong C, Brewer K, Song S, Zhang R, Lu W, Wen X, Li C. www.impactjournals.com/oncotarget 13 Oncotarget Peptide-based imaging agents targeting phosphatidylserine for the detection of apoptosis. J Med Chem. 2011; 54:1825-1835.
Yoo B, Kirshenbaum K. Peptoid architectures: elaboration, actuation, and application. Curr Opin Chem Biol. 2008; 12:714-721.
Huang X, Bennett M, Thorpe PE. A monoclonal antibody that binds anionic phospholipids on tumor blood vessels enhances the antitumor effect of docetaxel on human breast tumors in mice. Cancer Res. 2005; 65:4408-4416.
Landon L. A., and Deutscher, S. L. (2003) Combinatorial discovery of tumor targeting peptides using phage display, Journal of Cellular Biochemistry 90, 509-517.
Marconescu A, Thorpe PE. Coincident exposure of phosphatidylethanolamine and anionic phospholipids on the surface of irradiated cells. Biochim Biophys Acta. 2008; 1778:2217-2224.
Ran S, He J, Huang X, Soares M, Scothorn D, Thorpe PE. Antitumor effects of a monoclonal antibody that binds anionic phospholipids on the surface of tumor blood vessels in mice. Clin Cancer Res. 2005; 11:1551-1562.
Ran S, Downes A, Thorpe PE. Increased exposure of anionic phospholipids on the surface of tumor blood vessels. Cancer Res. 2002; 62:6132-6140.
Brown K. C. (2000) New approaches for cell-specific targeting: identification of cell-selective peptides from combinatorial libraries, Curr Opin Chem Biol 4, 16-21.
Gaspar D, Veiga AS, Castanho MRB. From antimicrobial to anticancer peptides. A review. Front Microbiol. 2013; 4.
He J, Luster TA, Thorpe PE. Radiation-enhanced vascular targeting of human lung cancers in mice with a monoclonal antibody that binds anionic phospholipids. Cancer Res. 2007; 13:5211-5218.
Hoskin DW, Ramamoorthy A. Studies on anticancer activities of antimicrobial peptides. BBA-Biomembranes. 2008; 1778:357-375.
Huang W, Seo J, Willingham SB, Czyzewski AM, Gonzalgo ML, Weissman IL, Barron AE. Learning from Host-Defense Peptides: Cationic, Amphipathic Peptoids with Potent Anticancer Activity. PloS one. 2014; 9.

* cited by examiner (A)

(B)

(C)

PPS1D1 - 1hr
 PPS1D1 - 4hr
 PC462D1 - 1hr
 PC462D1 - 4hr (A)

(B)

PPS1D1:

PPS1-DE2:

PPS1-RD1:

PPS1-2P3H:

PPS1-4P3H:

PPS1-Tri-1:

PPS1-Tet-1:

PPS2D1:

A   B

(A) Main Reactions:

(B) Synthesis of Azide-JM79:

A     B

2P3H-PPS1

2-4-PPS1

A

B

C

A

B

C

A

B

C

← 855.43

CANCER SPECIFIC LIPID TARGETED PEPTIDOMIMETICS

RELATED APPLICATIONS

This application is the National Stage of International Application No. PCT/US2016/43776, filed Jul. 23, 2016; which claims priority to U.S. Provisional Patent Application No. 62/199,107 filed on Jul. 30, 2015 and U.S. Provisional Patent Application No. 62/195,144 filed on Jul. 23, 2015, which are specifically incorporated by reference in their entirety herein.

GOVERNMENT FUNDING

This invention was made with government support under grant #1R01CA175779-01 awarded by the National Institutes of Health and grant #RP130258 awarded by the Cancer Prevention Research Institute of Texas. The government has certain rights in the invention.

FIELD

The disclosure relates generally to therapeutics. The disclosure relates specifically to the targeting of cancer cells.

BACKGROUND

Drug failures are common in cancer treatments and one of the major reasons is the heterogeneity of disease specific protein target expressions in cancer cells. The development of a targeted drug that can be effective on majority of the patient population has not yet been achieved. Conventional drug development approaches target protein biomolecules including but not limited to receptors, enzymes, and hormones, and depend on the prior knowledge of their biological roles.

Despite extraordinary advances in our understanding of the biology of cancer as well as potential molecular targets for its treatment, more than 90% of all new oncology drugs that enter clinical development do not obtain marketing approval. Even the approved drugs only act on a small percentage of the patient population and have considerable side effects and high prices. Most of the targets of these conventional drug leads are 'protein' biomarkers and their expression levels are highly heterogeneous from patient to patient. Effective cancer treatments will need to address: (a) patient-specific molecular defects, and (b) aspects of the overall tumor microenvironment.

Targeted molecular therapy has been suggested as a better approach than the chemo and radiotherapy for treating cancer. Protein biomolecules have been targeted. Unfortunately, expression of cancer specific protein biomolecules is highly heterogeneous and unpredictable from patient to patient. This limits the usefulness of targeted drugs to selected groups of patients.

It would be advantageous to target 'non-protein' biomarkers that are globally expressed in the tumor microenvironment by using a biologically amenable, easy to synthesize and optimize, low cost emerging class of peptidomimetic molecules called peptoids.

SUMMARY

An embodiment of the disclosure is a composition of matter comprising a phosphatidylserine-targeting peptoid consisting of at least one selected from 2P3H-PPS1 and 2-4-PPS1.

An embodiment of the disclosure is a composition of matter comprising a phosphatidic acid-targeting peptoid, phosphatidylinositol-targeting peptoid, or phosphotidylglycerol-targeting peptoid. In an embodiment, the peptoid is PPS1D1. In an embodiment, the peptoid is 2P3H-PPS1 and 2-4-PPS1.

An embodiment of the disclosure is a method of treating cancer comprising administering to a patient a composition of matter comprising the phosphatidylserine-targeting peptoid. In an embodiment, docetaxel is also administered to the patient.

An embodiment of the disclosure is a method of treating cancer comprising administering to a patient a composition of matter comprising at least one of the phosphatidic acid-targeting peptoid, phosphatidylinositol-targeting peptoid, or phosphotidylglycerol-targeting peptoid. In an embodiment, docetaxel is also administered to the patient.

An embodiment of the disclosure is a method of treating cancer comprising screening for a high specificity compound to bind to a biomolecule presented on a cancer cell comprising binding a first peptoid to a first bead to create a peptoid bead; repeating step (a) for the number of peptoids to be screened; exposing the peptoid bead to cancer cells from a patient; exposing the peptoid bead to non-cancer cells from the patient; measuring the specific binding of the peptoid bead to the cancer cells and non-cancer cells; selecting a peptoid displaying high specific binding for cancer cells and not displaying high specific binding for non-cancer cells; and administering the peptoid to the patient in need of cancer treatment. In an embodiment, the selected peptoid is PPS1 or a derivative thereof and targets phosphatidic acid, phosphotidylinositol, or phosphotidylglycerol. In an embodiment, the selected peptoid is 2P3H-PPS1 and 2-4-PPS1. In an embodiment, the PPS1 or a derivative thereof is dimerized. In an embodiment, the PPS1 or a derivative thereof is dimerized by covalently conjugating two PPS1 through a lysine residue. In an embodiment, the selected peptoid is dimerized. In an embodiment, the selected peptoid is dimerized by covalently conjugating two of the peptoids through a lysine residue.

An embodiment of the disclosure is a method of treating a viral condition comprising administering to a patient a composition of matter comprising a phosphatidylserine-targeting peptoid consisting of at least one selected from 2P3H-PPS1 and 2-4-PPS1.

An embodiment of the disclosure is a method of treating a viral condition comprising administering to a patient a composition of matter comprising a phosphatidic acid-targeting peptoid, phosphatidylinositol-targeting peptoid, or phosphotidylglycerol-targeting peptoid.

An embodiment of the disclosure is a method of detecting a condition comprising administering to a patient a composition of matter comprising a peptoid from the group consisting of phosphatidic acid-targeting peptoid, phosphatidylinositol-targeting peptoid, phosphotidylglycerol-targeting peptoid, the phosphatidylserine-targeting peptoid 2P3H-PPS1, and the phosphatidylserine-targeting peptoid 2-4-PPS1 conjugated to a fluorescent label; and visualizing the location of the fluorescent label in the patient. In an embodiment, the condition is cancer. In an embodiment, the condition is selected from the group consisting of a viral condition, diabetes, and apoptotic cells.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

In order that the manner in which the above-recited and other enhancements and objects of the disclosure are obtained, a more particular description of the disclosure briefly described above will be rendered by reference to specific embodiments thereof which are illustrated in the appended drawings. Understanding that these drawings depict only typical embodiments of the disclosure and are therefore not to be considered limiting of its scope, the disclosure will be described with additional specificity and detail through the use of the accompanying drawings in which.

FACS analysis of cytotoxicity of FITC-PPS1D1 on H460 cell line with 1 hr incubation (D) Number of FITC-PPS1D1 positive H460 cells at different concentration.

Figure 14:
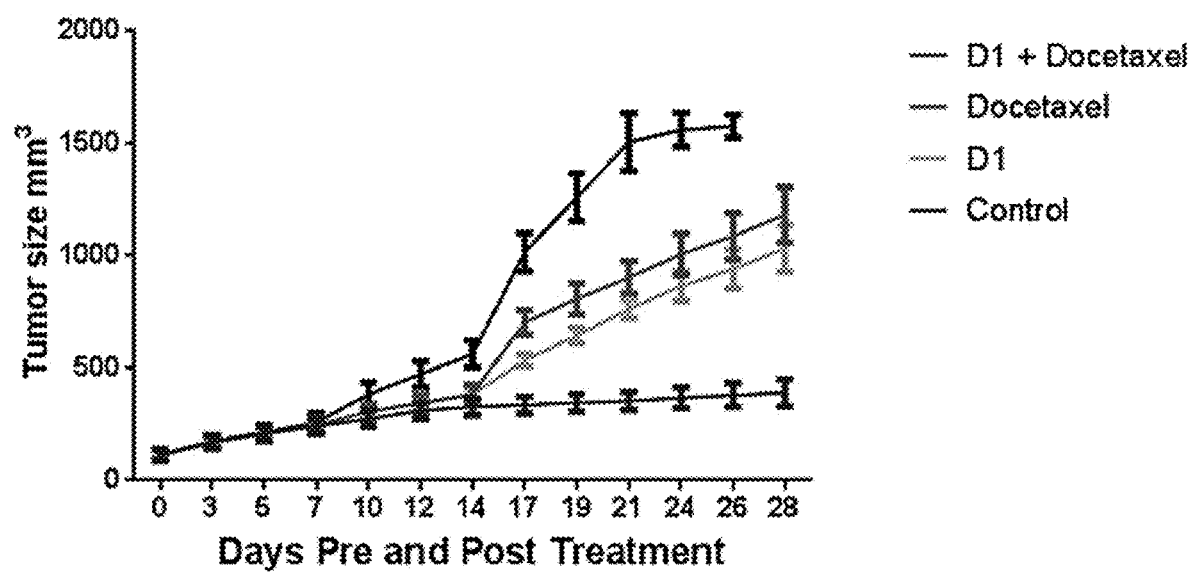

FIG. 14 Tumor size reduction of H460 tumor bearing mice with Docetaxel (red line, PPS1D1 (green line), Docetaxel+PPS1D1 (blue line) and PC462D1 treatment (black line). PPS1D1 displayed potent tumor burden effect with and without Docetaxel.

Figure 15:
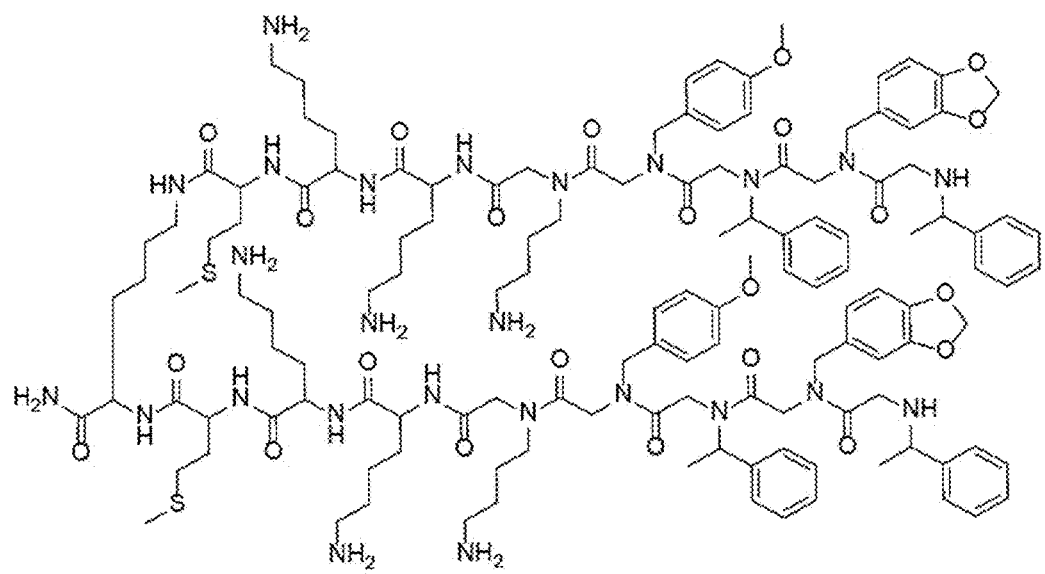

FIG. 15 depicts the structure of PPS1D1.

Figure 16:
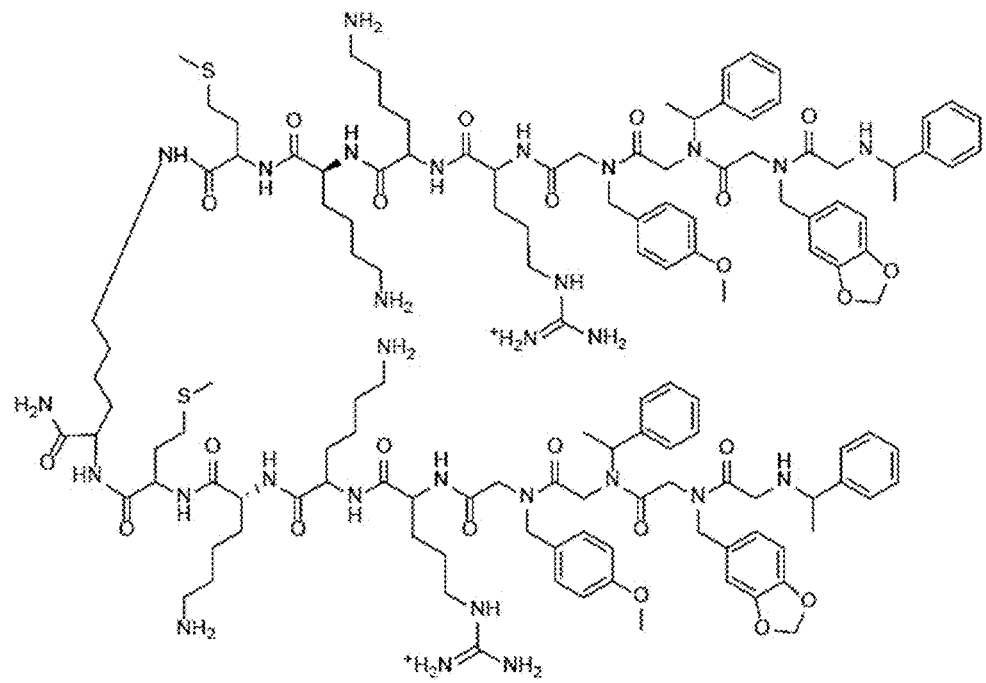

FIG. 16 depicts the structure of PPS1-DE2.

Figure 17:
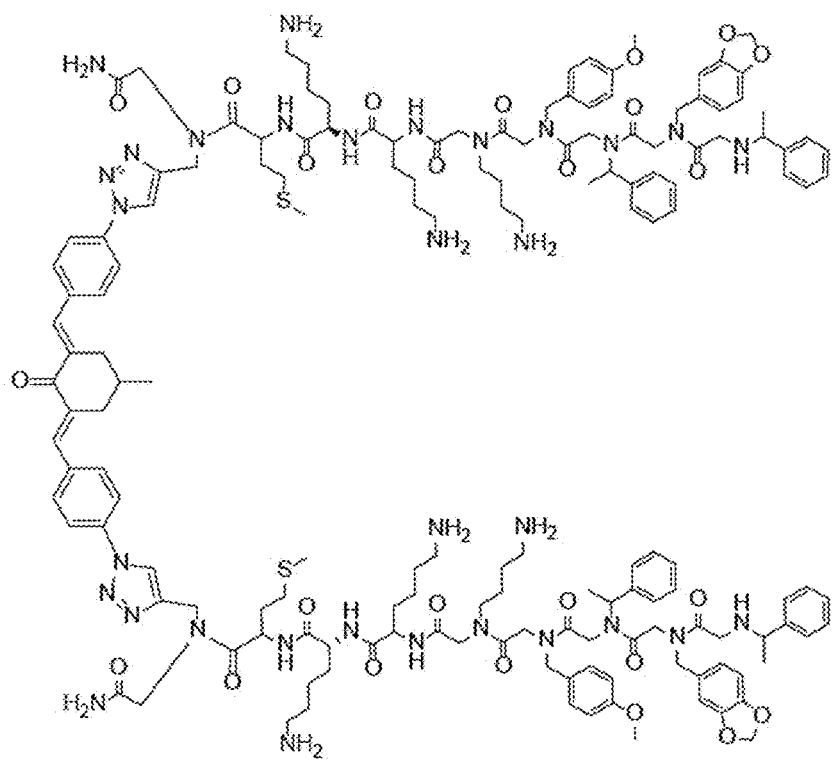

FIG. 17 depicts the structure of PPS1-RD1.

Figure 18:
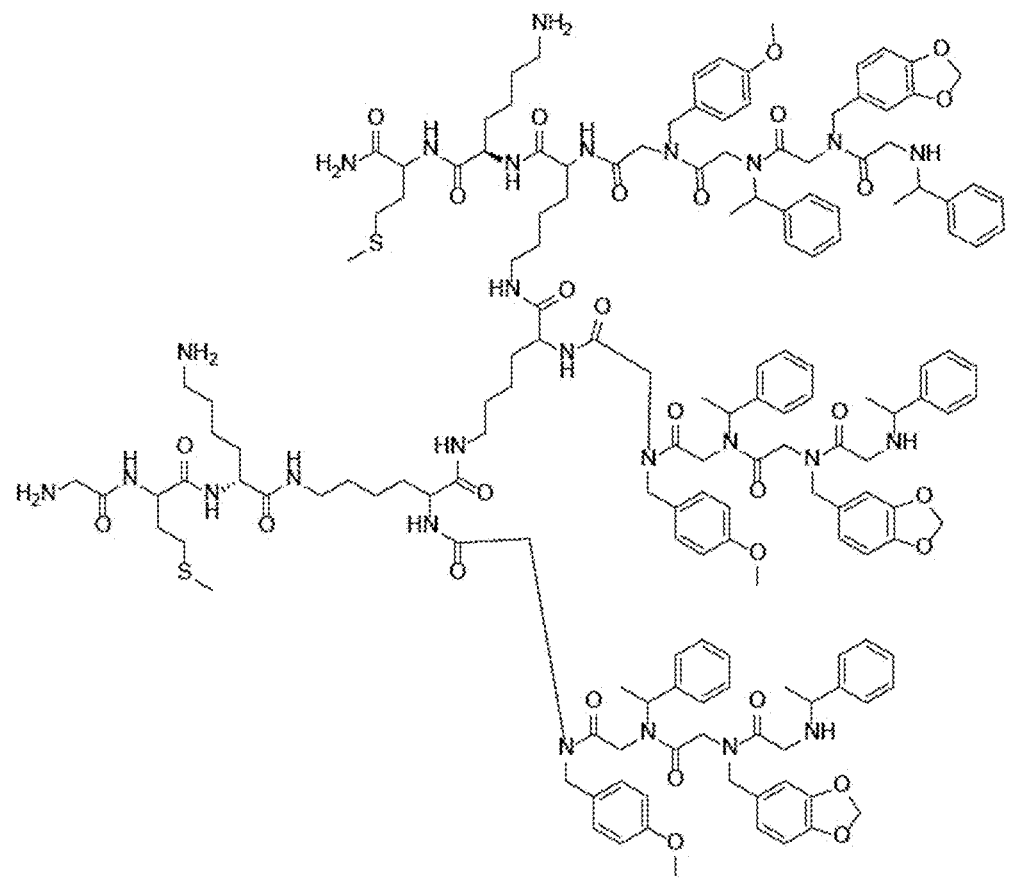

FIG. 18 depicts the structure of PPS1-2P3H.

Figure 19:
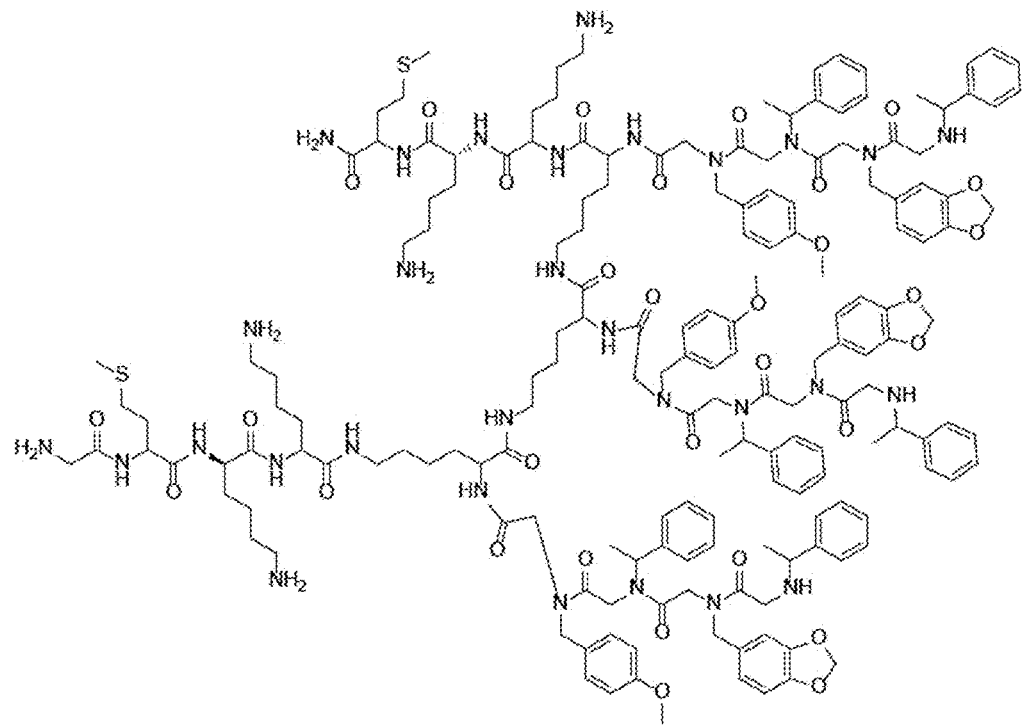

FIG. 19 depicts the structure of PPS1-4P3H.

Figure 20:
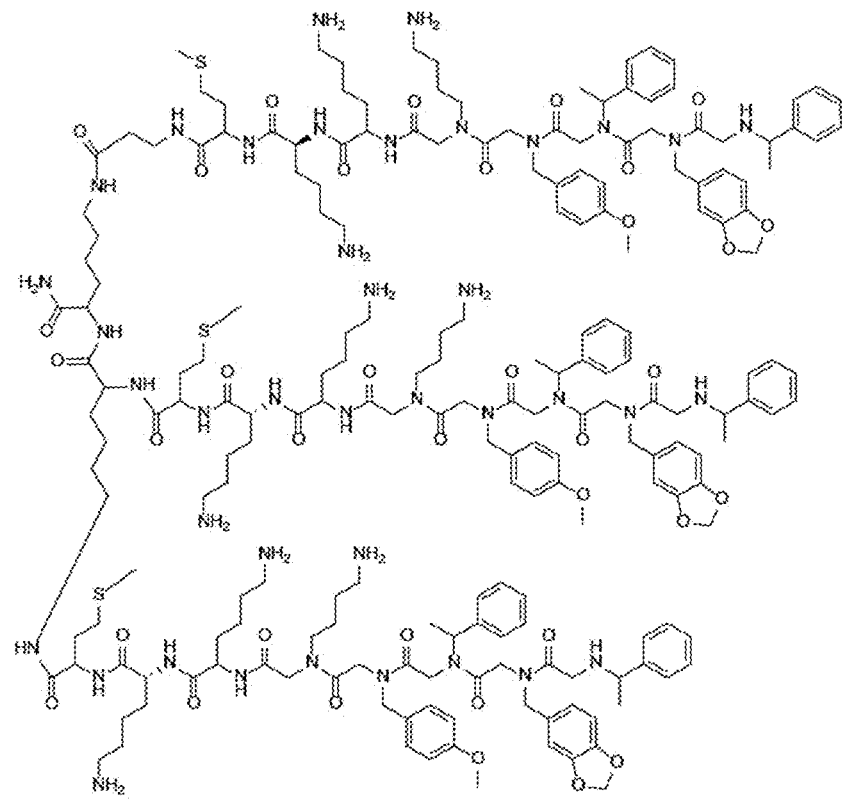

FIG. 20 depicts the structure of PPS1-Tri-1.

Figure 21:
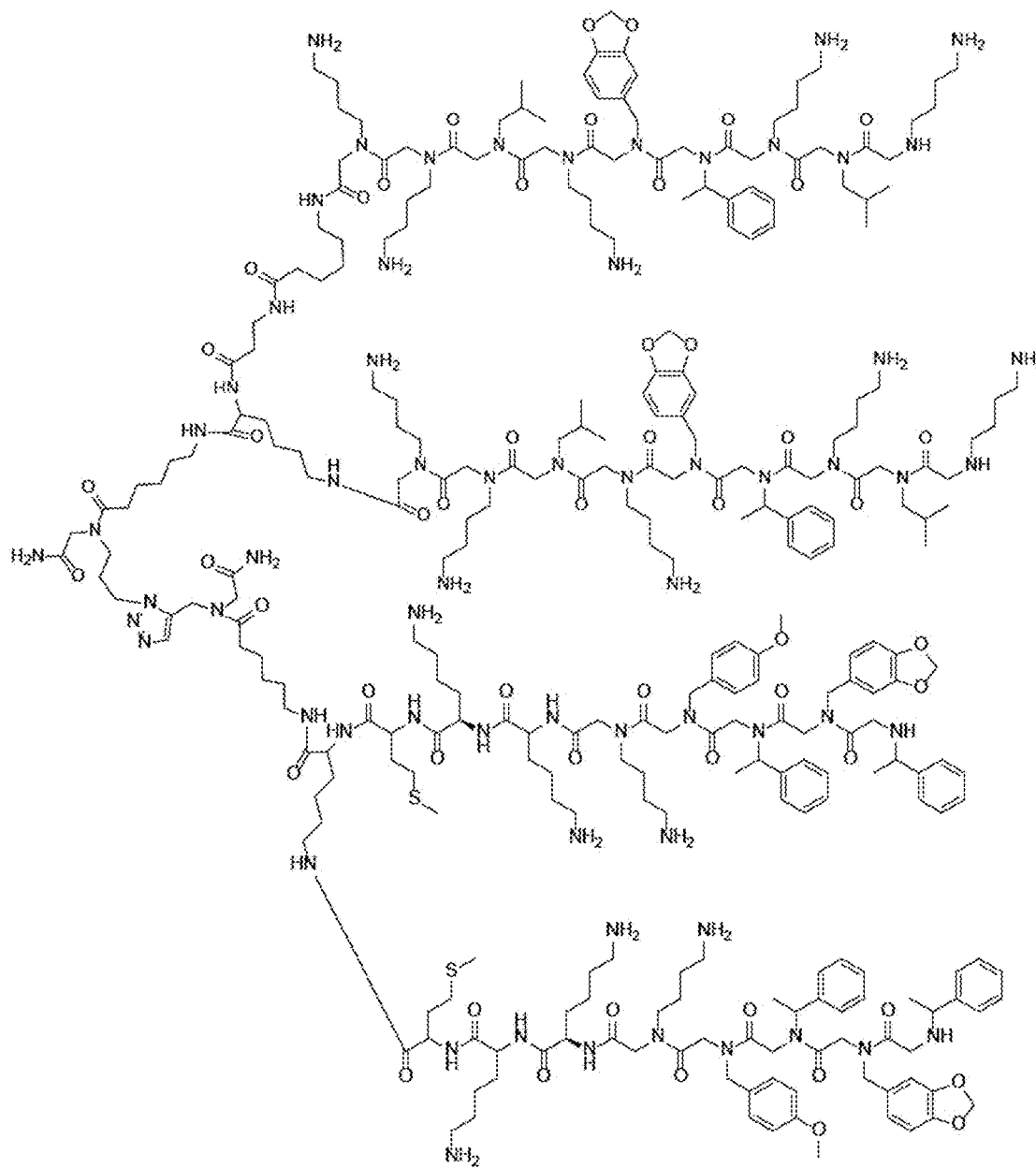

FIG. 21 depicts the structure of PPS1-Tet-1.

Figure 22:
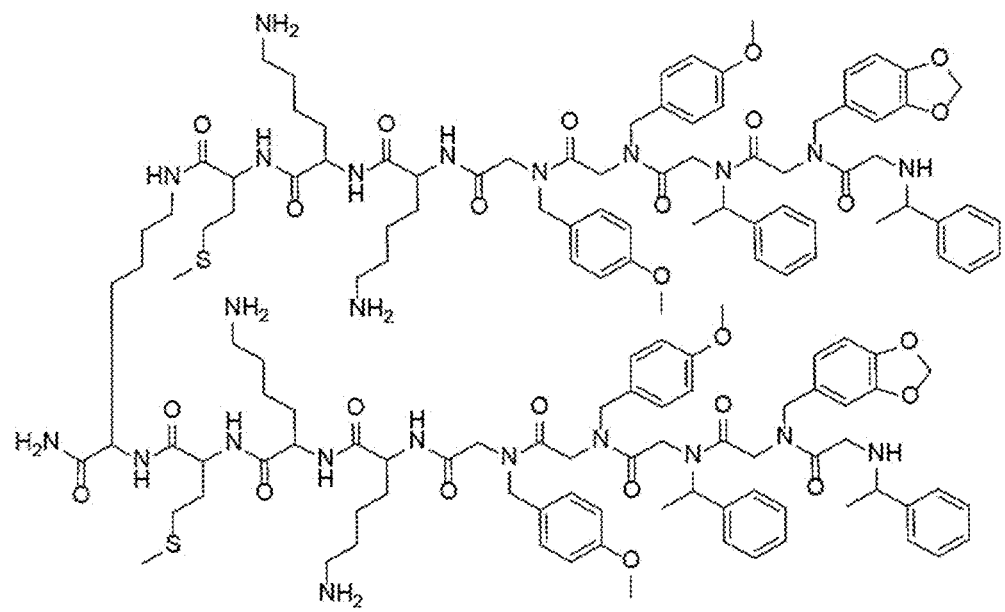

FIG. 22 depicts the structure of PPS2D1.

Figure 23:
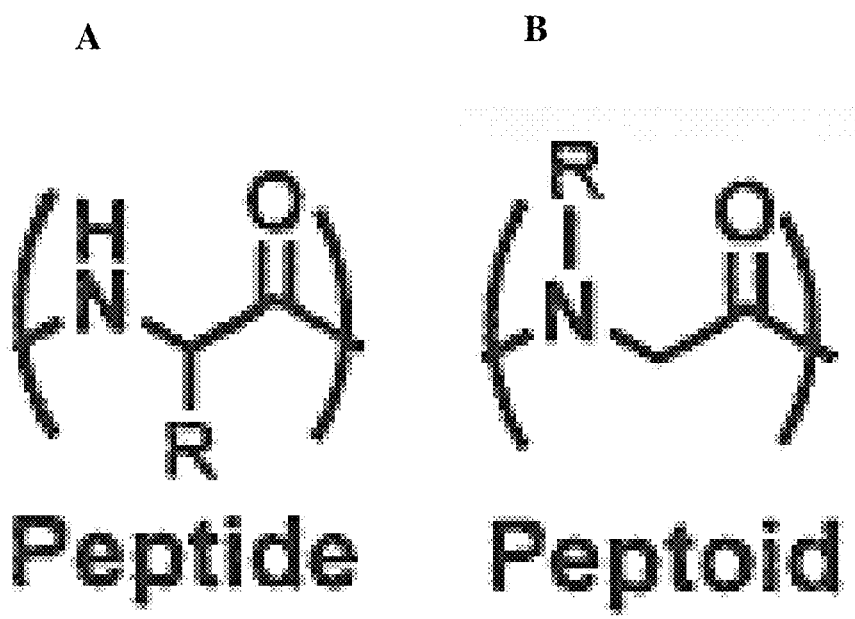

FIG. 23 (A) depicts the structure of a peptide; (B) depicts the structure of a peptoid.

Figure 24:
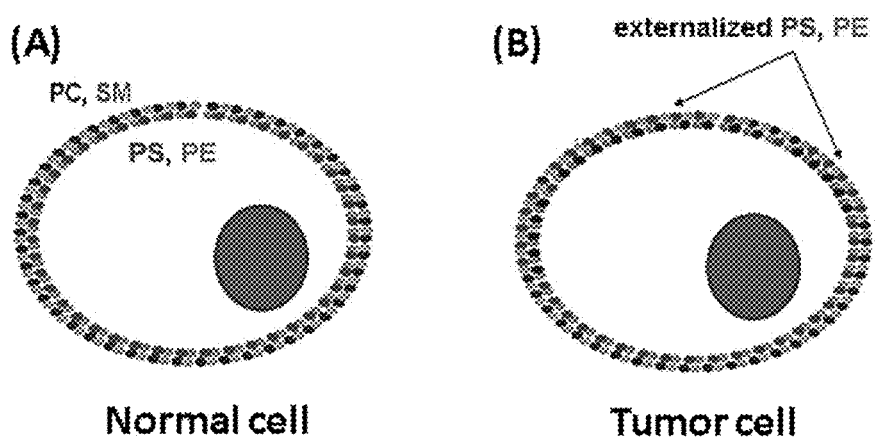

FIG. 24 depicts the different expression pattern of PS on normal and tumor cells.

Figure 25:
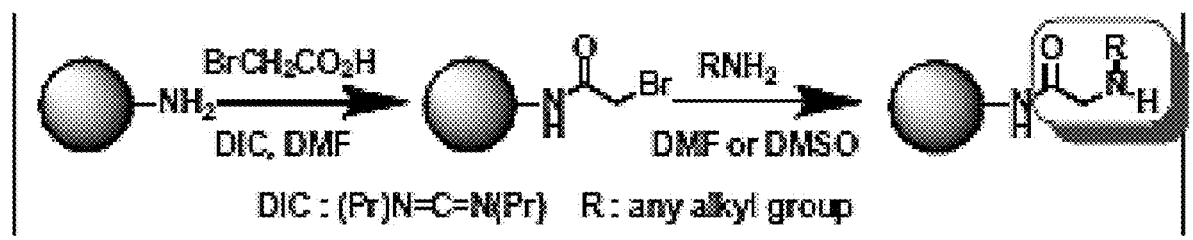

FIG. 25 depicts a peptoid synthesis outline.

Figure 26:
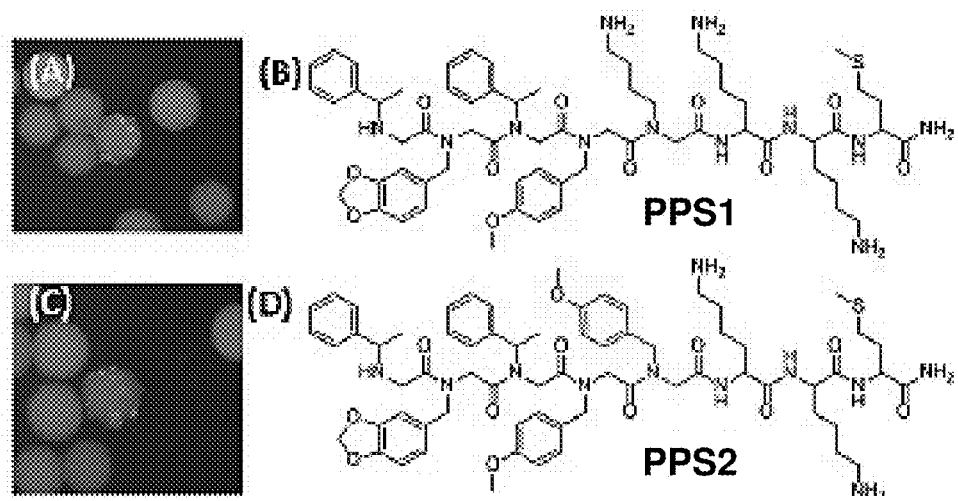

FIG. 26 depicts the hit beads (A) and (C); chemical structures of PPS1 (B) and PPS2 (D).

Figure 27:
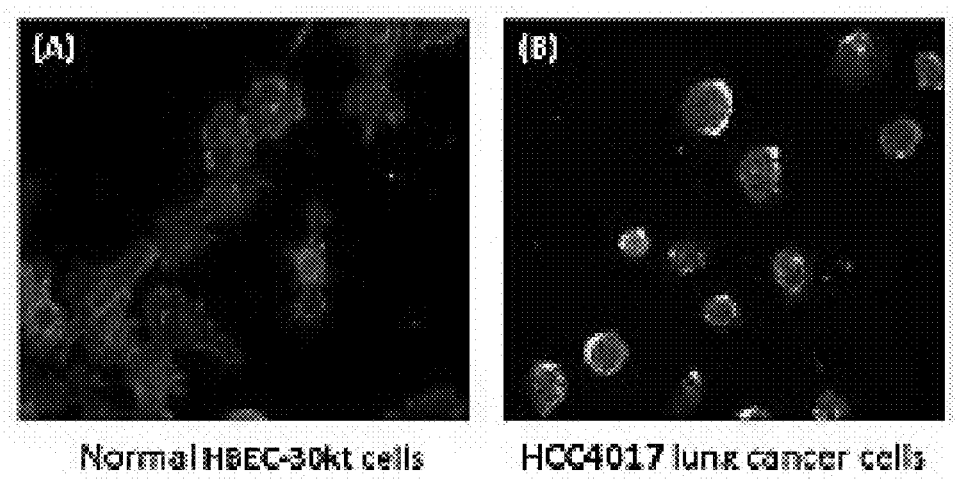

FIG. 27 depicts that PS is (A) not expressed on normal HBEC30kt cells, but (B) highly expressed on HCC4017 lung cancer cells (green stain).

Figure 28:
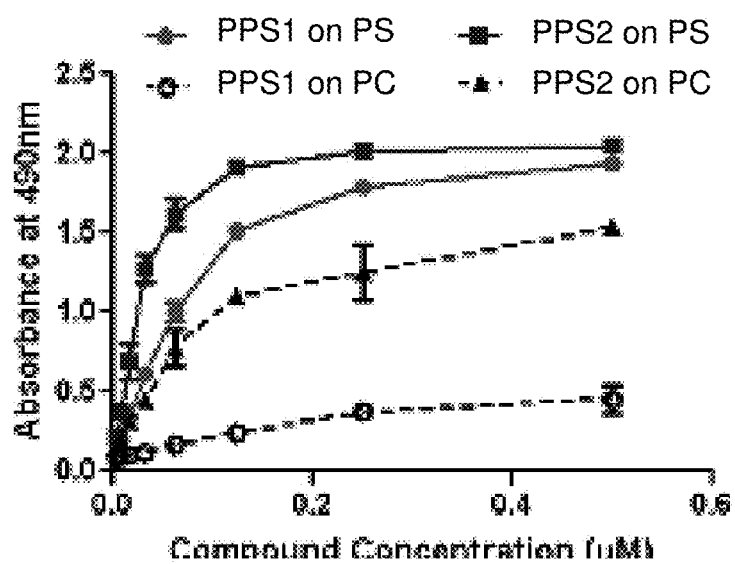

FIG. 28 depicts that PPS1 and PPS2 strongly bind to PS but not to PC.

Figure 29:
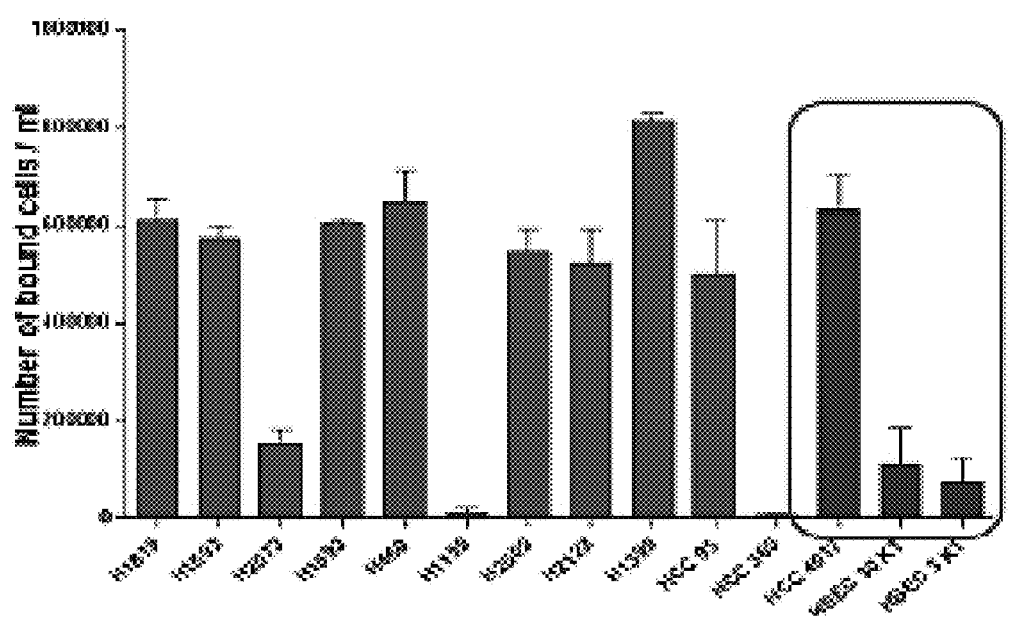

FIG. 29 depicts that PPS1 pulls down a series of lung cancer cell lines but not normal HBEC cell types.

Figure 30:
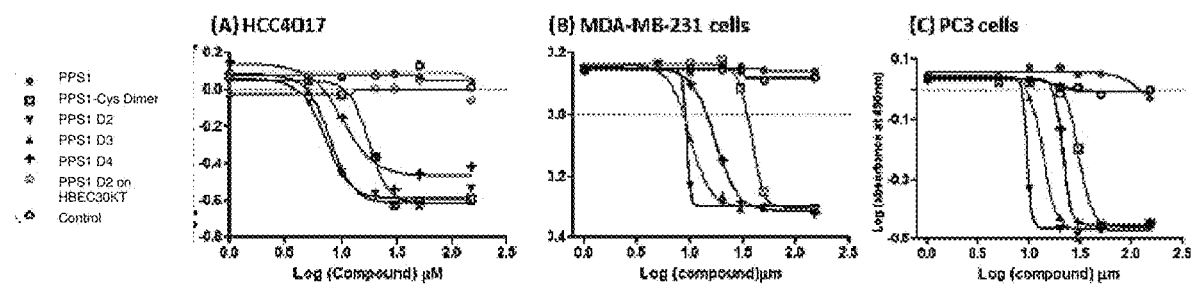

FIG. 30 Cell lytic activities of PPS1 and PPS1-dimers on (A) HCC4017, (B) MDA-MB-231, and (C) PC3 cells.

Figure 31:
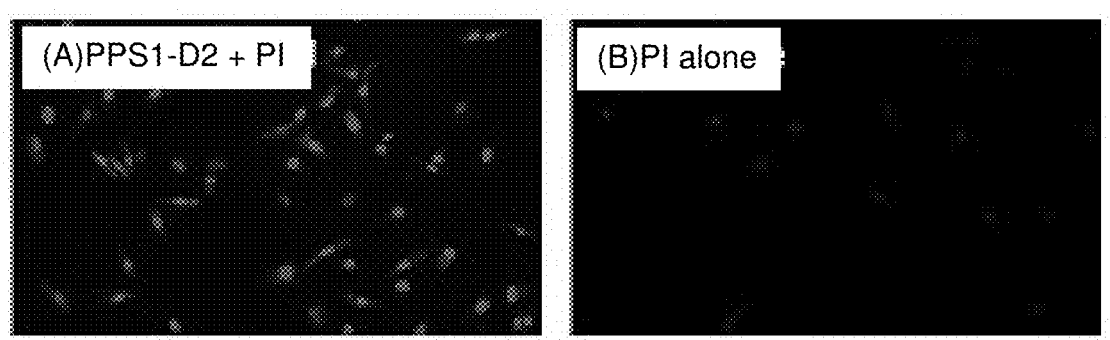

FIG. 31 Cell lytic activity confirmation with propidium iodide treatment (A) staining occurred only with PPS1-D2 treatment, (B) but not in the absence of the peptoid.

Figure 32:
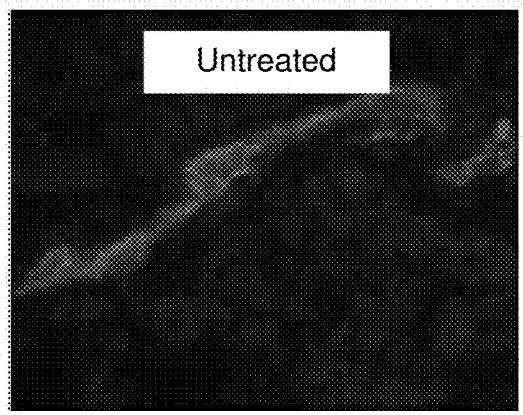
Figure 32:
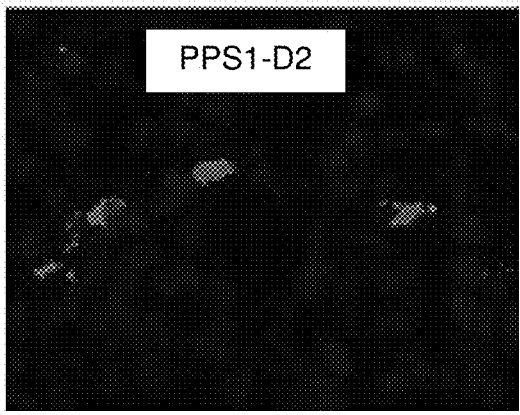

FIG. 32 Disruption of tumor vascular endothelium by PS-targeting peptoid dimer PPS1-D2. Mice bearing subcutaneous HCC4017 tumors were injected i.v. with 20 µg of PPS1-D2. 24 hrs later the mice were sacrificed and frozen sections of the tumors were stained with antibodies to CD31 (red). Vessels in the untreated control tumors had normal morphology (A), whereas disruption of vascular endothelium was observed in numerous tumor vessels (B).

Figure 33:
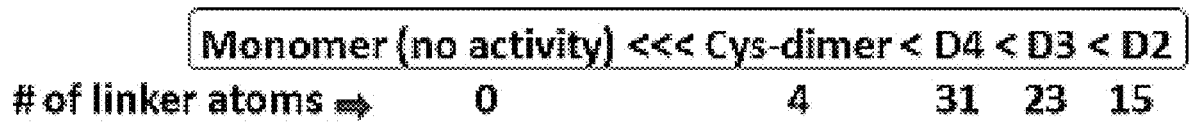

FIG. 33 depicts different PPS1 dimers and the number of atoms in each linker.

Figure 34:
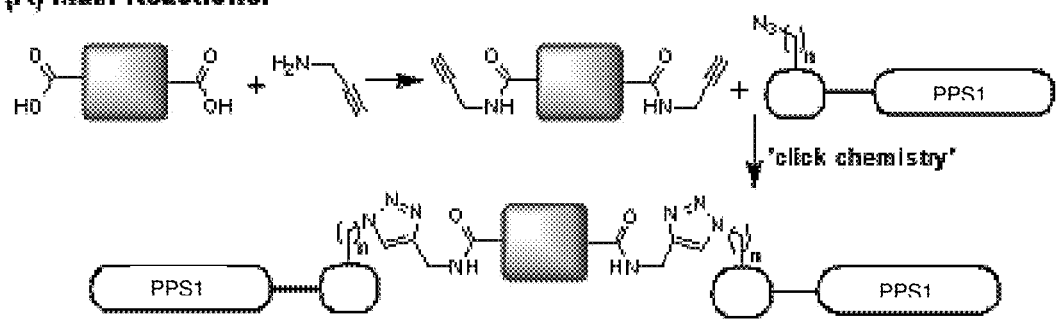
Figure 34:
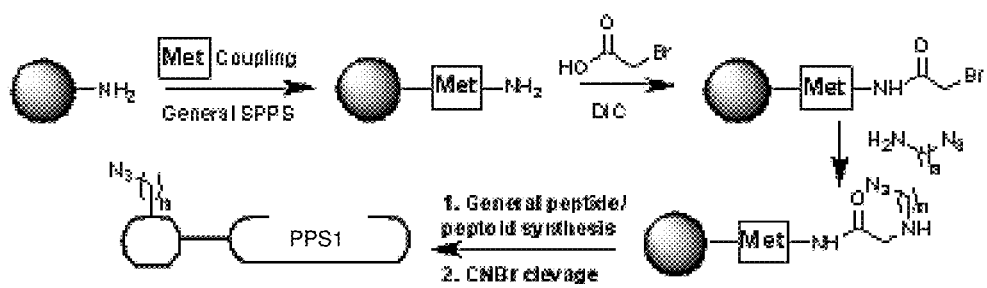

FIG. 34 (A) Two solution phase reactions involve in PPS1 dimer synthesis (B) Solid phase synthesis of azide-PPS1.

Figure 35:
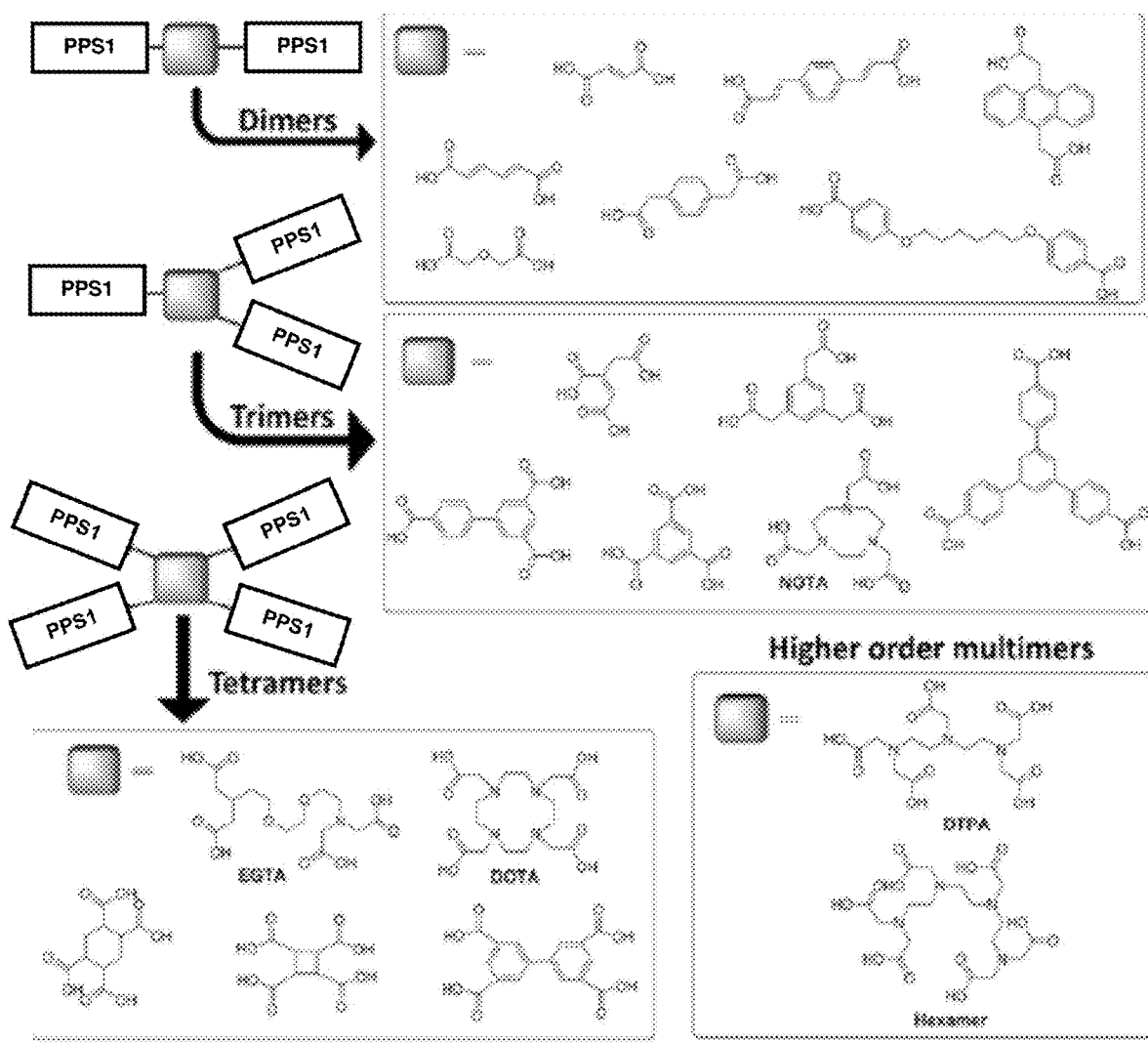

FIG. 35 List of different carboxylic acid scaffolds used in multimer synthesis.

Figure 36:
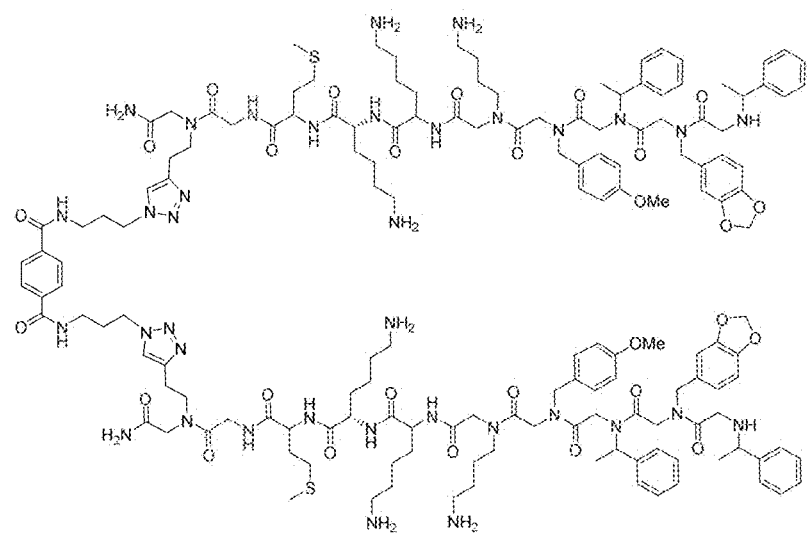

FIG. 36 depicts a new derivative peptoid.

Figure 37:
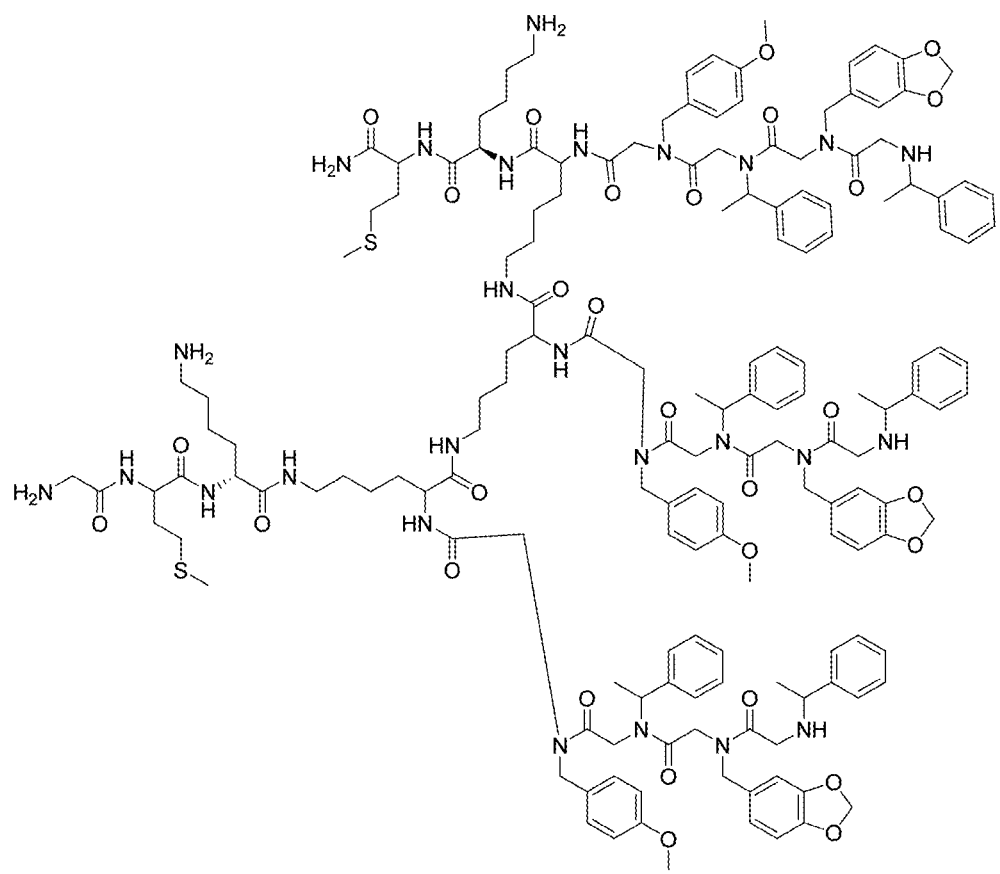

FIG. 37 depicts a new derivative peptoid.

Figure 38:
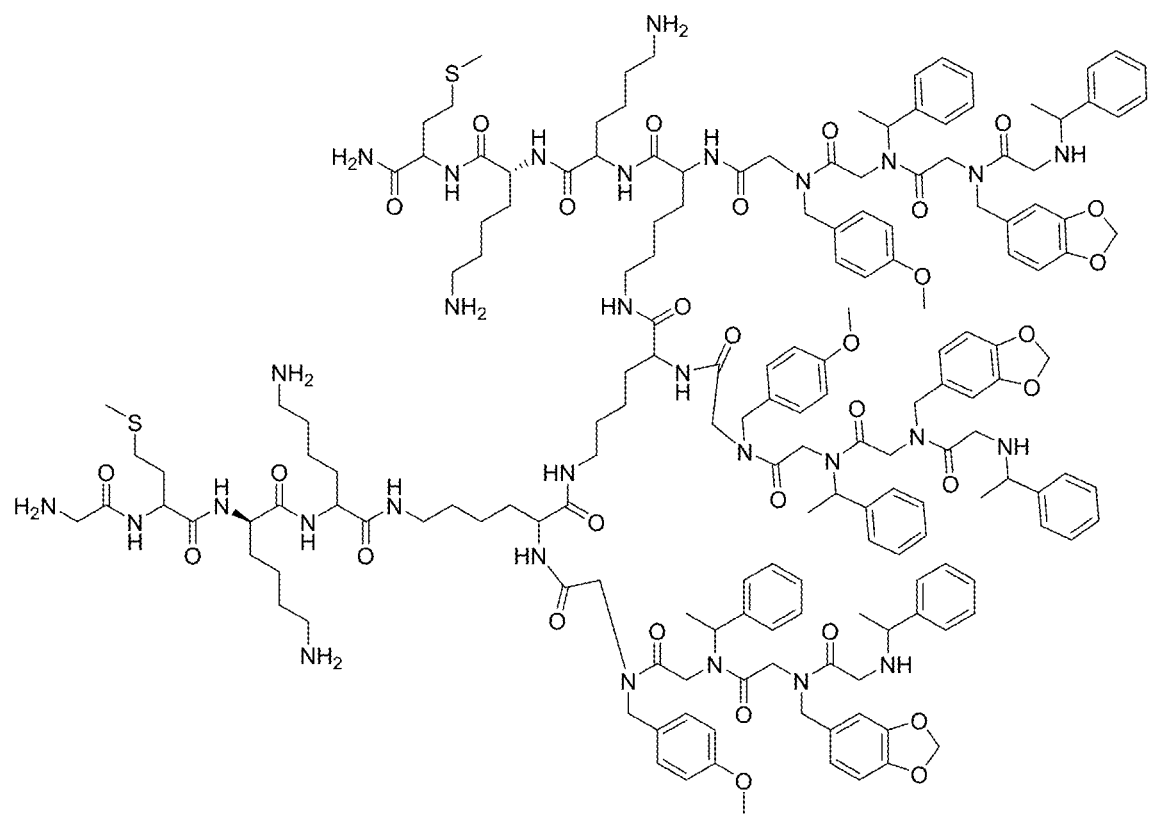

FIG. 38 depicts a new derivative peptoid.

Figure 39:
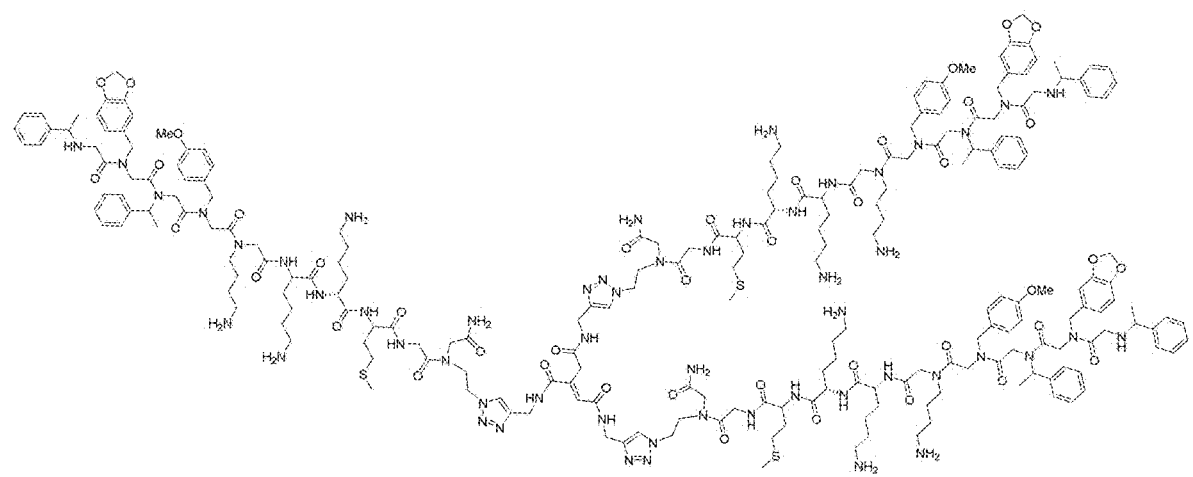

FIG. 39 depicts a new derivative peptoid.

Figure 40:
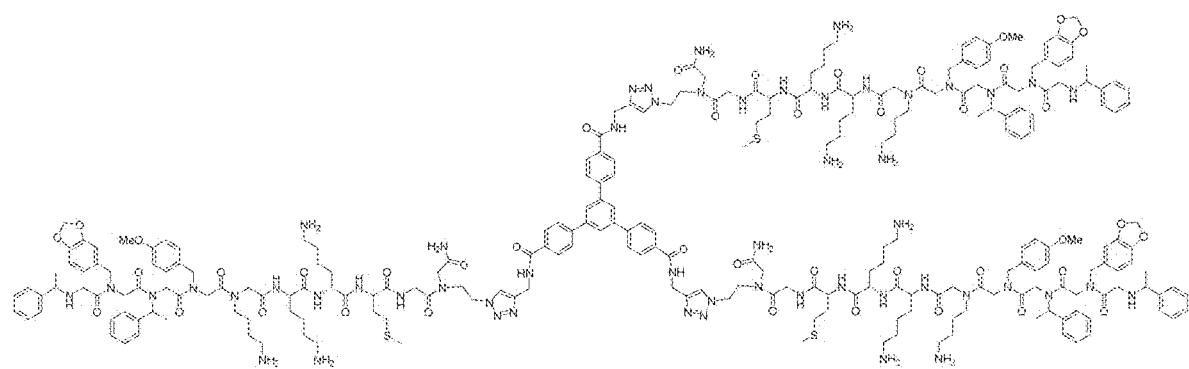

FIG. 40 depicts a new derivative peptoid.

Figure 41:
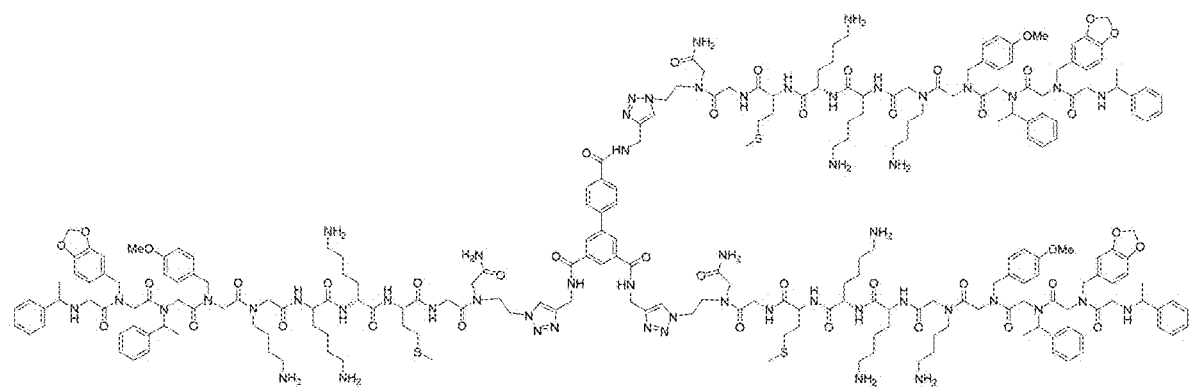

FIG. 41 depicts a new derivative peptoid.

Figure 42:
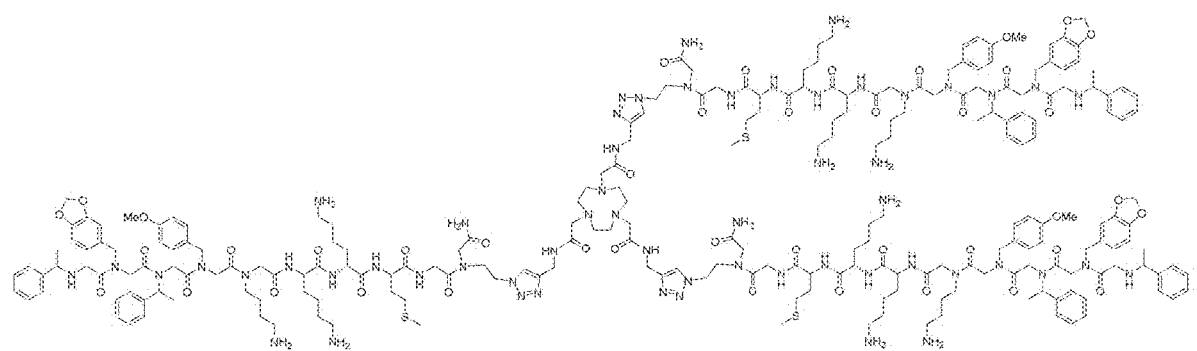

FIG. 42 depicts a new derivative peptoid.

Figure 43:
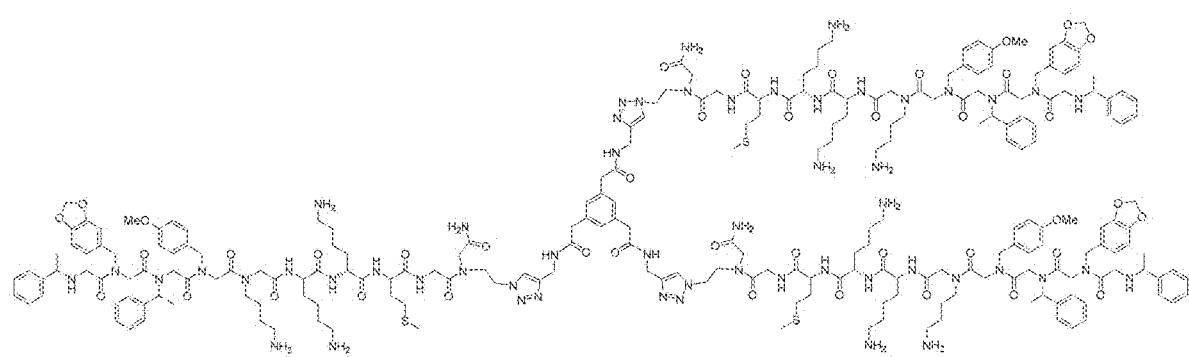

FIG. 43 depicts a new derivative peptoid.

Figure 44:
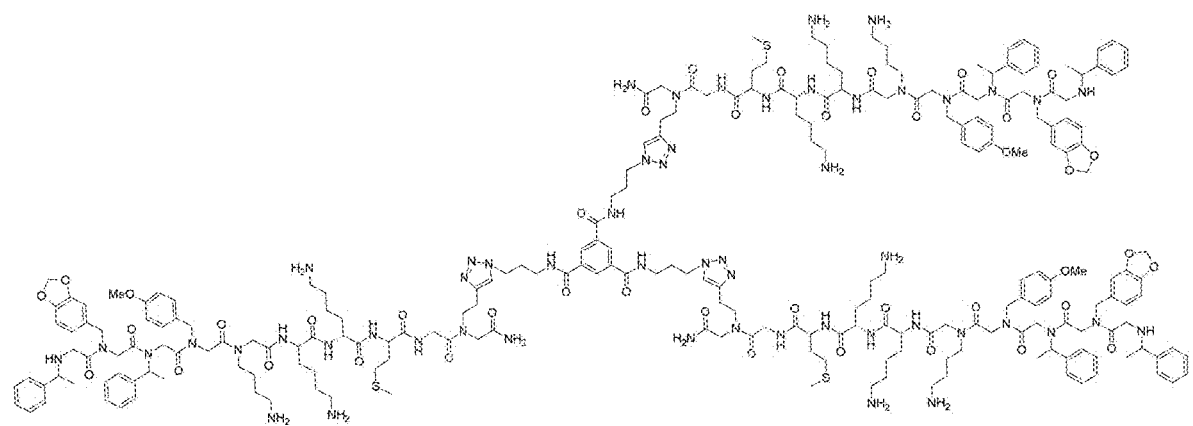

FIG. 44 depicts a new derivative peptoid.

Figure 45:
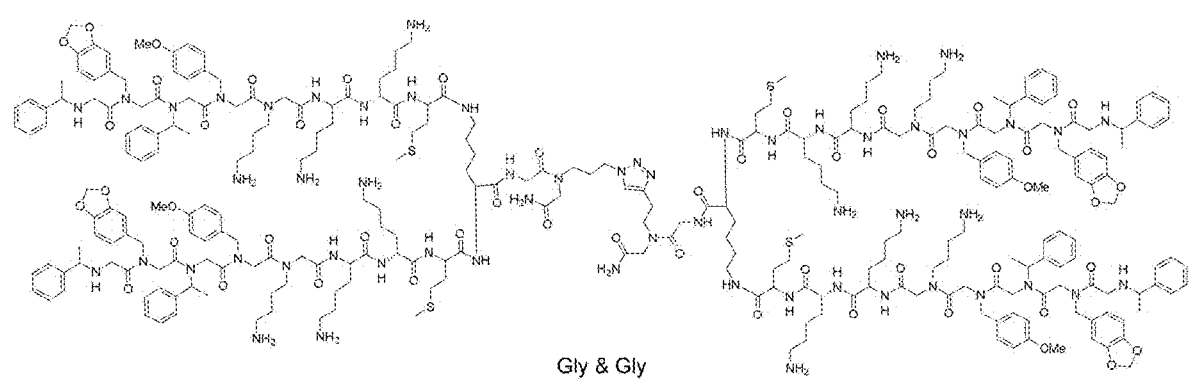

FIG. 45 depicts a new derivative peptoid.

Figure 46:
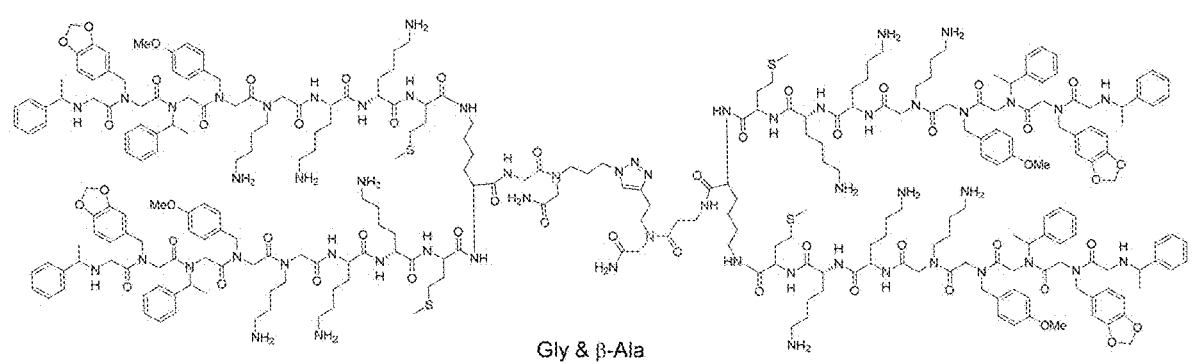

FIG. 46 depicts a new derivative peptoid.

Figure 47:
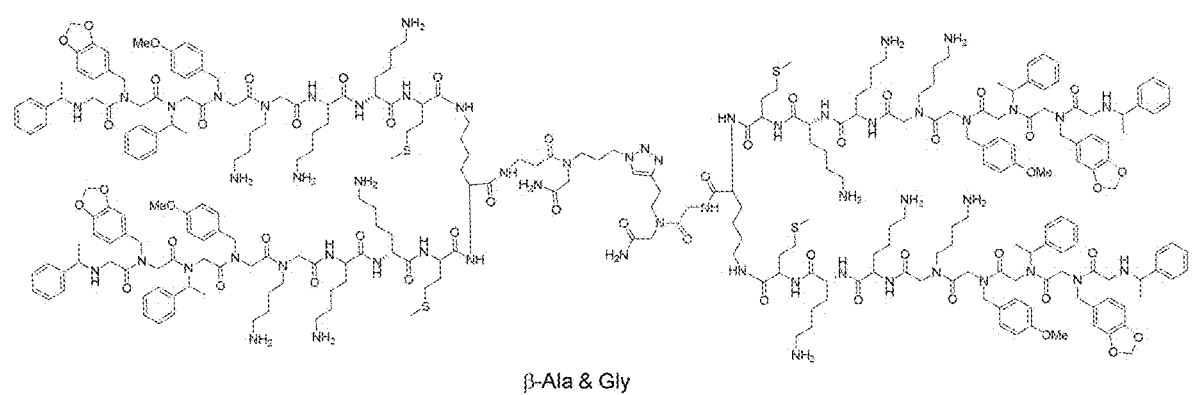

FIG. 47 depicts a new derivative peptoid.

Figure 48:
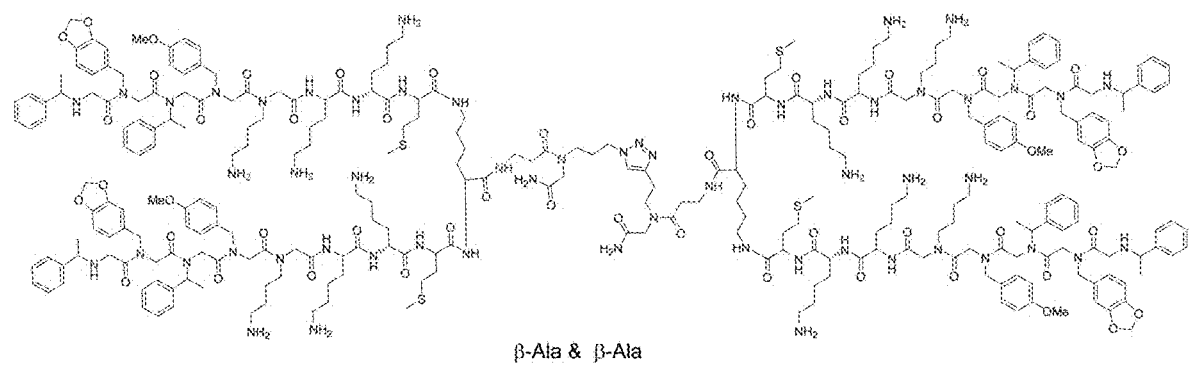

FIG. 48 depicts a new derivative peptoid.

Figure 49:
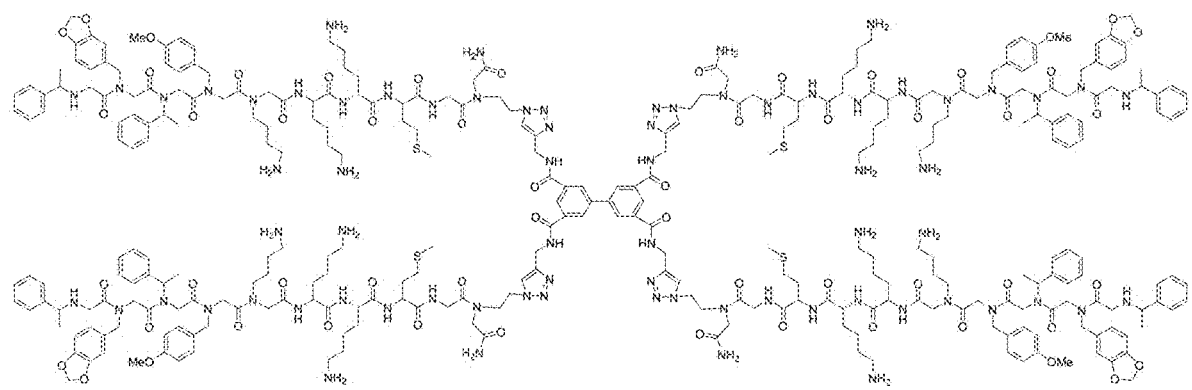

FIG. 49 depicts a new derivative peptoid.

Figure 50:
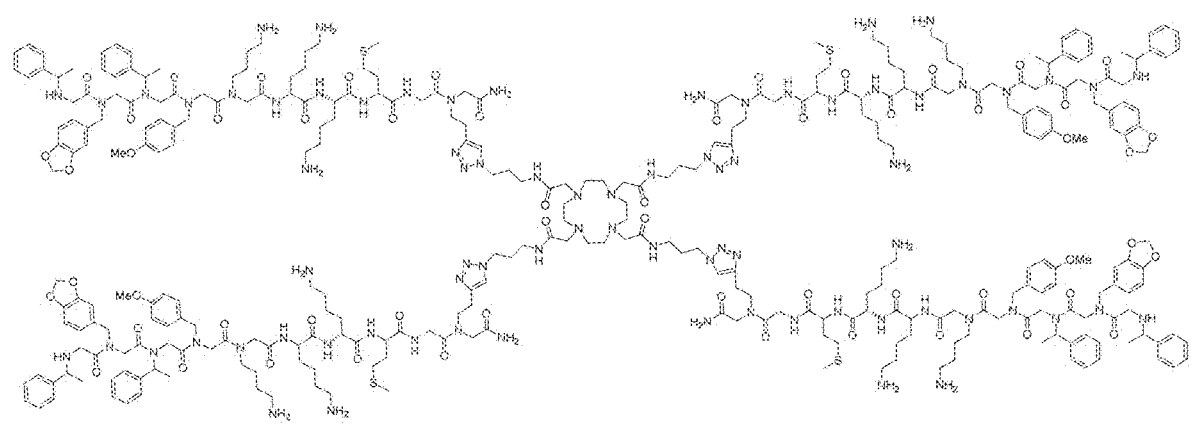

FIG. 50 depicts a new derivative peptoid.

Figure 51:
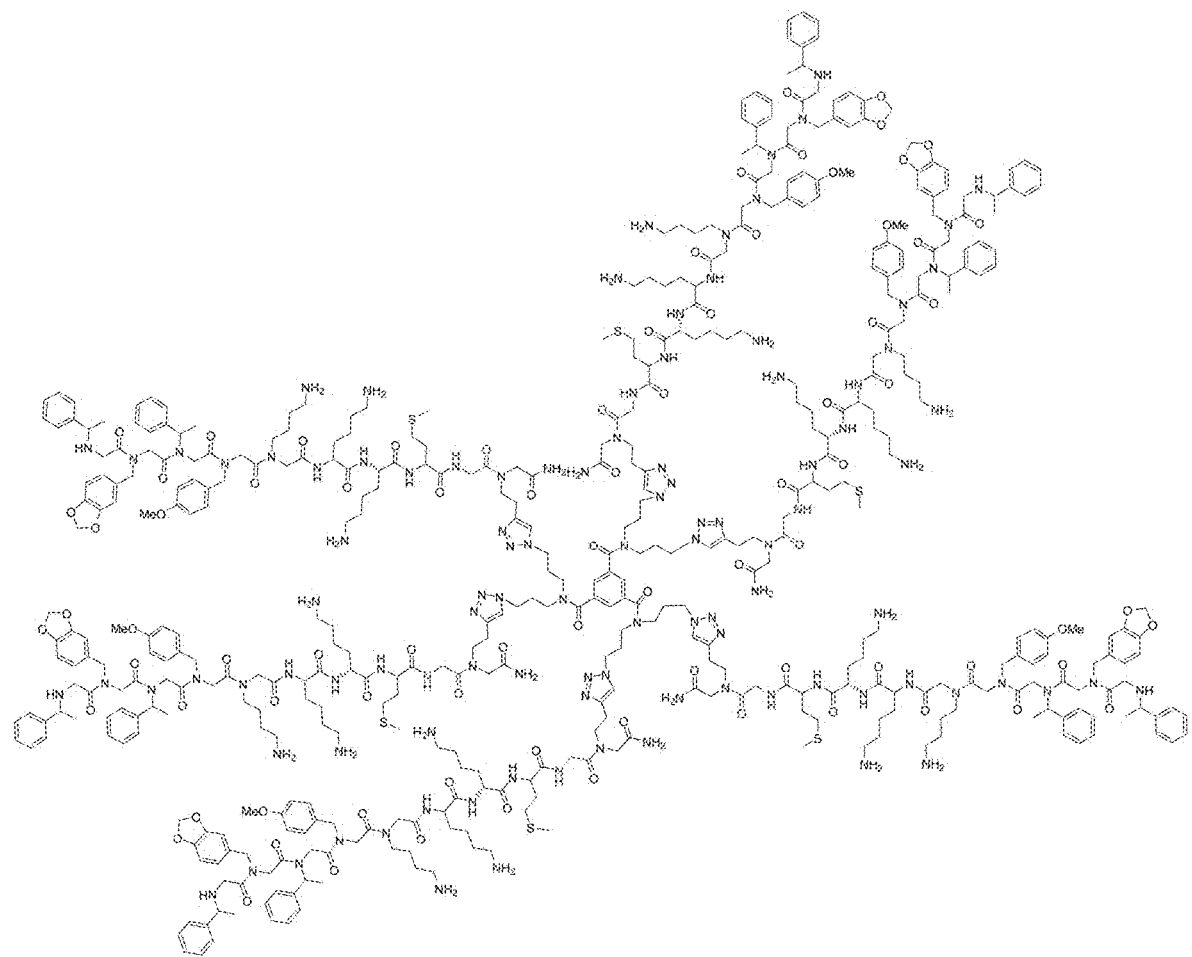

FIG. 51 depicts a new derivative peptoid.

Figure 52:
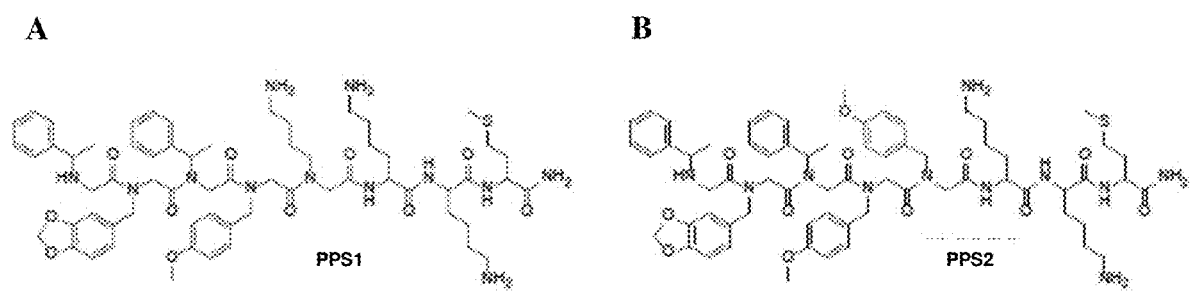

FIG. 52 depicts the structure of PPS1 and PPS2.

Figure 53:
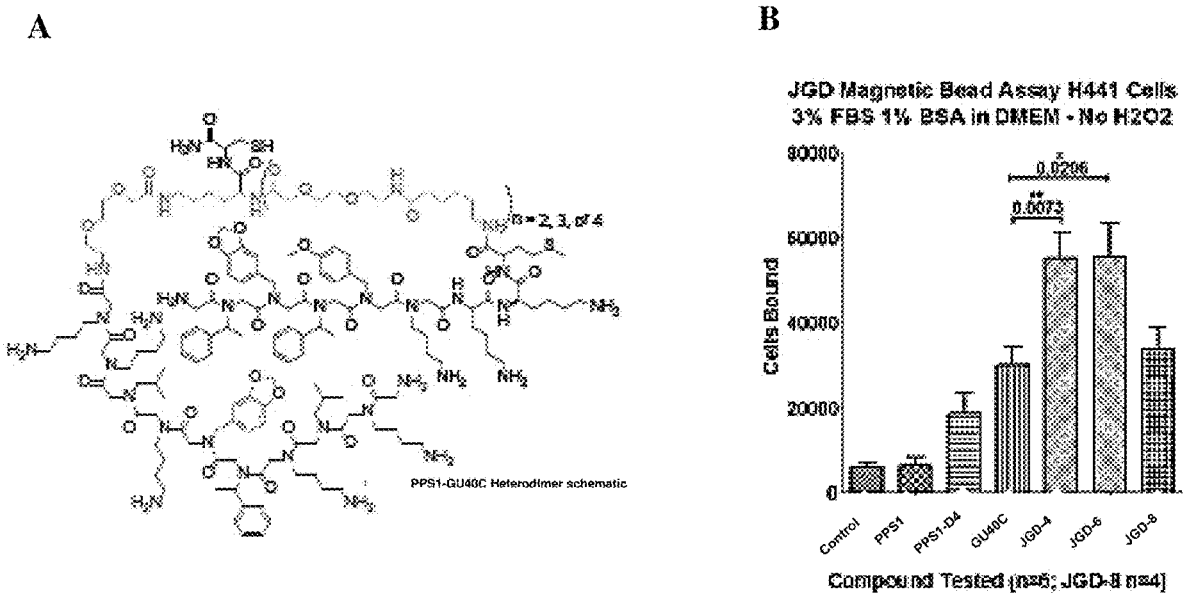

FIG. 53 depicts development of hetero-dimers targeting VEGFR2(GU40C) and PS (PPS1); (A) structure of PPS1-GU40C heterodimer (B) JGD Magnetic bead assay with H441 cells.

Figure 54:
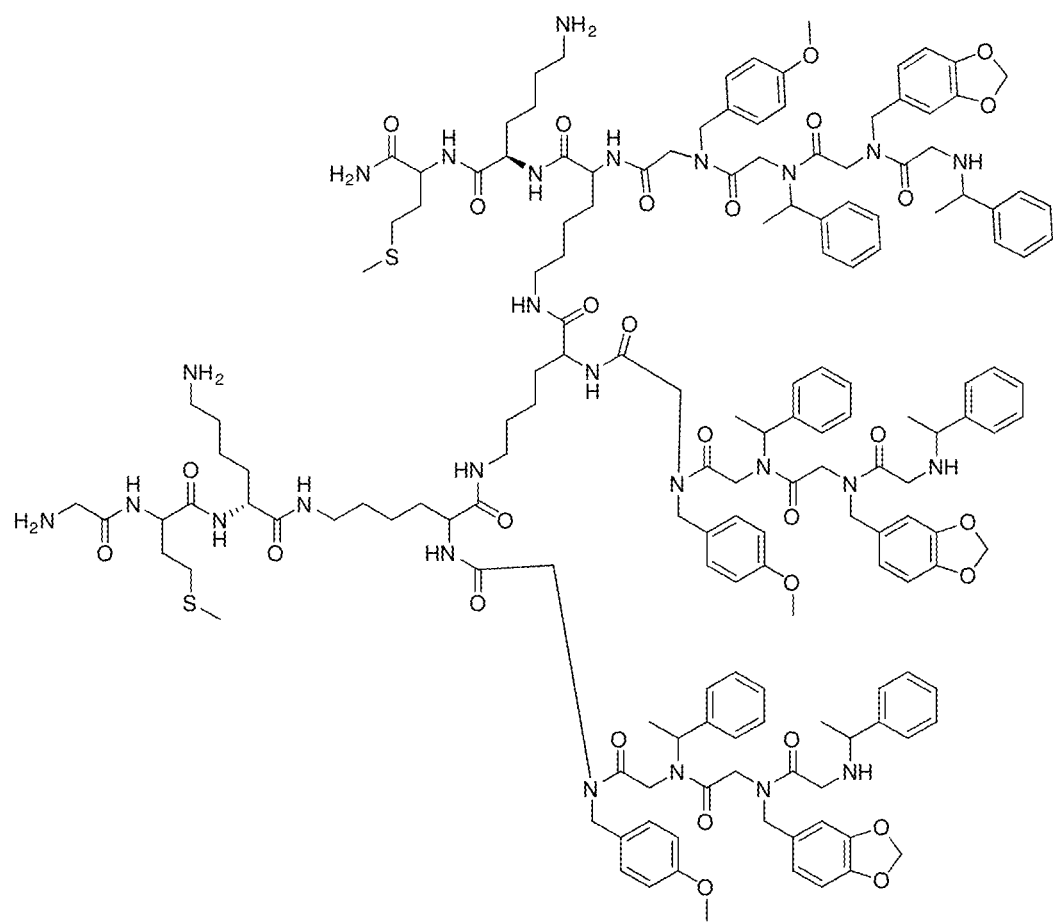

FIG. 54 depicts the structure of 2P3H-PPPS1.

Figure 55:
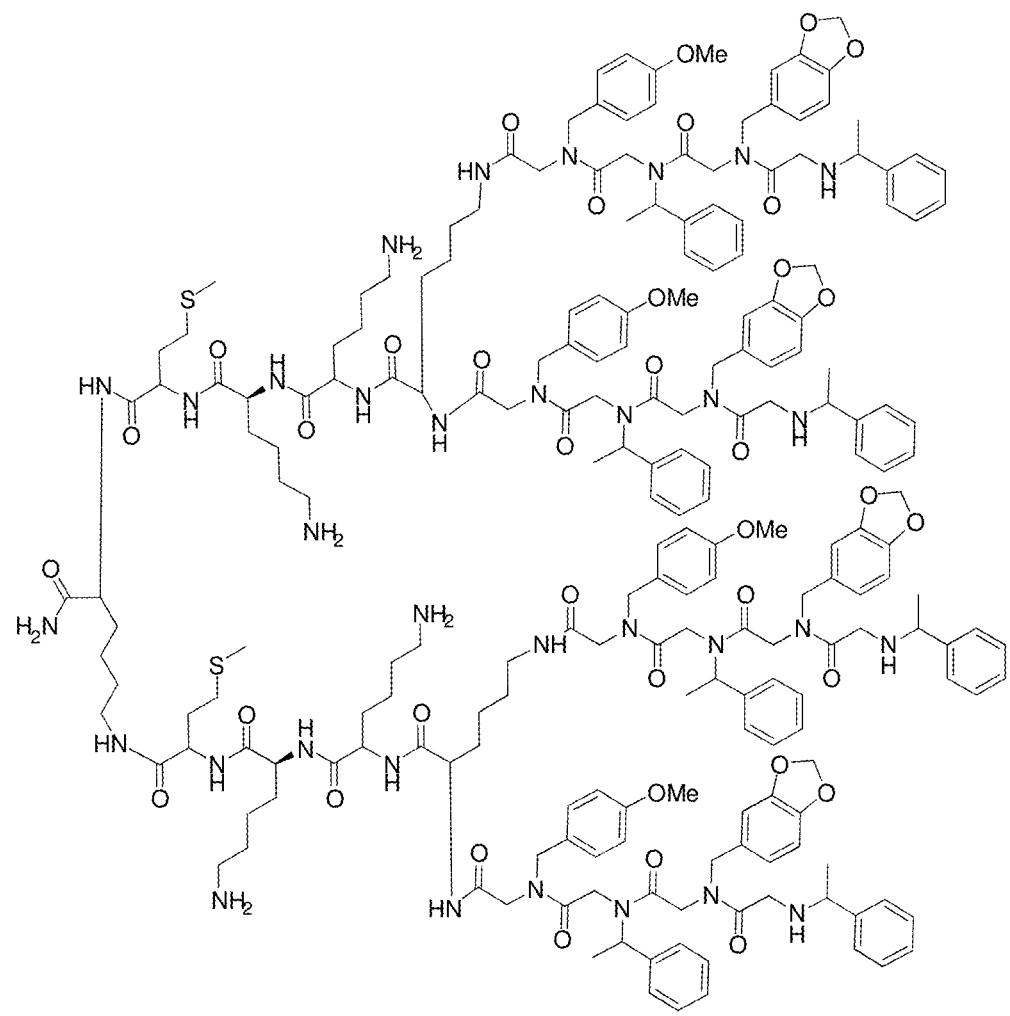

FIG. 55 depicts the structure of 2-4-PPS1.

Figure 56:
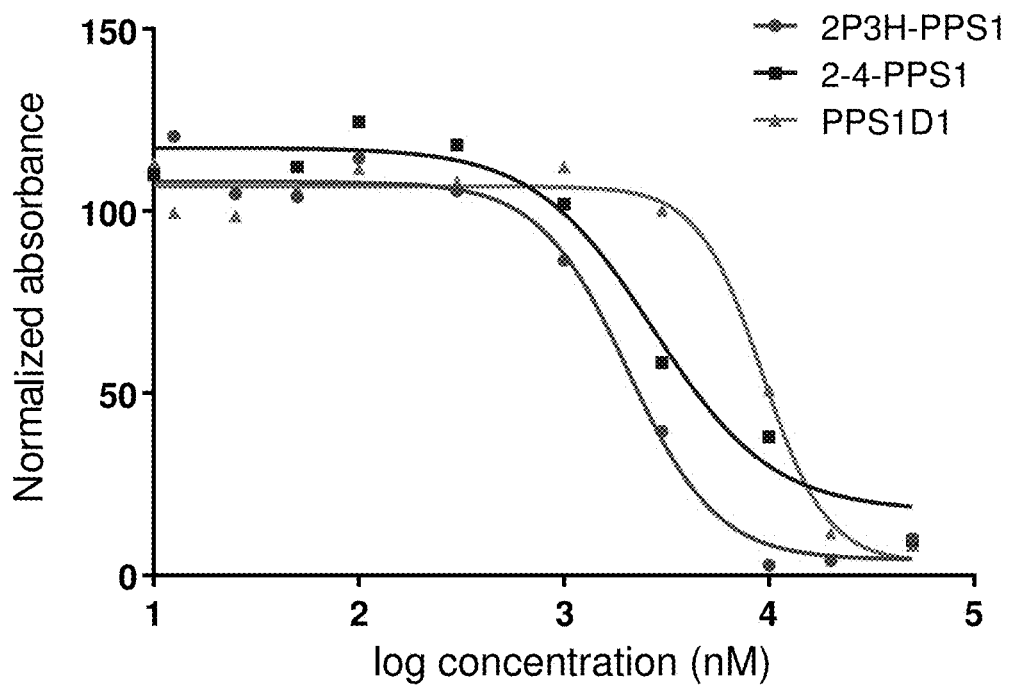

FIG. 56 depicts a graph of the HCC4017 cancer cell killing activity (MTS) of 2P3H-PPPS1 and 2-4-PPS1.

Figure 57:
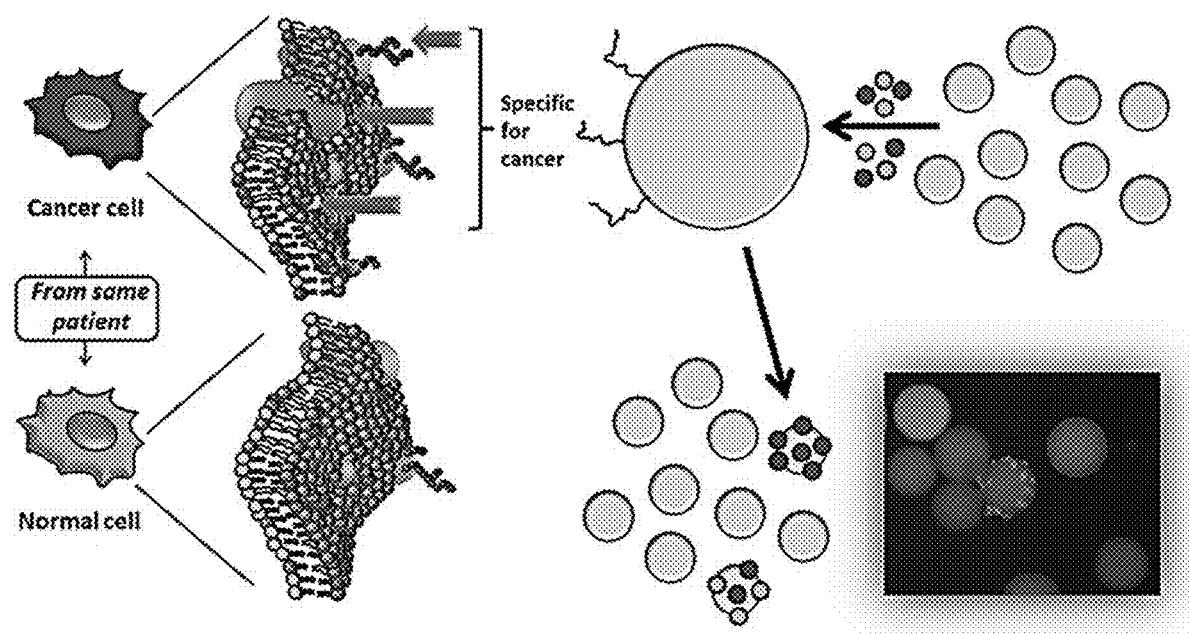

FIG. 57 depicts a peptidomimetic based on-bead two-color (OBTC) combinatorial cell screen that can detect differences between two cell surfaces at high accuracy by looking for beads (where each bead in the library had one peptide-peptoid hybrid on the surface) that only bound cancer but not normal cells.

Figure 58:
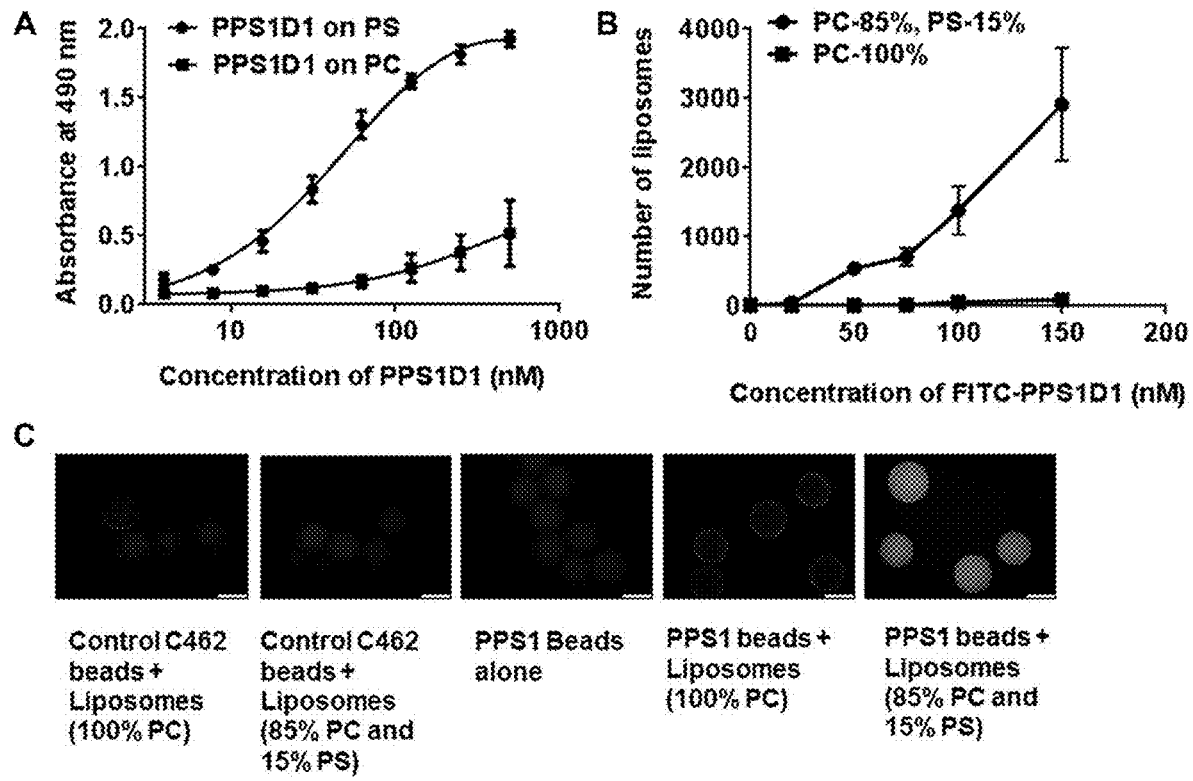

FIG. 58 depicts (A) ELISA binding assay of FITC-PPS1D1 with phosphatidylcholine (PC) and phosphatidylserine (PS) indicates that FITC-PPS1D1 only binds to PS. (B) Binding of liposomes made of 100% PC and 85% PC-15% PS to PPS1D1-FITC. Only 15% PS containing liposomes bound to FITC-PPS1D1 (Error bars represent standard deviation). (C) Binding of liposomes made of 100% PC and 85% PC-15% PS to PPS1 and control PC462 carrying tentagel beads. Only 15% PS containing liposomes bound to PPS1 beads, but not liposomes with no PS (100% PC). Control PC462 does not bind to both liposome types.

Figure 59:
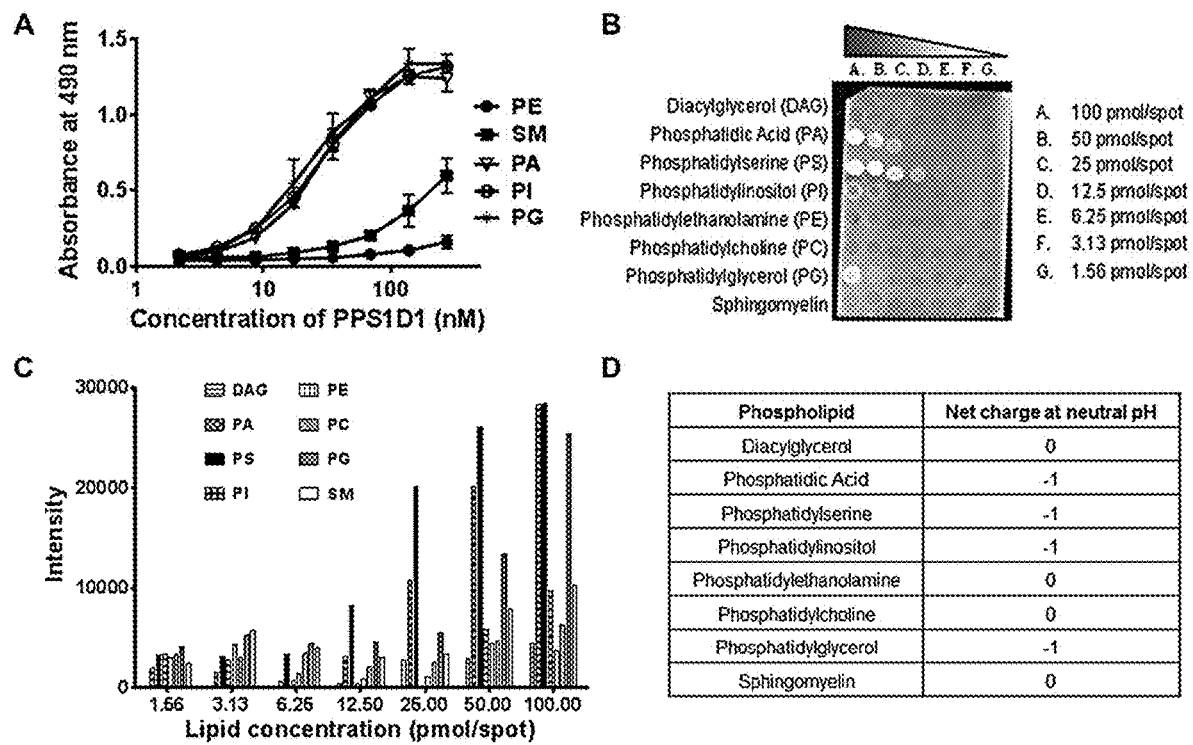

FIG. 59 depicts (A) ELISA binding assay of PPS1D1-FITC with Phosphatidylethanolamine (PE), Sphingomyelin (SM), Phosphatidic Acid (PA), Phosphatidylinositol (PI) and Phosphatidylglycerol (PG). Only PA, PI and PG showed binding to PPS1D1-FITC (Error bars represent standard deviation) (B) Lipid dot blot showing binding of biotinylated-PPS1D1 with membrane phospholipids PS, PA, PG and PI, but not to PC, DAG, PE and SM. (C) Quantification of lipid-blot assay figure shown in (B). (D) Net charges of PA, PE, PC, PS, PG, PI and DAG lipids at neutral pH.

Figure 60:
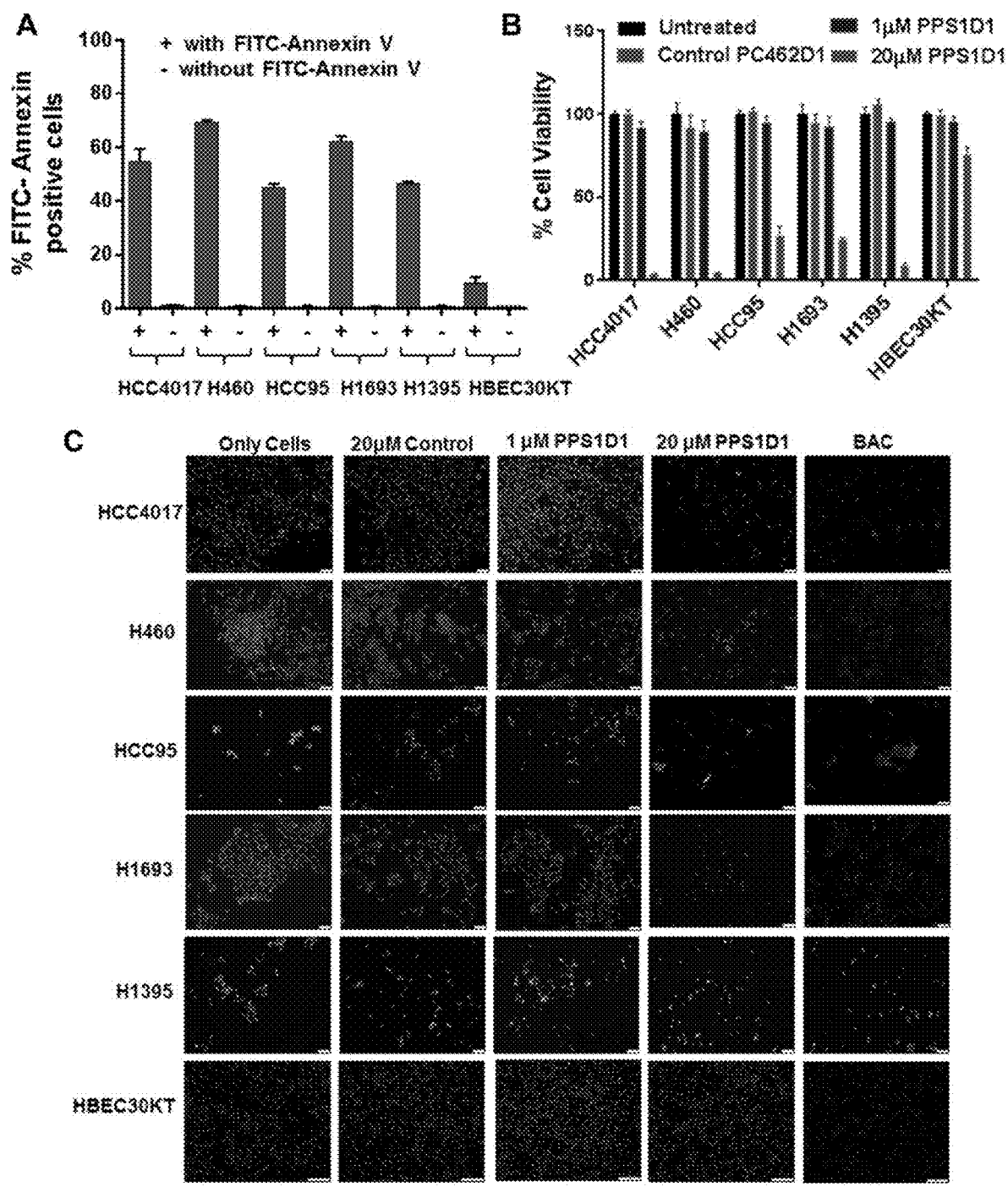

FIG. 60 depicts (A) PS expression levels of lung cancer cell lines HCC4017, H460, HCC95, H1693, H1395 and normal HBEC30KT by binding with FITC-Annexin V. Lung cancer cells exhibited high PS levels while HBEC30KT has lower levels of PS (Error bars represent standard deviation). (B) Standard MTS cell viability data for the treatment of PPS1D1 and control PC462D1 on same lung cancer cells lines and HBEC30KT cells shown in (A). PPS1D1 at 20 µM caused strong cell cytotoxicity on cancer cells, but not on HBEC30KT. (C) Treatment of same lung cancer cells lines and HBEC30KT shown in (A) with Propidium iodide (PI) and Hoechst 33342 dyes. PI stained nuclei of all the cancer cell lines at 20 µM of PPS1D1, but not HBEC30KT cells. A known cell membrane damaging agent, BAC treatment caused PI stain on all the cells lines tested.

Figure 61:
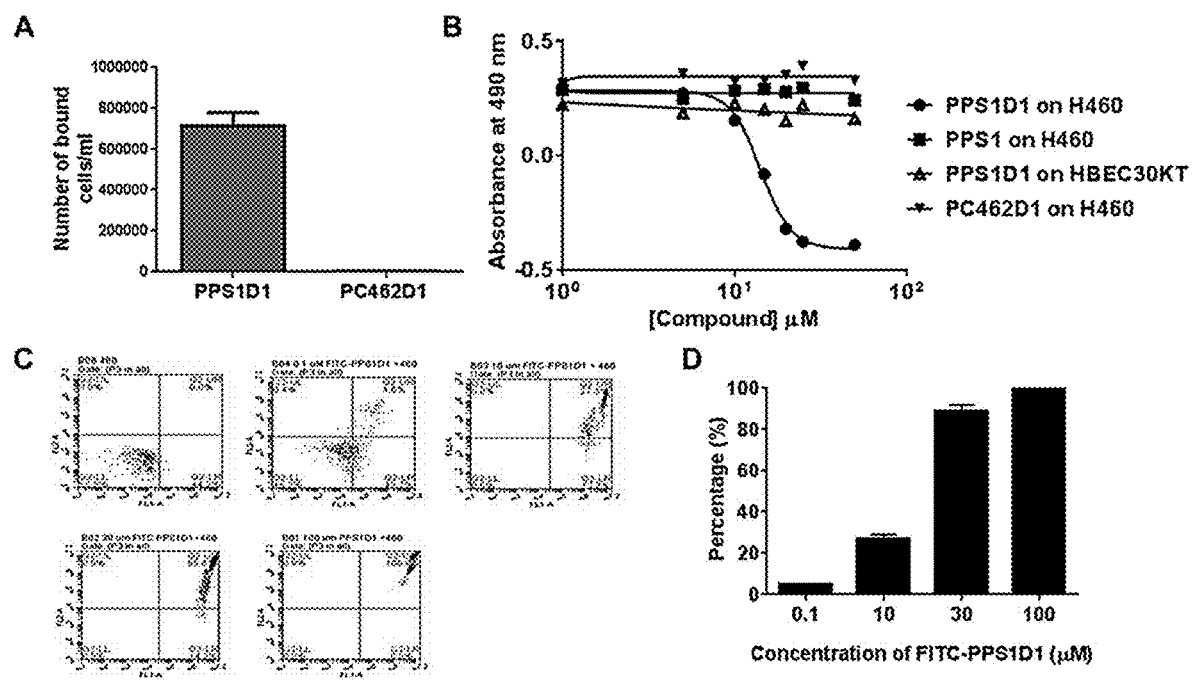

FIG. 61 depicts (A) Magnetic bead pulls down of H460 with PPS1D1, but not with control compound PC462D1 (Error bars represent standard deviation). (B) Standard MTS cell viability assay of H460 and normal HBEC30KT cells treated with PPS1D1, PPS1 and PC462D1. Only PPS1D1 induce the cell cytotoxicity on HCC4017, while no effect on normal HBEC30KT cells. (C) Flow cytometry studies of PPS1D1-FITC binding to H460 cells in the presence of Propidium iodide (PI). H460 cell population significantly moved to double positive region when PPS1D1-FITC concentration increases. (D) Quantification of FITC and PI double stained region.

Figure 62:
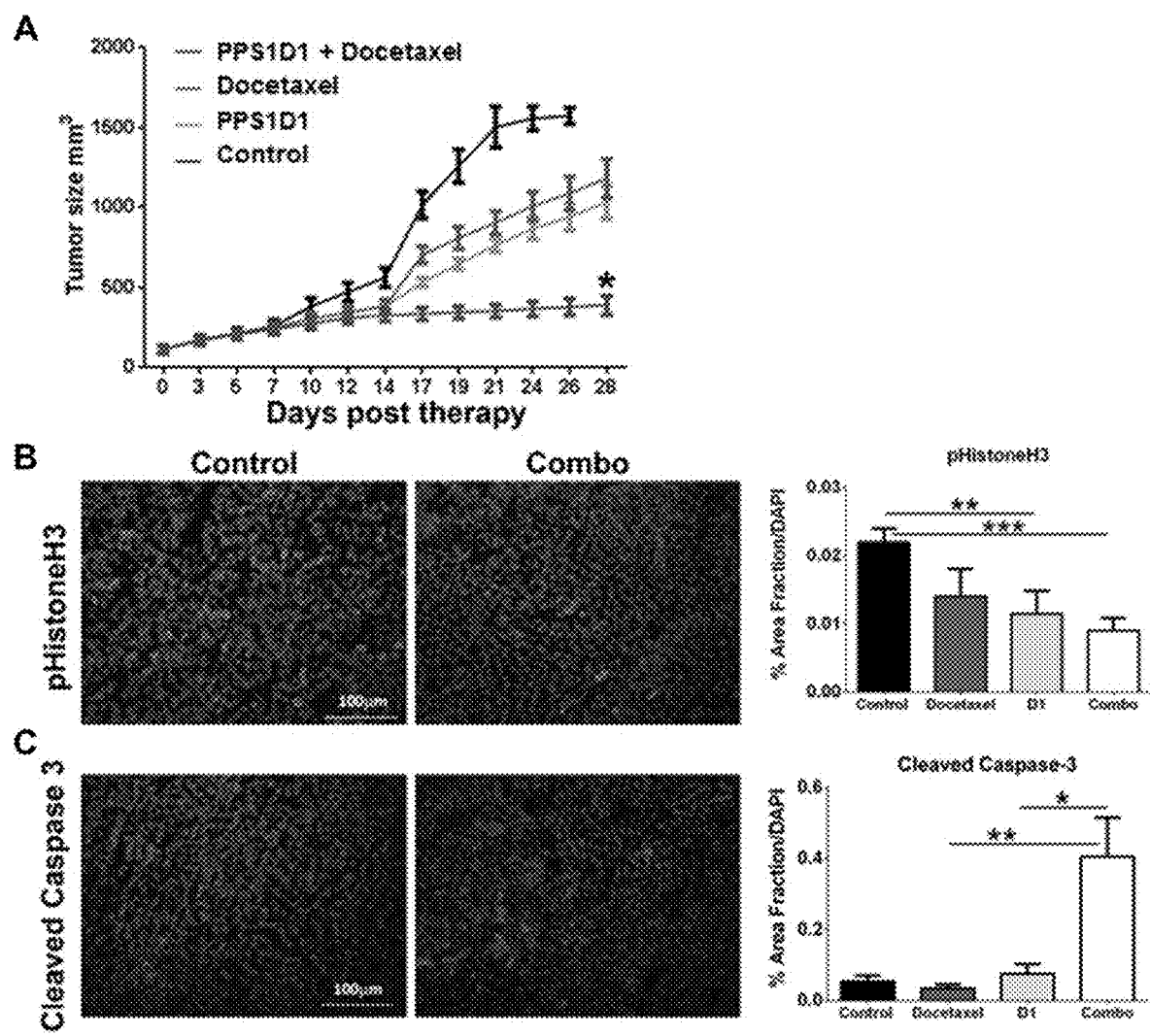

FIG. 62 depicts (A) Mice bearing subcutaneous H460 xenografts were treated with PPS1D1 (D1, n=8, 0.25 mg/mouse, 3 times per week on a M-W-F schedule), PC462D1 (Control, n=8, 0.25 mg/mouse, 3 times per week on a M-W-F schedule), docetaxel (n=8, 5 mg/kg, 2×/week), or the combination of PPS1D1 and docetaxel (n=8, combo). Mean +/−SEM tumor volume is displayed. PPS1D1 displayed tumor burden effects as a single agent as well as in combination with docetaxel. (B, C) Tumor tissue harvested after 4 weeks of therapy was evaluated for cell proliferation (B, phopsho-histone H3) and apoptosis (C, cleaved caspase-3) by immunofluorescence. DAPI was used as a counterstain and to normalize quantification of reactivity. *$p<0.05$; $p<0.01$; *$p<0.005$. The PPS1D1 and docetaxel combination therapy strongly reduce cell proliferation and induce apoptosis.

Figure 63:
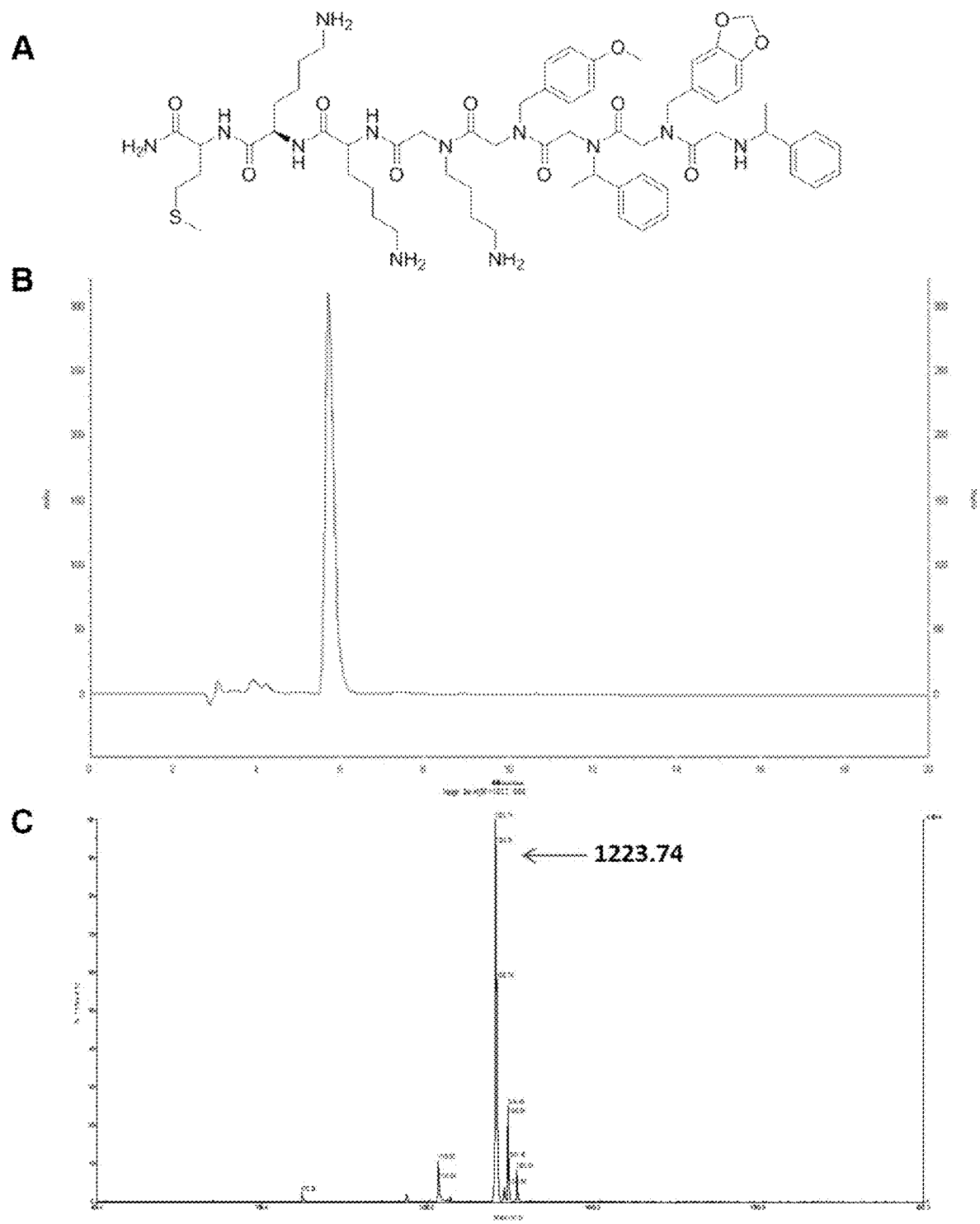

FIG. 63 depicts characterization of PPS1: (A) Chemical structure of PPS1, (B) Analytical HPLC of PPS1, (C) MALDI-TOF spectrum of PPS1.

Figure 64:
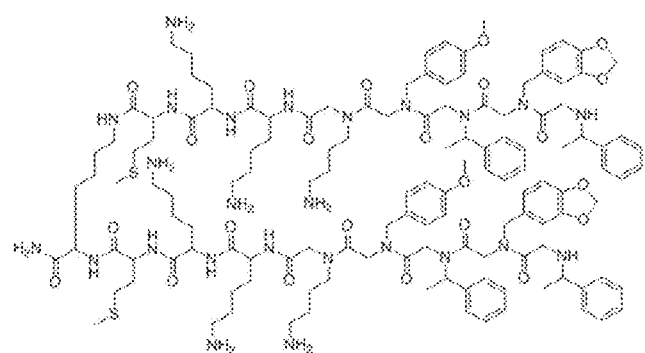
Figure 64:
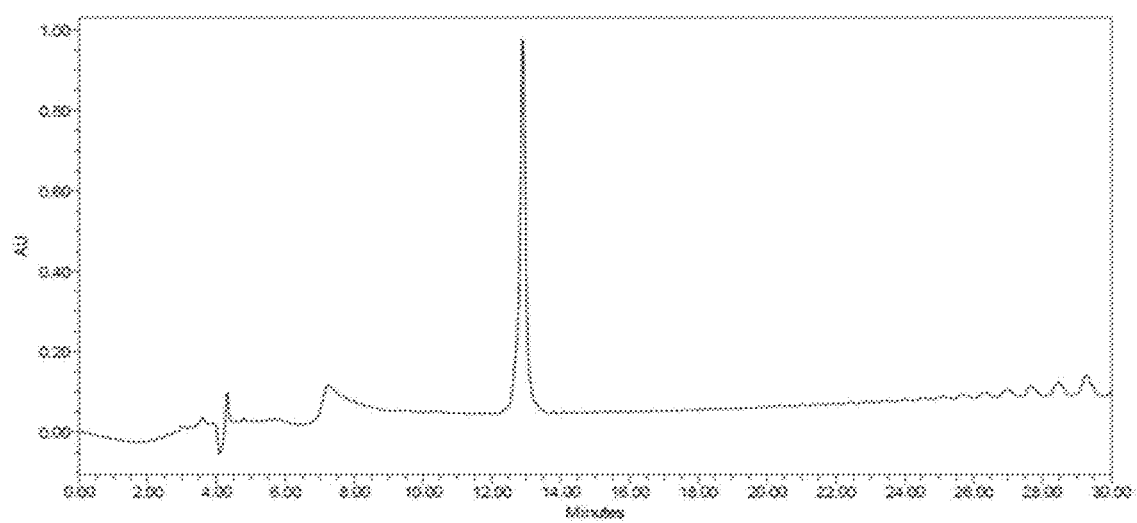
Figure 64:
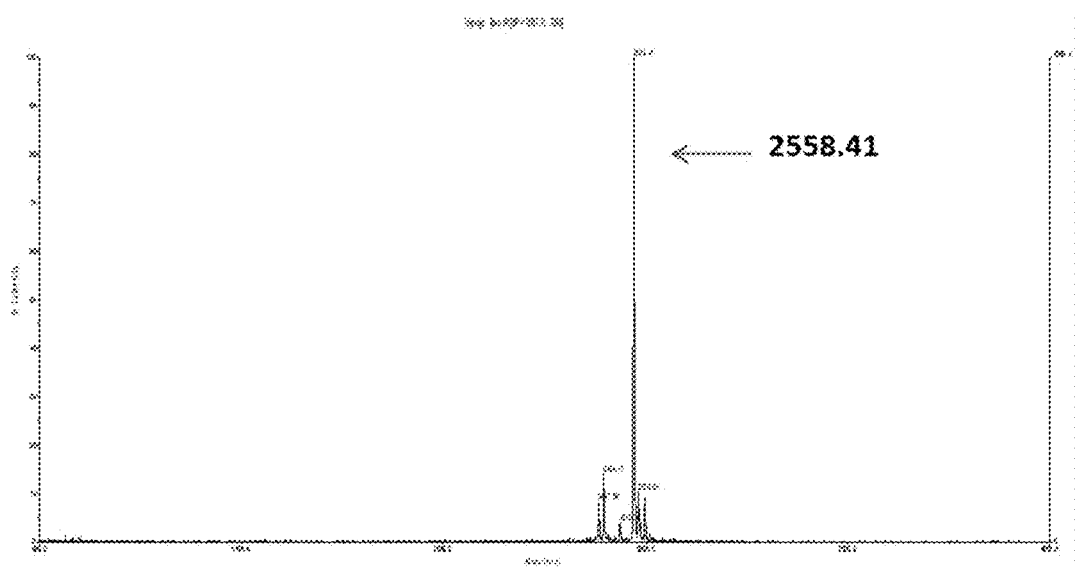

FIG. 64 depicts characterization of PPS1D1: (A) Chemical structure of PPS1D1, (B) Analytical HPLC of PPS1D1, (C) MALDI-TOF spectrum of PPS1D1.

Figure 65:
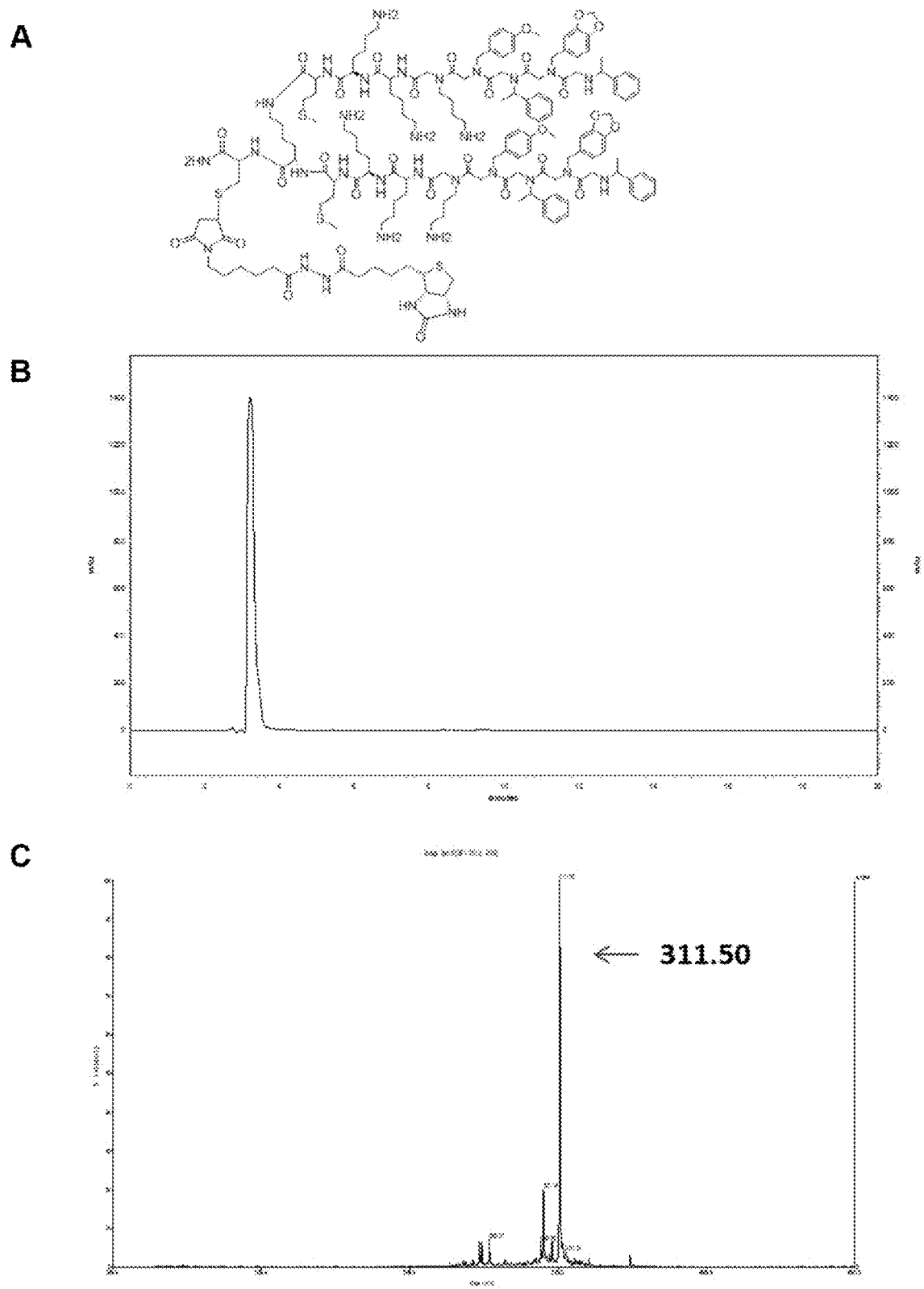

FIG. 65 depicts characterization of biotinylated PPS1D1: (A) Chemical structure of biotinylated PPS1D1, (B) Analytical HPLC of biotinylated PPS1D1, (C) MALDI-TOF spectrum of biotinylated PPS1D1.

Figure 66:
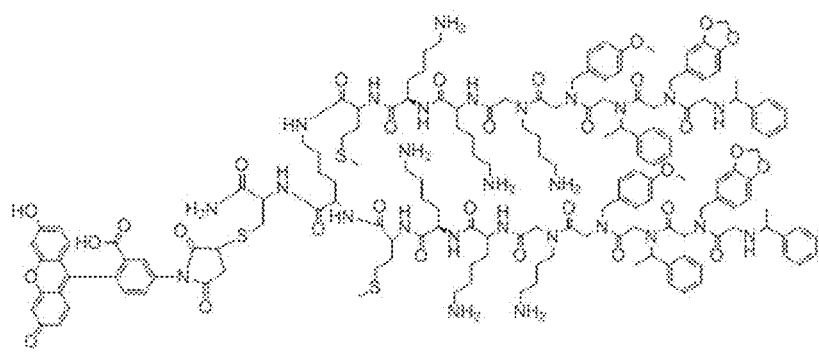
Figure 66:
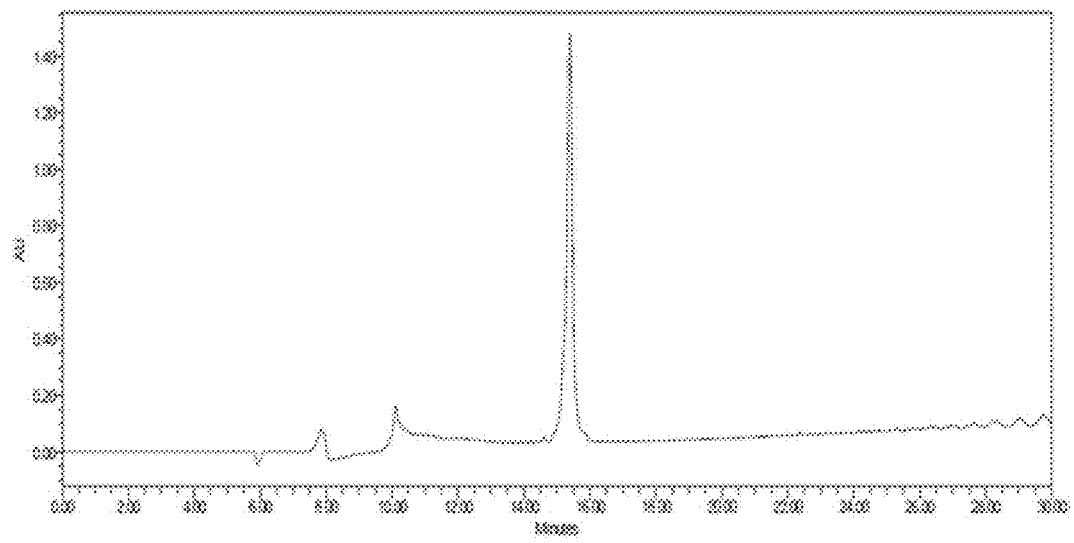
Figure 66:
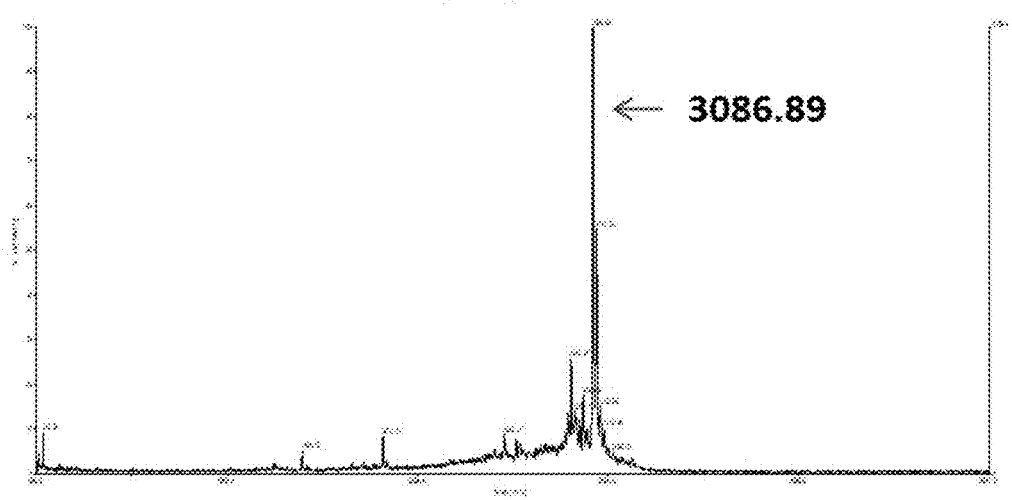

FIG. 66 depicts characterization of FITC-PPS1D1: (A) Chemical structure of FITC-PPS1D1, (B) Analytical HPLC of FITC-PPS1D1, (C) MALDI-TOF spectrum of FITC-PPS1D1.

Figure 67:
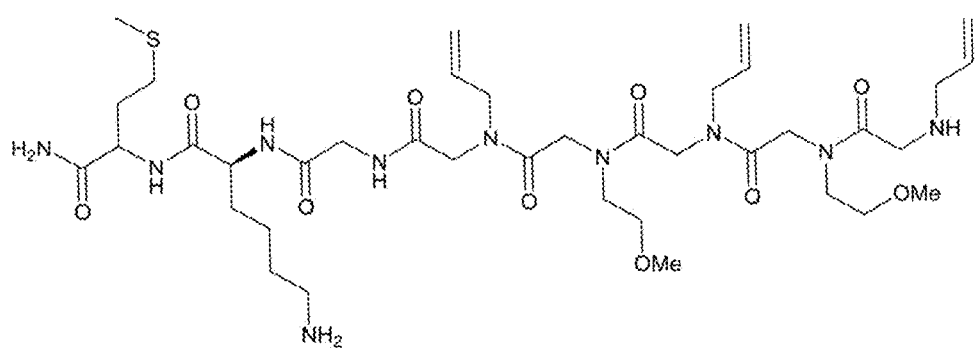
Figure 67:
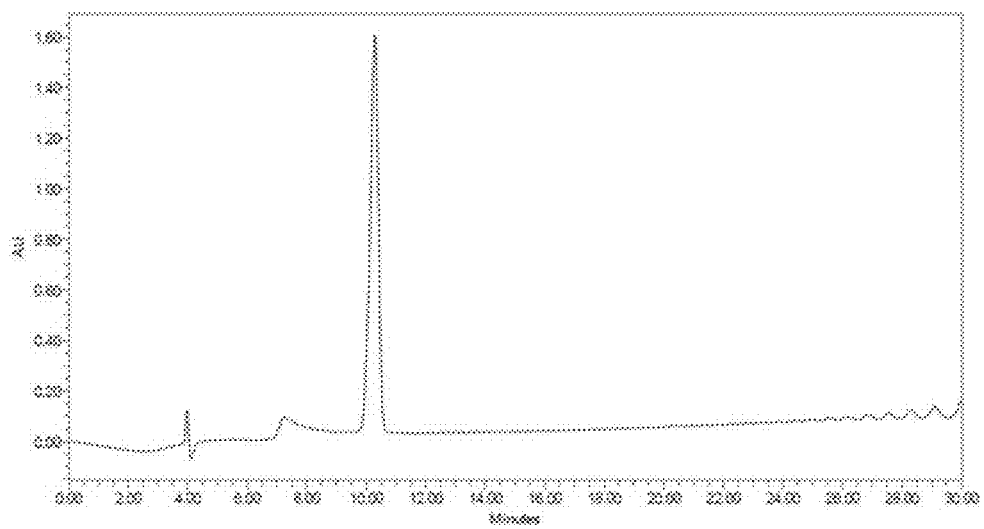
Figure 67:
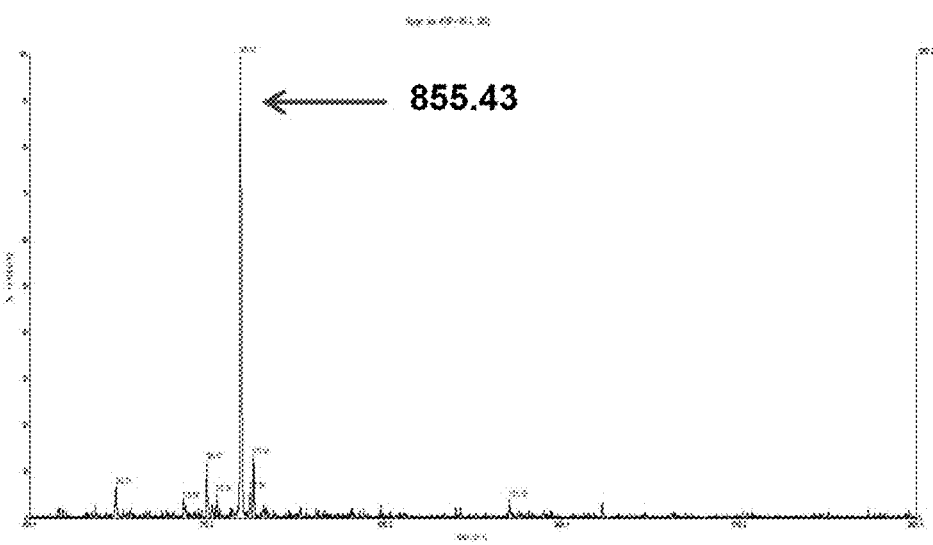

FIG. 67 depicts characterization of PC462: (A) Chemical structure of PC462, (B) Analytical HPLC of PC462, (C) MALDI-TOF spectrum of PC462.

Figure 68:
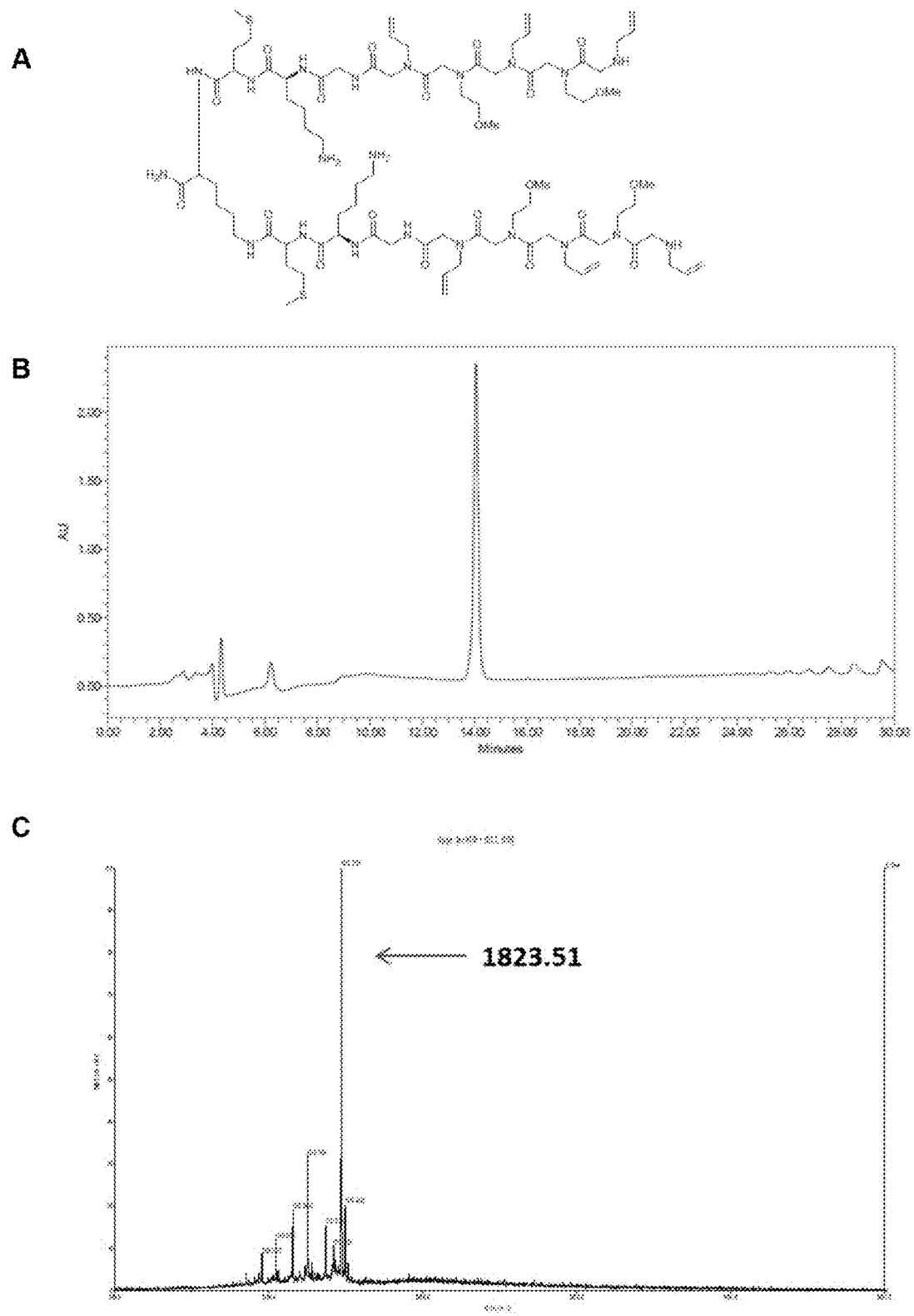

FIG. 68 depicts characterization of PC462D1: (A) Chemical structure of PC462D1, (B) Analytical HPLC of PC462D1, (C) MALDI-TOF spectrum of PC462D1.

Figure 69:
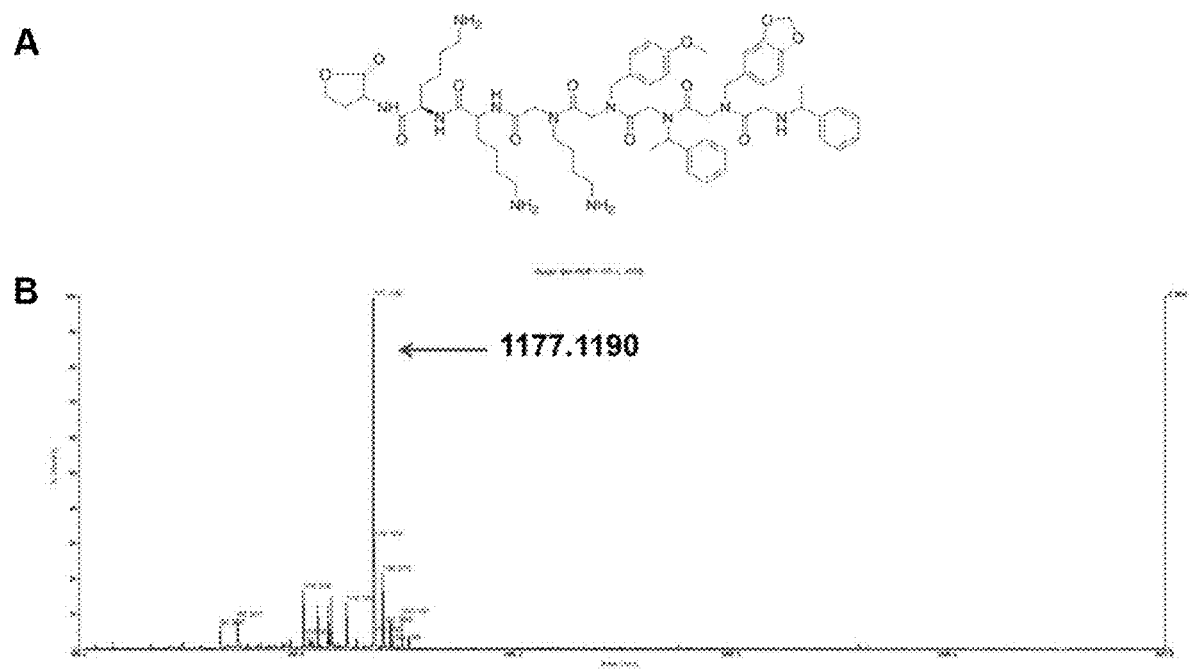

FIG. 69 depicts characterization of PPS1: (A) Chemical structure of PPS1 (cleaved with cyanogen bromide) synthesized on Tentagel MB-NH2 beads, (B) MALDI-TOF spectrum of PPS1 after cleavage from Tentagel MB-NH2 beads.

Figure 70:
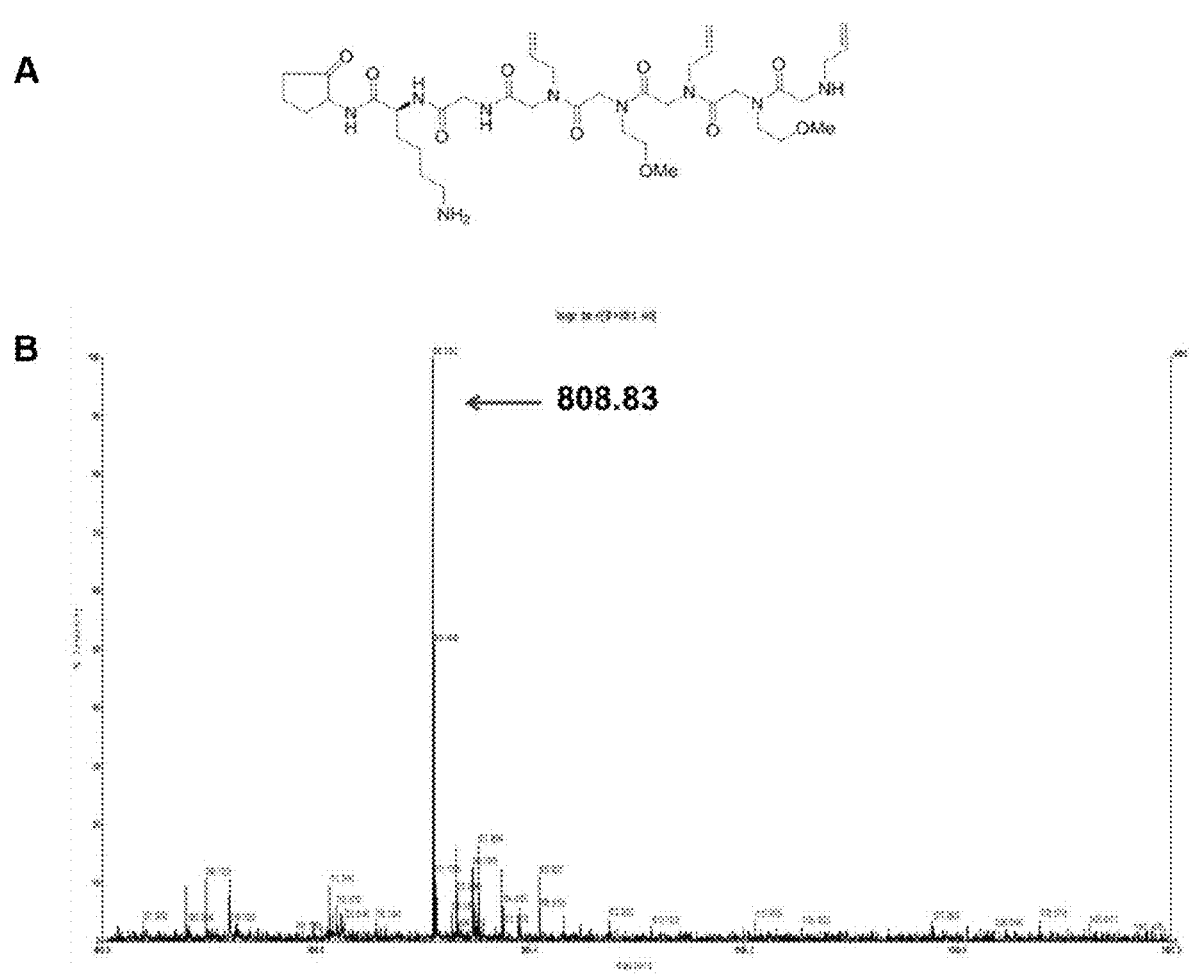

FIG. 70 depicts characterization of PC462: (A) Chemical structure of PC462 (cleaved with cyanogen bromide) synthesized on Tentagel MB-NH2 beads, (B) MALDI-TOF spectrum of PC462 after cleavage from Tentagel MB-NH2 beads.

Figure 71:
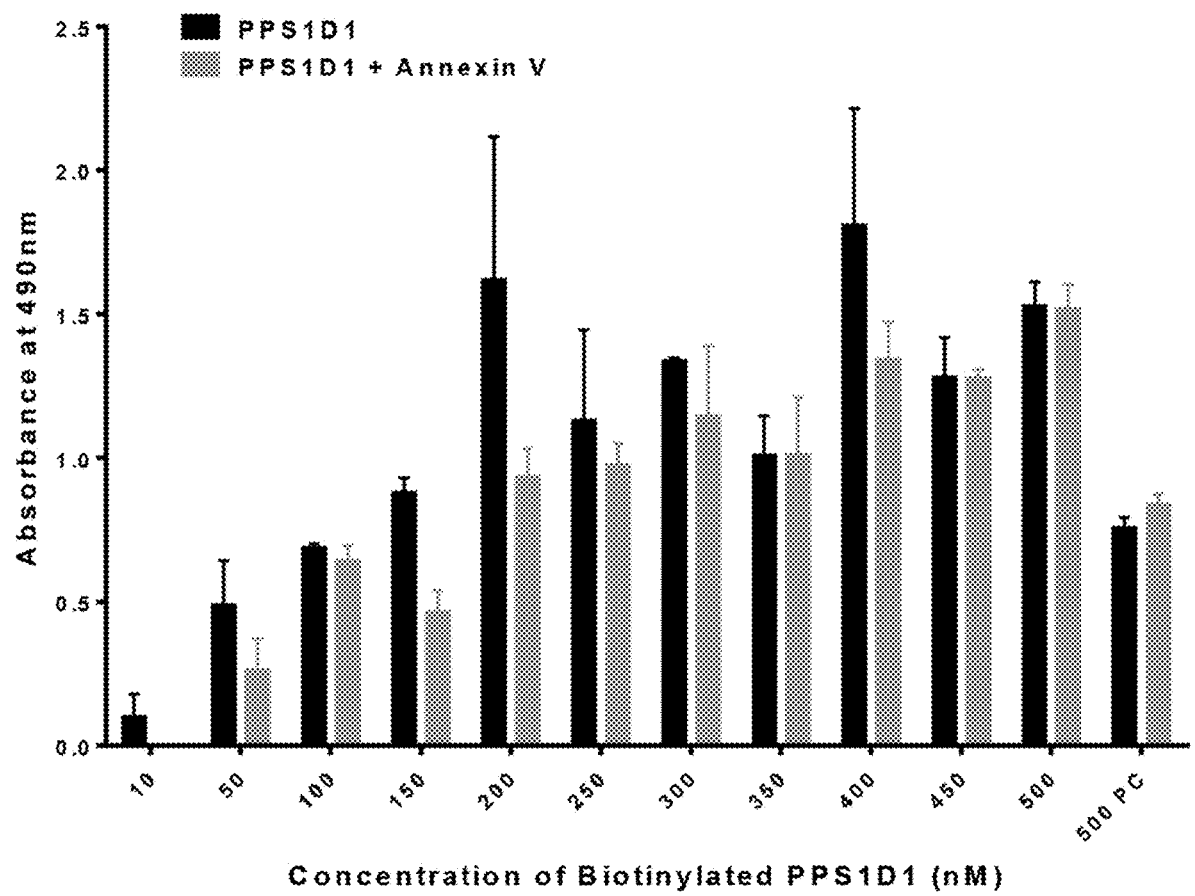

FIG. 71 depicts unlabeled Annexin V did not compete with FITC-PPS1D1 binding on an ELISA-like binding assay.

Figure 72:
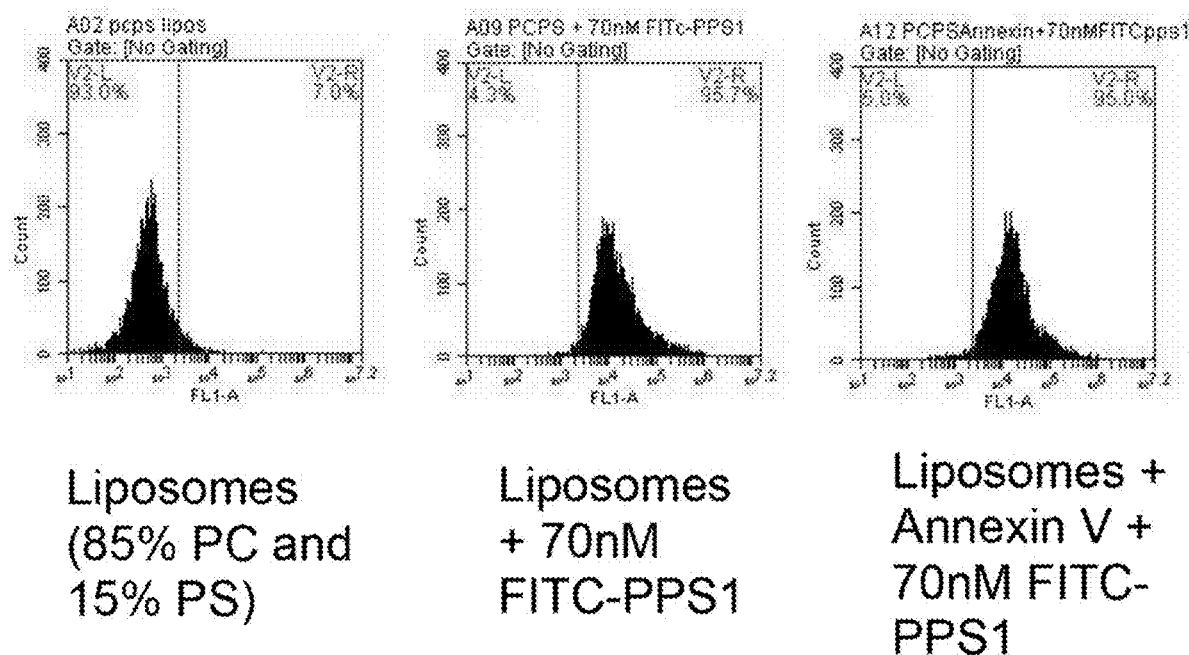

FIG. 72 depicts unlabeled Annexin V did not compete with FITC-PPS1 binding to liposomes made with 85% PC-15% PS.

Figure 73:
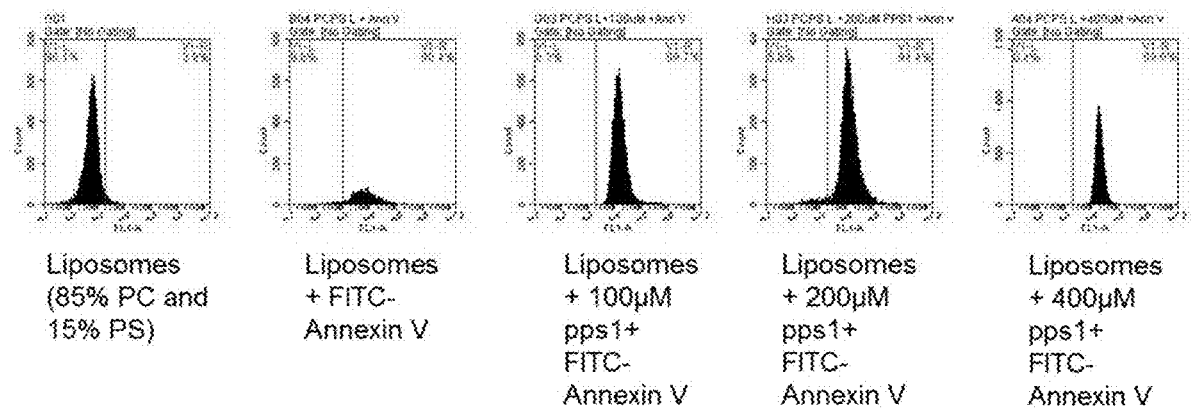

FIG. 73 depicts unlabeled PPS1 did not compete with FITC-Annexin V binding to liposomes made with 85% PC-15% PS.

Figure 74:
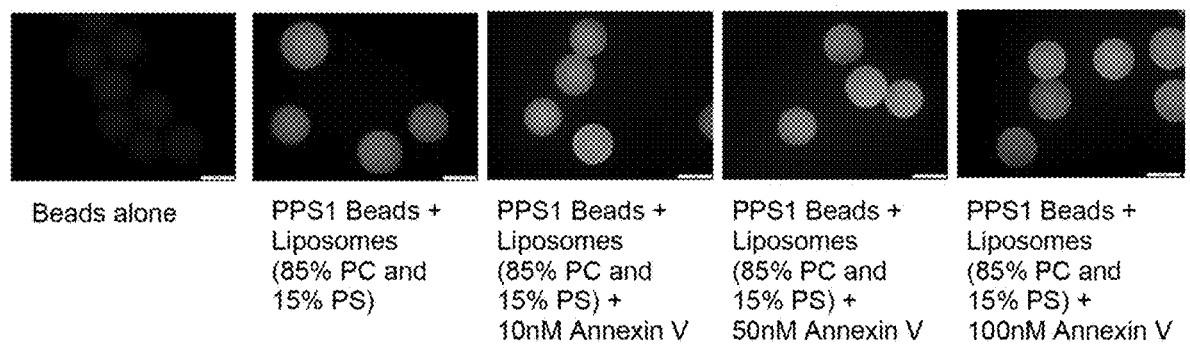

FIG. 74 depicts liposomes (85% PC-15% PS) incorporated with fluorophore NBD and then competed with Annexin V at 10, 50 and 100 nM. None of these conditions were able to remove liposomes from beads.

Figure 75:
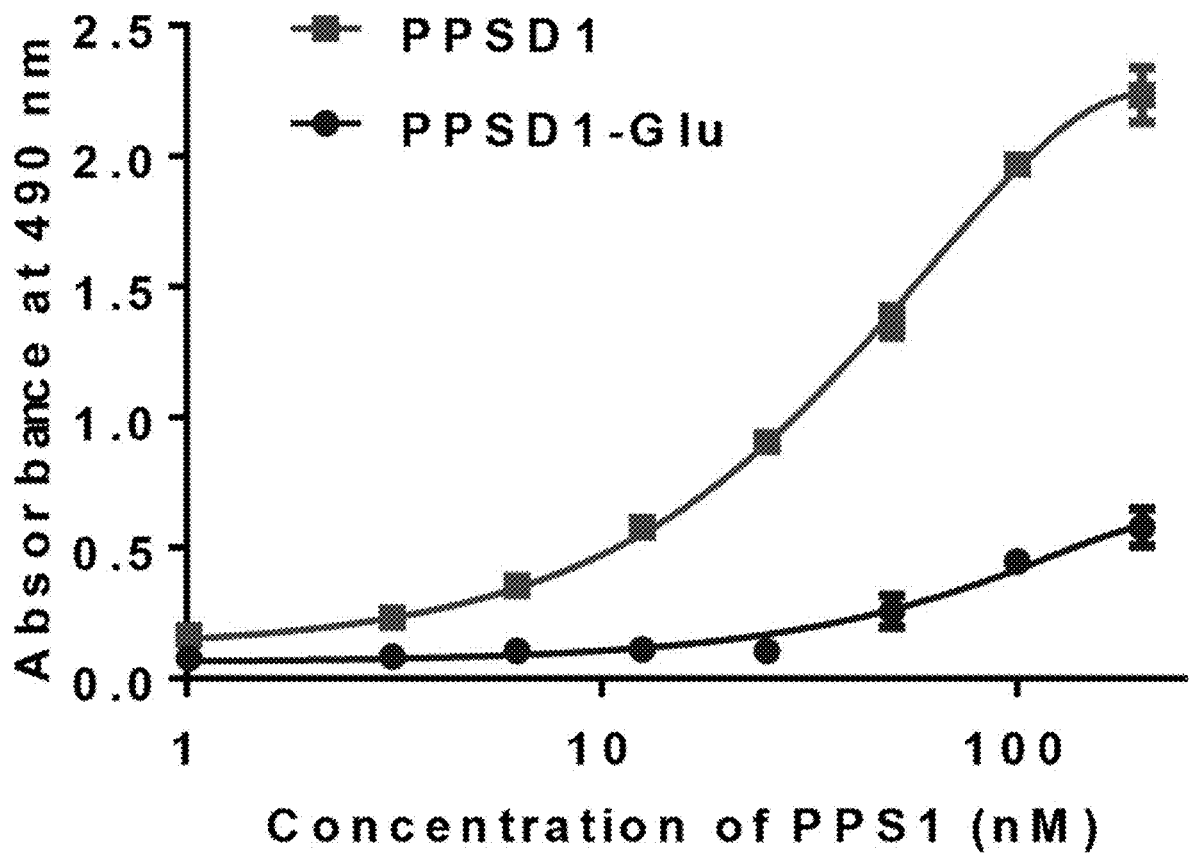

FIG. 75 depicts ELISA binding assay of PPS1D1-FITC and PPS1D1-Glu-FITC [replacing one of the positively charged lysine residues (3rd residue from C-terminal) of PPS1D1] with phosphotidylserine (PS) indicates that PPS1D1-Glu-FITC loses its binding ability when positive charges are converted to negative charges.

Figure 76:
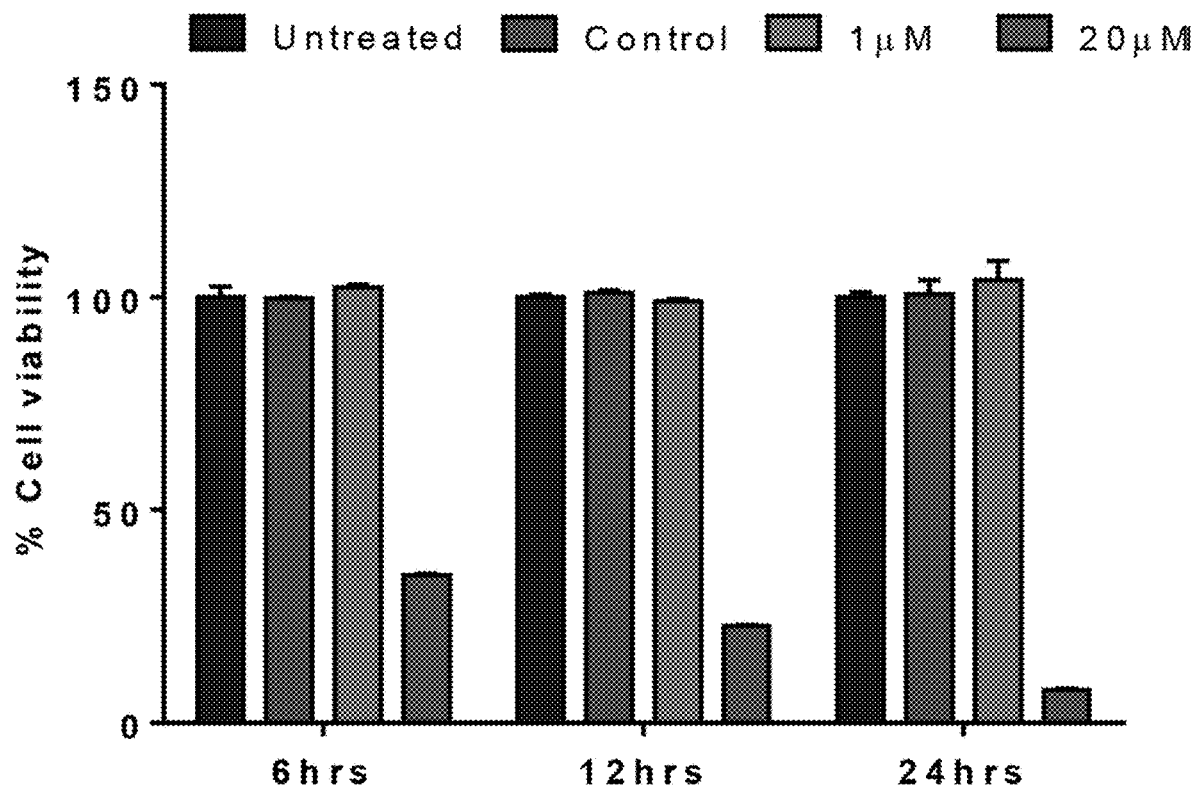

FIG. 76 depicts MTS assay results of PPS1D1 and control PC462D1 on HCC4017 cell line evaluated at 6, 12 and 24 hours.

Figure 77:
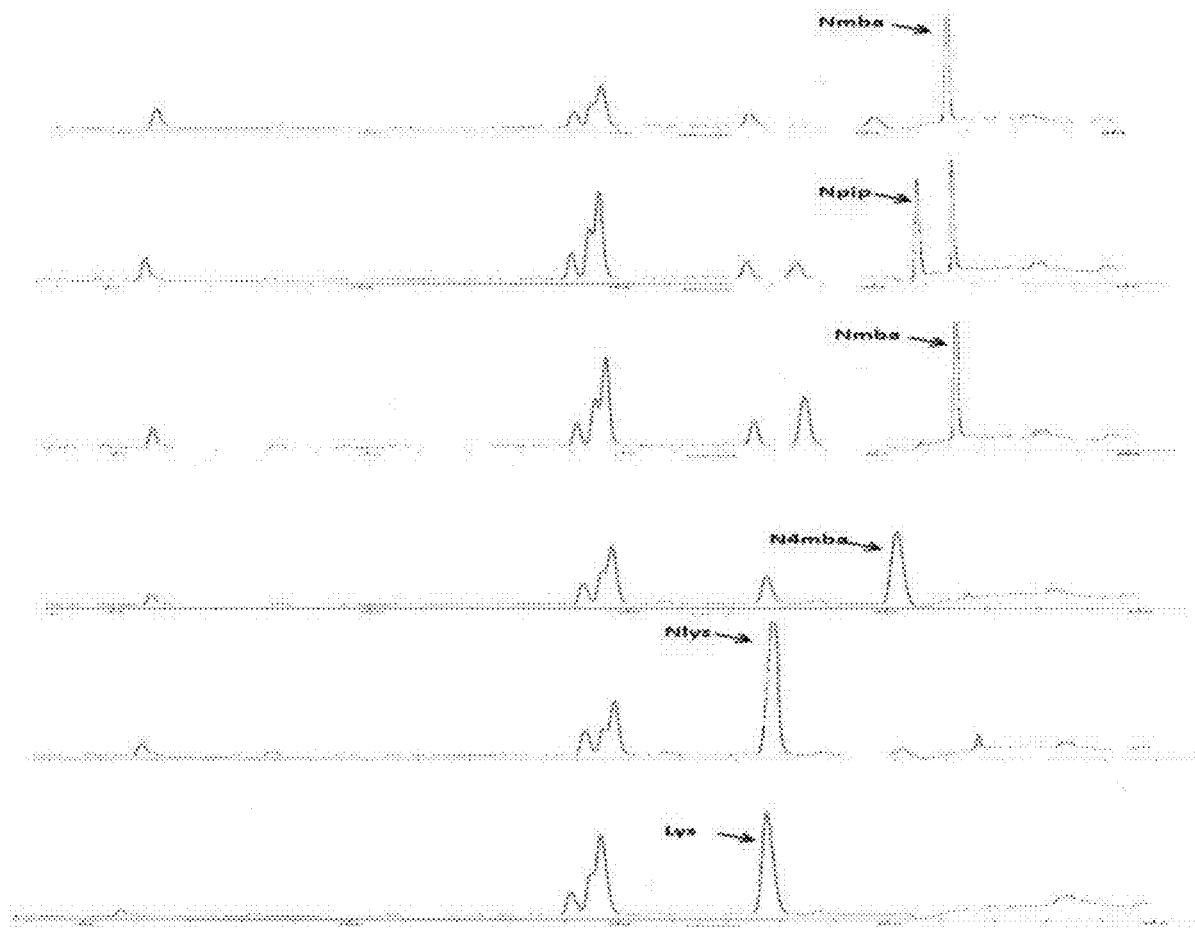

FIG. 77 depicts Edman sequencing graphs of PPS1 structure elucidation.

Figure 78:
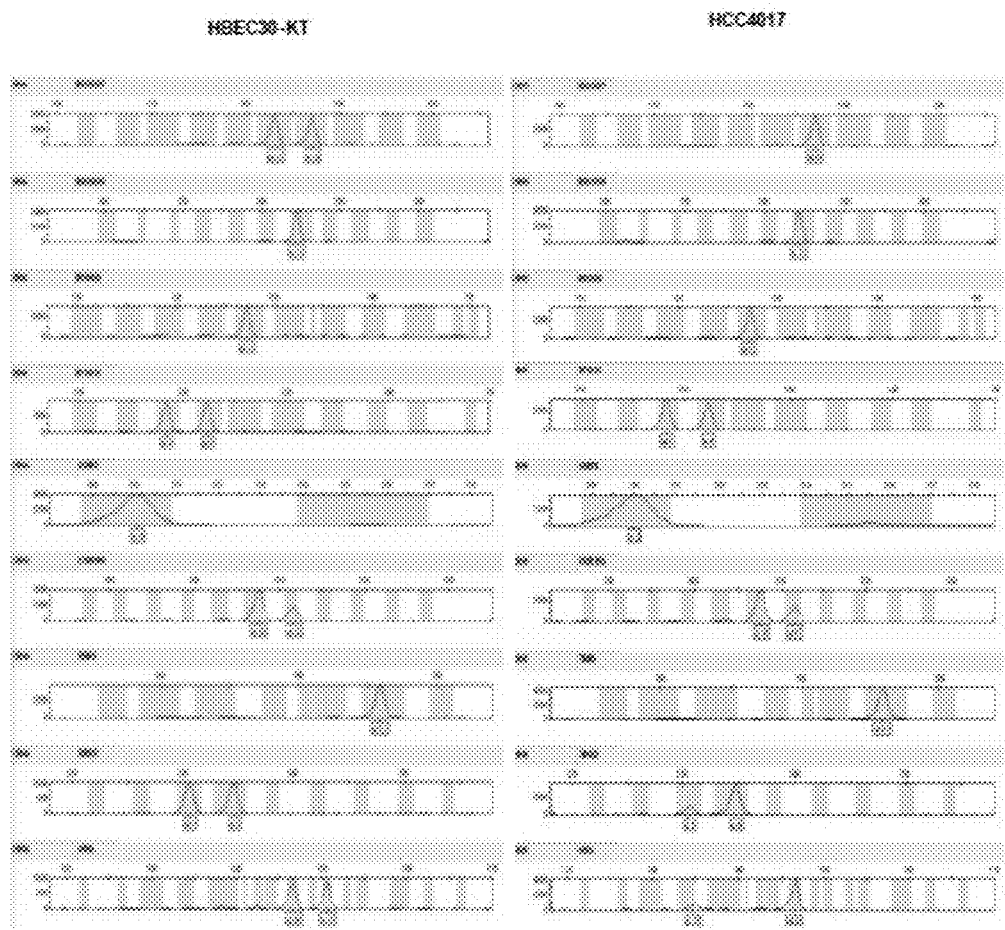

FIG. 78 depicts the PowerPlex 1.2 STR Fingerprinting results for HBEC30-KT and HCC4017 showing identity at 7/9 markers. The remaining two markers DS13S317 and vWA show loss of heterozygosity (red lines) in the tumor derived cell line (HCC4017).

Figure 79:
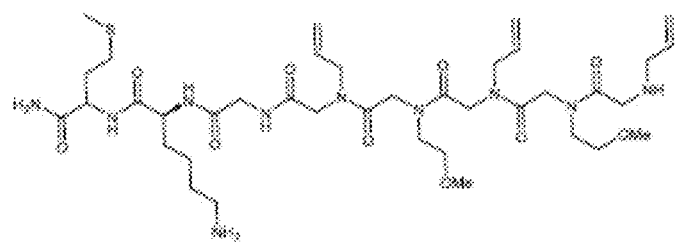
Figure 80:
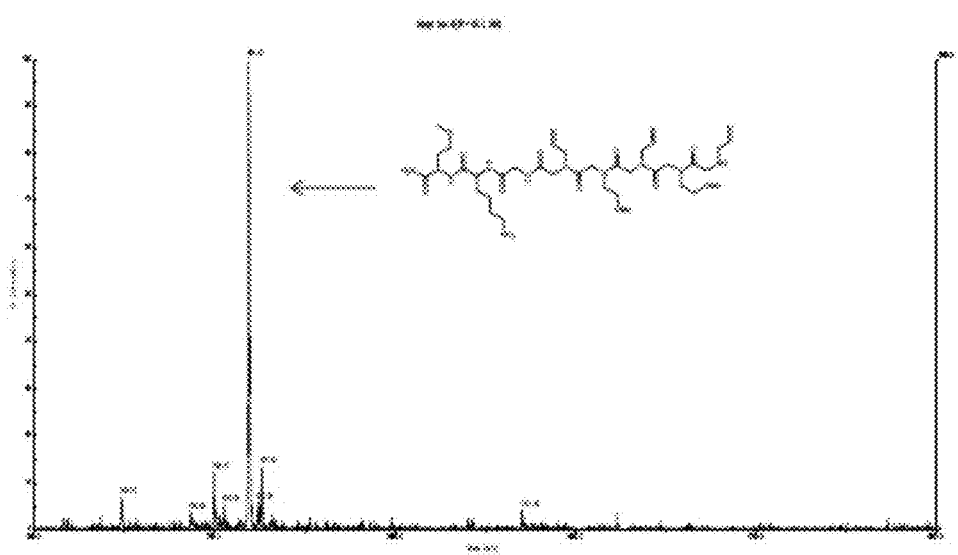
Figure 81:
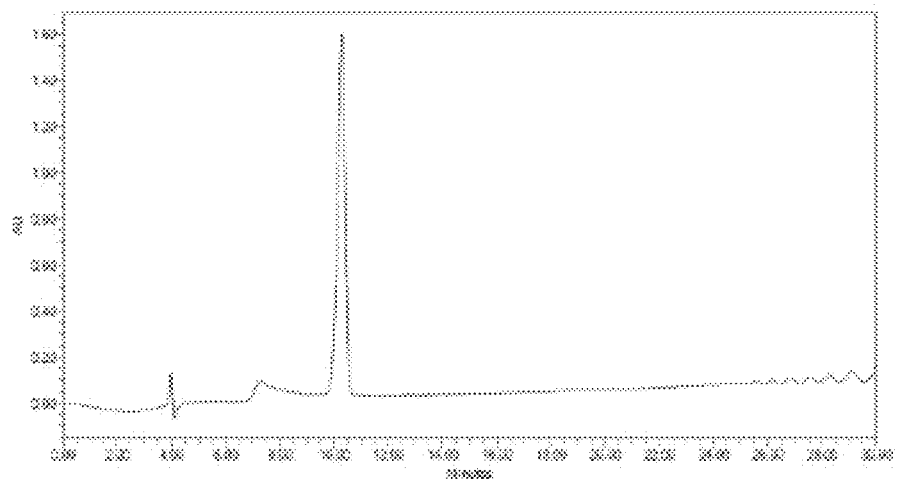
Figure 82:
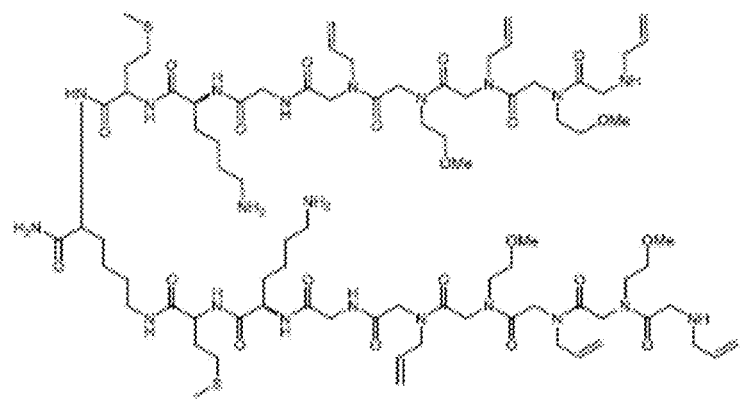
Figure 83:
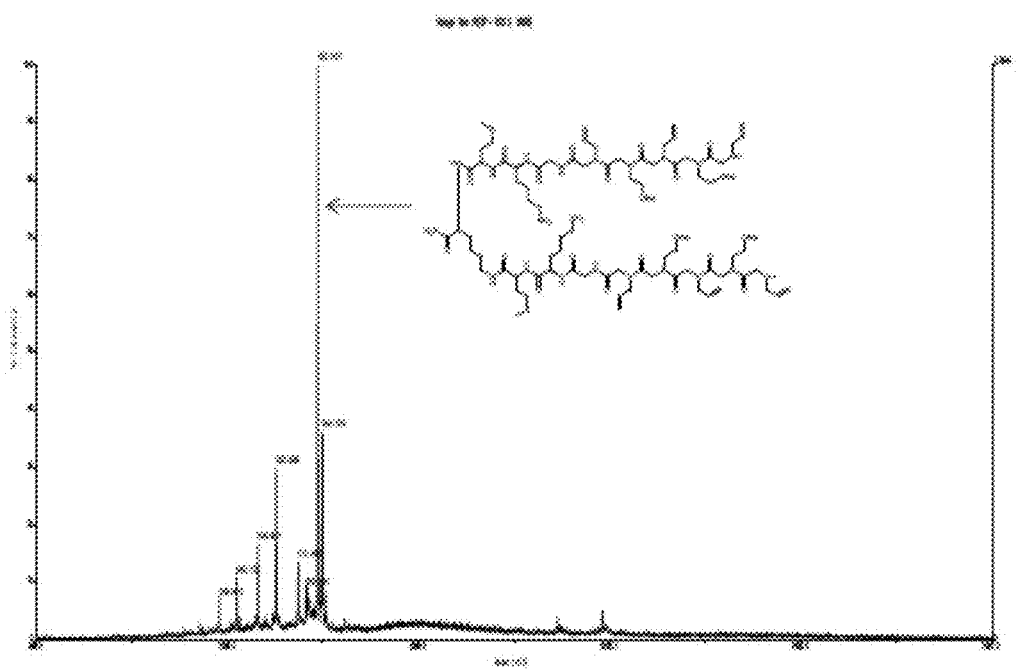
Figure 84:
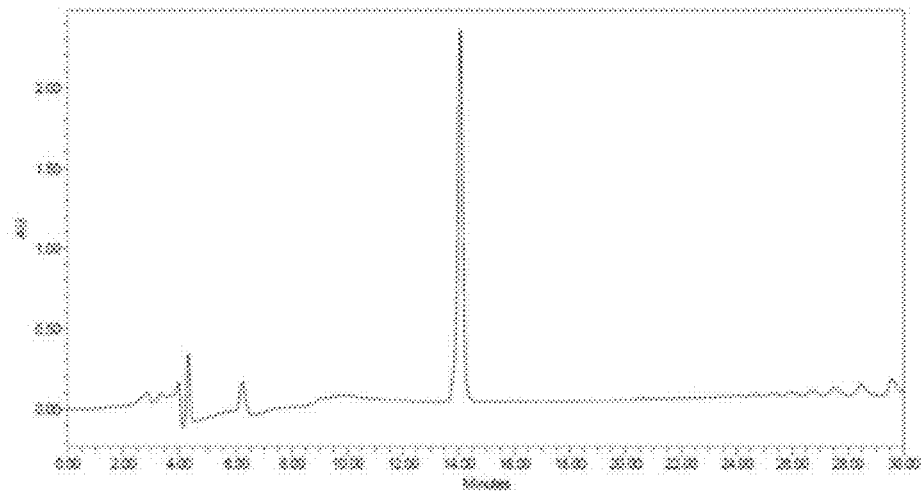
Figure 85:
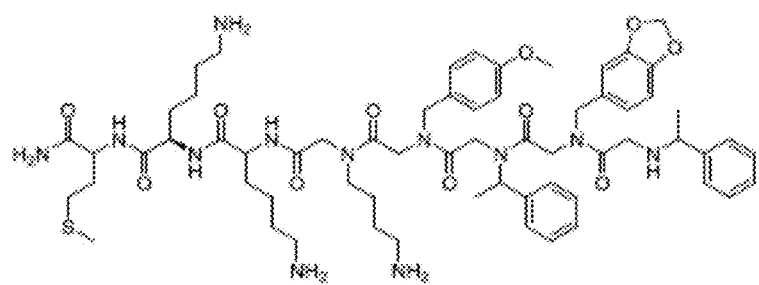
Figure 86:
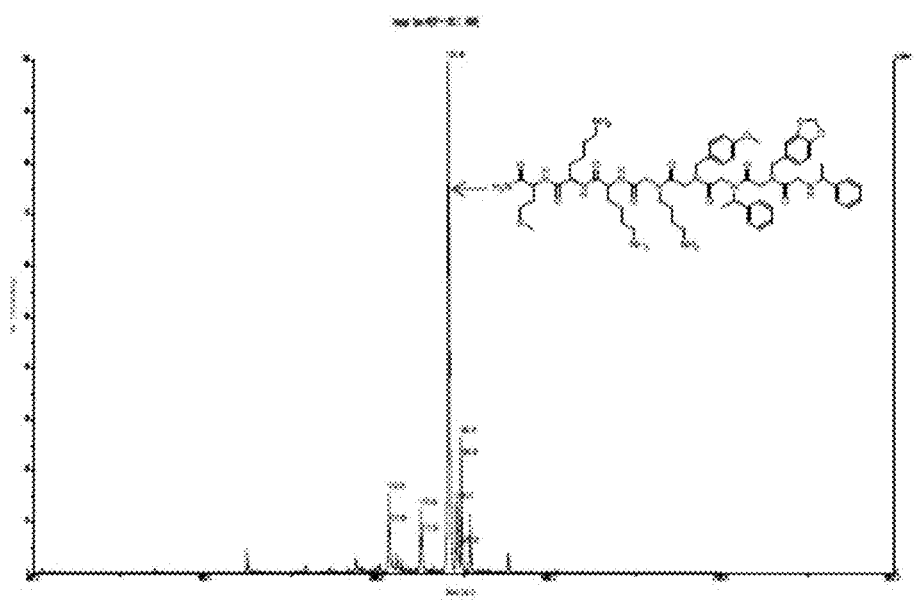
Figure 87:
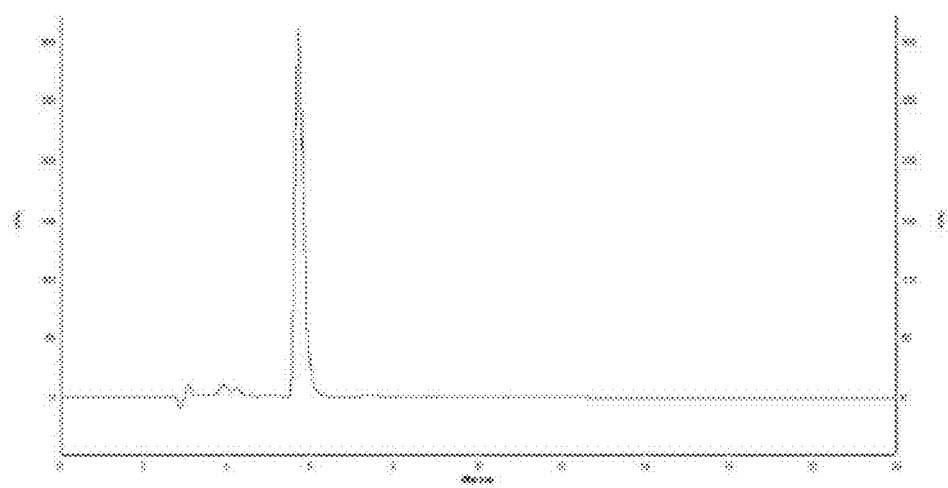
Figure 88:
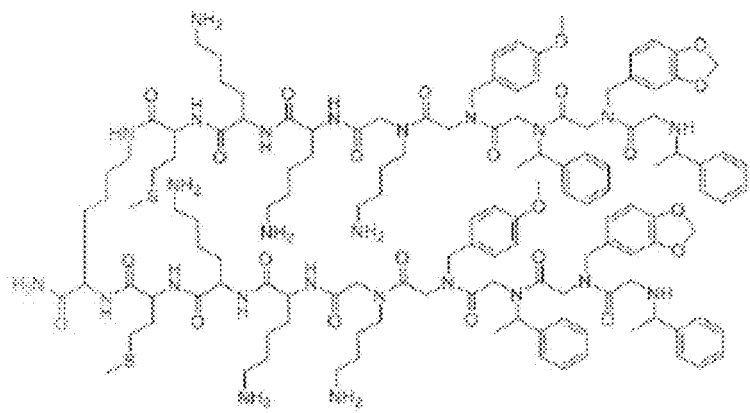
Figure 89:
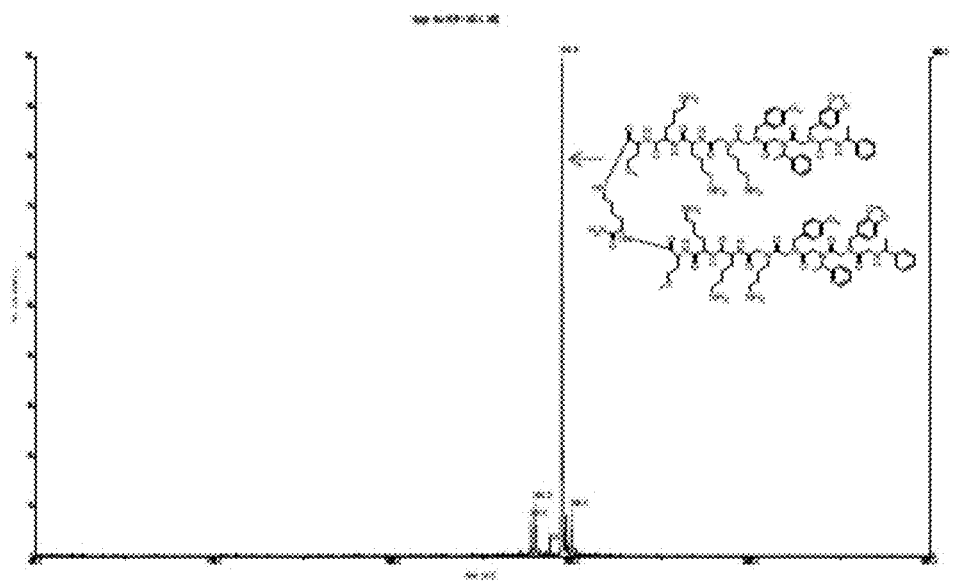
Figure 90:
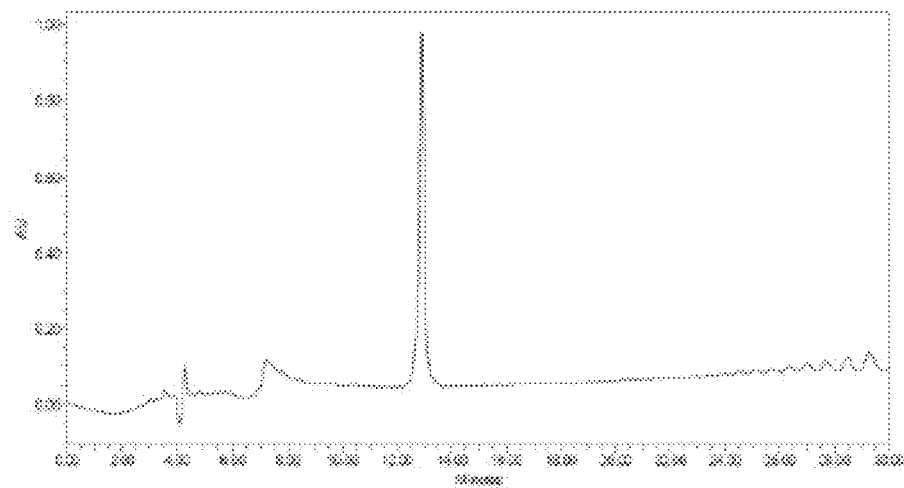
Figure 91:
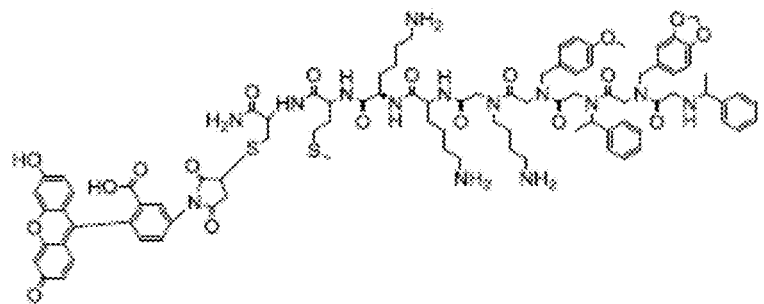
Figure 92:
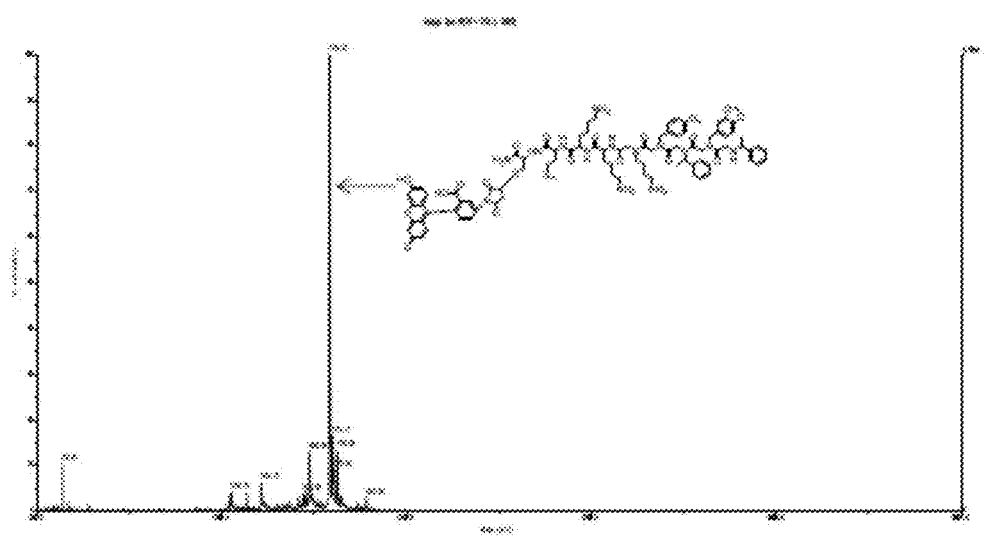
Figure 93:
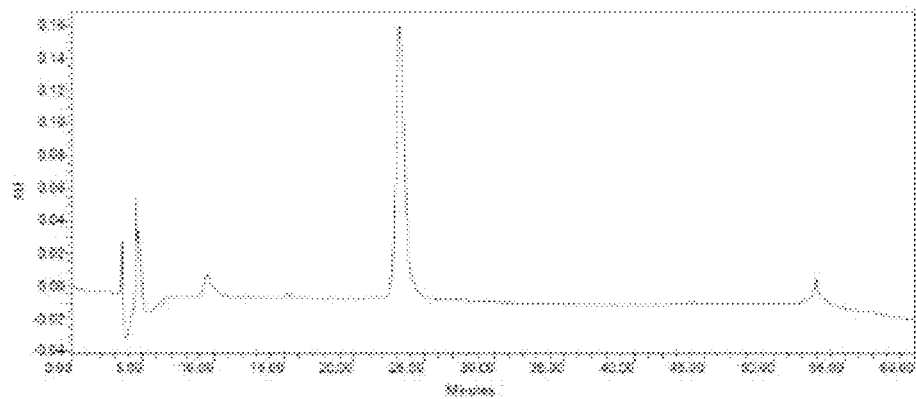
Figure 94:
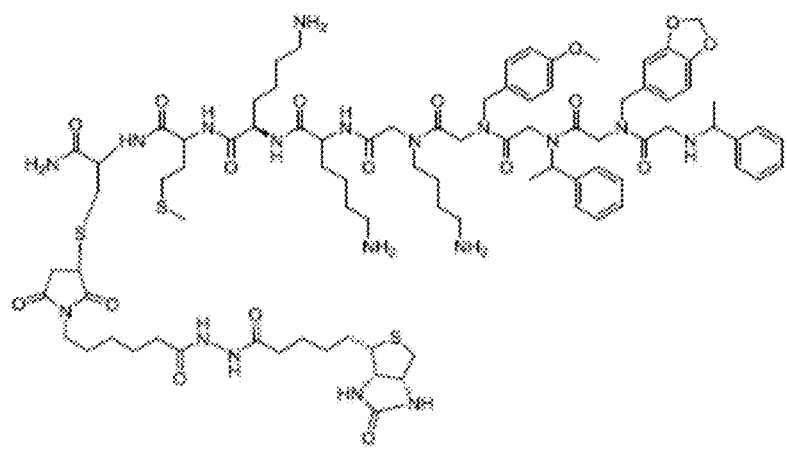
Figure 95:
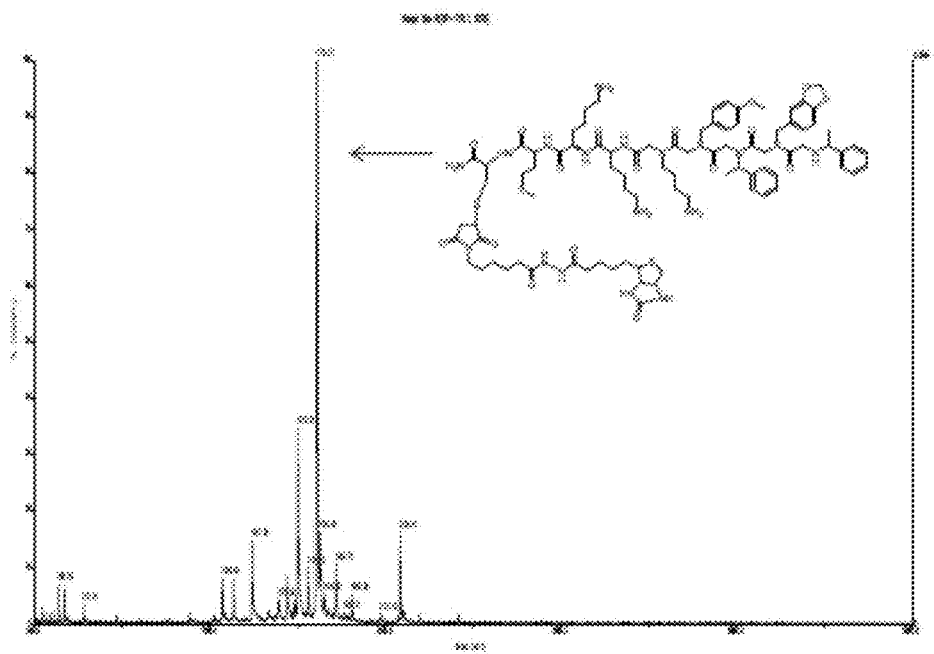
Figure 96:
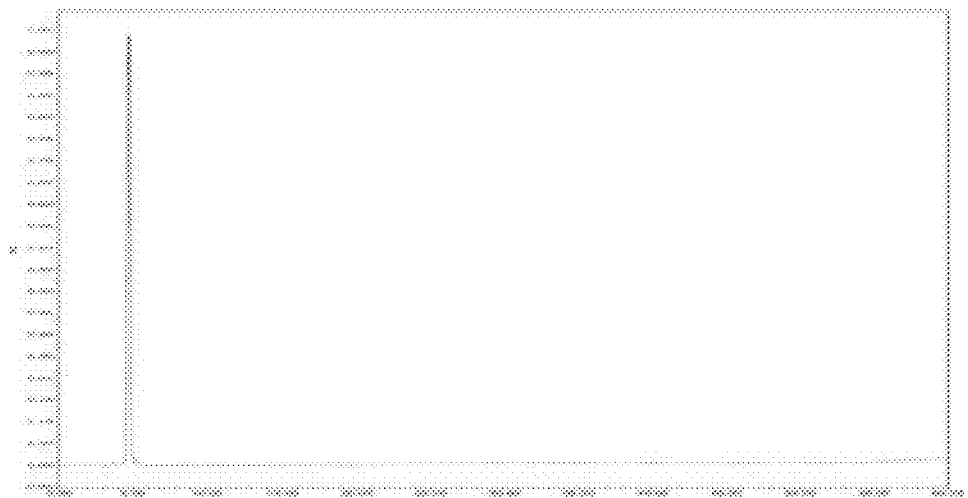
Figure 97:
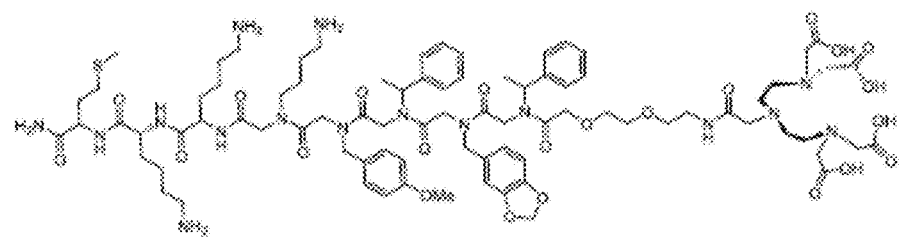
Figure 98:
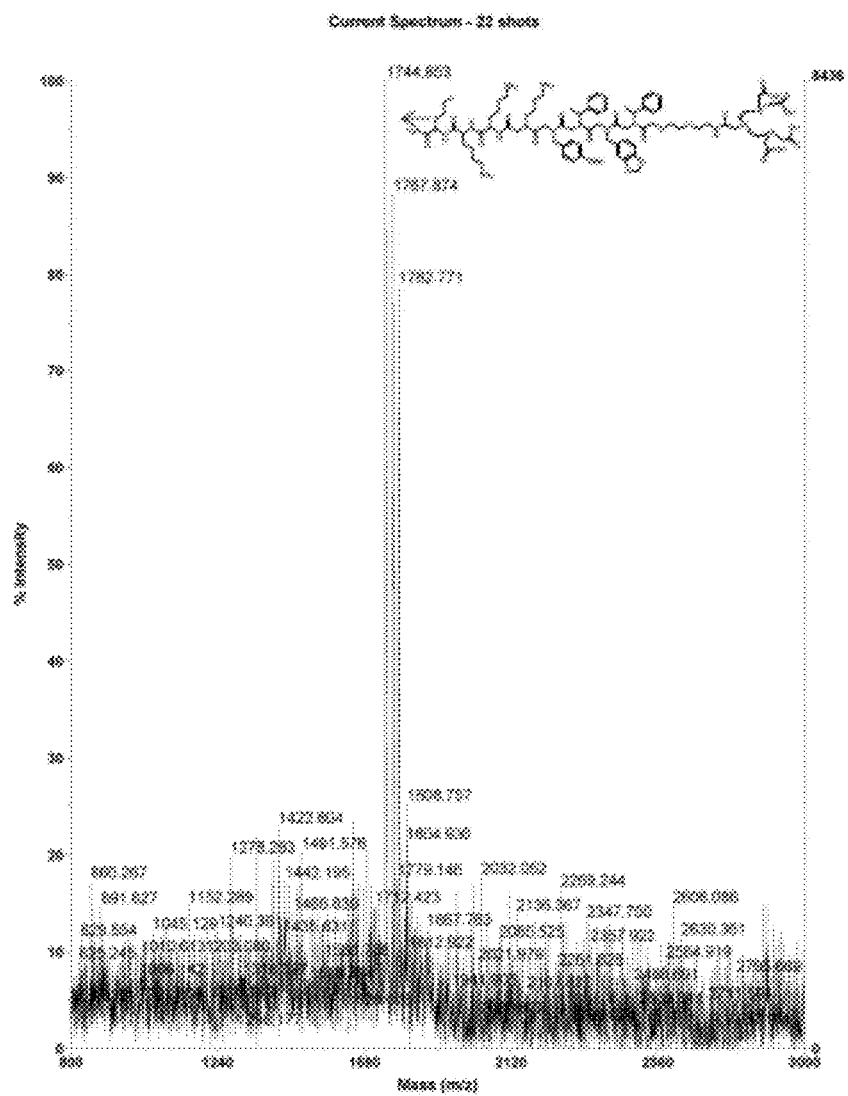
Figure 99:
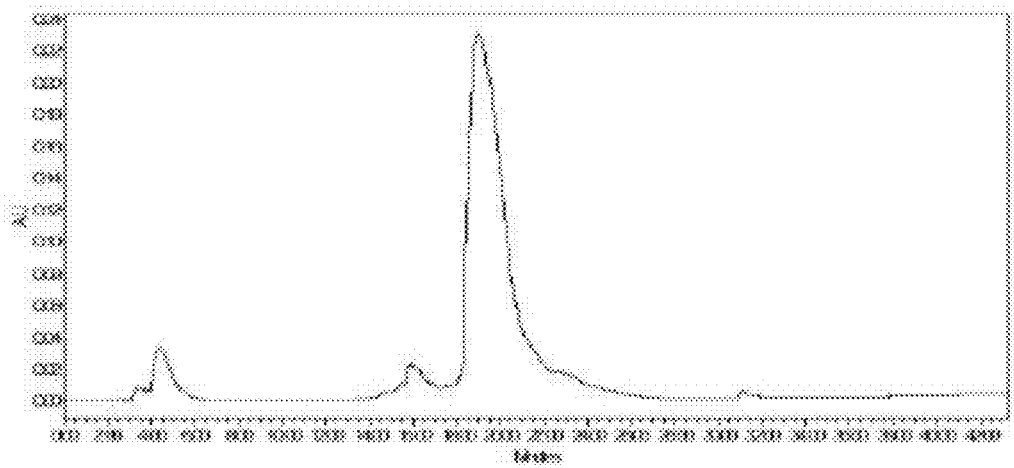
Figure 100:
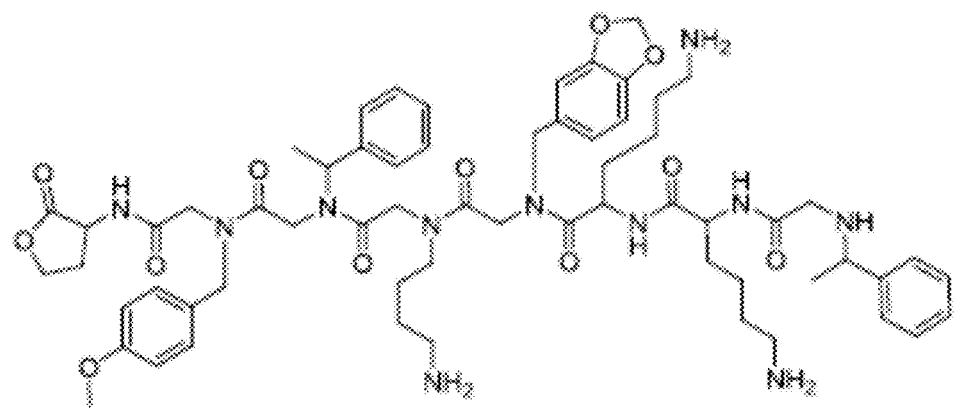
Figure 101:
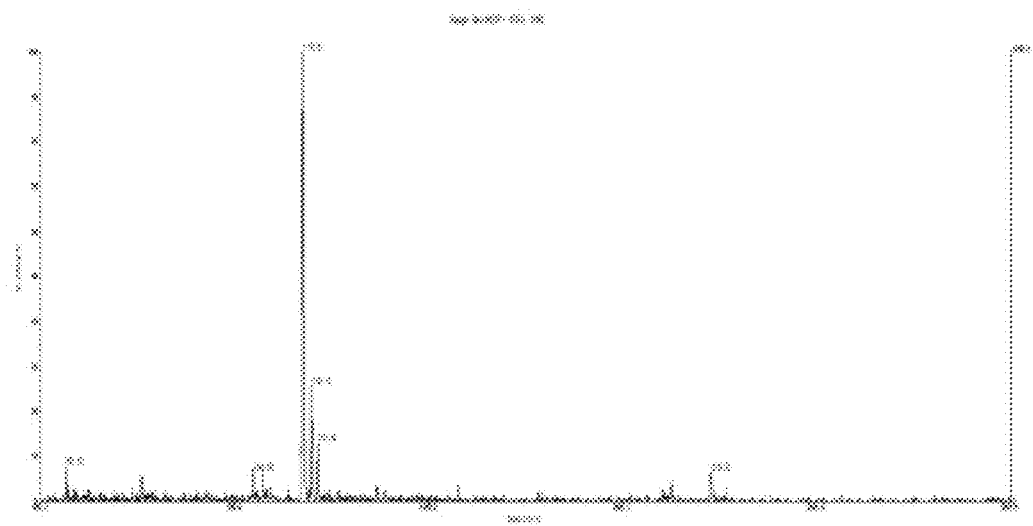
Figure 102:
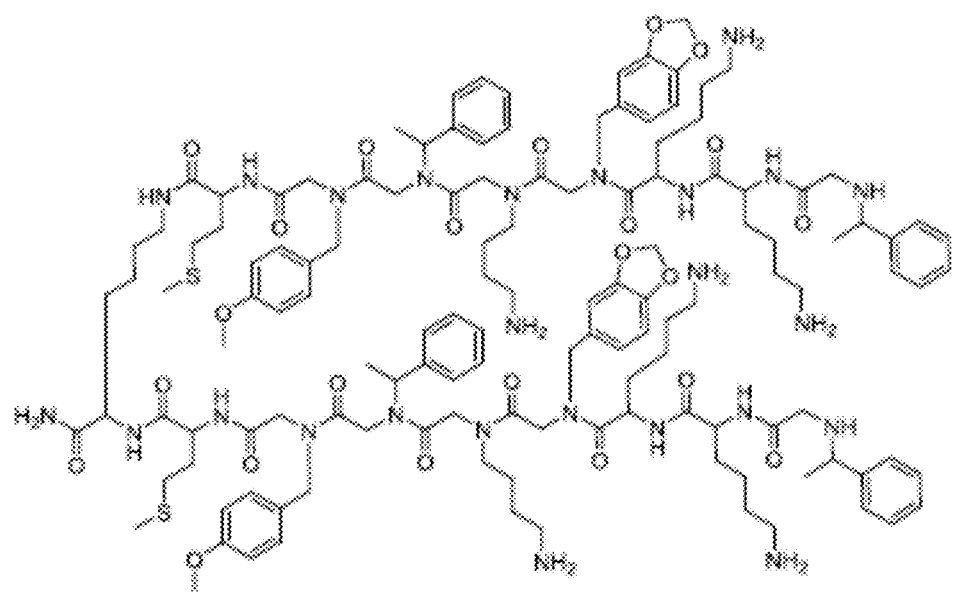
Figure 103:
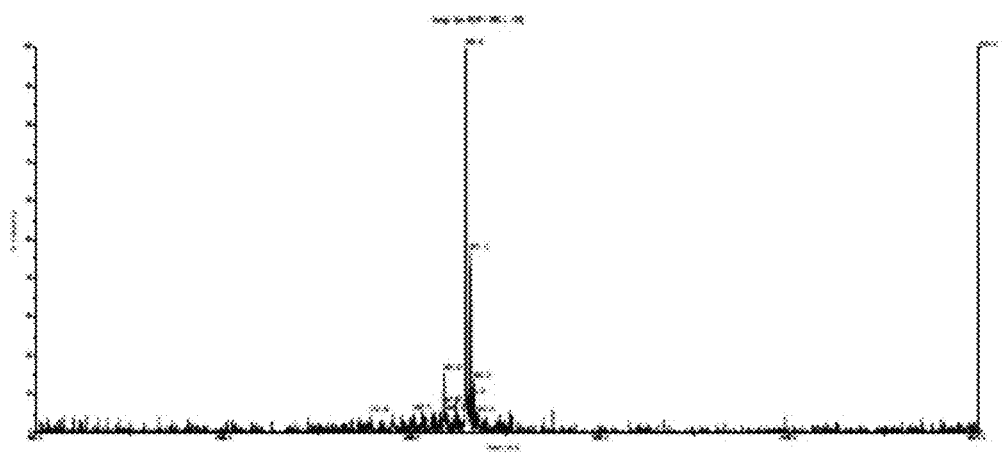
Figure 104:
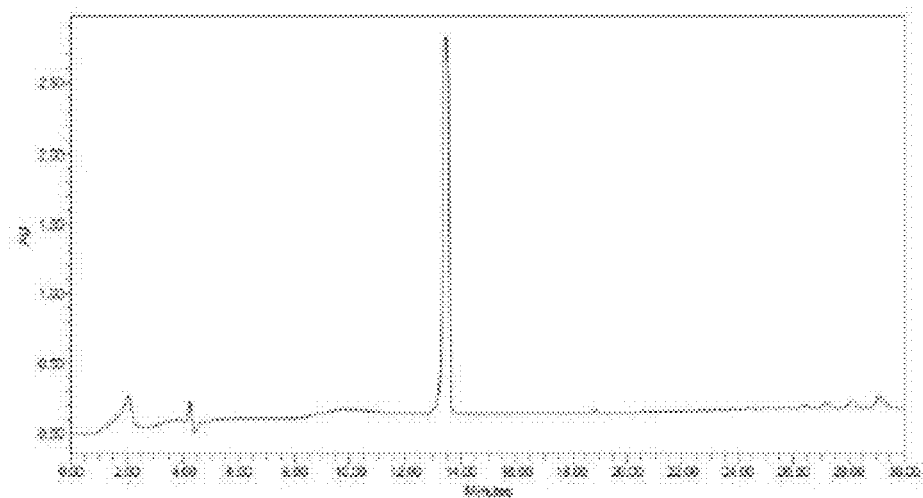

FIG. 79 depicts the Chemical structure of PC462.
FIG. 80 depicts the MALDI-TOF spectrum of PC462.
FIG. 81 depicts the Analytical HPLC of PC462.
FIG. 82 depicts the Chemical structure of PC462D1.
FIG. 83 depicts the MALDI-TOF spectrum of PC462D1.
FIG. 84 depicts the Analytical HPLC of PC462D1.
FIG. 85 depicts the Chemical structure of PPS1.
FIG. 86 depicts the MALDI-TOF spectrum of PPS1.
FIG. 87 depicts the Analytical HPLC of PPS1.
FIG. 88 depicts the Chemical structure of PPS1D1.
FIG. 89 depicts the MALDI-TOF spectrum of PPS1D1.
FIG. 90 Analytical HPLC of PPS1D1.
FIG. 91 depicts the Chemical structure of FITC-PPS1.
FIG. 92: depicts the MALDI-TOF spectrum of FITC-PPS1.
FIG. 93 depicts the Analytical HPLC of FITC-PPS1.
FIG. 94 depicts the Chemical structure of biotinylated PPS1.
FIG. 95: depicts the MALDI-TOF spectrum of biotinylated PPS1.
FIG. 96: depicts the Analytical HPLC of biotinylated PPS1.
FIG. 97 depicts the Chemical structure of PPS1-(Eu3+)-DTPA.
FIG. 98 depicts the MALDI-TOF spectrum of PPS1-(Eu3+)-DTPA.
FIG. 99 depicts the Analytical HPLC of PPS1-(Eu3+)-DTPA.
FIG. 100 depicts the Chemical structure of PC2.
FIG. 101 depicts the MALDI-TOF spectrum of PC2.
FIG. 102 depicts the Chemical structure of PC2D1.
FIG. 103 depicts the MALDI-TOF spectrum of PC2D1.
FIG. 104 depicts the Analytical HPLC of PC2D1.

DETAILED DESCRIPTION

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure. In this regard, no attempt is made to show structural details of the disclosure in more detail than is necessary for the fundamental understanding of the disclosure, the description taken with the drawings making apparent to those skilled in the art how the several forms of the disclosure may be embodied in practice.

The following definitions and explanations are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary 3$^{rd}$ Edition.

As used herein, the term "peptoid" means and refers to a structure that closely resembles a peptide except that the side chain extends from the main chain nitrogen rather than the a-carbon.

As used herein, the term "patient" means and refers to an animal, including but not limited to human beings.

Developing drugs based on known cancer related protein bio-molecules under conventional drug development approaches fails in delivering a concrete solution for battling cancer.

Figure 1:
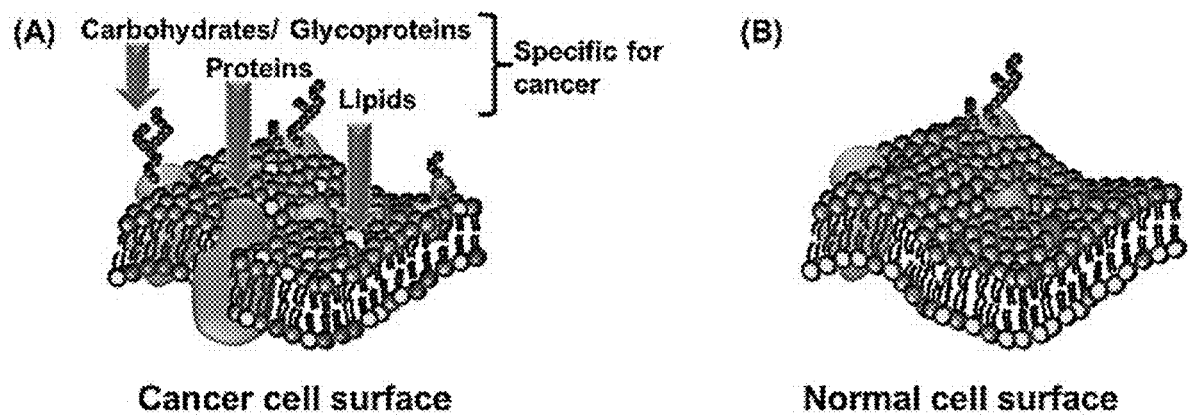
FIG. 1 Schematic comparison of cell membrane bimolecular asymmetry in cancer and normal cells. A cancer cell surface may display specific protein, lipid, carbohydrates and glycoproteins that are expressed in a cancerous situation that may be absent or minimal on the normal cell surface under healthy biological conditions.

The current understanding about cancer specific bio-molecules mainly comes through various aspects such as m-RNA data profiles, etc. All of these approaches have their own limitations. For example, one of the most powerful technologies to-date; genome-wide m-RNA data profiling, can only give direct information about protein expressions, and not about other molecular classes—such as lipids or carbohydrates—especially on cell surfaces. Anionic phospholipids, sialic acid residues and heparin sulfates are a few examples of other molecular classes overexpressed on cancer cell surfaces over the normal cells and present universally in cancer cells. Therefore, targeting such non-protein biomolecules may provide a unique answer to failures in drugs that target heterogeneously expressing proteins in cancer. Unfortunately, non-protein bio-molecules are overlooked in conventional drug development approaches due to overemphasis on targeting proteins. Also, there are not many appropriate technologies or methods to develop compounds targeting cancer specific molecular classes such as lipids or carbohydrates, as both rational design and combinatorial high throughput techniques are typically based on structural characteristics of proteins. Therefore, one potentially viable option is to consider cellular differences by directly targeting cancer cells over normal cells derived from same source, in a suitable combinatorial high throughput screening approach (FIG. 1). The goal would be to develop an unbiased selection method that could recognize 'something' on the cancer cell surface that is not found on the normal cell surface, comparing cancer cell vs normal cell simultaneously. This 'something' could still be a protein, but if selection criterion are applied carefully, it will give an equal chance to recognize a lipid or a carbohydrate specifically found on the cancer cell surface (FIG. 1). This approach may even find compounds that may target combinations of biomolecules or higher order structural arrangements of those biomolecules that are unique for cancerous situation as they present naturally on the cancer cell surface. The key point is to apply a method that can eliminate compounds targeting all the bio-molecules on a normal cell surface and pick a compound that targets any additionally expressed biomolecule on the surface of a cancer cell. This approach does not require any prior knowledge of the biomolecule being targeted. The biomolecule being targeted can be identified later.

The cell membrane is a phospholipid bilayer. It is composed of the major phospholipids, phosphatidylcholine (PC), sphingomyelin (SM), phosphatidylserine (PS), and phosphatidylethanolamine (PE). PC and SM, with choline head groups, are primarily in the outer membrane leaflet. PS and PE, with amine head groups, are primarily in the inner membrane leaflet. Phosphatidylinositol (PI), phosphatidylinositiol-4,5-bisphosphate (PIP2) and phosphatidic acid (PA) are also found in the inner membrane leaflet. Phospholipids can exchange positions in the same side of the membrane with the adjoining phospholipids extremely quickly. It can take hours for the phospholipids to flip from one side of the membrane to another. PS is found in the outer membrane leaflet at least during apoptosis, necrosis, activation of platelets, and malignant transformation. PS presence in the outer membrane leaflet is caused by high concentrations of calcium, possibly due to cellular stress.

PS expresses on the outer layer of every tumor endothelium, tumor cells, and apoptotic and necrotic cells. PS is known to express on the outer layer of a cell under hypoxia, cytokines, reactive oxygen species (ROS), chemotherapy, and radiotherapy.

At present there are only very few peptides, small molecules, and antibodies that have been reported as PS targeting agents. There are only a few PS specific compounds, small molecules such as butyl-2-methyl-malonic acid (ML-9), peptides (CLSYYPSYC and FNFRLKAGAKIRFG), and proteins and antibodies (annexin V and Bavituximab). Many of these do not show any activity and only one antibody (Bavituximab) shows some promise as an antagonist. Those molecules targeting PS typically have several issues including, poor pharmacokinetics, low in vivo stability, slow on-rates, high cost, and difficulty in production.

Compounds were selected that target cancer cells (e.g. HCC4017 lung cancer) only in the presence of normal bronchial epithelial cells (e.g. HBEC30KT) derived from the same patient, applying a unique on-bead two-color combinatorial cell screen. The approach is "unbiased", not knowing what is targeted at the beginning. The selected compounds are targeting 'something' only found in cancer cell surface that is absent in normal cells and this 'something' can be a protein, lipid, carbohydrate, glycoprotein etc. This approach bypasses the time and resource consuming conventional drug development approach, which relies on prior knowledge of the targeted biomolecule.

Two peptidomimetic (peptoid) compounds, PPS1 (previously named as JM79) and PPS2 (previously named as JM258) were identified. These two compounds were identified in two separate screens, but have very similar structures. Both compounds are mainly targeting phosphatidylserine (PS), a lipid that predominantly expresses on the outer layer of tumor cells, tumor endothelium and apoptotic cells. In normal cells in the body, PS is limited to the inner layer of the cell membrane. Since PS is universally found in tumors, it can be considered as a global target for potential cancer therapeutics.

The compounds display low nanomolar binding affinity ($K_d$ 15-20 nM) for PS with great specificity over phosphatidylcholine (PC—the typical lipid found on normal cells) on ELISA-like and liposome binding assays. The compound PPS1 binds around low μM on HCC4017 and H460 lung cancer cells expressing PS. The simple dimeric version of this compound (PPS1D1) displays improvement (about 175-fold) with binding at 80 nM (FACS studies) on the HCC4017 lung cancer cells. Compounds PPS1 and PPS2 are able to pull down HCC4017 cells as well as a spectrum of lung cancer lines (about 10 cell lines) selectively over normal HBEC30-kt and HBEC-3kt cells, validated on magnetic bead pull down assay.

PPS1D1 displays strong in vitro cancer cell killing activity on lung cancer (e.g. HCC4017, H460, H358, H441, H1819, H1993, H2122 cells), breast cancer (MD-MB-231 cells) and prostate cancer (PC3 cells), validated to date using standard MTS cell viability assays and FACS studies. In vivo studies indicated that PPS1D1 strongly accumulated in HCC4017 tumor xenografts in mice. PPS1D1 displayed strong tumor burden effect on H460 lung cancer xenografts, even better than docetaxel—a standard chemotherapy. More importantly, the combination treatment of PPS1D1 with docetaxel almost completely eliminated the tumor. Various derivatives of PPS1 have been developed that have similar and improved activities. FIGS. 15-22, 36-51. Structural studies indicate that these compounds have a secondary structure in solution and mechanism of action studies indicates that these compounds are highly cell permeable with rapid cell killing activity.

PS has been reported as a universal biomarker for tumors and the tumor-microenvironment. Following radiation and chemotherapy therapy, up to 95% of the tumor vessels can become PS-positive, making this an ideal and global candidate for both therapeutic and diagnostic applications. PS is known to express on viral as well as infected cells. Therefore applications can be extended to anti-viral therapy as well. Furthermore, these peptoids are serum stable, non-immunogenic, highly diverse, more economical to synthesize and can be optimized at will, displaying a collection of drug-like characteristics. Cancer is one of the leading causes of deaths in the United States. Developing economical, biologically amenable, and highly specific agents globally targeting cancer for diagnostic and therapeutic applications is a top clinical market in the United States at this time.

The current technology solves the following concerns:

(1) Targeted cancer drugs are only applicable on a very limited portion of patient populations. The technology represents a development of a "global" cancer targeted drug. Targeted therapies in cancer have specific effects on tumors, but the patient population that can be targeted is very limited for a particular drug. No universally targeted cancer drug is available, even just to a particular cancer type. Current cancer drugs target 'protein' biomolecules and cancer specific protein biomolecules have high heterogeneity in their expression levels. No protein is specific to a particular cancer and not every tumor will cause an elevation of these biomolecules. Therefore developing an agent that targets a single receptor or a protein is not adequate. PS appears to be a global bio-marker for the tumor microenvironment and could be used to target larger populations of cancer patients. For example, almost all animal and human tumors reported to date are express PS in their tumor microenvironment and chemo and radiation therapy steeply enhances this expression, making PS a precise global biomarker to target.

(2) To be used as "global" cancer imaging and diagnostic tool development: Peptoid compounds that target cancer biomolecules such as VEGFR2 (JACS, 2008) can easily be modified with imaging agents such as OOTA and can be used in standard PET and MRI applications in cancer imaging. Since PS is a globally expressing biomarker in the tumor microenvironment, "global" tumor imaging/diagnostic tools can be developed. Effective targeted imaging tools capable of globally targeting tumors are not currently available and only the non-specific tumor accumulating agents such as DOTA and 18F-FDG are used in the clinic. Imaging derivatives of the compounds of the disclosure can be used in both PET and MRI applications. The PPS1 monomeric version binds PS and does not have activity, while the dimeric version PPS1D1 binds and display strong activity. Depending on the application, the compound version can be selected for just imaging/diagnostic use or for real-time therapy monitoring with intrinsic therapeutic activity.

(3) To be used as an anti-viral therapy: PS is known to express viral and infected mammalian cells, and therefore applications can be extended to anti-viral therapy as well. Conventional drugs are based on protein targeting and viruses change their structures very rapidly, therefore developing effective anti-viral drugs is a daunting task. But, lipid-PS is a major component of the cell membrane and targeting globally expressed PS can be a creative solution for major hurdles in anti-viral drug discovery.

(4) To be used as a tool to detect apoptotic and stressed cells (e.g. dying cells, identification of dying β-cells in diabetes etc.): PS flipping from the inner layer of the cell membrane of a normal cell to the outer layer is due to various reasons that include stress, environmental factors such as ROS, hypoxia and apoptosis. PS is an apoptosis marker—one commercially available product is Annexin V. Annexin V is a protein and there is need for an easy to handle, low cost product). These compounds can be used to identify such cells in biological systems. One interesting application is to use these compounds to identify and map dying β-cells in diabetes, an invaluable tool to detect early phases of diabetes that may help in taking preventive measures.

The current disclosure is better than existing technologies because:

(1) PPS1 and PPS2 are the first peptoid molecules identified and validated for targeting lipid-PS. Peptoids are an emerging class of novel drug leads with a precise collection of drug-like properties. Peptoids (oligo-N-substituted glycines) closely resemble peptides except that the side chains extend from the main chain nitrogen rather than the α-carbon (FIG. 23). These oligomers are protease resistant, non-immunogenic, and can permeate the cell better. Peptoid synthesis is straightforward as microwave synthesis needs less than one minute for each reaction, making it highly efficient and economical. Large combinatorial libraries of peptoids (in the millions) can be synthesized easily, inexpensively, and rapidly (within 2-3 days). Peptoids are rich sources of antagonists for many pathological states such as cancer, antimicrobial, neurological and auto-immune diseases. Taken together, peptoids can be considered as excellent alternatives for drug development as compared to expensive and problematic conventional molecular classes such as small organics, antibodies, and peptides.

(2) Targeting lipid-PS over highly heterogeneously expressing protein-biomolecules: The effectiveness of protein targeted conventional cancer drugs are limited to small patient populations. But lipid-PS is reported to express in every tumor microenvironment, making PS a global target. The compounds of this disclosure not only recognize PS in tumors over normal tissues, they display intrinsic antagonist activity as well.

(3) To use peptoids targeting PS as a novel targeted anti-viral therapy: Conventional drugs are based on protein targeting and viruses change their structures very rapidly. Therefore developing an effective anti-viral drug is a daunting task. But, lipid-PS is a major component of the cell membrane and is also known to express on viral and infected mammalian cells. Therefore, applications can be extended to antiviral therapy as well. Targeting globally expressing PS can be a creative solution for major hurdles faced in anti-viral drug discovery.

(4) Development of theranostic agents that have both therapeutic and diagnostic capability for real-time therapy and monitoring of cancer. Theranostic agents, built with both therapeutic and imaging capacities, are an extremely valuable tool in oncology for monitoring drug localizations and actions in real time. But developing such compounds faces major synthesis challenges as well as other pharmacological problems such as stability, tissue penetration, biodistribution, and clearance issues. Since peptoid compounds have intrinsic activity, as well as being easier to modify with imaging agents, theranostic agents can be made for use for real-time therapy monitoring of the tumors. More importantly, if a therapy does not work, stops responding at any stage, or resistances are developed, those can be identified immediately and the treatment can be switched without a delay, potentially saving the patient's life.

Unbiased selection and validation of a lung cancer specific peptide-peptoid hybrid over the normal bronchial epithelial cells from the same patient.

Using an emerging class of biologically manipulable and cost effective peptidomimetics, called peptoids, non-protein biomarkers are targeted that globally present in the tumor microenvironment and are absent in normal tissues,. Conventional drug development tools are not readily available to target non-protein biomolecules.

The standard approach in drug development is to target bio-molecules that have known functions related to a given disease state. With the completion of the human genome sequence, understanding of the disease states at the molecular level advanced exponentially. In turn, this provides an important resource for drug development research, by providing a huge number of possible drug targets for various diseases. The majority of these bio-molecules are proteins such as enzymes, hormones, receptors, signaling molecules etc. While this approach has been successful in less complex diseases, handling immensely diverse pathological states like cancer through this conventional approach is extremely challenging for many reasons. The expression levels of these protein bio-molecules are highly variable not only between the main cancer types such as lung, breast, prostate, etc., but even between different cancer cells within a single tumor of an individual. Adding additional difficulty to protein targeted drug discovery, the signaling cascades in cancer cells are often cross-talking with each other, creating a highly sophisticated signaling network. This means the use of an antagonist drug targeting a certain protein to block that signaling event will not really effective due to: (I) variable presence of that protein (drug target) among cancer cells, and (II) the blockage of that signal at that particular point will simply be bypassed by another protein-protein interaction of the complex circuit.

There are several reported methods for unbiased selection of cell surface targeted compounds. Phage display, has proven to be an excellent method to identify high specificity peptides for cell surface markers. This unbiased peptide selection has been able to target a particular cell surface without a prior knowledge of the targeted receptor, which can later be identified. The methodology used in the studies is time consuming and more importantly limited to natural peptides, which still is a questionable class of molecules in the drug development given their limited serum stability and immunogenicity. Live cell screening methods using large combinatorial libraries of natural and unnatural amino acid containing synthetic peptides have been reported. Even though some of these methods contain secondary screening steps to eliminate compounds bind to control cells, these were applied as a subsequent step and need more time and resources.

A rapid and convenient on-bead two-color (OBTC) cell screen technology to directly identify high specificity ligands for cell surface receptors and identified high specificity peptoid ligands for VEGFR2 has been reported. This assay was subsequently used to select high specificity peptoid ligands for EAE responsive T-cell receptors that are elevated as compared with normal cell T-cell populations. A complete unbiased application of our OBTC cell screen is being utilized to identify peptide-peptoid hybrids targeting lung cancer cells over the normal bronchial epithelial cell from the same patient. This helps to reduce side effects and cytotoxicity of the drug as well, which is another extremely important factor that ultimately has to be optimized for each an individual drug.

Also, the development of next generation cancer therapeutic agents will require rapid optimization of affinity, specificity, biological amenabilities, such as serum stability, bio-distribution, tissue penetration, toxicity, clearance, etc. In addition, when considering the number of people affected, the strengths and high growth rates of tumors, rapid and cost effective developments of anti-cancer drugs become high priority. The attempts that do not consider all these very important aspects of the cancer drug development from the front end, usually fail without producing clinically feasible compounds. Therefore, it is quite clear that new approaches and novel molecular classes are needed to combat extremely complex pathological states like cancer.

Peptoids are emerging as a novel class of biologically acquiescent compounds with rapid and cost effective synthesis and optimization. They are protease insensitive, cell permeable, highly diverse, and less immunogenic than peptides and antibodies and recently reported as antagonists for various bio-molecules. The minimum pharmacophore of these peptoids can be easily identified and that knowledge can be used to rapidly optimize activities. Initially identified peptoids can easily be modified and optimized to produce molecules that are applicable in both therapeutic and diagnostic applications in vivo.

A peptide-peptoid hybrid on-bead combinatorial library of 393,216 compounds was developed and applied to a unique on-bead two-color (OBTC) cell screen. The OBTC screen can recognize differences between two cell surfaces at high sensitivity. High specific compound(s) were unbiasedly selected that target something only present in a cancer cell and not on normal cells. This something can be a protein, lipid, carbohydrate, etc. HCC4017 lung cancer cells were targeted over normal bronchial epithelial cells (HBEC30KT) derived from the same patient and peptide-peptoid hybrid PPS1 was identified. PPS1 displayed low micro-molar binding affinity and high selectivity towards HCC4017 cancer cells over normal HBEC30KT cells. The simple dimeric version, PPS1D1, displayed strong cytotoxic activity on HCC4017 cells, but no effect on normal cells. Also, PPS1D1 accumulated strongly in the tumor microenvironment, in particular tumor cell surfaces, on HCC4017 lung cancer xenografts implanted in NUDE mice as compared to controls used.

The strategy for unbiased selection of high specificity ligands that may target bio-molecules beyond proteins on the cancer cell surface involves the following steps: (I) Design and synthesize of peptide-peptoid combinatorial library (introduce a few amino acid positions to the library to increase structural diversity); (II) selection of a suitable cancer and normal cell line pair (cancer (test) and normal (control) cells were selected from the same patient to eliminate genetic variability between two cell groups and help specifically targeting only the cancer specific molecular alterations on the cancer cell surface over the normal cells); (III) exploration of a rapid, reliable, and economical way to unbiasedly select ligands (a unique OBTC cell screen was applied, as it has a unique capability of recognizing molecular differences on two cell surfaces in real time); and (IV) use standard validation methods to confirm the binding, specificity and activity of the compounds selected.

Design and synthesis of peptide-peptoid hybrid library

As mentioned, peptoids have a greater potential to rapidly move from the "bench to bedside", thus, they were chosen as the most suitable molecular class for study. A unique one-bead-one-compound combinatorial library with theoretical diversity of 393,216 permutations was developed. Peptoids are oligo-N-substituted glycines and closely resemble peptides except that the side chains extend from the main chain nitrogen rather than the a-carbon. Peptoid synthesis is straightforward; bromoacetic acid coupling brings the 2 carbon unit and the Br can be replaced by any amine group, completing each of these reactions in less than 1 min using microwave assisted protocol. An unique one-bead—one-compound combinatorial library with theoretical diversity of 393,216 permutations was developed. Each of those sequences contains three amino acids followed by a 5-mer highly diversified peptoid region (FIG. 2A). Methionine at the first position supports CNBr cleavage from tentagel beads for mass spectroscopic sequencing and D-Lysine at the second position acts as a linker. In addition, the positive charged Lys at the base of the library structure reduces aggregation of library molecules and displays properly to be recognized by the incoming bio-molecules during the on-bead screen. The third position was randomly filled with one of the 12 different amino acids to improve diversity. The third position can be any amino acid that provides targeting of PS. All three amino acid positions were carefully designed to avoid vulnerability towards serum proteases and should be stable in biological systems. The next five positions were completely randomized and contain peptoid units developed using eight highly diverse organic amines (FIG. 2B). The next five positions can be any amino acid that provides targeting of PS. The "peptide-peptoid" sequence scaffold can bring additional structural features leading to interesting biological activities.

Phosphatidylserine (PS) is a global marker of tumors: The cellular phospholipid bilayer is composed of four major phospholipids that are arranged asymmetrically. Two lipids with choline head groups, phosphatidylcholine (PC) and sphingomyelin (SM), are enriched in the outer membrane leaflet whereas two lipids with amine head groups, phosphatidylserine (PS) and phosphatidylethanolamine (PE), are largely confined to the inner leaflet (FIG. 24A). During cell activation, apoptosis, necrosis, and malignant transformation, PS and PE become externalized (FIG. 24B) due to activation of PS and PE exporters and inhibition of importers caused by the elevated intracellular Ca2+ associated with these conditions.

PS is exposed on the surface of vascular endothelial cells (EC) in almost all tumor models examined so far, whereas it is absent from vascular endothelium in normal tissues. Orthotopic, syngeneic, and spontaneous human and rodent tumors growing in mice or rats all have PS-positive vasculature. PS exposure dramatically increases when tumors are treated with chemotherapy, radiation, or androgen deprivation therapy. After treatment, up to 95% of the vessels become PS-positive. Tumors also generate high levels of reactive oxygen species (ROS) from a number of different dysregulated metabolic processes, including aberrant signaling from tyrosine kinase receptors.) Tumor cells and tumor stromal cells secrete growth factors and cytokines that activate tumor EC. Activated tumor EC is more responsive to stress than their quiescent counterparts in normal tissues and are more likely to externalize PS in response to environmental stress, and any additional stress, presented by therapy.

PS becomes exposed on many different types of cancer cells. Utsugi et al. were the first to show that tumor cells exhibit 3-7 fold increase in cell-surface PS as compared to normal keratinocytes. PS has since been reported to be a cell-surface marker for ovarian carcinoma, gastric carcinoma, melanoma, leukemia, prostate carcinoma, renal cell carcinoma, glioblastoma, and rhabdomyosacrcoma. The outer membrane of tumor cells can contain as much as 9% PS and high levels of PS exposure have been correlated with progression of melanoma and poor outcome. In addition, tumor cells have been shown to release PS-positive microvesicles and exosomes that can be detected in serum and ascites fluid collected from cancer patients.

Taken together, PS is consistently present on tumor endothelium, tumor cells, and on other components of the tumor microenvironment. Therefore, PS can be considered as a global biomarker for the development of targeted drugs for the treatment of a high percentage of cancer patients.

FIG. 23 Peptide vs peptoid

FIG. 24. Different expression pattern of PS on normal and tumor cells.

Current PS-targeting molecules: One of the most widely studied PS-binding molecules is annexin V, a 35.8 kDa protein. The C2A domain of synaptotagmin I also binds PS and other anionic phospholipids by coordinating Ca2+ much like annexin V. Both annexin V and synaptotagmin have been used successfully in the clinic for the detection of ischemia. However, both proteins have unfavorable pharmodynamics, with major uptake being observed in the liver, kidneys and bone marrow. Recently, several low molecular weight imaging probes have been developed based on nonpeptidic small molecules such as butyl-2-methyl-malonic acid (ML-9) and 18F-5-fluoropentyl-2-methyl-malonic acid (18F-ML-10), and used to visualize irradiated brain metastases in human patients.

A human-mouse chimeric antibody known as bavituximab has previously been developed for targeting PS for clinical use, initially for the treatment of solid tumors. Bavituximab family members recognize two molecules of a PS binding serum protein beta2-glycoprotein 1 (β2GP1) and the resulting complexes bind PS with a high affinity (Kd=0.4 nM). Bavituximab inhibits tumor growth in multiple rodent models of cancer. The safety profile of bavituximab is well established and has been administered to human patients in several phase I and phase II clinical trials. In a phase II trial, 61% (28/46) of breast cancer patients given a combination of bavituximab and docetaxel achieved an objective response compared to a 41% response rate reported for breast cancer patients treated with docetaxel alone in a separate study. Bavituximab was also given to non-small cell lung cancer (NSCLC) patients in combination with carboplatin and paclitaxel and 65% (11/17) of evaluated patients achieved anobjective response. Recently, bavituximab labeled with the positron emitting isotope arsenic-74 (74As) (18) and another PS-targeting monoclonal antibody labeled with the near-infrared (NIR) dye (IRDye800CW), were also successfully used for in vivo imaging of tumor vasculature.

The PS-specific peptide sequence CLSYYPSYC was identified by screening a M13 phage display library. Another PS-binding peptide (PSBP-6) with 14 residues (FNFRLKA-GAKIRFG) has also been reported.(44) In another study, systemic injection of a lytic cationic PS-binding peptide, D-K6L9 (MW=1.8 kDa), composed of 6 lysines and 9 leucines in both their D and L isomeric forms, inhibited the growth of 22RV1 & MDA-MB-231 tumors in mice. Although the PS-targeted agents described in the current literature have demonstrated some prognostic value, there is a need to develop better agents as their clinical use is limited by several issues including: 1) poor pharmacokinetics, 2) low in vivo stability, 3) low affinities 4) high cost, and 5) difficulty in production.

Peptoids as a promising class of therapeutic agents: Peptoids (oligo-N-substituted glycines) closely resemble peptides except that the side chains extend from the main chain nitrogen rather than the α-carbon (FIG. 25). These oligomers are achiral, protease resistant, more cell permeable and adopt different conformations than peptides, yet retain the same density of functionality and backbone polarity. Peptoid synthesis is straightforward (FIG. 25) as in order to add one residue (equivalent to an amino acid of a peptide), it needs only two chemical steps and each of these can be completed by 2×15 second microwave pulses (FIG. 25). Bromoacetic acid coupling brings the 2 carbon units and the Br can be replaced by any amine group (FIG. 25), which dramatically expands the repertoire of chemical space. Large combinatorial libraries of peptoids (in millions) can be synthesized easily, inexpensively, and rapidly (within 2-3 days). Peptoid sequences can be deduced sensitively by Edman degradation or mass spectrometry. Peptoids are rich sources of protein-binding ligands that exhibit antagonist effects on receptors and intracellular protein molecules. Many antimicrobial peptoids are also reported. In addition, peptoids are non-immunogenic in mice. Taken together, peptoids can be considered as excellent alternatives for drug development as compared to expensive conventional molecular classes such as small organics, antibodies and peptides.

FIG. 25 depicts a peptoid synthesis outline.

Unbiased selection of peptide-peptoid hybrid compounds for cancer cells over normal cells The main aim is to identify peptide-peptoid hybrid compounds that can target any type of bio-molecules uniquely present on a cancer cell surface that are absent or of low abundance on normal cells. The OBTC cell assay was originally developed by exposing two identical cell groups (from the same cell line) that differ only by the presence (red stained) or absence of a certain receptor (green stained), to millions of tentagel beads, each carrying a unique peptoid with large number of copies in 'one-bead-one-compound' format. A bead bound with only red stained/receptor overexpressed cells indicated that the peptoid on this bead binds only to overexpressed receptor and not to any other cell surface molecule on the cell surface. If binding to any other cell surface molecule occurs, those are found on the green stained original cells as well and it will register as both red and green cells. Therefore, highly specific receptor ligands can rapidly be selected discarding non-specifics. This unique capability of recognizing differences between two cell surfaces of our BOTC assay is the main hypothesis in this study. That is to expose red stained cancer cells and green stained normal cells as a 1:1 mixture to the library and pick only the red cell bound beads (FIG. 3A). This means the identified compound binds to 'something' on the cancer cell surface, which is not found on the normal cell surface, and more importantly it can be a protein, lipid, carbohydrate or any kind of a molecular or structural arrangements unique to cancer cell surface. One critically important factor here is to have both cancer and normal cells derived from same individual. Otherwise, the differences found here may be due to the genetic differences of individuals, and not cancerous cell vs normal cell differences. The HCC4017 lung cancer cell line was used as the target, since the HBEC30KT normal immortalized bronchial epithelial cell line that is originated from the lungs of the same patient is available. The genetic analysis of both cell lines was obtained to make sure both cell lines are derived from the same patient. (FIG. 78).

The practical use of primary normal human cells for studies is a difficult task due to several reasons. These include complications in obtaining and maintaining primary normal human cells, and even less availability of well suited immortalized normal human cells. As already mentioned, use of normal cells from the same organ/tissue where the cancer is growing of the same person is critical. The lung cancer cell line HCC4017 was used as a target, since the 'normal' immortalized bronchial epithelial cell line (HBEC30KT) that is originated from the lungs of the same patient is available. A genetic analysis of both cell lines was obtained to make sure both cell lines are derived from the same patient. Both these cell lines are immortalized, easy to handle, and fit all criteria set for the study.

Applying the OBTC assay, HCC4017 cells were stained with Qtracker 655 quantum dots (red) and HBEC30kt cells were stained with Qtracker 565 quantum dots (green). Both cells were mixed in a 1:1 ratio and exposed to approximately 100,000 library beads (FIG. 3A). After 30 minutes incubation with shaking at room temperature, unbound cells were washed off and beads bound only with red-labeled cells (HCC4017) were selected (FIG. 3B) as candidates that have high specificity towards HCC4017 cells. These are the compounds binding to 'something' present on red stained HCC4017 cancer cells that are not found on green stained normal HBEC30kt cells. Once again, this 'something' can be a protein, lipid, carbohydrate or even combinations of biomolecules or higher order structural arrangements of those biomolecules. Beads that bound to both cell types (red and green) were ignored as compounds that targets non-tumor specific cell surface bio-molecules (FIG. 3C). This assay was repeated four times, each time using approximately 100,000 beads to roughly cover the total theoretical diversity of the library. Red cell bound beads were extremely rare. Out of the four panning attempts, only three beads that were bound exclusively by HCC4017 cells were identified out of the approximately 400,000 bead screen. This indicates the highest amount of stringency applied in the OBTC assay and the paucity of purely cancer specific bio-molecules. Single bead Edmann sequencing identified the sequences of those candidates for HCC4017 and the structure of one specific peptide-peptoid hybrid—PPS1, is shown in FIG. 3D.

The PPS1 compound consists of four hydrophobic residues towards the N-terminus and three positively charged residues towards the C-terminus. All four hydrophobic residues are peptoid residues and contain bulkier aromatic rings on each side chain. Two of them contain oxygen as heteroatoms. From three positive charges, one was the fixed D-lysine at the 2nd position of the library. The next position was the variable amino acid region and lysine was selected for this 3rd position during the screen. The remaining positive charge at the 4th position from the C-terminus is a peptoid residue with a lysine-like side chain. One of the other two 'hits' identified had almost the same structure as PPS1, differing only by a single residue. Both of these other two compounds are under investigation.

Binding and specificity validation of the identified peptide-peptoid hybrid PPS1

After structural identification, binding specificity was confirmed. The targeted bio-molecule was not known at this point. After sequence determination, both qualitative and quantitative methods were used to characterize the binding of PPS1 to cells. A basic qualitative method was used. The PPS1 compound was re-synthesized on Tentagel beads and exposed to red quantum dot labeled HCC4017 cells alone (FIG. 4A), green quantum dot labeled HBEC30kt cells alone (FIG. 4B), and a 1:1 mixture of red and green labeled cells (FIG. 4C). PPS1 bearing beads readily bound to HCC4017 lung cancer cells (FIGS. 4A & C) but rarely bound to green labeled HBEC30kt normal lung cells (FIGS. 4B & C), validating the high specificity of PPS1 to HCC4017 lung cancer cells compared with the paired HBEC30kt normal lung cells. Red stained HCC4017 cells did not bind to tentagel beads carrying scrambled version PC2. (FIG. 4F). The scrambled version of PPS1, PC2, bearing beads did not show any binding to HCC4017, indicating the sequence specificity (FIG. 4F). A semi-quantitative magnetic bead pulldown assay was developed to further confirm the specificity of PPS1. PPS1 and a non-binding control compound, C462, were synthesized with a biotin tag at the C-terminus (commercially available biotinylted glutamine was used and coupled at the C-terminal). Biotin-PPS1 and biotin-C462 were used to coat streptavidin-magnetic beads to provide PPS1 and C462 coated magnetic beads. An equal number of these PPS1 and C462 coated magnetic beads were equilibrated with 1 million cells of lung cancer HCC4017 cells and normal HBEC30kt and HBEC3kt cells (another normal bronchial epithelial cell line) separately. When this equilibrium mixture was brought close to a magnet, all the magnetic bead-bound cells (through PPS1) get attracted to the magnetic field and the non-bound cells were removed by a washing step. The retained cells were counted and quantified. As shown in FIG. 4D, PPS1 coated magnetic beads readily pulled down about 70-75% of the HCC4017 cells, while only about 10% of the normal HBEC30kt and HBEC3kt cells were pulled down. The control compound C462 coated magnetic beads were unable to pulldown either of the HCC4017 or HBEC cells types, indicating the pulldown event is very specific to the PPS1 compound. This further confirms the high specificity of the PPS1 compound toward HCC4017 cancer cells over the normal HBEC30kt and HBEC3kt cells.

After qualitative and semi-quantitative binding and specificity validation of PPS1 to HCC4017 cells over normal HBEC cells, two different assays were performed to validate this binding event quantitatively. An ELISA-like standard assay using fluorescein isothiocyanate (FITC) labelled PPS1 (FIG. 5A) was used. PPS1 was synthesized with C-terminal Cys and the thiol group was used to attach FITC through standard maleimide chemistry. HCC4017 cells were grown in 96 well plates, fixed and blocked for nonspecific binding. The PPS1-FITC was added in serial dilution to these wells, the compounds were left to bind for 1 hour, and washing occurred to remove the unbound compound. The remaining fluorescence was detected at 520 nm. As shown in FIG. 5C this assay indicated that the PPS1-FITC binds to HCC4017 cells around Kd=5 µM.

A europium (Eu3+) labelled diethylenetriaminepentaacetic acid (DTPA) based cell surface binding detection assay was used (33, 34). Lanthanide-based (e.g. Eu3+) luminescent ligand binding assays are superior to traditional radio-labelled and FITC-labelled assays due to improved sensitivity and also the capability of eliminating the autofluorescence of the cells. The DTPA labelled PPS1 was synthesized and the DTPA with Eu3+ was chelated (FIG. 5B). The binding assay was conducted in standard ELISA-like approach. HCC4017 cells were grown in 96 well plates, fixed and blocked for nonspecific binding. The PPS1-(Eu3+)-DTPA was added in serial dilution to these wells, the compounds were left to bind for 1 hour and the unbound compound washed. The enhancement solution of Eu3+ was added and the bound PPS1-(Eu3+)-DTPA was detected at 610 nm as previously reported. The binding curve obtained from these data (FIG. 5D) indicated that the PPS1 compound binds to HCC4017 cell around Kd=7 µM. Both of these different quantitative binding assays indicated that PPS1 binds to HCC4017 cells with a Kd ranging around Kd=5-7 µM.

Further improvements and in vitro activity validation of the peptide-peptoid hybrid PPS1

After confirming the binding and specificity of the PPS1 on HCC4017 lung cancer cells, whether this compound has any biological effects on HCC4017 lung cancer cells was assayed. The gold standard cell viability (MTS) assay was used. HCC4017 cells and HBEC30kt and HBEC3kt cells were grown in 96 well plates on day 1, then treated by serial dilution of PPS1 and control compound C462 on day 2, and the viable cell count was measured using MTS reagent on day 3. This assay did not indicate any activity of these compounds on any of the cell lines up to the maximum of 100 µM concentration treated. On one of the repetitive experiments of this assay, Cystinylated-PPS1 compound was included (FIG. 6A). This was the intermediate compound used to attach the FITC-malemide for binding assays described previously. To our biggest surprise, this compound started showing moderate cell killing activity on HCC4017 cells that was not found with PPS1 (FIG. 6B). The only difference between this Cystinylated-PPS1 and the original PPS1 compound was just a single cysteine amino acid at the C-terminal. It was difficult to rationalize having a single amino acid residue at the terminus of the sequence causing a large difference of activity, other possibilities were considered. Cysteine has sulfur (—SH) group on the side chain and two of these can easily form disulfide bonds. When there are two Cysteines in C-terminals of PPS1, these could form a disulfide bond to create a dimeric structure of the PPS1 (FIG. 6A). As reported many times in the literature, multimerizations can drastically improve binding and activities of compounds over their monomeric counterparts. Over a 90-fold activity improvement through homo-dimerizations of a VEG-Receptor-2 targeted peptoid was observed using the same OBTC assay (24).

A homo-dimeric version of PPS1 was synthesized. On-bead synthesis protocols for various types of homo-dimers of these peptoids can include loading a central lysine residue onto beads and continuing synthesis of two monomeric copies of the same compound on two available amine functionalities of this bead bound lysine simultaneously. By performing this protocol a simple dimeric version of PSP1 compound was synthesized and named PPS1D1 (FIG. 6C). The analogous dimeric version of control compound C462 also synthesized as C462D1. The resulting dimeric version of the PPS1 compound, PPS1D1 (FIG. 6C), and the analogous dimeric versions of scrambled PC2, PC2D1 (FIG. 6E), and control compound C462, PC462D1 (FIG. 82), were then evaluated for activity. The standard MTS assay was performed using these two dimeric versions as compared to their monomeric counterparts on HCC4017 lung cancer cells using HBEC normal cells as control targets. As described above, HCC4017 cells and HBEC30kt and HBEC3kt cells were grown in 96 well plates on day 1, treated serial dilutions of PPS1, PPS1D1, C462 and C462D1 on day 2, and viable cell count was measured using MTS reagent on day 3. Also as previously observed, the PPS1 monomer did not affect the cell viability of HCC4017 whereas the PPS1D1 dimer was able to clearly affect the cell viability of HCC4017 cancer cells with IC50 value around 10 µM (FIG. 6D). This activity was stronger than: (I) the activity shown by Cystinylated-PPS1; which was speculated as acting as a dimer formed through disulfide bonds, and (II) PPS1 monomer, which has not shown any activity over the concentration range tested. The dimerization improved the activity of the PPS1. The lower activity of the dimer formed through disulfide bonds may be due to the lower stability of disulfide bonds. But PPS1D1, which was synthesized with a perfect covalent linkage through a central lysine, displayed the strongest activity on HCC4017. Furthermore, PPS1D1 did not have any activity on both of the normal HBEC cells lines tested (FIG. 6D), further confirming the observations of previously described binding specificity studies. Neither of the monomeric (C462) nor dimeric (D462D1) compounds displayed activity on any of the cell lines tested (FIG. 6D).

A scrambled version of PPS1D1 and PC2D1 (FIG. 6E). Importantly, PPS1D1 did not have any activity on either of the normal HBEC cells lines tested (FIG. 6E). Additionally, PC2D1 or PC462D1 had no effect on cell viability (FIG. 6E). This further supports the hypothesis of unbiased selection of tPPS1, which may target a biomolecule found only on HCC4017 cell surface and not on the HBEC30kt normal cells. These data demonstrate that PPS1 has a high specificity binding toward a biomolecule presented on HCC4017 cells, which is not found or is substantially less abundant in normal HBEC cells. Moreover, upon dimerization, PPS1D1 displays considerable cell killing activity on HCC4017 cancer cells and has no effect on HBEC normal cells within the concentration range tested. In addition, the activity improvement through dimerization indicates the avidity effect may be playing a role. If true, the actual targeted biomolecule on the HCC4017 cell line also has a higher chance of found to be in dimeric, multimeric, or even complex higher order structural forms.

FACS binding assays were conducted to further quantify the binding event of the PPS1 monomer and PPS1D1 dimer. PPS1 displayed a Kd of 14 µM while the PPS1D1 displayed a much improved 80 nM.

Figure 7:
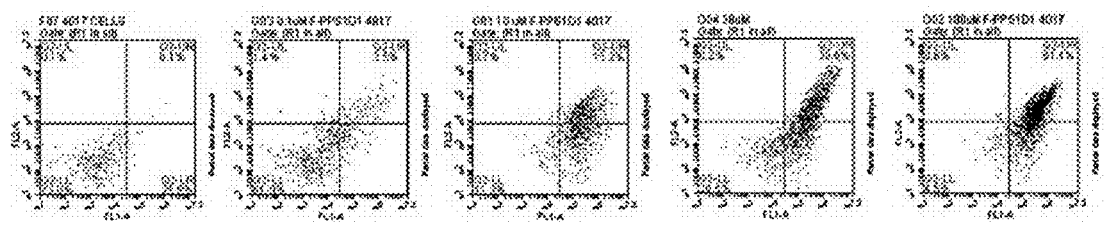
FIG. 7 (A) FACS analysis of cytotoxicity of FITC-PPS1D1 on H460 cell line with 1 hr incubation (B) Histogram depicting percentage of FITC-PPS1 and PI positive cells after 1 hr incubation (C) Schematic representation of effect of PPS1D1 on HCC4017 cells.
Figure 7:
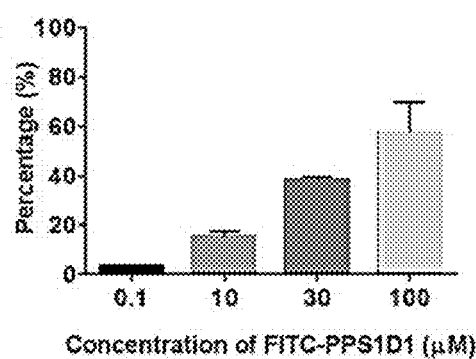
Figure 7:
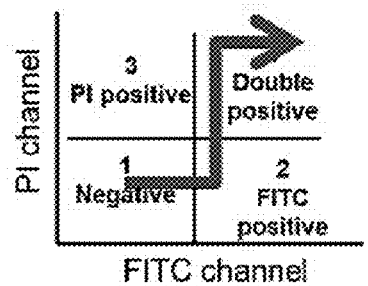

The FACS assay was used to further confirm the activity of PPS1D1 compound. Propidium Iodide (PI) is known to bind to nucleic acids inside the cells but is not cell permeable alone. If the cells are damaged or killed by a compound treatment, PI can get into cells and stain the nucleus. The FACS binding assay was performed in the presence of PI to investigate the activity of PPS1D1 towards the HCC4017 cells. Serial dilutions of PPS1D1-FITC on HCC4017 cells were performed in the presence of PI and the FACS assay was conducted by acquiring signals from both the PI and fluorescein channels. The percentage of stained cell populations were plotted with PI staining on the Y axis and fluorescein staining on the X axis. In this format, the moving of the stained cell pollution toward the X-axis indicates the increased binding event of the compound on the cells. If the stained cells move toward the Y-axis, indicates the compound has some activity that affects the integrity of the cells. Moving of the stained cell population towards the double-positive range confirms the binding as well as the functional activity of the compound. As shown in FIG. 7, upon treatment of PPS1D1-FITC, the stained cell population starts moving towards the X-axis at lower concentrations of the compound. This indicates the binding of the compound on HCC4017 cells. But at higher concentrations of the PPS1D1, the stained cell population clearly moves in the direction of Y-axis as well, ultimately ending up in the double-positive area. This clearly indicates the PPS1D1 not only binds strongly around the lower micromolar concentration range, but has the functional effect that disturbs the cell integrity as well. This observation occurs around the 5-15 µM range, perfectly matching the 10 µM IC50 value observed in the MTS assay that directly measures the cell viability.

PPS1 has high specificity binding towards a bio-molecule predominantly found on the HCC4017 cell surface, which is not found or less abundant in normal HBEC cells. Moreover, upon dimerization, PPS1D1 displays considerable cell killing activity on HCC4017 cancer cells but has no effect on HBEC normal cells within the concentration range tested.

In vivo validations of the peptide-peptoid hybrid PPS1D1

PPS1D1 compound binding, specificity and activity was validated through in vivo animal model levels. The PPS1 targeting HCC4017 lung cancer model, was validated using HCC4017 xenografts.

Tumor localization was investigated using PPS1D1. PPS1D1 and the control compound C462D were biotinylated at the C-terminal and mice were treated. The mice were sacrificed at 1 hr and 4 hr time points and the tumor sections were evaluated by treating Streptavidin-Cy3. (FIG. 8) The nucleus was stained with DAPI. PPS1D1 strongly accumulated in HCC4017 tumor sections. This accumulation was higher at the 4 h time point than the 1 hr time point, indicating this phenomenon is not due to a non-specific accumulation. More strikingly, very prominent staining surrounding tumor cells strongly indicated that the PPS1D1 is recognizing a bio-molecule presented on the tumor cell surface rather than just accumulation in the tumor microenvironment. Our non-HCC4017 binding control peptide was almost not found any of the tumor sections studied, again supporting the specific binding of PPS1D1 to HCC4017 cells.

The actual tumor burden effects of PPS1D1 on HCC4017 xenografts were studied. The study was planned with 4 groups. Unfortunately, the HCC4017 cells did not grow properly in mice. It took a long time to grow and created a very heterogeneous xenograft population. PPS1D1 treatment was performed, but due to the high heterogeneity of the tumors, most of the mice in every group had to be sacrificed as they reached the maximum allowed limits. Some of the same group displayed less growth. The initial data showed that the compound is capable of reducing the tumor growth.

Minimum tolerance does (MTD) studies were performed by injecting PPS1D1 into mice. Initial MTD studies indicated that the MTD for nontumor bearing animals was 5 mg/kg and 1 mg/kg for mice bearing subcutaneous HCC4017 xenografts. In vivo localization studies were performed with biotinylated versions of PPS1D1 and PC462D1. Animals were injected intravenously with 100 µL of biotinylated PPS1D1 or PC462D1 (500 µg/mL) and sacrificed at 1 and 4 h post injection. Tissue was collected, snap frozen, and sectioned and the presence of the PPS1D1 and PC462D1 determined by streptavidin-Cy3. Biotinylated PPS1D1 accumulated in the tumor microenvironment at 1 h and with increased signal intensity at 4 h (FIG. 8E). There was no detectable signal from the control compound at either time point. This indicates that the specificity of PPS1D1 toward HCC4017 cells was promptly maintained in vivo as well.

A unique OBTC combinatorial cell screening technology was applied through an unbiased approach and a highly specific peptide-peptoid hybrid PPS1D1 for HCC4017 lung cancer cells (that does not recognize normal HBEC30-KT bronchial epithelial cells from the same lung of the same patient) was successfully identified. Due to the unique capability of the OBTC assay in recognizing differences of two cell surfaces, the hypothesis was to apply this assay to identify compounds that can recognize any type of bio-molecule (e.g. protein, lipid or carbohydrate) present only on the HCC4017 lung cancer cell surface and not on the normal HEBC30kt cell surface. PPS1D1 displayed cell killing activity of HCC4017 lung cancer cells, but not on normal HEBC30kt and HEBC3kt cells. Also, PPS1D1 strongly accumulated in HCC4017 tumor xenografts grown in mice.

Furthermore, the OBTC unbiased selection approach effectively bypasses the time and resource consuming conventional drug/lead development approach, where knowledge of the targeted bio-molecule is a prerequisite. The OBTC combinatorial cell screening technology is rapid and cost effective as compared to most other drug/lead development approaches, including the phage display method, which has the capability of apply in unbiased selections. More importantly, This technology can be applied to other cancer types providing a platform for unbiased selection of high specificity ligands for various disease specific biological targets, providing a global platform for unbiased selection of high specificity ligands.

FIG. 1. Schematic comparison of cell membrane bimolecular asymmetry in cancer and normal cells. Cancer cell surface may display specific protein, lipid, carbohydrates and glycoproteins that are expressed under cancerous situation that may be absent or minimal on normal cell surface under healthy biological conditions.

Figure 2:
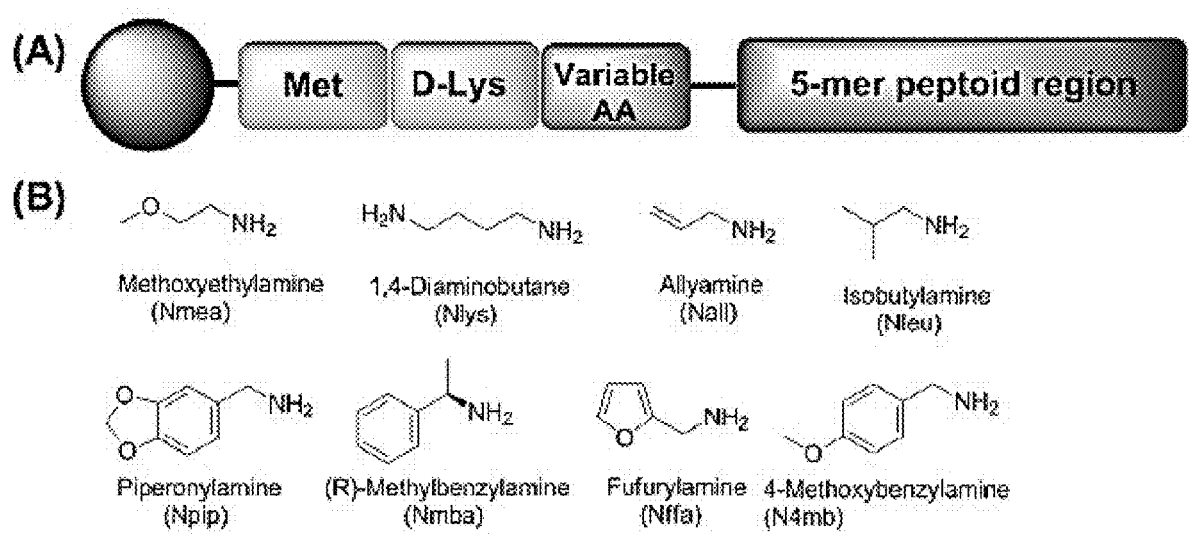
FIG. 2 The basic structure of the on-bead peptide-peptoid hybrid library of 393,216 compounds developed using split-pool synthesis. (A) Each compound of the library is built with three C-terminal amino acids residues, followed by 5-mer peptoid region towards the N-terminal. Initial methionine and D-Lys were fixed at the first and second positions. The third position was varied with 12 amino acids and the 5-mer peptoid region was diversified with 8 different amines. (B) The chemical structures of the 8 different amines employed in the 5-mer diversified peptoid region. The nitrogens become the main chain nitrogens of the amide bonds in the peptoid backbone, allowing the rest of the moiety to become 'R' groups that help recognize the target biomolecule.

FIG. 2. The basic structure of the on-bead peptide-peptoid hybrid library of 393,216 compounds developed using split-pool synthesis. (A) Each compound of the library is built with three C-terminal amino acids residues, followed by 5-mer peptoid region towards the N-terminal. Initial methionine and D-Lys were fixed. 3rd position was varied with 12 amino acids and 5-mer peptoid region was diversified with 8 different amines. (B) The chemical structures of the amines employed in the 5-mer diversified peptoid region. The nitrogens shown in blue color becomes the main chain nitrogens of the amide bonds in the peptoid backbone, allowing rest of the moiety to become 'R' groups that helps recognizing target biomolecule.

Figure 3:
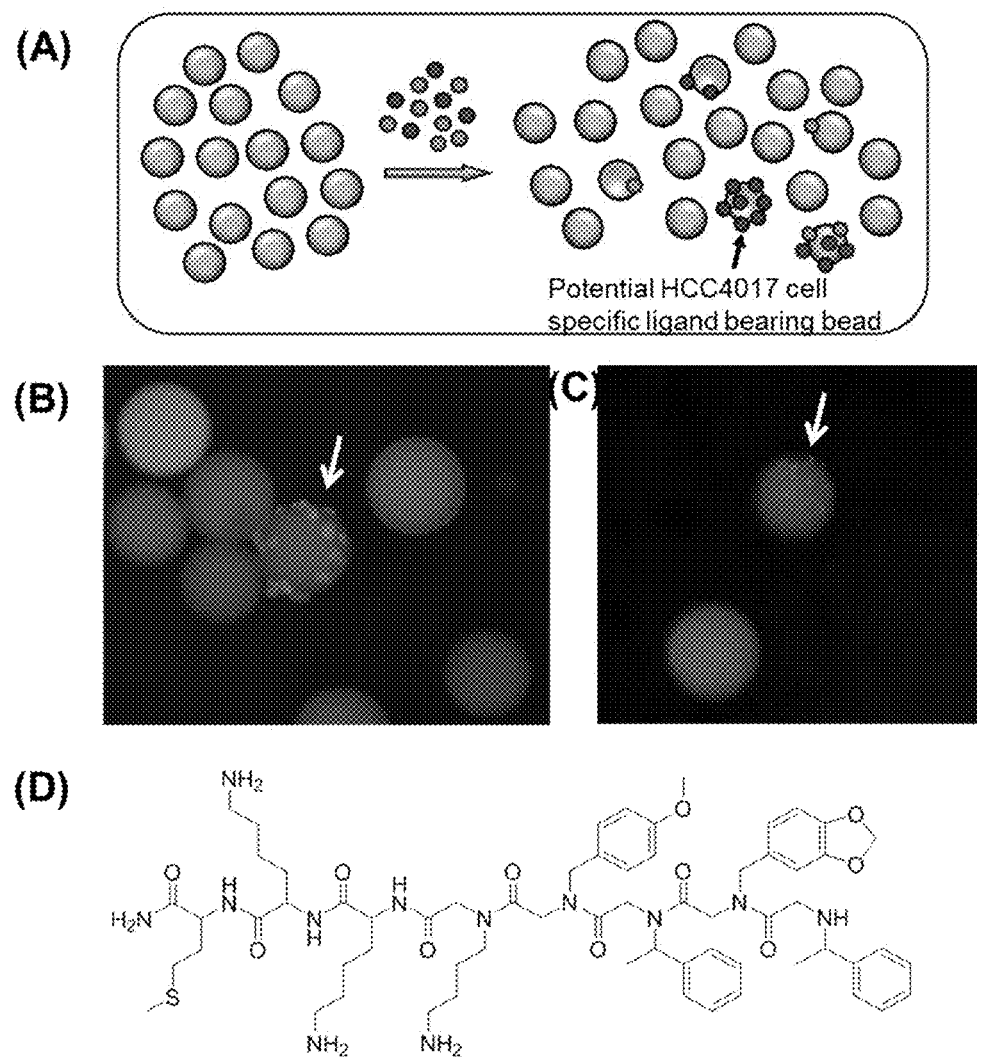
FIG. 3 The On-Bead Two-Color (OBTC) combinatorial cell screen was used to identify HCC4017 lung cancer cell specific ligands over normal HBEC30KT cells from the same patient. (A) Schematic representation of the assay. In a single assay, a 100,000 batch of one-bead one-compound library beads (large blue circles) was treated with 1:1 mixture of red and green quantum dot stained HCC4017 cells and HBEC30KT cells respectively. Only red cell bound beads indicate that the compound on that bead recognized 'something' uniquely present on HCC4017 lung cancer cell surface that is absent (or negligible) in HBEC30KT cell surface. (B) and (C) Fluorescent microscopic images of beads at the end of the assay after screening and washing the cells (100× total magnification, DAPI-longpass Filter). (B) One of the three beads found with only red stained HCC4017 cells bound (shown by arrow), out of total ~400,000 beads screened in four rounds. (C) A bead bound to both red and green stained cells, discarded as non-specific compound carrying beads that may have recognized biomolecules common to both cell surfaces. (D) The structure of one of the 'hits', the peptide-peptoid hybrid PPS1 that was identified from the screen.

FIG. 3. The On-Bead Two-Color (OBTC) combinatorial cell screen to identify HCC4017 lung cancer cell specific ligands over normal HBEC30KT cells from the same patient. (A) Schematic representation of the assay. In a single assay, a 100,000 batch of one-bead one-compound library beads (large blue circles) was treated with 1:1 mixture of red and green quantum dot stained HCC4017 cells and HBEC30KT cells respectively. Only red cells bound bead indicates that the compound on that bead recognized 'something' uniquely present on HCC4017 cell surface that is absent (or negligible) in HBEC30KT cell surface. (B & C) Fluorescent microscopic images of beads at the end of the assay after screening and washing off cells (100× total magnification, DAPI-longpass Filter). (B) One of the three beads found with only red stained HCC4017 cells bound (shown in arrow), out of total ~400,000 beads screened in four rounds. (C) A bead bound to both red and green stained cells, discarded as non-specific compound carrying beads that may have recognized biomolecules common to both cell surfaces. (D) The structure of one of the 'hit' peptide-peptoid hybrid PPS1 identified from the screen.

Figure 4:
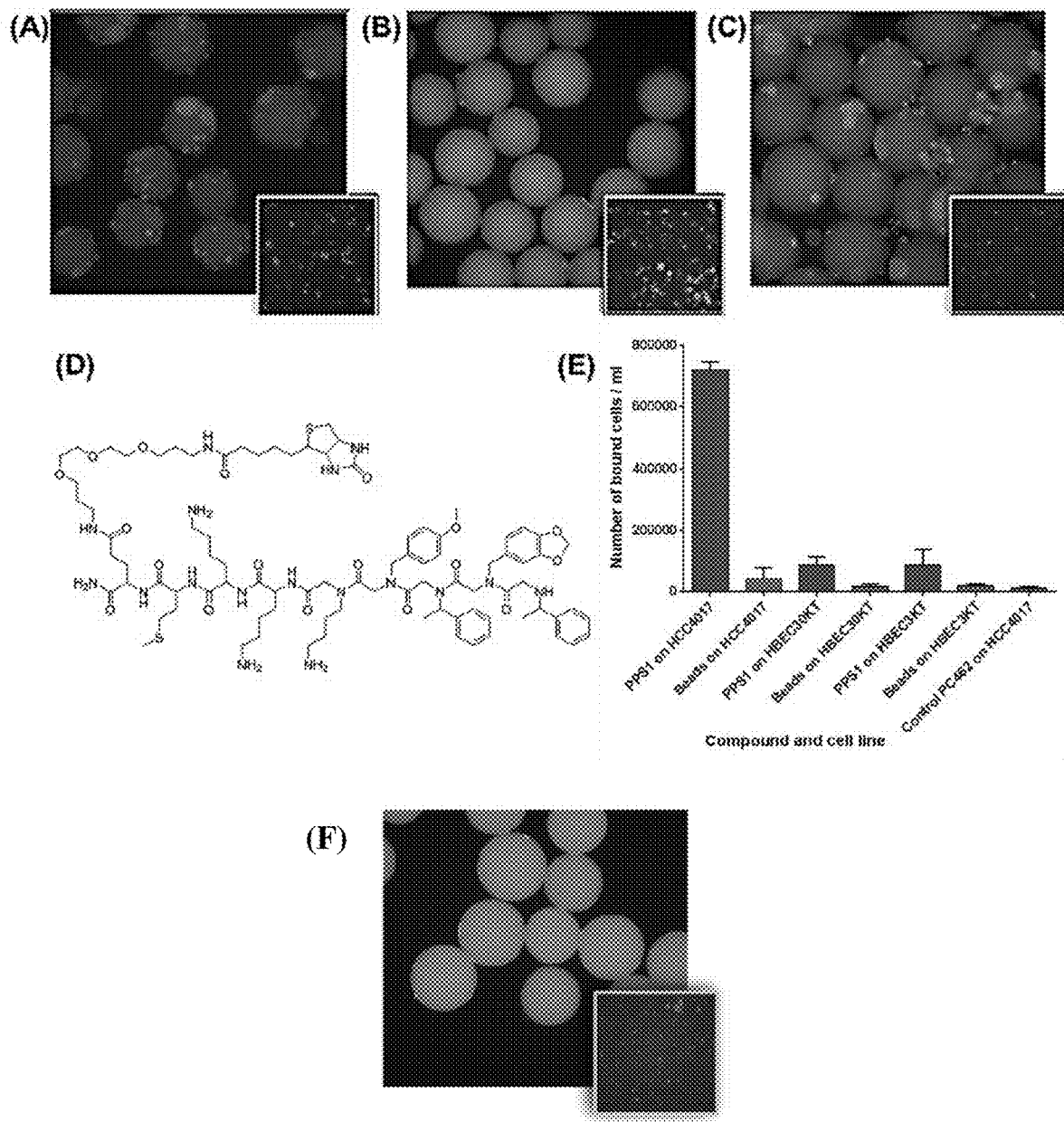
FIG. 4 Qualitative binding and specificity validation of the identified peptide-peptoid hybrid PPS1. First, PPS1 was re-synthesized on tentagel beads and exposed to: (A) Red quantum dot labeled HCC4017 cells alone (B) Green quantum dot labeled HBEC30KT cells alone (C) Both red labeled HCC4017 and green labeled HBEC30KT at 1:1 mixture. PPS1 predominantly bound to red stained HCC4017 cells over HBEC30KT cells. (D) Chemical structure of the c-terminus biotinylated PPS1. (E) Streptavidin-magnetic beads coated with biotinylated PPS1 pulled down only HCC4017, but not HBEC30KT or HBEC3KT cells. (F) Red stained HCC4017 cells did not bind to tentagel beads carrying scrambled version PC2. The control non-binding PC462 compound coated magnetic beads fail to pull down any of the tested cell lines.

FIG. 4. Qualitative binding and specificity validation of the identified peptide-peptoid hybrid PPS1. First, PPS1 was re-synthesized on tentagel beads and exposed to: (A) Red quantum dot labeled HCC4017 cells alone (B) Green quantum dot labeled HBEC30KT cells alone (C) Both red labeled HCC4017 and green labeled HBEC30KT at 1:1 mixture. PPS1 predominantly bound to red stained HCC4017 cells over HBEC30KT cells. (D) Chemical structure of the c-terminus biotinylated PPS1. (E) Streptavidin-magnetic beads coated with biotinylated PPS1 pulled down only HCC4017, but not HBEC30KT or HBEC3KT cells. The control non-binding PC462 compound coated magnetic beads fail to pulldown any of the cell lines.

Figure 5:
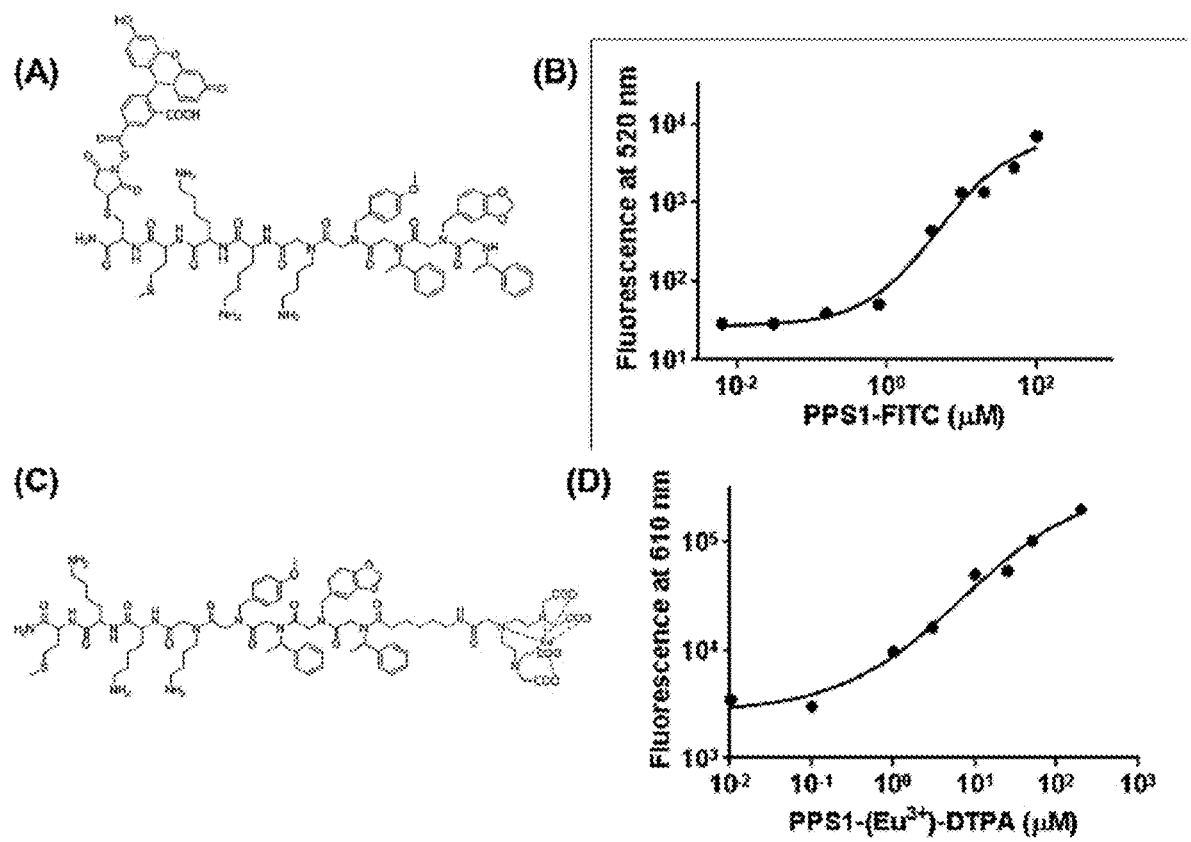
FIG. 5 ELISA-like quantitative binding and specificity validation of the identified peptide-peptoid hybrid PPS1. (A) Chemical structure of c-terminal fluorescein isothiocyanate (FITC)-labelled PPS1 (FITC-PPS1). (B) Binding curve of HCC4017 cells with PPS1-FITC indicates a $K_d$ around 5 µM. (C) Chemical structure of N-terminus modified Eu3+-chelated DTPA-labelled PPS1 (D) Binding curve of HCC4017 cells with PPS1-(Eu3+)-DTPA indicates a $K_d$ around 5-7 µM.

FIG. 5. ELISA-like quantitative binding and specificity validation of the identified peptide-peptoid hybrid PPS1. (A) Chemical structure of c-terminus fluorescein isothiocyanate (FITC) labelled PPS1 (FITC-PPS1). (B) Binding curve of HCC4017 cells with PPS1-FITC indicates KD around 5 μM. (C) Chemical structure of N-terminus modified Eu3+-chelated DTPA labelled PPS1 (D) Binding curve of HCC4017 cells with PPS1-(Eu3+)-DTPA indicates KD around 5-7 μM.

Figure 6:
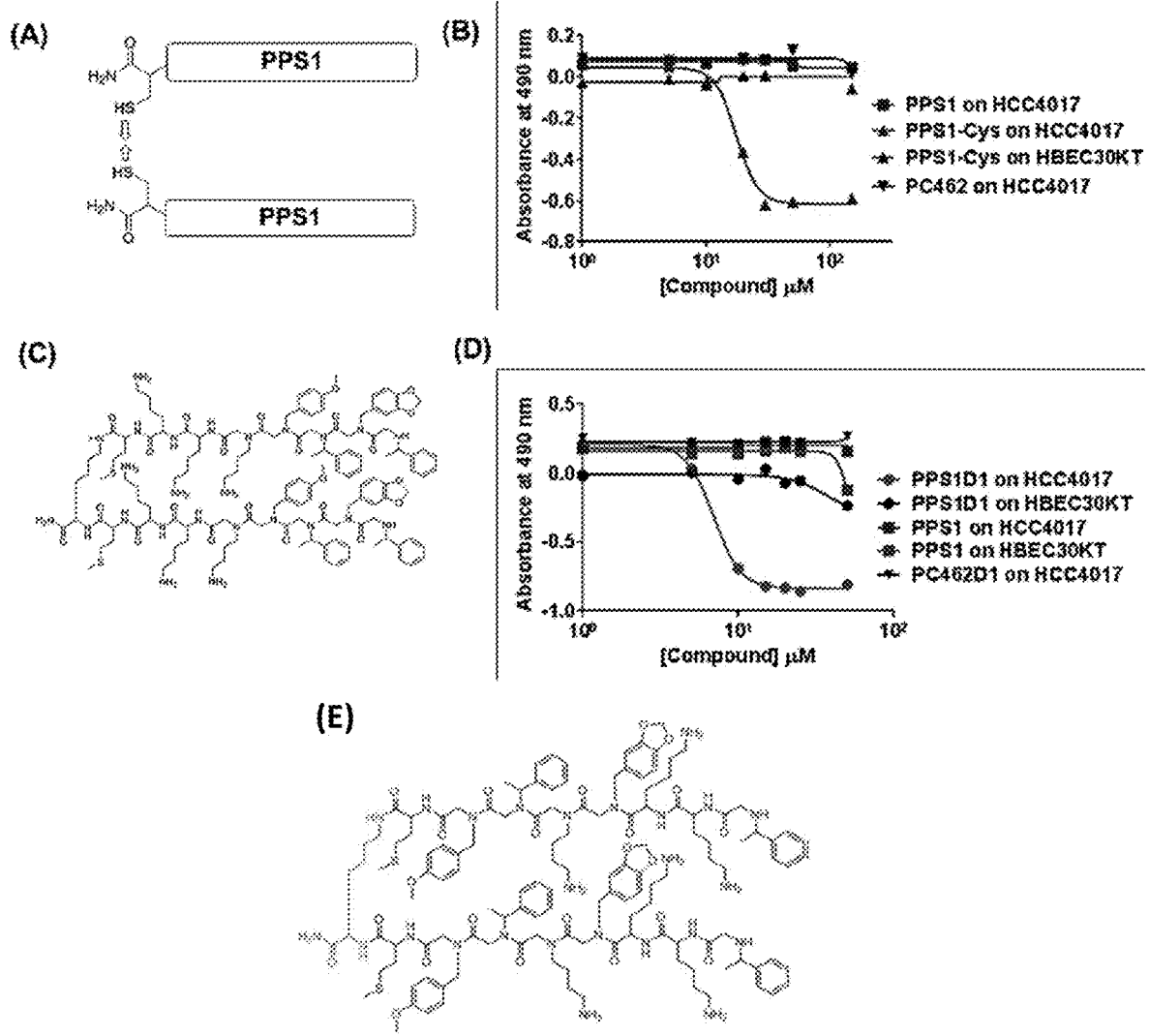
FIG. 6 Dimerization of PPS1 triggers PPS1 activity. (A) Cartoon depicting the suspected disulfide bond formation between two c-terminal cysteinylated PPS1 (B) Standard MTS cell viability assay results on HCC4017 with the treatment of PPS1 (blue line), PPS1-cys (red line) and PC462 (black line) and PPS1-Cys treated on HBEC30KT as a control (green line). Only PPS1-Cys treated with HCC4017 displayed cell killing activity. (C) Chemical structure of the PPS1 homo-dimer PPS1D1. Each of the two monomeric units of PPS1 is linked through a central lysine residue at the C-termini. (D) Standard MTS cell viability assay results on HCC4017 and HBEC30KT treated with PPS1D1 (red line and black line respectively), PPS1 (blue line and green line) and PC462D1 (black line). (E) Scrambled version of PPS1D1 and PC2D1. Only PPS1D1 treated with HCC4017 displayed cell killing activity.

FIG. 6. Dimerization of PPS1 triggers the activity of PPS1. (A) Cartoon depicting the suspected disulfide bond formation between two c-terminal cysteinylated PPS1 (B) Standard MTS cell viability assay results on HCC4017 with the treatment of PPS1 (blue line), PPS1-cys (red line) and PC462 (black line) and PPS1-Cys treated on HBEC30KT as a control (green line). Only PPS1-Cys treated with HCC4017 displayed cell killing activity. (C) Chemical structure of PPS1 homo-dimer PPS1D1. Each of the two monomeric units of PPS1 is linked through a central lysine residue at the C-termini. (D) Standard MTS cell viability assay results on HCC4017 and HBEC30KT treated with PPS1D1, PPS1, and PC462D1. Only PPS1D1 treated with HCC4017 displayed cell killing activity.

FIG. 7. (A) FACS analysis of cytotoxicity of FITC-PPS1D1 on H460 cell line with 1 hr incubation (B) Histogram depicting percentage of FITC-PPS1 and PI positive cells after 1 hr incubation (C) Schematic representation of effect of PPS1D1 on HCC4017 cells.

Figure 8:
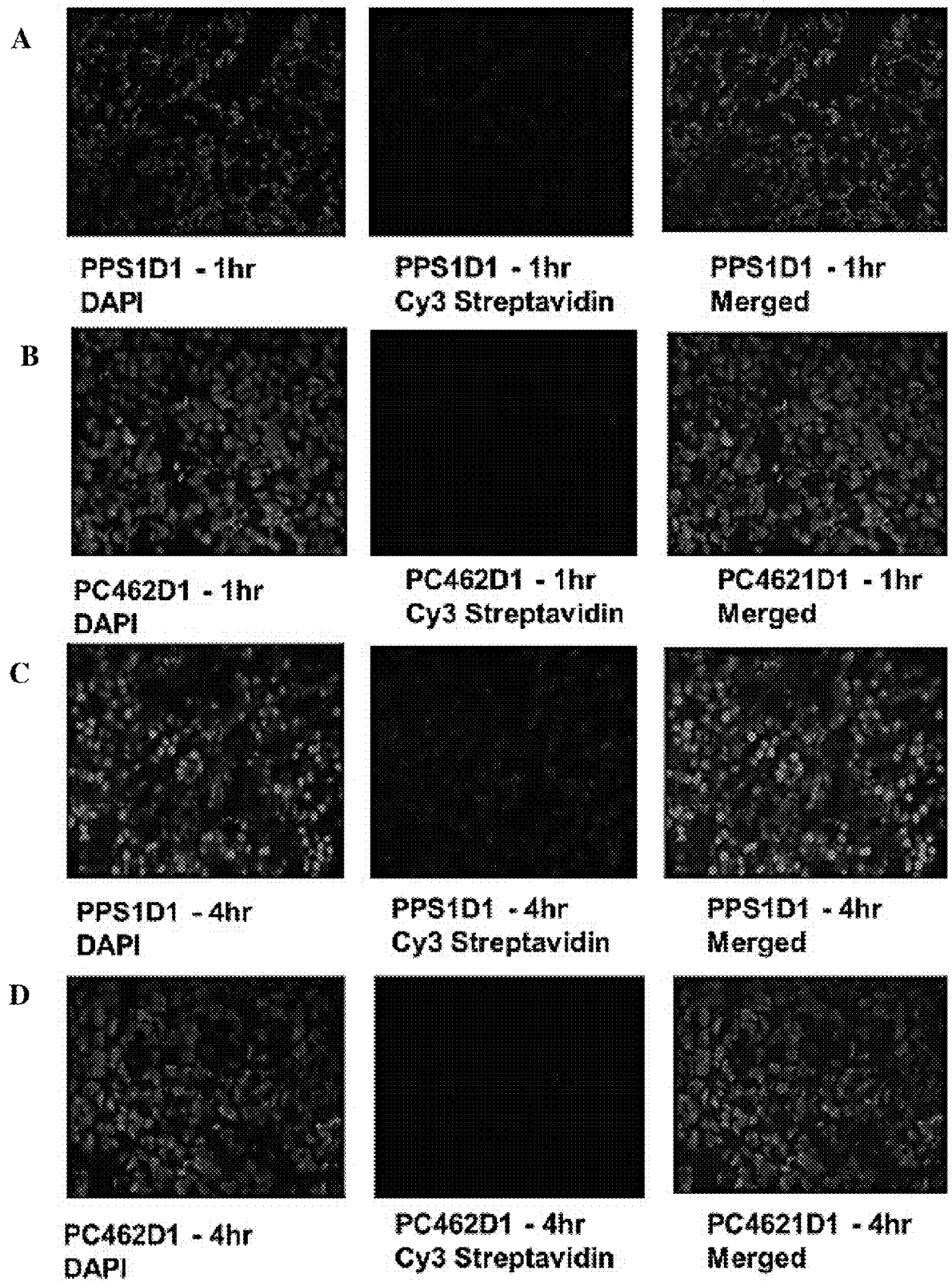
FIG. 8 Tumor accumulation of PPS1D1 in HCC4017 xenograft in mice. PPS1D1 strongly accumulated in tumors at both 1 h (A) and 4 h (C) time points as compared to no accumulation of the control non-binding compound PC462D1 (B) and (D). (E) Tumor accumulation studies of PPS1D1 and control P462D1 compounds on HCC4017 xenografts in NOD/SCID mice. PPS1D1 strongly accumulated in the tumor at both 1 and 4 h time points, while the control PC462D1 was not detected.
Figure 8E:
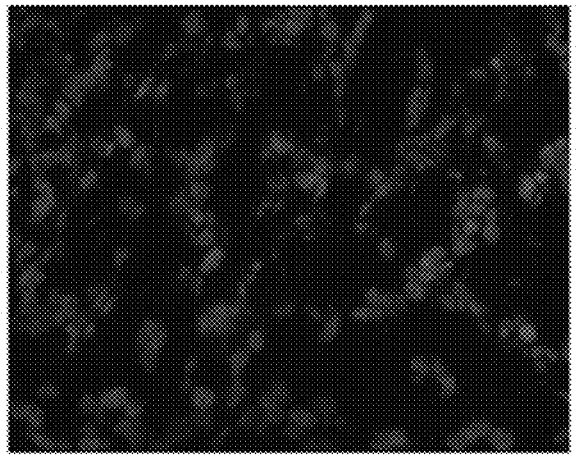
Figure 8E:
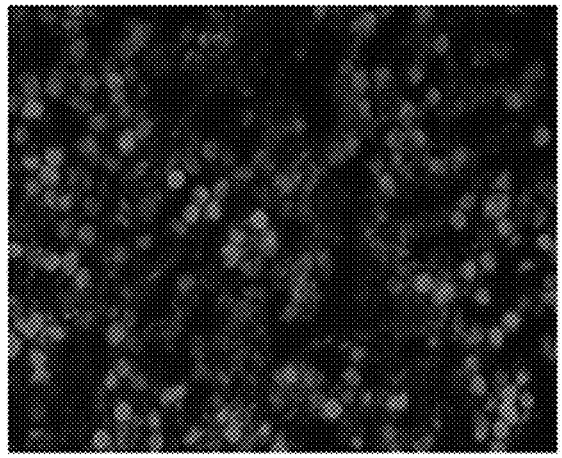
Figure 8E:
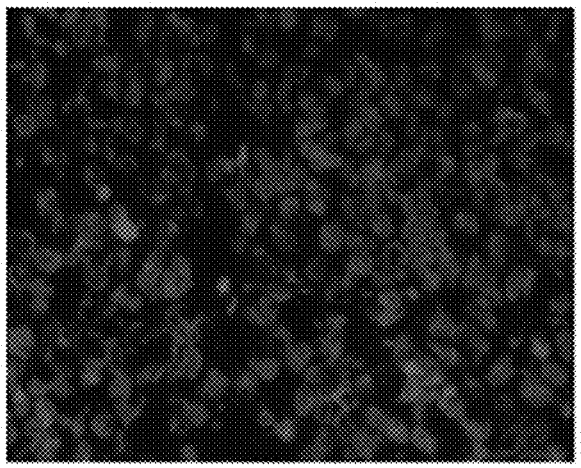
Figure 8E:

FIG. 8: Tumor accumulation of PPS1D1 in HCC4017 xenografts in mice. PPS1D1 strongly accumulated in tumors at both 1 h and 4 h time points as compared to no accumulation of control non-binding compound. FIG. 8E shows the results of tumor accumulation studies of PPS1D1 and control P462D1 compounds on HCC4017 xenografts in NOD/SCID mice. PPS1D1 strongly accumulated in the tumor at both 1 and 4 h time points, while the control PC462D1 was not detected.

Validation of Lipid-Phosphatidylserine (PS) as the target of unbiasedly selected cancer specific peptide-peptoid hybrid PPS1

Asymmetry of phospholipids on normal and cancer cell plasma membrane is one of the features that distinguishes them from one another. Phosphatidylserine (PS), one of the most abundant anionic phospholipids is typically found on the inner leaflet of the normal cell membrane, flips onto outer leaflet in cancerous situation. PS is the target of PPS1. HCC017 lung cancer cells strongly express PS on the cell surface, while normal HBEC30KT cells do not. PPS1 coated magnetic beads are able to strongly pull down HCC017 lung cancer cells and not HBECE30KT cells, further indicating PPS1 can bind to PS. PPS1 binding to PS has been confirmed using ELISA-like assays, lipid dot blot, and liposome based binding assays as well as competitive binding studies with the known PS targeting molecule annexin V. Cytotoxicity effects of simple dimeric version PPS1D1 were observed on HCC4017 cells and also on another lung cancer cell line H460, which also strongly expresses PS. PPS1D1 has a strong cytotoxicity on H460 through MTS and FACS based assays in vitro. Treatment of PPS1D1 on H460 xenografts displays strong tumor burden effects with and without docetaxel, a preferred chemotherapy for lung cancer.

Targeted cancer drug development is far more challenging due to the diversity and complexity of the disease. A unique unbiased selection approach using on-bead two-color (OBTC) combinatorial cell screen was used to identify a peptide-peptoid hybrid PPS1 (FIG. 9A) targeting HCC4017 lung cancer cells in the presence of normal HBEC30kt cells from the same lung of the same patient. PPS1 had specific binding and upon simple dimerization (PPS1D1) (FIG. 9B), this compound displayed strong cytotoxicity on HCC4017 lung cancer cells but had no detectable binding or activity on normal HBEC30kt cells. PPS1D1 was identified as targeting lipid-phosphatidylserine (PS), uniquely found on cancer cell surfaces as compared to normal cells (FIG. 10A).

Figure 9:
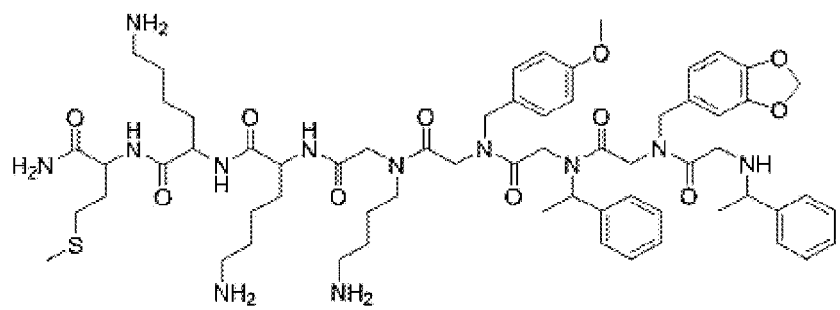
FIG. 9 Chemical structure of (A) PPS1 monomer and (B) PPS1D1, a dimer containing two PPS1 molecules linked through a central lysine residue at the C-termini.
Figure 9:
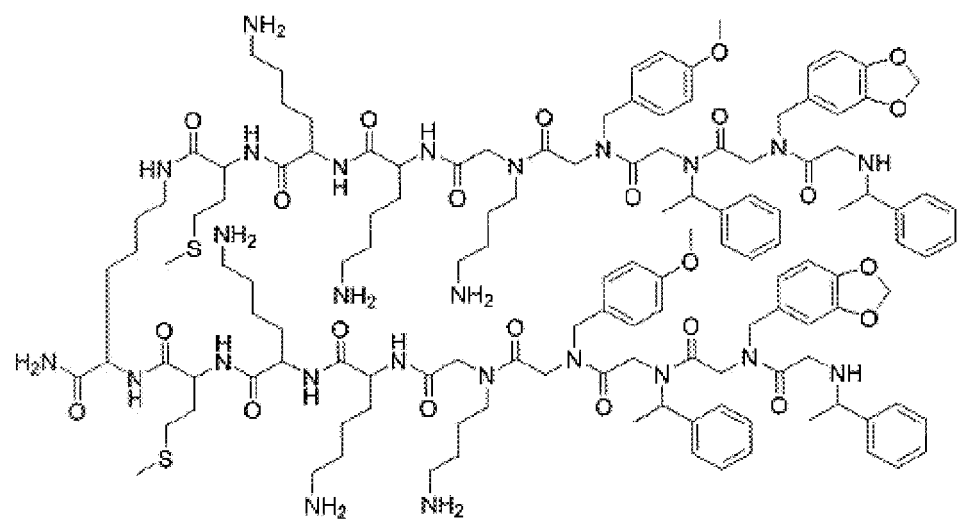

FIG. 9: Chemical structure of (A) PPS1 monomer and (B) PPS1D1, a dimer containing two PPS1 molecules linked with cysteine residue.

Figure 10:
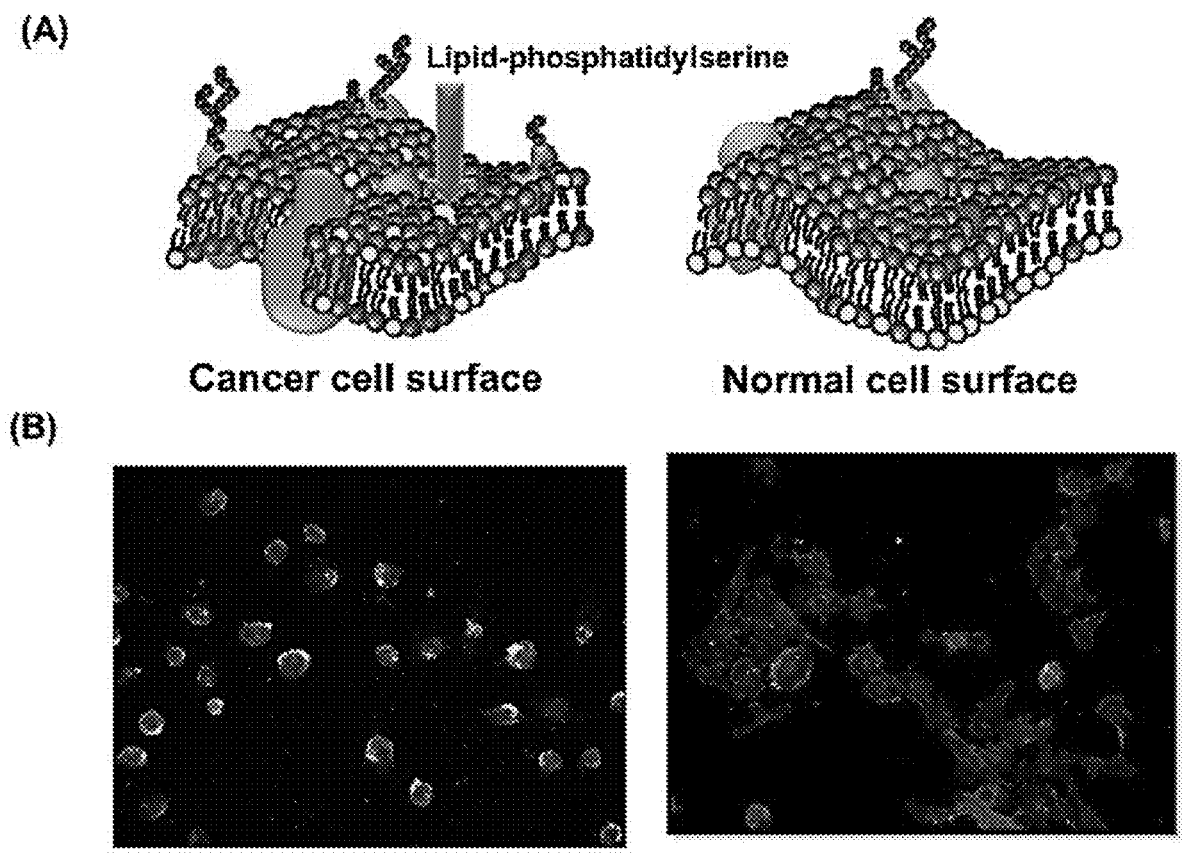
FIG. 10 (A) schematic representation of membrane lipid asymmetry in cancer and normal cells. (B) Staining of HCC4017 (left) and HBEC30KT (right) with PS targeting bavituximab antibody.

FIG. 10: (A) schematic representation of membrane lipid asymmetry in cancer and normal cells. (B) Staining of HCC4017 (left) and HBEC30KT (right) with PS targeting bavituximab antibody.

Identifying compounds that may target biomolecules beyond proteins was achieved by directly targeting cancer cells over normal cells derived from same patient, in a suitable combinatorial high throughput screening approach. The approach was to use an OBTC combinatorial cell screen that has the unique capability of sensitizing differences of two cell surfaces and performing an unbiased selection that could recognize 'something' on the cancer cell surface which is most importantly not found on the normal cell surface (as indicated in FIG. 10A), comparing red stained cancer cells vs green stained normal cells simultaneously. Proteins, lipids or carbohydrates were given an equal chance to be the 'something' that was specifically found only on the cancer cell surface. The OBTC assay eliminated compounds that targets all the bio-molecules on a normal cell surface at the same time and any compound that targets any bio-molecule that is over expressed on the cancer cell surface. The target of PPS1 is lipid-phosphatidylserine (FIG. 10A).

It was assumed that the compound bound to a specific protein and the compound was used to bind, trigger cross-linking, pull down and was identified through western blotting, sequential digestions and mass spectrometry analysis. The compound was not pulling down any specific protein. Therefore attention was paid to other classes of bio-molecules on the cell surface such as lipids and carbohydrates. In particular, anionic phospholipids, sialic acid residues and heparin sulfates are some known examples of these other molecular classes that over are expressed in cancer cell surface over the normal cells. There was non-availability of such a direct pulldown type technique to identify lipids targeted by PPS1D1. Membrane lipid composition of every tissue is unique, having a mix of anionic and cationic lipids. Mostly phosphotidylcholine (PC) and sphingomyelin (SM) are located on outer leaflet, while anionic phospholipids phosphotidylserine (PS) and phosphotidylethanolamine (PE) are more abundant in inner leaflet of a typical normal cell. The distribution of phospholipid is highly dynamic; it changes in response to physiological and pathophysiological events. Movement of lipids across the membrane is controlled by aminophospholipid translocases, scramblases, ATP binding cassette group of transporters and Ca2+ concentration. The movement across membrane is most well studied during apoptosis, malignancy and cell damage. Anionic phospholipid PS has been extensively reported as a universal marker of tumor vasculature. This is because PS is usually present in the inner layer of the normal cell membrane and flips to the outer layer (FIG. 10A) during apoptosis, necrosis, and cell activation, malignant transformation under hypoxia, ROS and cytokine activations.

There have been several efforts to target PS for imaging and therapeutic applications in cancer. Peptides, antibodies and small molecules targeting PS have been reported. A PS binding peptide identified by screening a M13 phage library was used for H460 tumors imaging in mice. Another peptide was identified by screening of library of compounds for their binding to PS—coated surface plasmon resonance sensor chips. This peptide was conjugated with 99mTc and was shown to bind to cancer cells. Zinc containing small molecules targeting PS have been used for optical imaging of tumors. PS presence is one of the important markers observed in the tumor microenvironment. It has been observed in almost all mice and human tumor models studied. In most tumors PS presence is strongly observed on endothelial cells of the tumor vasculature. Depending on tumor type, there can be as much as 50% vessels showing PS presence. It has been shown that when tumors are treated with conventional cancer treatments like chemotherapy, radiation or hormone deprivation more and more tumor vessels become PS positive.

Current drug classes such as peptides, small organic molecules, and antibodies, all have their own drawbacks. Antibodies have high cost of production and offer poor biodistribution and penetration. Small organic molecules are difficult to synthesize and optimize. Peptides have poor serum stability as most of them are rapidly degraded in vivo. Under these circumstances, peptidomimetic compounds with peptide-like characteristics have emerged as important therapeutic molecules for anti-cancer drug development. Peptoids have peptide like backbone and each residue is N-substituted glycines, equivalent to an amino acid of a peptide. The R group of a peptoid residue is placed on a nitrogen instead of the alpha carbon. This arrangement makes peptoids protease resistant, more cell permeable, and non-immunogenic. Large peptoid libraries containing millions of molecules can rapidly and be easily synthesized at low cost and has been reported to use in identification of potential drug leads targeting various cancer targets.

HCC4017 lung cancer cells have more PS than normal cells

It is well known that PS flipping to outer leaflet occurs due to significant alterations in a cell as well as its environment. In a normal situation, this flipping occurs in cells undergoing apoptosis and PS expression on cell surface serves as a bait for macrophages to remove those cells. In a cancerous situation, PS moves to outer leaflet and serves as a signal to invade immune system recognition as a malignant cell and this helps as a survival methods. This PS asymmetry between normal and cancer cell provides a platform to uniquely develop cancer specific therapeutics.

HCC4017 cancer cells express PS on its surface and PS is absent in the normal HBEC30KT cells. Both cells were stained with a PS specific antiobody, bavituximab. It is well characterized for its PS specificity. Both HCC4017 and HBEC30KT cell lines were grown in an 8 well glass chamber place at 37° C. overnight. The next day, 2 µg/ml Bavituximab and β2-glycoprotein, needed for the antibody binding, was added. After 1 hr incubation at 37° C., cells were fixed with paraformaldehyde. Cells were washed and stained with the fluorescently conjugated secondary antibody goat-anti human Cy2. Cells were then permeabilized and stained with Texas red conjugated phalloidin. After appropriate drying, the slides were mounted with Prolong Gold with DAPI (Invitrogen) and imaged with a fluorescence microscope. Bavituximab staining was predominantly present in HCC4017 compared to HBEC30KT (FIG. 10B), which almost did not stained. This result showed the significantly elevated levels of PS on outer leaflet of HCC4017 compared to normal HBEC30KT. This observation is in-line with the data published on other tumor cell lines, which show elevated PS levels on lymphoma, melanoma and colon carcinoma cell lines. These results show that although derived from same patient, HCC4017 and HBEC30KT have different amount of PS on their outer leaflet, which can only be attributed to the cancerous situation of HCC4017, whereas HBEC30KT was isolated from the healthy lung of that same individual. This observation perfectly aligned with the capacity of the OBTC assay to recognize 'something' unique to a cancer cell surface that is not found on the normal cell surface during an initial unbiased selection.

PPSD1 shows higher affinity to PS

The direct binding of PPS1 to PS was tested. An ELISA-like assay was used. Two main lipids typically found on cell membrane, PS and PC, were immobilized separately on a 96-well plates and biotinylated PPS1 was incubated at an increasing concentration gradient. Presence of bound PPS1 was detected by HRP-streptavidin after appropriate blocking and washing. (FIG. 11A), PC was selected as the control because it is the most abundant neutral phospholipid found in the outer leaflet of the normal cell membranes. PPS1 binds to PS coated ELISA plates at around a 20 nM binding constant ($K_d$), while no significant binding to PC occurred during the concentration gradient tested (FIG. 11A). This indicates PS has specificity to PS over PC.

Structural features of PPS1and PS were compared to determine why PPS1 preferred PS over PC. PPS1 has three positive charged residues aligned together and a hydrophobic region with four consecutive aromatic rings (FIG. 9A). This can perfectly form both electrostatic and hydrophobic interactions with opposing negatively charged PS head groups and its hydrophobic tail regions. A question was why PC and all other lipids also have somewhat similar negative charged head groups through phosphorus groups, even though the capacity may be different, and the same hydrophobic tails. To answer why amphipathic type PPS1 does not recognize PC and probably other lipids the ELISA-like binding assay was expanded to include other membrane phospholipids like Phosphotidylethanolamine (PE), sphingomyelin (SM), Phosphatidic acid (PA), Phosphotidylinositol (PI) and phosphotidylglycerol.

As shown in FIG. 11B, PPSD1 displayed binding with PS, PA, PI and PG with the strongest affinity to PS. PPS1 did not bind to PC, PE and SM. (FIGS. 11A and 11B). This suggests that the PPS1 interaction with PS is not due to simple positive-negative interactions through typically negatively charged lipid head groups common to every membrane lipid, but to a true specific recognition event. All of the bound lipids PS, PA, PI and PG have an overall negative charge as compared to unbound PC, PE and SM, which are neutral. This extra negative charge is responsible for interacting with positively charged region of PPS1, while the hydrophobic regions of both PPS1 and lipids may interact through van der Waals forces. To further validate these results on a different platform, the ability of PPS1D1 to bind to phospholipid at different lipid concentrations was investigated using commercially available membrane lipid arrays (Echelon, USA). The membrane was first blocked with 3% BSA in TBS-T for 1 hr. After washing with TBS-T, 2.5 µg/ml of biotin labeled PPS1D1 was added. Binding of biotin-PPS1D1 was detected by immunoblotting with streptavidin-HRP antibody. In this membrane lipid array PPS1D1 shows strongest binding affinity to PS, while PA followed with a little weaker binding than that (FIG. 11D). This assay also shows PPSD1 binding to PG and PI at a very weak level, but clearly not binding to PC, PE and SM. This data confirmed the same pattern of binding observed with previous ELISA data, distinguishing two lipid groups that have overall negative, neutral and positive charges. The binding affinity of PPS1D1 to PS appears to be strongest among all phospholipids as even at low lipid concentrations, PPS1D1 efficiently binds to it. (FIG. 11D). It did not show binding to neutral phospholipids like phosphotidylcholine (PC), phosphotidylethanolamine (PE), sphingomyelin (SM) and diacylglycerol (DAG) at tested concentrations. It is well documented that these phospholipids are predominantly present in the inner leaflet in normal cells. FIG. 11C shows asymmetric distribution of anionic and neutral phospholipids in plasma membrane of erythrocytes. PC, PE, SM and PS are the most abundant phospholipids. Among these, only PS is an anionic phospholipid. PC and SM are present mostly in the outer leaflet, whereas PE and PS occupy most of inner leaflet with a variety of other anionic phospholipids. However, in stress conditions and in most tumor studied to date, PS and PE flip to the outer leaflet. PPS1D1 has six positively charged residues along with a hydrophobic region. The overall positive charge of PPS1D1 might explain its binding more efficiently to negatively charged phospholipids. However the binding affinity of PPSD1 to these anionic phospholipids is different. It binds to PS more efficiently than other anionic phospholipid (FIG. 11B). PPS1D1 could have a structure beyond a simple linear sequence contributing various levels of binding to PS, PA, PI and PG, maintaining highest binding affinity to PS. It could contribute in how charge is displayed and which residues come into direct contact with the interacting lipid.

Figure 11:
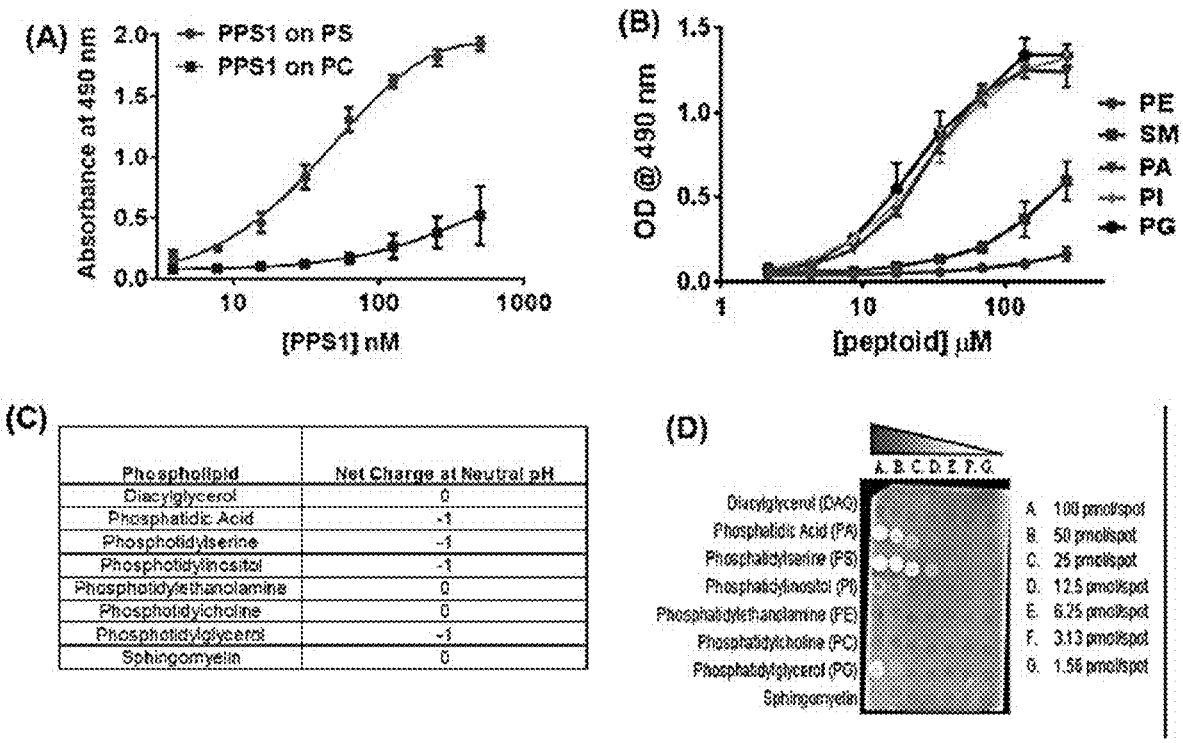
FIG. 11 (A) ELISA binding assay of PPS1 with Phosphotidylcholine (PC) and Phosphotidylserine (PS) (B) ELISA binding assay of PPS1 with Phosphotidylethanolamine (PE), Sphingomyelin (SM), Phosphatidic Acid (PA), Phosphotidylinositol (PI) and Phosphotidylglycerol (PG) (C) Table depicting net charge of PA, PE, PC, PS, PG and PI at neutral pH (adapted from Lehninger, Principles of Biochemistry, $2^{nd}$ edition, Chapter 8) (D) Lipid Dot Blot showing binding of biotinylated PPS1D1 with membrane phospholipids at different lipid concentrations.

FIG. 11: (A) ELISA binding assay of PPS1 with phosphotidylcholine (PC, red line) and Phosphotidylserine (PS, blue line) (B) ELISA binding assay of PPS1 with Phosphotidylethanolamine (PE, pink line), Sphingomyelin (SM, green line), Phosphatidic Acid (PA, purple line), Phosphotidylinositol (PI, orange line) and Phosphatidylglycerol (PG, black line) (C) Table depicting net charge of PA,PE, PC, PS, PG and PI at neutral pH (D) Lipid Dot Blot showing binding of biotinylated PPS1D1 with membrane phospholipids at different lipid concentrations.

Lipid membranes are not static and fully composed of one type of lipid as in ELISA-like or lipid-blot assays. Therefore, liposomes were made out of different % of these lipids to mimic an actual cell surface better than the two platforms above. Binding of FITC tagged PPS1D1 with liposomes containing 100% PC and 85% PC:15% PS was examined. Liposomes provide a 3D surface that closely mimics the cell membrane, thus binding on their surface closely correlates with cell membrane binding. 1 mM liposomes in Tris Buffer with 3% BSA were incubated with FITC-PPS1D1 at 20, 50, 75, 100 and 150 nM for 1 hour. Following incubation, binding of liposomes to FITC-PPS1D1 was analyzed by flow cytometry by detecting the FITC signal (FIG. 12A). FITC-PPS1D1 specifically bound to 15% PS containing liposomes and the binding was improved as the concentration of FITC-PPS1D1 is increased. Binding to 100% PC containing liposomes was not observed within the concentration level studied. These results further confirm that PPS1D1 is truly recognizing PS over PC as it strongly bound to PS expressing HCC4017 cells while not binding to mostly PC expressing normal HBEC30KT cells.

Figure 12:
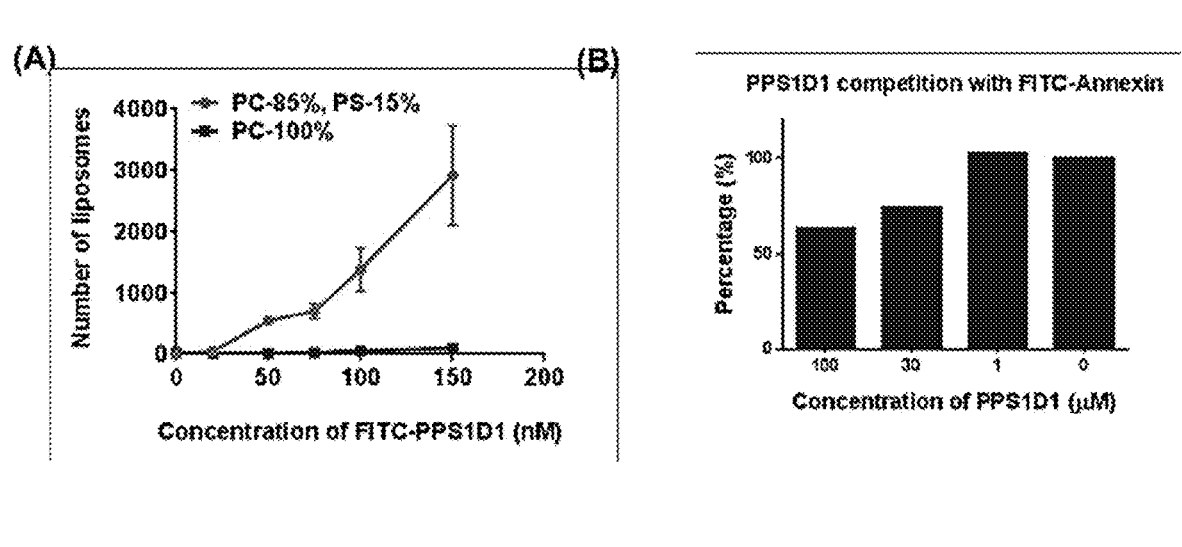
FIG. 12 (A) Binding of liposome made of 100% Phosphotidylcholine and 85% Phosphotidylcholine-15% Phosphotidylserine to FITC-PPS1D1 (B) Competition of PPS1D1 with FITC-Annexin in binding HCC4017.

FIG. 12: (A) ELISA binding assay of PPS1 with phosphotidylcholine (PC,red line) and Phosphotidylserine (PS, blue line) (B) ELISA binding assay of PPS1 with Phosphotidylethanolamine (PE, pink line), Sphingomyelin (SM, green line), Phosphatidic Acid (PA, purple line), Phosphotidylinositol (PI, orange line) and Phosphatidylglycerol (PG, black line) (C) Table depicting net charge of PA,PE, PC, PS, PG and PI at neutral pH (D) Lipid Dot Blot showing binding of biotinylated PPS1D1 with membrane phospholipids at different lipid concentrations.

Validation of PPS1D1 on H460

On the basis of in vitro data for PPS1D1, the effect of PPS1D1 in a mouse model was examined. HCC4017 cells were previously used for validation and binding of PPS1D1 but HCC4017 are not an effective xenograft cell line as they grow very slowly and do not produce good sized tumors.

Tumor inducement in mice using HCC4017 formed hugely variable tumors over a period of more than two months. H460, a non-small cell carcinoma cell line, was used as it is more effective in producing tumors in mice. Before moving to animal studies with PPS1D1, comprehensive validation of cytotoxic effect of PPS1D1 on H460 was performed (Fig: 13). The PS expression levels of H460 using FITC-Annexin V staining detected by FACS was checked. H460 also strongly expresses PS (FIG. 13A). A magnetic bead pull down, cell proliferation assay, and flow cytometry were performed on the H460 cell line. PPS1D1 coated magnetic beads were incubated with the H460 cell line for 30 minutes. The supernatant was removed by immobilizing beads on side of the tube with a magnet. The number of cells bound to beads were counted with a hemocytometer. PPS1D1 coated magnetic beads pulled down H460 cells more efficiently compared to normal lung cell line HBEC30KT (FIG. 13A). Cell proliferation assays on a H460 cell line were performed by treating them with PPS1D1, PPS1, and the control compound, PC462D1. In cell proliferation assays, PPS1D1 was very potent in inhibiting growth of H460 cells compared to monomer PPS1, and the control peptoid PC462D1 (FIG. 13B). Most cytotoxicity was seen at the concentration of ~10 μM and above. This activity was very similar to the PPS1D1 activity observed on HCC4017 cells. Binding and cytotoxicity of fluoresceinated PPS1D1 was examined using flow cytometry. Efficiency of PPS1D1 cytotoxicity on H460 cancer cells at different concentrations with 1 hour incubation with PPS1D1 was examined. Assays were performed to determine whether there were cells that were double positive for FITC (bound to PPS1D1) and PI, to evaluate cell viability. FITC tagged PPS1D1 was incubated for 1 hr with H460 cells at 0.1, 10, 30 and 100 μM concentrations. At the end of incubation period, propidium iodide (PI) was added to stain dead cells. With increasing concentrations of PPS1D1, the number of cells positive for FITC-PPS1D1 and PI increased (FIG. 13C). At 0.1 μM FITC-PPS1D1 concentration nearly ~4.6% cells were double positive this number increased significantly to 27.3% and 85.8% in cells treated at 10 and 30 μM FITC-PPS1D1. All cells were double positive at the highest treatment concentration of 100 μM. These results indicate that PPS1D1 is not only binding to but is cytotoxic to H460. The cytotoxic effect showed strong co-relation to concentration of PPS1D1 as with increasing concentration. More cells were positive for both FITC-PPS1D1 and PI (FIG. 13D). FITC-PPS1D1 binds to H460 cell surface and cytotoxicity is initiated.

Figure 13:
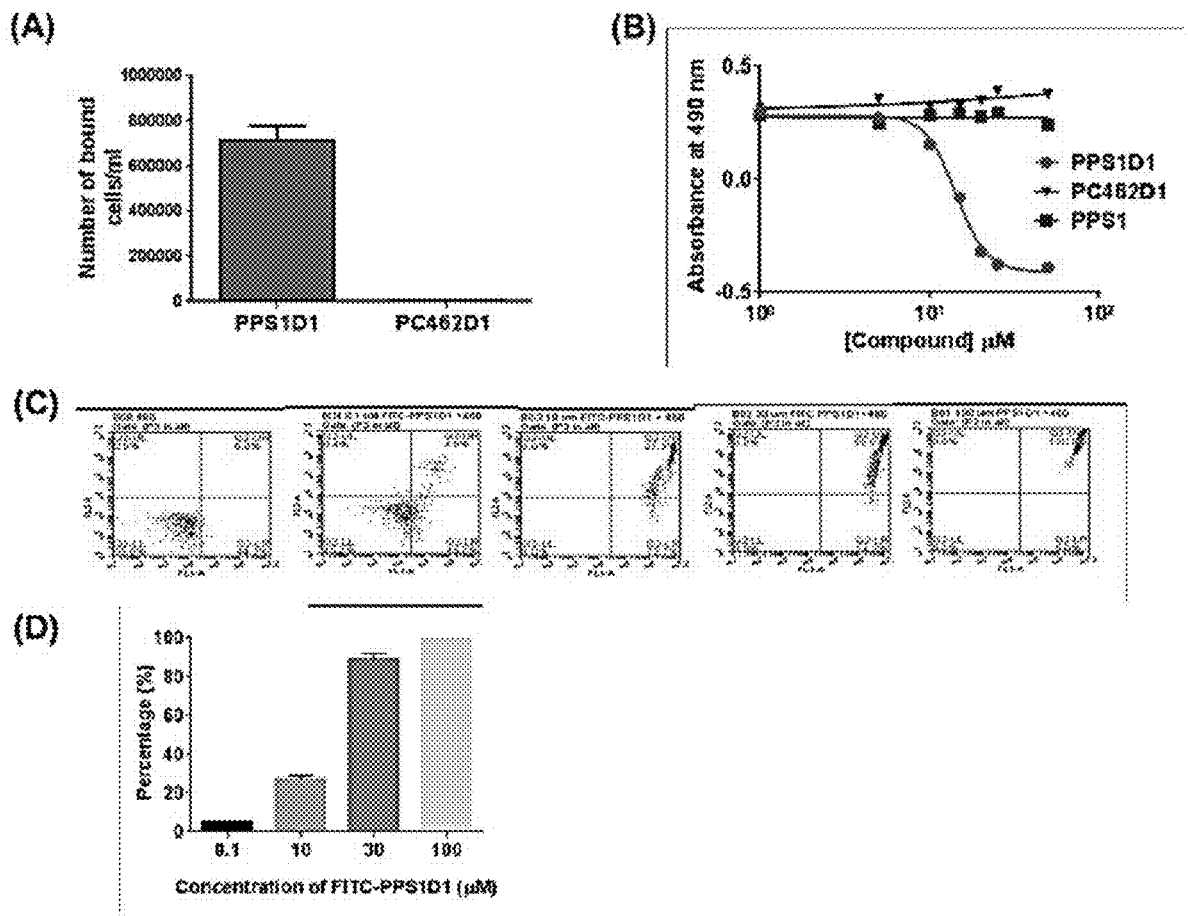
FIG. 13 Comprehensive validation of PPS1D1 on H460 (A) Magnetic bead pull down H460 with PPS1D1 and control compound PC462D1 (B) Cell proliferation assay on H460 in presence of PPS1D1, PPS1, and PC462D1 (C)

FIG. 13: Comprehensive validation of PPS1D1 on H460 (A) Magnetic bead pull down H460 with PPS1D1 and control compound PC462D1 (B) Cell proliferation assay on H460 in presence of PPS1D1 (red line), PPS1 (blue line) and PC462D1 (black line) (C) FACS analysis of cytotoxicity of FITC-PPS1D1 on H460 cell line with 1 hr incubation (D) Number of FITC-PPS1D1 positive H460 cells at different concentration (E) schematic representation of effect of PPS1D1 on H460 cells.

Inhibition of Growth of Mice Xenograft by PPS

Whether PPS1D1 would inhibit tumor growth in a murine model was examined. H460 cells were implanted in nude mice. Tumors were allowed grow until it reach 0.5 mm. These xenografts were then treated with a daily dose of 0.5 mg/mL in four different groups that consist of PPS1D1 alone, docetaxel alone, PPS1D1 and docetaxel together or with the control peptoid (PC462D1) alone. Docetaxel is a standard chemotherapeutic treatment for non-small cell carcinoma. The activity of PPSD1 and its ability to work as a combination treatment were examined. PPS1D1 and Docetaxel were equally effective in reducing the size of the tumors but PPSD1 has a slightly better effect (FIG. 14). The maximum reduction in tumor size was seen with mice which had been treated PPS1D1 and Docetaxel as a combination. This effect was extremely potent and the tumor growth was completely controlled. These results suggest that PPS1D1 can improve response to standard chemotherapy. It has been reported that chemotherapy and radiation therapy increase the PS flipping in tumor microenvironment. Therefore, Docetaxel might have helped improve binding of PPS1D1 on cancer cell surface that is now displaying an increased amount of PS to be targeted. After the standard chemotherapy and radiation therapy, the target PS is highly abundant for the drug to recognize and attack.

FIG. 14: Tumor size reduction of H460 tumor bearing mice with Docetaxel (red line, PPS1D1 (green line), Docetaxel+PPS1D1 (blue line) and PC462D1 treatment (black line). PPS1D1 displayed potent tumor burden effect with and without Docetaxel.

Anionic lipid phosphotidylserine is the target of the anti-cancer peptide-peptoid hybrid PPS1 selected through an unbiased selection approach. PPS1 preferentially binds to anionic phospholipids most specifically to PS. Preferential binding ability of PPS1 to PS allows it to differentiate between cancer and normal cells. PPS1 was effective as an anti-cancer compound with in vitro and in vivo models. There is an increasing need for anti-cancer agents that are effective against broad types of cancers. Phospholipid asymmetry is observed in most cancers analyzed to date. Although antibodies targeting PS have been reported, these often show poor tumor penetration and their cost of production is very high compared to peptide-peptoids hybrids.

All the amino acids were purchased from EMD4 Biosciences and all the primary amines from Aldrich. O-Benzotriazole-N,N,N',N'-tetramethyl-uronium-hexafluoro-phosphate (HBTU) and N-Hydroxybenzotriazole.H2O (HOBt) from AnaSpec. All the other reagents were purchased from Sigma-Aldrich.

An Applied Biosystems Voyager—6115 mass spectrometer was used in positive reflector mode to acquire MALDI-TOF mass spectra. Alpha-Cyano-4-hydroxycinnamic acid was used as matrix. HPLC purification was performed in a Waters 1525 Binary HPLC pump connected to Waters 2487 Dual λ Absorbance Detector using Protein & Peptide C18 300A°, 22×250 mm, 10 micron column from Grace Davison Discovery Sciences. Compound separation was carried out at room temperature using Acetonitrile (ACN; Honeywell) and water containing 0.1% Trifluoroacetic acid (TFA; Sigma-Aldrich).

All lung cancer cell except HCC4017 were grown in RPMI 1640 (Sigma) supplemented with 10% FBS (Sigma). HCC4017 was grown in RPMI supplemented with 5% FBS.

Lung cell line HBEC30KT and HBEC3KT were grown with keratinocyte serum free media supplemented with human recombinant epidermal growth factor and bovine pituitary extract (Life Technologies).

The basic structure of the library consist of three amino acids followed by 5-mer diversified peptoid region (FIG. 1A). TentaGel macrobeads (140-170 microm; substitution: 0.48 mmol/g resin; Rapp Polymere) were swelled in 5 ml of extra pure dimethylformamide-(DMF; Acros Organics) for 30 min at room temperature in a reaction column (Intavis AG). The reaction column was drained and treated with premixed 0.4M amino acid in anhydrous DMF (12 ml) (Sigma-Aldrich) and 0.4M HBTU in anhydrous DMF containing 0.8M N-methyl morphaline (NMM; 12 ml; Sigma- Aldrich). Then the reaction column was placed on a shaker for 2 hours, drained and washed with DMF. Fmoc group was removed by treating the beads with 20% piperidine (Sigma-Aldrich) for 10 minutes×2 on the shaker. After washing the reaction column next amino acid was added and Fmoc group was removed as described previously. Then the beads were equally distributed into 12 reaction columns and each of the following amino acids was added to each of them. Fmoc-Gly-OH, Fmoc-Leu-OH, Fmoc-Val-OH, Fmoc-Phe-OH, Fmoc-Asn-OH, Fmoc-Glu(Trt)OH, Fmoc-Gln(otBu)OH, Fmoc-Asp (otBu)OH, Fmoc-His(Trt)OH, Fmoc-Ser(tBu) OH, Fmoc-Thr(tBu)OH, Fmoc-Lys(Boc)OH. All the beads from 12 reaction columns were pooled together Fmoc group was removed and divided equally into 8 reaction columns for microwave (1000W) assisted peptoid synthesis.

Each of the reaction columns were treated with 2 M Bromocetic acid in anhydrous DMF (1 ml) and 2M DIC in anhydrous DMF (1 ml), gently shaken for about 30 seconds and micro waved for 15 seconds with the power set at 10%. Then the beads were shaken again for about 15 seconds and micro waved as described above. The reaction columns were drained and washed with DMF (2 ml×10). Then each of the reaction column was treated with 1M solution of each of the primary amines 2 ml (FIG. 1B) and microwaved 2×15 sec after gentle shaking. The beads were washed, pooled and divided equally into 8 reaction columns again and subjected to the addition of next peptoid residue. This procedure was repeated until 5-mer peptoid region is completed.

At the end of synthesis beads were washed with Dichloromethane (DCM) (3×2 ml), treated with 2.5 ml of cleavage cocktail containing 95% Triflouoroacetic acid (TFA), 2.5% water and 2.5% Triisopropylsialine (TIS) on the shaker for 2 hours to remove the side chain protection. Reaction column was drained, washed with DMF (3×2 ml) and stored in anhydrous DMF in 4C.

On bead two color binding assay for combinatorial library screen using HCC 4017 cells and HBEC30KT cells.

About 100,000 peptoid library beads were washed 2 times in RPMI medium with 5% FBS and equilibrated in the same medium containing 2% Bovine Serum Albumin (BSA; Sigma Aldrich) for 1 hour in three polypropylene tubes.

HCC 4017 and HBEC 30 KT cells were removed from culture plates by treating with GIBCO enzyme free cell dissociation buffer (Invitrogen) 2 ml per plate (5 minutes for HCC 4017 and 20 minutes for HBEC 30 KT) at 37° C. HCC 4017 cells were washed and suspended in RPMI medium with 5% FBS. HBEC 30 KT cells were washed and suspended in KSFM medium. Cells were counted and distributed in two 1.5 ml microcentrifuge tubes (total of four tubes for both cell lines) in $1 \times 10^6$ cells in 1 ml of media per each tube.

Then the cell labeling procedure was conducted as follows. To prepare 10 nM labeling solution (typical working concentration is 2-15 nM), pre-mixed 1 µl each of Qtracker reagent (Invitrogen) A and B in a 1.5 ml microcentrifuge tube (prepared two tubes for each color) and incubated for 5 minutes at room temperature. 0.2 ml of respective medium was added to each tube and vortex for 30 seconds. $1 \times 10^{106}$ cells were added to each tube (two HCC 4017 and two HBEC 30 KT) containing the labeling solution and incubated at 37° C. for 60 minutes. Washed the cells twice using RPMI medium with 5% FBS and re-suspended each cell line in 2.5 ml of same medium containing 1% BSAHCC 4017 cells labeled with Qtracker 655 were visualized in red color and HBEC 30KT cells labeled with Qtracker 565 were visualized in green color via DAPI filter in fluorescence microscopy (Olympus BX-51, with a color camera).

The incubation medium was removed from bead containing polypropylene tubes. Two 2.5 ml portions of both cell types were mixed thoroughly and pipetted up and down several times to break the clumps. 1.6 ml of cell suspension mixture was added to each of the beads containing three polypropylene tubes and incubated at room temperature with gentle shaking for 20 minutes. (Final cell density for each cell type was $0.4 \times 10^6$ and the total was $0.8 \times 10^6$.) During incubation cell binding to beads was checked time to time in about 5 minutes intervals to make sure not to over equilibrate, which could increase non-specific binding of cells to beads. Beads were gently washed two times with RPMI medium and visualized under the fluorescent microscope equipped with the DAPI filter.

Isolation and Preparation of Beads for Edmann Sequencing: Single positive beads containing fluorescently tagged cells (red color) were identified using a fluorescent microscope under 2.5× objective magnification and removed manually with a 20 µl pipette using medium size pipette tips. Careful attention was needed to avoid picking up of beads that bound to both red and green cell types.

Selected beads were washed three times with 1% SDS and boiled in same solution for 45 minutes to strip off bound cells and proteins. Finally beads were washed three times with water. Single beads placed on Edman sequencing cartridges were used for sequencing.

Resynthesis of PPS1 compound: Resynthesis of PPS1 compound was done on TentaGel beads. First the three amino acids Fmoc-Met-OH Fmoc-Dlys (Boc) and Fmoc-Lys(Boc) were loaded to the resin respective Fmoc groups were removed. Then the 5-mer peptoid region containing following primary amines was synthesized using microwave assisted peptoid synthesis protocol as described previously; Boc-Diaminobutane, 4-methoxybenzylamine, (R)-Methylbenzylamine, Piperonylamine and (R)-Methylbenzylamine. At the end of synthesis beads were washed with Dichloromethane (DCM) (3×2 ml) and treated with 2.5 ml of cleavage cocktail on the shaker for 2 hours to remove the side chain protection. Then the beads were washed with DMF (3×2 ml) and stored in anhydrous DMF in 4° C.

Cyanogen Bromide (CNBr) cleavage of beads: Small amounts of beads were removed from reaction vessel before storage and washed with DCM (3×2 ml) 30 mg/ml CNBr solution (1 ml) was prepared in 5:4:1 Acetonitrile:Acetic acid:water. 50 µl from this solution was added to beads and kept on the shaker overnight. CNBr solution was allowed to evaporate and 1:1 mixture of acetonitrile and water was added to the beads and resulting solution was used for confirmation of mass.

On bead two color (OBTC) binding assay for binding confirmation of HCC4017 cells to PPS1 compound 200 µl of TentaGel beads containing JM 79 compound were transferred into each of three 1.5 microcentrifuge tubes. The beads were washed 2 times in RPMI medium with 5% FBS and equilibrated in same medium containing 2% Bovine Serum Albumin for 1 hour.

HCC 4017 and HBEC 30 KT cells were removed from culture plates, counted and 0.4×106 cells from each cell type were distributed in 1.5 ml microcentrifuge tube and subjected to labeling procedure as described in library screening. At the end of the labeling procedure cells were suspended in 0.5 ml of RPMI medium containing 10% FBS and pipetted several times to break cell clumps. Red and green cells separately added to two tubes and 1:1 mixture to third tube. Cell density for each cell type was kept as $0.4 \times 10^6$ in each tube. Then the beads were incubated at room temperature with gentle shaking for 20 minutes. During incubation cell binding to beads was checked time to time in about 5 minutes intervals and HCC cells demonstrated significant binding within 10 minutes. Then the beads were gently washed and visualized under the fluorescent microscope equipped with the DAPI filter.

Resynthesis of flourescienated PPS1D1 (FITC-PPS1D1): This synthesis was carried out on Rink amide MBHA resin (EMD4 Biosciences). Fmoc-Cys(Trt)-OH (HOBt, HBTU, DIPEA) was loaded as first amino acid on to the resin and the rest of the synthesis was conducted as described previously. At the end 95% TFA, 2.5% water and 2.5% TIS mixture was used to cleave the compound from resin as well as to remove the side chain protection. Then the TFA was evaporated and resulting solid compound was dissolved in 1:1 water:ACN mixture. This solution was subjected to HPLC purification using the solvent conditions starting from 100:0 water:ACN to 50:50 water:ACN. The purified compound was lyophilized to obtain the dry product.

Fluorescein-5-maleimide (Thermofisher) was dissolved in DMSO was coupled to this compound (1M:1 M ratio) in buffer solution at pH 7. The resulted PPS1D1-FITC compound was purified again using the same solvent conditions and lyophilized to obtain the final product.

Live cell staining of HCC 4017 and HBEC 30KT cells using Bavituximab anti-PS antibody: On day 1, 20,000 HCC 4017 and HBEC 30KT cells were added to each well of an 8-well glass chamber plate. Left the chamber plate in incubator at 37° C. overnight. On day 2 cell staining was carried out as follows. 300 µl of 2 µg/ml Bavi and β2-Glycoprotein was added to each chamber and Incubated for 1 hr at 37° C. Media were removed from and chambers were removed to obtain the glass slide. Then slide was gently washed 2× in PBS by submersion in a Coplin jar. Fixed the cells in a Coplin jar filled with warm 4% paraformaldehyde (PFA) for 5-10 min at r.t. Removed slides from fixative and wash 3× in PBS and quenched the PFA with 50 mM NH4Cl (in PBS) for 5 min. Washed 3× PBS. Dried the area surrounding each well and incubate cells with 50 ul goat-anti human Cy2 secondary antibody 1:1000 dilution in PBS+1% BSA for 1 hr at 37° C. Removed the secondary antibody and washed 3× in PBS by submersion. Cells were permeabilized for cytoskeletal staining using 50 ul PBS+0.5% Triton-X100 for 5 min at r.t. Wash 2× in PBS. Stained the cells with Texas Red conjugated phalloidin 1:200 dilution in PBS+1% BSA 50 µl for 20 min and washed 3× in PBS. Slide was allowed to air dry and mounted with Prolong Gold with DAPI (Invitrogen) Results were visualized under fluorescence microscope.

Magnetic bead binding assay: The assay was done using Dynabeads M-280 Streptavidin (Invitrogen life technologies). First beads were resuspended in the original vial by vortexing and 14 µl of beads (approximately $9 \times 10^6$ beads) transferred to a microtube and added 500 µl of PBS with 0.1% BSA. Then placed the microcentrifuge tube containing beads on the magnet for 2 minutes and removed the supernatant by aspiration. Again added 500 µl of PBS with 0.1% BSA and washed the beads total 3 times. Then divided the beads into 6 vials and 1000 pmol of biotinylated PPS1 Monomer, D1, D2, D3 and Tetramer 1 was added to each vial and incubated for 30 minutes at RT with gentle shaking. Then the beads were washed 3 times with 500 µl of PBS with 0.1% BSA and HCC 4017 cells ($0.5 \times 10^6$ cells in 1ml of RPMI with 1% BSA) were added to each vial and incubated for 30 minutes at RT with gentle shaking. Then removed the supernatant using magnet and number of bead bound cells were calculated using hemocytometer.

ELISA binding assay on PS and PC: PS and PC (Avanti Polar Lipids) were dissolved in hexane at 10 µg/ml concentration and added to Immulon 1B "U" bottom microtiter plates (Thermo) 50 µl/well. hexane was allowed to evaporate at room temp (in the hood). Plates were blocked by adding 200 µl 1% BSA in PBS to each well and incubated for 1 hour. Each well was washed with 3× w/200 µl PBS. Serial dilutions (0.5 µM to 0.0078 µM) of biotinylated PPS1 and PPS2 were dissolved in blocking buffer (100 µl/well) and incubated for 1 hr on shaker. Washed 5× w/200 µl PBS. Added 100 µl streptavidin-HRP (1:2000 in blocking buffer) to each well and incubated for 30 min. Washed 8× w/200 µl PBS. Developed with 100 µl OPD (1 plate=10 ml=5 ml 0.1M Citric Acid+5 ml 0.2M Na2HPO4+5 mg OPD, +5 µl H2O2) for 3 min. Stopped the reaction with 100 µl 0.18M H2SO4 Read OD at 490 nm.

Liposome Production: Liposomes were made by extrusion. Lipid mixes used were (1) lipid mixes (POPC100 mole %) and (2) (POPC:DOPS; 85:15 molar ratio) and All the lipid mixes in chloroform were dried under a stream of $N_2$ gas followed by further drying in a vacuum for overnight. The lipid films were re-suspended in 10 mM Tris Buffer (pH 7.4) to a final total lipid concentration of ~10 mM. Unilamellar vesicles were formed by 10 freeze-thaw cycles in liquid N2 and room temperature water. Large unilamellar vesicles were formed by extrusion through polycarbonate filters with 1000-nm pore size (Avanti Polar Lipids).

Flow Cytometry

With cells: HCC4017 and H460 cells were grown on 10 cm culture dishes (BD Falcon) to approximately 70% confluence in RPMI media supplemented with 10%. Cells were then treated with PPS1D1 to a final concentration of 100, 30, 10 µM and allowed to incubate at 37° C. for 1 hr. Following treatment, cells were washed with PBS and suspended in it. Propidium iodide was added and cells were analyzed by flow cytometry (Becton-Dickinson AccuriC6). All data were analyzed using BDAccuriC6 software.

With liposomes: 1 mM liposomes in Tris Buffer with 3% BSA were incubated with FITC-PPS1D1 at 20, 50,75,100 and 150 nM for 1 hour. Following incubation binding of liposomes to FITC-PPS1D1 was analyzed by flow cytometry (Becton-Dickinson AccuriC6). All data were analyzed using BDAccuriC6 software.

Membrane lipid array: Membrane lipid arrays were purchased from Echelon Biosciences. Membranes were blocked in 3% BSA in TBS-T for one hour then incubated with 2.5 µg/ml of biotin-PPS1D1 for two hours. After washing unbound peptoid using TBS-T, bound biotin-PPS1D1 was detected by immunoblotting with Streptavidin-HRP antibody at 1:750 dilution (BioLegend).

ELISA binding assay: 500,000 cells of HCC 4017 cells were grown in 12 wells of white clear bottom 96 well plate (Corning Inc) 24 hours prior to the experiment. Each well was blocked with 100 µl of 5% BSA in Phosphate Buffered Saline (PBS; Invitrogen) for 15 minutes at room temperature. Then the BSA was removed from wells and each well was treated with 50 µl of graded concentrations of FITC labeled JM 79 compound prepared in 1% BSA containing PBS (10 concentration ranging from 500 to 0.0064 µm, each one is done in duplicates) and incubated for 45 minutes at room temperature. Wells were washed 2×100 µl of PBS and remaining fluorescence was measured at 520 nm using a plate reader (Fluostar Optima, BMG Laboratories, Durham, N.C.).

Proliferation assay on HCC 4017 cells treated with PPS1D1 and Control compound: 5000 cells of HCC 4017 cells were grown in 54 wells of white clear bottom 96 well plate (Corning, Inc.) on day 1 of the experiment. On day 2, two experimental sets were designed to treat the wells with graded concentrations of PPS1 and control compound prepared in 5% FBS containing RPMI medium. Eight graded concentrations ranging from 50 to 0.01 μm was used from both compounds and each point is done in triplicates. 6 wells left untreated as controls On day 4 medium was removed from each well and treatment was repeated as described previously On day 5, 20 μl of CellTiter 96® AQueous One Solution Cell Proliferation Assay (Promega) was added to each well and absorbance was measured at 492 nm using a plate reader 2 hours after treatment.

Peptoid compounds include but are not limited to PPS1D1 (FIG. 15), PPS1-DE2 (FIG. 16), PPS1-RD1 (FIG. 17), PPS1-2P3H (FIG. 18), PPS1-4P3H (FIG. 19), PPS1-Tri-1 (FIG. 20), PPS1-Tet-1 (FIG. 21), and PPS2D1 (FIG. 22). These compounds are PS targeted, strong agonist that have a validated in vitro cellular activity. PPS1D1 has a validated in vivo animal tumor burden activity.

PPS1 can also binding to other cancer specific lipids such as phosphatidic acid (PA), phosphotidylinositol (PI) and phosphotidylglycerol (PG). PPS1 can target cancer specific phosphatidic acid (PA), phosphotidylinositol (PI) and phosphotidylglycerol (PG).

EXAMPLES

Example 1

An on-bead two-color (OBTC) combinatorial cell screen was utilized to identify peptoid ligands targeting HCC4017 lung cancer cells in the presence of normal HBEC3kt bronchial epithelia cells from the same patient. The idea was to use a completely unbiased assay to identify ligands that bind to 'something' specifically found on the cancer cell that is not present on the normal cell. The HCC4017 cells were stained with red Qdots and normal cells with green Qdots, mixed 1:1, and exposed to the peptoid library beads (total 400,000 in 4 rounds, 100,000 each time). Only the red cell bound beads (FIGS. 26(A) and (C)), were selected, which indicated the peptoid on that bead had bound to something only found on the red (HCC4017) cells. Two highly structurally related peptoids were identified; PPS1 and PPS2 (which only differ at the 4th position) on two separate screens from the same peptoid library (FIGS. 26(B) and (D)). Later it was found that HCC4017 cells significantly express PS whereas HBEC cells do not (FIG. 27). The binding of PPS1 and PPS2 to PS was evaluated. PPS1 and PPS2 displayed low nanomolar binding affinity (Kd~15-20 nM) on PS-coated ELISA plates but not to plates coated with PC, the main lipid found in the outer bilayer leaflet of normal cells (FIG. 28). The peptoid PPS1 pulled down HCC4017 and a series of lung cancer cell lines preferentially over normal HBEC cell lines on a magnetic bead pull down assay (FIG. 29). Importantly, monomeric PPS1 and PPS2 had no toxic effect on cancer cells, whereas dimeric versions of PPS1 and PPS2 were highly toxic. The dimers displayed low micromolar level toxicity towards HCC4017 (lung), MDA-MB-231 (breast), and PC3 (prostate) cancer cells, but were not toxic to normal HBEC30KT cells (FIG. 30). This activity was due to cell lysis as indicated by sharp activity curves and clear destruction of cells that can be visualized under the microscope. The simple propidium iodide (PI) test also confirmed that the nuclear staining happens only when PPS1-D2 is treated (FIG. 31(A)). The untreated non-permeabilized cells did not get stained upon propidium iodide treatment [Figure 31(B)]. Furthermore, the minimum pharmacophore studies revealed that the 1st and $4^{th}$ residues are minimally important for the PS recognition (data not shown). This is the first validated lipid binding cancer-specific peptoid.

FIG. 26 (A), (C) The 'hit' beads identified, and chemical structures of (B) PPS1, (D) PPS2.

FIG. 27 PS is (A) not expressed on normal HBEC30kt cells, but (B) highly expressed on HCC4017 lung cancer cells (green stain).

FIG. 28 PPS1 and PPS2 strongly bind to PS but not to PC.

FIG. 29 PPS1 pull down series of lung cancer cell lines and not normal HBEC cell types.

FIG. 30 Cell lytic activities of PPS1 and PPS1-dimers on (A) HCC4017, (B) MDA-MB-231, and (C) PC3 cells.

The in vivo vascular disrupting effects of PPS1-D2 were explored. Mice bearing HCC4017 tumors growing subcutaneously were injected i.v. with 20 μg of PPS1-D2. Twenty four hours later, the tumors were removed, cryosectioned, and stained for CD31 to detect vascular endothelium. Numerous vessels in the PPS1-D2 treated tumors had disrupted tumor endothelium, whereas vessels in the untreated control animals appeared intact (FIG. 32). Also, mice treated with 50 μg of PPS1-D2 show no signs of toxicity. This dose can be calculated to give an initial blood concentration that is roughly 10-fold higher than needed for maximal lysis of PS-expressing cell in vitro.

PS has been reported to be a globally expressed biomarker in the tumor microenvironment. Targeting PS with high specificity molecules provides a high chance of finding diagnostic and treatment applications in a broad patient population, while protein-targeted approaches are limited by the high heterogeneity in biomarker expression. Peptoid multimers can be synthesized that are powerfully and specifically toxic to PS-expressing tumor vascular endothelial cells and tumor cells. The cell lytic activity of the PS targeted peptoids will be improved by dimerization or multimerization (e.g. trimers, tetramers, dendrimers, etc.) via various rigid or non-rigid linkers. Any linker can be used that provide a peptoid that targets PS. These peptoids will enjoy the same advantageous properties inherent in peptoids in general, notably high serum stability, non-immunogenicity, simpler and less costly synthesis, and ease of optimization.

Example 2

Multimers of PPS1 will be synthesized. Twenty or more different multimers of PPS1 (dimers, trimers, tetramers and higher order multimers) will be synthesized using flexible and rigid linkers.

Example 3

It will be demonstrated that the multimeric derivatives developed in Example 2 are selectively lytic towards PS expressing tumor cells but not to PS-negative normal cells. The peptoid multimers will be screened for lytic activity on a limited panel of PS-positive and negative cells. The most potent and specific peptoids will then enter comprehensive testing on a larger panel of malignant and normal cells. Finally, it will be determined whether the peptoids selectively lyse cultured endothelial cells that have been treated with 5 Gy irradiation to render them PS-positive.

FIG. 31 Cell lytic activity confirmation with propidium iodide treatment (A) staining occurred only with PPS1-D2 treatment, (B) but not in the absence of the peptoid.

FIG. 32. Disruption of tumor vascular endothelium by PS targeting peptoid dimer PPS1-D2. Mice bearing subcutaneous HCC4017 tumors were injected i.v. with 20 μg of PPS1-D2. 24 hr later the mice were sacrificed and frozen sections of the tumors were stained with antibodies to CD31 (red). Disruption of vascular endothelium was observed in numerous tumor vessels, whereas vessels in the untreated control tumors had normal morphology.

Example 4

It will be determined whether the in vivo biodistribution, tumor localization, and antitumor activity of PPS1-D2 (our current leading compound) and the best five peptoid derivatives identified in Example 2. The peptoids will be tested in the following tumor models: orthotopic PC3 human prostate cancer, orthotopic MDA-MB-231 human breast cancer, and HCC4017 lung cancer. The effect of combining the peptoids with docetaxel, which amplifies PS-exposure on tumor blood vessels and tumor cells, will also be determined.

Example 5

It appears that dimerization of PPS1 and PPS2 triggers the cell lytic activity. Most surface active lytic peptides disrupt phospholipid membranes by inserting into the membrane and assembling into ion-conducting pores or by forcing disruptive changes in membrane curvature. Typically, a threshold concentration has to be exceeded on the cell membrane for lysis to occur. This should also apply to peptoids. If so, lytic activity will depend on factors such as: whether the interaction with the membrane is electrostatically or hydrophobically driven; whether the peptoids associate with one another before binding to the cells or whether PS-binding is needed for oligomerization; whether there is cooperation in the peptide binding process; whether the peptide inserts into the hydrophobic core of the phospholipid membrane or lays on the surface, or both; and whether the peptoids need cause curvature changes in the membrane for lysis to occur.

Several possible cell lytic mechanisms have been proposed in the literature; (i) carpet model, (ii) barrel stave mechanism and (iii) toroidal pore model. Mechanisms (i) and (ii) are based on reaching a threshold level of peptide-like molecules on the membrane to initiate the lytic activity, while the toroidal pore model suggests those molecules affect the local curvature of the membrane cooperatively such that a peptide-lipid toroid of high curvature forms. It is not clear which mechanism is involved with the activity of our peptoids. Dimerizations might help to reach the threshold concentration earlier, or support the cooperative mechanism or even act through a completely different mechanism. 3 dimers composed of central lysine residues and a flexible linker region which is made out of β-alanine moieties to manipulate the distance between two monomeric units have already been synthesized. A very short dimer made by disulfide bonds through two Cys units on the monomers has been validated. While all 4 dimers showed lytic activity, the smallest linker (4 atom long Cys-dimer) and the longest linker (31 atom long D4) seemed to have lower activity than the intermediate-length linkers containing 15-23 atoms (FIG. 33). Multimers will be developed that have: (i) intermediate-length linkers, (ii) specifically with added rigidity which may support the lytic activity even further. This could lead to identifying the most improved peptoid derivative of PPS1 and PPS2.

Example 6

To synthesize focused multimers of PPS1: (I) Methods: Two simple and well established solution phase reactions and a straightforward solid phase synthesis protocol will be used. Each multimer will be synthesized by reacting two basic components using 'click chemistry' (FIG. 34(A): (1) central linker scaffold ready with different numbers of alkyne moieties (2 for dimers, 3 for trimers etc.) (2) monomeric peptoid portion synthesized with C-terminal azide moiety.

Example 7

Preparation of central linker scaffold:
As shown in FIGS. 34 and 35, various numbers of carboxylic groups on central scaffolds will be reacted with propargylamine (FIG. 34A—first reaction) as previously reported. Briefly, central scaffolds will be suspended in DMF, followed by addition of HBTU and diisopropylethylamine (DIPEA). Propargylamine will be added to this mixture and stirred at room temperature overnight. DMF will be removed under high vacuum. The resultant residue will be taken into dichloromethane and the organic phase will be washed with MilliQ water and NaOH. This organic phase will be dried (anhydrous $NaCO_3$), filtered, and solvent will be removed by rotary evaporation. Compounds will be further purified by reverse phase HPLC. MALDI mass and NMR analysis will be conducted to confirm the product. All of the above work out protocols and solvents will be adjusted according to the properties of the scaffold. All reagents are commercially available.

FIG. 33 Different PPS1 dimers and number of atoms in each linker

Example 8

Synthesis of peptoid portion with c-terminal azide moiety: Manual Fmoc-based solid phase peptide synthesis (for peptide portion) and microwave assisted peptoid synthesis (for peptoid portion) methods will be utilized with each synthesis using a 100 mg of Rink amide resin. All peptide coupling steps will be performed by mixing a Fmoc-protected amino acid (5n) with coupling reagents [HBTU (4.9n), HOBt (5n), DIPEA (10n)] in DMF using disposable reaction vessel (Intavis) gently shaken for 2 hrs. Fmoc deprotection will be done by 20% (v/v) piperidine in DMF. For peptoid portions; each peptoid unit will be coupled using the two successive reactions, previously shown in FIG. 25, by performing microwave-assisted synthesis protocol. First, beads will be treated with 2 M bromoacetic acid and 3.2 M DIC, and the coupling will be performed for 2×15 sec using 100W microwave power. Following a subsequent DMF wash, the primary amine (2 M) will be treated and the same microwave procedure will be used.

In this particular synthesis; first, the azide moiety will be added to the resin exactly following the peptoid synthesis protocol [FIG. 34(B)]. Bromoacetic acid addition will be followed by proper azido amine (the 'n' depicts no. of carbons and it will be 2 or 4). Then, normal PPS1 sequence will be synthesized. The first 3 amino acid coupling [Fmoc-met-OH, Fmoc-D-lys-Boc, Fmoc-lys-Boc] will be followed by addition of 5 peptoid residues (amines used are: Boc-1, 4diaminobutane, 4-methoxybenzylamine, (R)-Methylbenzylamine, Piperonylamine—please refer to the PPS1 structure: FIG. 26B). On completion of each compound, the TFA/TIS/ddH2O [95:2.5:2.5 (v/v/v); 2 mL] cleavage cocktail will be treated for 2 hrs to remove all TFA labile protecting groups and cleave the compound from the resin. Product will be confirmed by MALDI, purified by reverse phase HPLC and lyophilized. All reagents are commercially available.

FIG. 34. (A) Two solution phase reactions involve in PPS1 dimer synthesis (B) Solid phase synthesis of azide-PPS1

FIG. 35 List of different carboxylic acid scaffolds used in multimer synthesis.

Example 9

'Click' chemistry to form multimers: The resulting central scaffolds with alkyne moieties will be reacted with PPS1 peptoid with C-terminal azide groups [FIG. (34A)—second reaction]. A click chemistry protocol supported by microwave irradiation to successfully synthesize a tetrameric peptoid has been adopted. All reactions will be performed with 1:5 equivalent of alkyne:azide and the Tetrakis(acetonitrile)copper(I) hexafluorophosphate catalyst in water-tert-butanol mixture. The reaction mixture will be microwaved under 100 W power for 2-10 minutes depending on the reaction. This will be repeated 1-2 rounds as needed. Then the reaction will be allowed to shake at room temperature overnight. The final product will be purified by reverse phase HPLC and confirmed by MALDI. All reagents are commercially available.

Example 10

Twenty derivatives of alkyne containing scaffolds starting from 20 different carboxylic acids shown in FIG. 35 will be synthesized. Then, the azide containing PPS1 will be synthesized on a large scale to get enough material for all 20 click chemistry reactions. Twenty different multimers (7 dimers, 6 trimers, 5 tetramers, 1 pentamer and 1 hexamer) of PPS1 will be developed.

Example 11

Different solvents and work up conditions may be needed due to the different hydrophobicities of the central scaffolds. Also, the same challenges will exist in click chemistry and the reaction conditions need to be optimized for different systems. For some cases, the whole click chemistry procedure may fail due to the steric bulkiness of central scaffolds.

Example 12

An imidazoline(mesythyl)copper bromide (Imes) CuBr or $Cu(O)/CuSO_4$ (II) mixture can be used as catalysts.(83) Microwave and thermal conditions can be manipulated to optimize these reactions. In another embodiment, a Cys-maleimide approach can be used to bring 2 units together. The central carboxylic acid scaffolds can be reacted with 1-(2-aminoethyl)-pyrrole-2,5-dione (maleimide amine—Sigma Aldrich) and the PPS1 can simply be synthesized with a C-terminal cysteine. Then the two units can be coupled to form the PPS1 multimers (the maleimide double bond readily reacts with the thiol group on cysteine to form a stable carbon-sulfur bond). In addition, there are certain organic scaffolds available (Sigma Aldrich) to develop some of these multimers using a fully on-bead synthesis protocol as well.

Example 13

It will be demonstrated that the multimeric derivatives developed are selectively lytic towards PS-expressing tumor cells but not to PS-negative normal cells. (I) Methods: The MTS assay for cell viability and the CytoTox-Glo™ assay for lysis will be used to identify the most optimized lytic peptoid derivative. All 20 PPS1 multimers will be tested first for lytic activity on a limited panel of PS-positive cancer cell lines HCC4017, MDA-MB-231, and PC3 and for lack of lytic activity on PS-negative HUVEC cells. The most potent and specific peptoids (about 5-10) will then be tested against a large panel of malignant and normal cells as follows: (i) PS-positive cancer cell lines: H460, A549, H1993, H2009 (lung cancer); RM9 (prostate cancer); Raw264, J774, and Jurkat (leukemic); F98 (glioma). (ii) PS-negative normal cells: HBEC3kt, HBEC30kt, and HFF (fibroblasts); HUVEC, PAE, HBEC, BAEC, and HMVEC (endothelial). (iii) Cultured endothelial cells treated with 5 Gy irradiation to render them PS-positive.

Example 14

Cell viability-MTS assay: Different cell lines will be grown and maintained in suitable media (e.g. DMEM, RPMI etc.). Cells will be pre-seeded on 96-well plate at a density of $2 \times 10^3$ cells/well in 200 µL of media containing 5-10% FBS overnight. On the next day, 200 µL of peptoid solution with varying concentrations (0.1 nM-50 µM) will be added (in triplicate for each treatment) and the cells will be incubated for another 24 hrs. Wells treated with non-active control peptoid, PPS1, PPS1-D2 and without peptides will serve as controls. At end of the experiment, cell viability will be measured using 3-(4,5-dimethylthiazol-2-yl)-5-(3-carboxymethoxyphenyl)-2-(4-sulfophenyl)-2H-tetrazolium, inner salt assay (MTS assay) according to manufacturer's specification (Promega Corporation, Madison, Wis.). The percentage of cell viability will be calculated by dividing the absorbance value of treated cells by the absorbance value of control cells within each group. All experiments will be repeated 2-3 times.

Example 15

Cell lysis assay: The CytoTox-Glo™ Assay is a luminescent cytotoxicity assay that measures the extracellular activity of a distinct intracellular protease activity (dead-cell protease) when the protease is released from membrane-compromised cells. A luminogenic cell-impermeant peptide substrate (AAFaminoluciferin) is used to measure dead-cell protease activity. The liberated aminoluciferin product is measured using Ultra-Glo™ Recombinant Luciferase. The amount of luminescence directly correlates with the percentage of cells undergoing lysis. The experiments will be conducted as above. Percentage lysis is calculated by subtracting the luminescent dead-cell signal from the total luminescent value and expressing the difference as a percentage of the signal from cells treated with triton X-100 (100% lysis).

It will be determined whether the peptoids are selectively lytic towards PS-expressing endothelial cells by irradiating HUVE (large vessel EC) or HMVEC (microvascular EC) with 5 Gy. After 8 to 24 hours, when PS exposure peaks and the cells are still intact, they will be treated with the peptoids for 1 hour and lysis measured as above.

Example 16

Peptoids will be tested to see if they have stronger and/or more specific lytic activity than our current lead compound, PPS1-D2. Peptoids will also be tested to see if they lyse endothelial cells that have been rendered PS positive by irradiation.

Example 17

In addition to the MTS and lysis assays, fluorescent confocal microscopy and flow cytometry can be used to analyze damage cells treated with the optimized derivative. (45) If incorporating rigid or flexible linkers into the dimers does not improve their activity over that of the current leading compound, PPS1-D2, multimeric compounds using different residues in their linkers will be synthesized. It is possible that the linkers may also have fine specificity and that their optimal structure needs to be worked out through structure-activity relationship studies. The PPS1 monomeric unit will also be tested to see if it can be improved through knowledge gathered from minimum pharmacophore identification (e.g. changing the 4th position to find an optimized compound). These improved monomers will also be useful in ultimately developing improved multimers.

Example 18

In vivo biodistribution, tumor localization, and antitumor activity of PPS1-D2 and the peptoid derivatives will be determined. 1) Radioiodination of the peptoid derivatives: PPS1-D2 and five further peptoid derivatives having potent and specific lytic action on tumor versus normal cells in vitro will be resynthesized with an additional tyrosine residue (couple after the azide addition—FIG. 34(B)). The tyrosine derivative will be iodinated with $^{125}$I-iodide using standard methods.

2) Pharmacokinetic and biodistribution studies in tumor bearing mice: Groups of 5 female SCID mice will be injected with 2×106 MDA-MB-231 human breast cancer cells into the upper left mammary fat pad. When the tumors have grown to 1 cm in diameter, 125I-labeled peptoid (100 µg) will be injected i.v. At various later time points (5 min, 30 min, 1 h, 2 h, 4 h, 8 h, 24 h, 48 h, 72 h) 20 µl of blood will be collected from the tail vein into a heparinized tube and its radioactivity counted. The blood clearance curve of % injected radioactivity remaining in blood versus time will be analyzed using a two compartment pharmacokinetic algorithm. Pharmacokinetic parameters to be analyzed include: t½α, t½β, AUC0-∞, Vd, A, B (% C0), and mean residence time. To obtain biodistribution data, the experiment will be repeated with 6-9 groups of 4 mice, with groups being sacrificed at 5 min, 30 min, 1 h, 2 h, 4 h, 8 h, 24 h or longer if there is significant radioactivity still remaining. Normal organs and tumor will be dissected out, weighed, and their radioactivity counted. The % injected dose per gram of tissue will be calculated. Tumor localization will be calculated as tumor to normal ratio (T/N) using contralateral muscle as the normal tissue.

3) Localization to tumor vasculature: PS-binding dimeric peptoids will be synthesized carrying a biotin residue [Fmoc-Glu-Biotin (Novabiochem) will be added to the PPS1 portion as a simply amino acid incorporation after the azide addition—FIG. 34(B)]. The biotinylated derivative (50 µg) will be injected i.v. into mice bearing MDA-MB-231 breast tumors on the mammary fat pad. After 2 hours, the mice will be anesthetized, and their blood circulation perfused with heparinized saline through the left ventricle of the heart. Tumor and normal tissues will be dissected out, frozen and cryosections cut. The sections will be stained with hematoxylin and eosin. The peptoid will be detected immunohistochemically with Cy3-labeled streptavidin and counterstained with Cy5-labeled antibodies to CD31 to identify endothelium. Coincident staining of peptoid and CD31 will indicate peptoid bound to vascular endothelium.

4) Toxicity to mice: The maximum tolerated dose (MTD) of the peptoids will be determined by injecting graded doses of peptoid i.v. into groups of 4 BALB/c SCID mice. The MTD will be calculated as the highest dose at which all animals in the group survive. To determine the toxicity, mice will be injected with half of the MTD dose i.v. and 24 hours later will be sacrificed and organs fixed in formalin. Paraffin sections will be prepared for histology and examined. Effects on blood coagulation will be sought by determining the activated partial thromboplastin time (aPTT) and prothrombin time (PT).

5) Antitumor activity in mice: i) Hormone-refractory prostate cancer model. $10^6$ luciferase-labeled human PC3-luc cells will be injected into the prostate gland of male SCID mice (84, 85). Tumor growth will be followed over time by measuring the bioluminescence (BLI) produced after luciferrin is administered. When tumors reach 0.4 cm diameter, as judged from bioluminescence (BLI)-versus-tumor volume calibration curves, treatment will be initiated. Mice will be injected i.v. with half of the MTD of peptoid once a week, or 100 ug/25 g mouse if the peptoid is not toxic at 200 ug/mouse. Other groups of mice will receive peptoid plus docetaxel (5 or 10 mg/kg) or docetaxel alone. The docetaxel treatment increases PS exposure on tumor vessels and on tumor cells, thus amplifying the target for the peptoid. With other PS-targeting agents, docetaxel acts synergistically to enhance efficacy. Terminal tumor weights will be recorded.

ii) Breast cancer model. $10^6$ MDA-MB-231 cells will be injected into the upper left mammary fat pad of female SCID mice. When the tumors reach 0.5 cm diameter, therapy will be started. Half of the MTD of peptoids (or 100 ug/25 g mouse, if the peptoid is not toxic at 200 ug/mouse) will be administered i.v. once a week. Other groups of mice will receive peptoid plus docetaxel (5 or 10 mg/kg) or docetaxel alone. Tumor size measurements and terminal tumor weights will be recorded. Metastases, which spread primarily to the lungs in this model, will be counted after sacrifice.

iii) Lung cancer model. SCID mice will be injected with 106 human HCC4017 NSCLC cells subcutaneously. When tumors reach 0.8 cm diameter, the mice will be treated i.v. with half the MTD of the peptoid once a week, or 100 ug/25 g mouse if the peptoid is not toxic at 200 ug/mouse. Other groups of mice will receive peptoid plus docetaxel (5 or 10 mg/kg) or docetaxel alone. Tumor size measurements and terminal tumor weights will be recorded.

6) Disruption of tumor vasculature. Destruction of tumor vasculature will be assessed by counting microvascular density using CD31 to identify tumor endothelium and measuring total vascular area on histological sections of tumors. Co-staining with antibodies to collagen IV in the basement membrane will identify vessels denuded of endothelium. Changes in tumor blood volume (perfusion volume) will be estimated by injecting FITC-dextran (Mr 106) i.v. into the mice, removing the tumors, homogenizing them and quantifying total fluorescence. The % of vessels that are able to transport solutes will be quantified by injecting fluorescent tomato lectin and counting lectin positive vessels. Tumor perfusion will be assessed by injecting Hoechst 33342 dye i.v. and sacrificing the mice 1 min later and quantifying the area of Hoechst-staining on tumor sections.

Statistical Analyses: Tumor size reduction, microvascular density and vascular area on histological sections of tumors will be compared among the treatment groups using ANOVA tests or Kruskal-Wallis tests. If significant, Student's t-tests or Wilcoxon rank-sum tests will then be conducted to investigate which pairs of treatment groups yields significant results using Bonferrni corrections for multiple comparisons. Kaplan-Meier method will be used to estimate the survival times. Log-rank tests will be used to compare the survival time among treatment groups.

Treatment with a lytic PS-targeting peptoid induces vascular damage in tumors (PPS1-D2 initial data already displayed this activity—FIG. 32). The time course of damage is expected to be more rapid, however, because of the rapidity of lysis by peptoids in vitro. Damage is expected to cause collapse of tumor vasculature and tumor cell killing through deprivation of oxygen and nutrients and build-up of waste products. Docetaxel is expected to enhance the anti-vascular effects of the peptoid by amplifying PS-exposure on tumor endothelium and on the tumor cells themselves. Docetaxel will also destroy the viable rim of tumor cells that survives after targeting with PS-targeting antibodies, because these outer tumor regions are well vascularized and well-oxygenated tumor cells are sensitive to docetaxel-mediated killing. Direct tumor cell killing will be achieved with peptoids because peptoids are much small and likely to penetrate tumors more easily than antibodies. The pharmacokinetics of peptoids are unpredictable. The blood clearance rate could be rapid or slow depending on whether the peptoid interacts with serum proteins that extend their half-life.

Peptoids have already been established as having low inherent toxicity. Exposed PS itself is remarkably specific to tumors. Normal apoptotic PS-expressing cells are 'marked for clearance' so peptoid-mediated lysis of these dying cells is not expected to contribute to toxicity. The PPS1-D2 peptoid has an MTD of 2-4 mg/kg. In the unlikely event that toxicity is encountered, the structural components of the peptoid that contribute to toxicity will be examined and modifications will be made to these residues to reduce toxicity. It is possible that the peptoids will be cleared rapidly from the bloodstream by renal excretion and that this will reduce their opportunity to contact tumor cells. It should be possible to rectify an excessively short half-life by increasing the size of the peptoid by multimerization, or introducing a serum protein binding region. It should be remembered, however, that the primary target for the peptoid is likely to be the tumor vascular endothelium which is completely accessible to peptoid in the blood and therefore has time to be saturated by peptoid, even with one that is rapidly cleared.

FIGS. 36-52 depicts various peptoids. FIG. 52 depicts the structures of PPS1 and PPS2.

FIG. 53 depicts development of hetero-dimers targeting VEGFR2(GU40C) and PS (PPS1); (A) structure of PPS1-GU40C heterodimer (B) JGD Magnetic bead assay with H441 cells. All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the disclosure as defined by the appended claims.

Example 19

Two derivatives of PPS1D1, 2P3H-PPS1 (FIG. 54) and 2-4-PPS1 (FIG. 55) were found to have cancer cell killing activity.

FIG. 54 depicts the structure of 2P3H-PPS1.

FIG. 55 depicts the structure of 2-4-PPS1.

FIG. 56 depicts a graph of HCC4017 cancer killing activity (MTS) of 2P3H-PPS1, 2-4-PPS1, and PPS1D1. The activities of the two improved derivatives, 2P3H-PPS1 and 2-4-PPS1, are shown in red and blue lines respectively. The activity of PPSD1 is shown in a green line.

Example 20

FIG. 57 depicts a peptidomimetic based on-bead two-color (OBTC) combinatorial cell screen that can detect differences between two cell surfaces at high accuracy by looking for beads (where each bead in the library had one peptide-peptoid hybrid on the surface) that only bound cancer but not normal cells. A library of 393,216 compounds targeting HCC4017 lung adenocarcinoma cells (labeled in red) was screened in the presence of HBEC30KT normal bronchial epithelial cells (labeled in green) derived from the same tissue of the same patient. This screen identified a peptide—peptoid hybrid called PPS1 which displayed high specific binding for HCC4017 cancer cells over HBEC30KT cells. Specificity was validated through on-bead, ELISA-like and magnetic bead pulldown studies, while a scrambled version of PPS1 did not show any binding. The simple dimeric version (PPS1D1) displayed cytotoxic activity on HCC4017 cells, but not on normal HBEC30KT cells. PPS1D1 also strongly accumulated in HCC4017 lung cancer xenografts in mice over control constructs. Such combinatorial screens using tumor and normal cells from the same patient have significant potential to develop new reagents for cancer biology, diagnosis, and potentially therapy.

Example 21

Phosphatidylserine (PS) is an anionic phospholipid maintained on the inner—leaflet of the cell membrane and is externalized in malignant cells. A careful unbiased selection has been launched targeting biomolecules (e.g. protein, lipid or carbohydrate) distinct to cancer cells by exploiting HCC4017 lung cancer and HBEC30KT normal epithelial cells derived from the same patient, identifying HCC4017 specific peptide-peptoid hybrid PPS1. In this current study, PS is identified as the target of PPS1. Direct PPS1 binding to PS using ELISA-like assays, lipid dot blot and liposome based binding assays is validated. In addition, PPS1 recognized other negatively charged and cancer specific lipids such as phosphatidic acid, phosphatidylinositol and phosphatidylglycerol. PPS1 did not bind to neutral lipids such as phosphatidylethanolamine found in cancer and phosphatidylcholine and sphingomyelin found in normal cells. Further, the dimeric version of PPS1 (PPS1D1) displayed strong cytotoxicity towards lung cancer cell lines that externalize PS, but not normal cells. PPS1D1 showed potent single agent anti-tumor activity and enhanced the efficacy of docetaxel in mice bearing H460 lung cancer xenografts. Since PS and anionic phospholipid externalization is common across many cancer types, PPS1 may be an alternative to overcome limitations of protein targeted agents.

Conventional drug development targeting cell surface proteins is challenging in oncology due to the diversity and complexity of cancer. The heterogeneity of protein expression and cross-talk/compensation between signaling cascades present significant hurdles for the development of therapeutic agents that provide durable efficacy and are broadly effective. It is hypothesized that identifying compounds that target non-protein based cell surface bio-molecules that are widely expressed across many cancer types would address some of these challenges. Therefore, a unique unbiased selection approach was performed to target biomolecules such as proteins, lipids or carbohydrates present on the cancer cell surface, but not found or less abundant on normal cells. Bead two-color (OBTC) combinatorial cell screen was utilized to select peptide-peptoid hybrids that discriminate cell surface targets in closely related cell populations. This screening strategy is unbiased in terms of the nature of target selection allowing equal chance to recognize a protein, lipid or a carbohydrate specific to cancer cells. The OBTC cell screen was performed using a lung cancer cell line (HCC4017) and normal bronchial epithelial cells (HBEC30KT) derived from the same patient. A library of ~400,000 peptide-peptoid hybrids was screened against a mixture of HCC4017 and HBEC30KT cells. The cells were pre-labeled with fluorescent quantum dots such that HCC4017 cells were red and HBEC30KT cells were green. Beads that only bound to red stained HCC4017 cells were selected for further characterization. A peptide-peptoid hybrid was identified called PPS1 (FIG. 9A) that binds HCC4017 lung cancer cells with limited or no binding to normal HBEC30KT cells. The dimeric version of PPS1, PPS1D1 (FIG. 9B) displayed strong cytotoxic activity on HCC4017 cells, but not on HBEC30KT cells. Furthermore, PPS1D1 strongly accumulated in HCC4017 lung cancer xenografts.

Target identification of an unbiasedly selected compound is challenging and the first assumption is that the compound binds to a specific protein. An approach to identify the targeted protein is mass spectrometry after compound facilitated precipitation. In an embodiment, this path was not successful. Targets of other molecular classes such as lipids and carbohydrates that may be found in cancer were evaluated. In particular, anionic phospholipids, sialic acid residues and heparin sulfates are some known examples of other molecular classes that are elevated on the cancer cell surface.

Described herein are the target identification and binding of PPS1 to anionic phospholipids, principally, phosphatidylserine (PS). Typically the plasma membrane consists of phosphatidylcholine (PC) and sphingomyelin (SM) in the outer leaflet, while PS and phosphatidylethanolamine (PE) are segregated to the inner leaflet. This distribution is actively maintained but dynamically changes in response to physiological and pathophysiological events. Movement of lipid across the membrane is controlled by aminophospholipid translocases, scramblases, ATP binding cassette group of transporters and Ca2+ concentration, and is well studied during apoptosis, malignancy and cell damage. The anionic phospholipid PS has been reported as a marker of tumor vasculature. This is because PS is flipped to the outer leaflet of the plasma membrane in endothelial cells in the tumor microenvironment and also in some cancer cells due to oxidative stress, hypoxia/re-oxygenation, cytokine activation, cell trafficking and tumor cell metabolites. PS is also externalized during apoptosis, necrosis, and cell activation. Depending on tumor type, up to 50% of the blood vessels in the tumor can externalize PS. Further, PS exposure on tumor vasculature is elevated after therapy with chemotherapy, radiation, androgen deprivation or small molecules.

There are only a small number of PS targeted peptides, antibodies and small molecules that have been reported to date. The most widely studied PS-binding probe is annexin V, a 35.8 kDa protein that binds PS in a calcium-dependent manner with nanomolar affinity. A PS binding peptide identified by screening M13 phage library was used for H460 tumors imaging in mice. Another peptide was identified by screening a library of compounds for their binding to PS-coated surface plasmon resonance sensor chips. This peptide was conjugated with 99 mTc and was shown to bind to cancer cells. Zinc containing small molecules targeting PS has also been used for optical imaging of tumors. Bavituximab, a chimeric monoclonal antibody that binds PS via a co-factor, β2-glycoprotein-1 has been used for the therapy and imaging of solid tumors in preclinical models and is currently under clinical testing in cancer patients.

While small molecules, peptides and antibodies also displayed their own weaknesses in terms of developing as probes and/or drugs, emerging molecular class of peptidomimetics called peptoids were explored. Peptoids have peptide-like characteristics and have emerged as important alternative molecules for anti-cancer drug-lead development. Peptoids have peptide like backbone but each residue is N-substituted glycine, which is equivalent to an amino acid of a peptide. The R group of a peptoid residue is placed on nitrogen instead of the alpha carbon in a peptide. This arrangement confers protease resistance, cell permeability and reduced immunogenicity. Large peptoid libraries containing millions of molecules can be rapidly and easily synthesized at low cost. Peptoids are potential drug leads targeting various cancer targets and imaging agent carries. In this study, the target identification of peptide-peptoid hybrid PPS1 is described and it is demonstrated that PPS1 has potential as an anti-cancer therapeutic.

Results and Discussion

PS exposure on HCC4017 lung cancer cells

The amphipathic nature of PPS1 (FIG. 9A and FIG. 63) suggested that this compound may target cell membrane lipids, as many anti-microbial peptides reported to date typically display the same structural features. As described above, PS is well-known to be externalized in the tumor vascular endothelial cells and on some tumor cells as depicted in FIG. 10A compared to normal cells. PPS1 was selected for binding to HCC4017 cells over HBEC30KT cells, thus the level of PS exposure in HCC4017 and HBEC30KT cells using immunocytochemistry with the PS targeting antibody bavituximab was evaluated. HCC4017 cells were robustly positive for bavituximab staining while HBEC30KT showed little to no staining with this PS targeting agent (FIG. 10B), indicating significantly elevated levels of PS on outer leaflet of HCC4017 compared to normal HBEC30KT. This observation is consistent with PS exposure on other cancer cell types such as lymphoma, melanoma and colon carcinoma cell lines.

PPS1D1 binds PS

Since PS is selectively exposed on the surface of HCC4017 cells compared with HBEC30KT, it was examined if PPS1D1 (FIG. 9B and FIG. 72) binds to PS directly. In an ELISA-like assay, PS and PC were coated separately on 96-well plates, biotinylated PPS1D1 (FIG. 65) was introduced in a concentration gradient and the bound compound was detected using standard streptavidin-HRP system. It was observed that PPS1D1 bound to PS at KD ~55 nM with very high specificity over the PC in a concentration dependent manner (FIG. 58A).

While an ELISA-like assay using purified components provides some information regarding binding characteristics, it was possible that the cellular arrangement and dynamics of PS and PC might be different in a lipid bilayer. To partially address this issue, binding studies to liposomes with varying concentrations of PS were extended. Liposomes with 100% PC and 85% PC-15% PS were created. These liposomes were incubated with fluorescein labeled PPS1D1 (FITC-PPS1D1, FIG. 66) at 20, 50, 75, 100 and 150 nM for 1 hour and the fluorescein signal was detected by flow cytometry. FITC-PPS1D1 specifically bound to liposomes that contained 15% PS but did not bind liposomes that were 100% PC (FIG. 58B). These results demonstrated that PPS1D1 binds PS over PC. To confirm these observations, PPS1 and non-PS binding control compound PC462 were synthesized (FIGS. 67, 69 and 70) on Tentagel beads and exposed those beads to liposomes with 100% PC and 85% PC-15% PS that were incorporated with fluorophore 7-nitro-2-1,3-benzoxadiazol-4-yl (NBD) dye. As shown in FIG. 58C, only the beads with PPS1 exposed to liposomes with 85% PC-15% PS lit up indicating PPS1 binds to PS. No binding was observed on the beads with PPS1 exposed to liposomes with 100% PC or beads with control compounds (FIG. 58C).

Multiple competition assays were conducted to determine whether PPS1 (or PPS1D1) competes with Annexin V, a known PS binding agent. In ELISA-like competitive binding assay (FIG. 71) Annexin V did not compete with PPS1D1 for binding to PS. Competition between Annexin V and PPS1 for binding to PS in liposomes using flow cytometry was evaluated. Again in these assays there was no competition between Annexin V and PPS1 for binding to PS (FIG. 72 reduce the binding of NBD-PS containing liposomes on PPS1 displaying tentagel beads (FIG. 74). Prior reports have also found that PS targeting antibodies, including the IgM 9D2, do not cross block the binding of Annexin V to PS [10]. The lack of competition between PPS1 or antibody PS targeting agents with Annexin V for PS binding may be due to the different binding modes of these agents. Annexin V requires calcium to bind to PS. PS targeting agents such as 9D2 bind PS via the bridging protein β2-glycoprotein-1. However, PPS1 directly binds PS. Also, PS-ligand binding may be much more complex than that of a typical protein-ligand binding. Typical protein ligand binding occurs via a defined binding pocket, which facilitates clear competition by other ligands that interact with the same binding pocket. But PS is a lipid in a fluid membrane, which has no defined macromolecular structure further complicating possible binding modes.

The structural features of PPS1 and PS were compared. PPS1 monomer has three positively charged residues aligned together and a hydrophobic region with four consecutive aromatic rings (FIG. 9A), while the PPS1D1 dimer has twice the amount of those positive and hydrophobic regions. This structure is likely to form electrostatic and hydrophobic interactions with opposing negatively charged head groups on PS and its hydrophobic tail region, suggesting that PPS1 and PPS1D1 interact with negatively charged phospholipids. To test this, one of the positively charged lysine residues (3rd residue from C-terminal) was replaced with glutamate (which will bring opposing negative charge) and observed a major reduction of the binding activity as shown in FIG. 75.

PPS1D1 recognizes negatively charged phospholipids

One of the major questions arising at this point is how PPS1 or PPS1D1 specifically recognizes PS over PC, as both lipids have negatively charged phosphate head groups. To address this specificity concern, ELISA-like binding assay were expanded to include other membrane phospholipids such as phosphatidylethanolamine (PE), sphingomyelin (SM), phosphatidic acid (PA), phosphatidylinositol (PI) and phosphatidylglycerol (PG). As shown in FIG. 59A, PPS1 displayed binding to PA, PI and PG but did not bind to PE and SM. Interestingly, all of the lipids bound by PPS1 (PS, PA, PI and PG) have an overall negative charge as compared to unbound PC, PE and SM that are neutral at physiological pH (Table shown in FIG. 59D). This additional negative charge can be responsible for the interaction with the positively charged region of PPS1 or PPS1D1, while the hydrophobic regions of PPS1 or PPS1D1 may interact with hydrophobic tail groups of the lipids through van der Waals forces. To validate these results on a different platform, PPS1D1 binding to phospholipids at different lipid concentrations was investigated using commercially available membrane lipid arrays, lipid dot blots (Echelon, USA). The membrane was treated with biotin labeled PPS1D1 and binding was detected by immunoblotting with streptavidin-HRP. PPS1D1 showed the strongest binding to PS, while PA, PG and PI followed with weaker binding (FIGS. 59B and 59C). This assay confirmed that PPS1D1 does not bind to PC, PE, SM or diacylglycerol (DAG) and recapitulated the ELISA-like assay. Furthermore, the binding characteristics of PPS1D1 are varied on PS, PA, PG and PI in the lipid blot assay and this suggests that PPS1D1 may have a secondary structure beyond a simple linear sequence. It has been reported that PS can form a bilayer lamellar and reverse hexagonal phase. PS is mainly in a lamellar phase after hydration at physiological pH. By validating our binding through an ELISA-like assay and liposomes, PPS1D1 has an equal opportunity to bind to each phase of PS.

Activity validation of PPS1D1 on series of lung cancer cell lines

Previously, PPS1D1 showed cytotoxic activity against HCC4017 lung cancer cells but not normal HBEC epithelial cells. In this current study, the target of PPS1D1 is PS and HCC4017 strongly expresses PS. Our next goal was to evaluate the level of PS externalization on other lung cancer cell lines and the activity profile of PPS1D1 on those cell lines. A variety of lung cancer cell lines HCC4017 (lung adenocarcinoma), H460 (large cell lung cancer), H1395 (lung adenocarcinoma), HCC95 (squamous cell lung carcinoma), H1993 (adenocarcinoma; non-small cell lung cancer), H1695 and HBEC30KT (normal bronchial epithelial cells) were treated with fluorescein-labeled Annexin V (FITC-Annexin V) and the bound fluorescein signal was detected using flow cytometry. As shown in FIG. 60A, these cancer cell lines exhibited PS externalization with H460 and H1693 displaying the highest level (~65-70% cells PS positive) while HBEC30KT normal cells with minimum levels. Standard cell viability (MTS) assay by treating these cell lines with PPS1D1 (1 and 20 μM) and 20 μM of a control compound PC462D1 (FIG. 68) in 96-well plates were performed. PPS1D1 exhibited a strong cytotoxicity on all the cancer cell lines at 20 μM concentration but not at 1 μM (FIG. 60B). This activity was somewhat similar when tested at 6, 12 and 24 hours post treatment using HCC4017 cancer cell line (FIG. 76). PPS1D1 had no effect on normal HBEC30KT cells at either concentration. These data are consistent with our previous observations that PPS1D1 has an IC50~10 μM on HCC4017.

It was evaluated how PPS1D1 affects viability of these PS expressing cancer cell lines. While there are difficulties of narrowing down the exact mechanism of action of a compound targeting cell membrane lipids, whether PPS1D1 has any effect on cell membrane integrity was evaluated. Cells were treated with standard DNA staining dyes Propidium iodide (PI) and Hoechst 33342. While both bind DNA, only Hoechst is cell permeable. Therefore, when treating live cells only Hoechst will stain the nucleus while PI will stain the nucleus only if the cell membrane integrity is compromised. All the lung cancer cell lines and normal HBEC30KT cells were treated with these dyes in the presence of PPS1D1 (at 1 μM and 20 μM) or a control compound PC462D1 at 20 μM and evaluated fluorescence by microscopy without fixation. As shown in FIG. 60C, untreated cells were only stained by the Hoechst dye. The control peptoid and PPS1D1 at 1 μM also only show staining with Hoechst dye. In contrast, treatment of lung cancer cells with PPS1D1 at 20 μM resulted in staining of cells with PI demonstrating a loss of membrane integrity. This effect was not observed on normal HBEC30KT cells. Cells were treated with the known cell membrane damaging agent Benzalkonium chloride (BAC), which resulted in PI-positive nuclei as shown in FIG. 60C. These observations indicate that 20 μM PPS1D1 is selectively cytotoxic to PS-positive lung cancer cells.

The effect of PPS1D1 on H460 lung cancer cells was tested in detail using several in vitro assays. H460 is an aggressive lung cancer cell line harboring mutations in p53 and KRAS that has been used widely in xenograft studies. PS expression is elevated on H460 cells (FIG. 60A) and PPS1D1 shows cytotoxicity towards these cells (FIGS. 60B and 60C). A magnetic bead pulldown assay (Experimental procedure 9) was conducted by incubating 1×106 H460 cells with magnetic bead coated PPS1D1 and control PC462D1 separately. PPS1D1 coated magnetic beads readily retrieved about 75% of H460 cells compared to negligible amount pulled down by control compound PC462D1 (FIG. 61A). Standard cell viability (MTS) assays (Experimental procedure 10) on H460 cells performed by treating increasing concentrations of PPS1D1, PPS1 and control compound PC462D1 in 96-well plates. PPS1D1 displayed very similar cytotoxic activity on H460 cells (IC50=~10 μM) as was observed for HCC4017 cells, while monomeric PPS1 and control PC462D1 did not affect H460 cells (FIG. 61B). It was confirmed that PPS1D1 has no cytotoxicity on normal HBEC30KT cells (FIG. 61B). Next, how the efficiency of PPS1D1 cytotoxicity increased with respect to the binding on H460 cancer cells at different concentrations using flow cytometry was examined. PPS1D1-FITC was incubated for 1 hr with H460 cells at 0.1, 10, 30 and 100 μM concentrations and PI was added to stain dead cells. With increasing concentration of PPS1D1, the number of H460 cells double positive for PPS1D1-FITC and PI increased from ~5% to 100% (FIGS. 61C and 61D). These results indicate that PPS1D1 binds and is cytotoxic to H460 cells.

Inhibition of growth of H460 lung cancer xenograft by PPS

The effect of PPS1D1 on the growth of H460 xenografts implanted in NOD/SCID immunodeficient mice was examined. Immunodeficient animals were chosen to facilitate the growth of human tumor xenografts. Although previous studies with PS-targeting bavituximab showed antitumor response required immune activation against tumor cells, our in vitro data suggests that PPS1D1 has a direct cytotoxic effect on cancer cells. Therapy with a control peptoid (PC462D1, 0.25 mg/mouse, 3×/week ip), PPS1D1 (0.25 mg/mouse, 3×/week ip), docetaxel (0.5 mg/kg, 2×/week, ip) or the combination of PPS1D1+docetaxel was initiated when tumors were ~100 mm3 in volume. FIG. 62A shows tumor volume vs days post therapy initiation and demonstrates that PPS1D1 and docetaxel slowed tumor growth as single agents. However, combination therapy was more effective than either therapy alone (FIG. 62A). PPS1D1 at the doses used did not induce animal weight loss nor did it exacerbate toxicity induced by docetaxel (data not shown). Tumor tissue was harvested after 4 weeks of therapy and assessed for cell proliferation and apoptosis by immunohistochemistry. Combination therapy significantly reduced cell proliferation as measured by phosphorylated Histone H3 reactivity (FIG. 62B) and significantly elevated apoptosis as determined by cleaved caspase 3 reactivity (FIG. 62C). These data are consistent with the effect of other PS targeting agents (e.g., bavituximab), which showed enhanced activity in combination with standard therapy. It is clear from studies with bavituximab that standard chemotherapy (e.g., taxanes) increases the exposure of PS resulting in elevated binding of the PS targeting agent. A similar mechanism can underlie the enhanced activity of docetaxel and PPS1D1.

The anionic lipidphosphatidylserine (PS) is the target of the anti-cancer peptide-peptoid hybrid PPS1, which was initially selected through a unique unbiased selection approach (OBTC cell screen) that compared HCC4017 lung cancer cells and HBEC30KT normal cells derived from the same patient. This OBTC screening has many advantages for identification of targeting ligands specific for a selected cell population. The assay is dynamic with competing cell populations having equal access to targeting ligands. The screen is simple, rapid and economical and has been successfully employed to identify peptoids that bind therapeutically tractable targets previously. In the present study, PPS1 preferentially binds to anionic phospholipids, most specifically to PS and then to PA, PI and PG to some extent, but not to PC, SM and PE. PS is exposed on tumor cells and endothelial cells in the tumor microenvironment of wide-varieties of tumor types. A dimeric form of PPS1, PPS1D1, showed potent cytotoxicity towards series of lung cancer cells lines that express PS. PPS1D1 displayed potent cytotoxicity on H460 lung cancer cells in vitro and displayed single agent activity in H460 xenografts. PPS1D1 also potently enhanced the anti-tumor activity of docetaxel. There is an increasing need for anti-cancer agents that are effective against broad types of cancers, as the efficacy of protein targeted drugs are limited to certain subpopulations of cancer types due to the heterogeneous expressions of those protein drug targets. Phospholipid asymmetry and elevated PS levels is observed in the tumor microenvironments of most cancers analyzed to date. PPS1D1 can have efficacy in multiple tumor types and also has the potential to safely increase the efficacy of standard cancer therapy.

Materials and Methods

Synthesis of PPS1

Synthesis of PPS1 compound was done on NovaSyn TGR resin (EMD Millipore, MA). First three amino acids, Fmoc-Met-OH, Fmoc-D-Lys(Boc)-OH and Fmoc-Lys(Boc)-OH were loaded to the resin after Fmoc removal each time. Then 5-mer peptoid region containing Boc-Diaminobutane, 4-methoxybenzylamine, (R)-Methylbenzylamine, Piperonylamine and (R)-Methylbenzylamine was completed using microwave assisted peptoid synthesis protocol. At the end, beads were washed with DCM and cleaved off with TFA cleavage cocktail (See detailed experimental procedures below).

Synthesis of PPS1D1

PPS1D1 was synthesized on NovaSyn TGR resin. First, Fmoc-Lys(Fmoc)-OH was coupled overnight as the central linker, and both Fmoc groups were removed simultaneously allowing two copies of the sequence to be built on two amine groups of this central Lys. Beyond this point PPS1 synthesis procedure described above was utilized.

Cell lines

HCC4017, H460, HCC95, H1693, H1395, HBEC30KT and HBEC3KT cell lines were obtained from the cell collection of Dr. John Minna's research group at UTSouthwestern Medical Center. HCC4017, H460, HCC95, H1693, and H1395 was grown in RPMI supplemented with 5% FBS. Normal lung cell line HBEC30KT and HBEC3KT were grown with keratinocyte serum free media (KSFM) supplemented with human recombinant epidermal growth factor and bovine pituitary extract.

Cell staining 20,000 HCC4017 and HBEC30KT cells were plated in 8-well glass chamber plate. Incubation with control IgG or bavituximab (2 μg/ml, provided by Peregrine Pharmaceuticals, CA) was initiated 24 hrs post plating. The primary antibody was incubated for 1 hr 37° C. Slides were washed in PBS two times and fixed with warm 4% paraformaldehyde (PFA) for 5-10 min at room temperature (RT) followed by washing 3 times with PBS. PFA was quenched with 50 mM NH4Cl (in PBS) for 5 min and washed 3 times with PBS. Reactivity was detected with goat-anti human Cy2 secondary antibody (1:1000) for 1 hr at 37° C. To visualize the cytoskeleton cells were permeabilized with PBS+0.5% Triton-X100 for 5 min at room temperature, washed 2 times with PBS and stained with Texas Red conjugated phalloidin (1:200) for 20 min. Slides were then mounted with Prolong Gold with DAPI (Invitrogen), cover slipped and evaluated by Olympus BX43 fluorescence microscope.

Lipid ELISA-like binding assay

Lipids (Avanti Polar Lipids) were dissolved in hexane at 10 μg/ml and coated on to Immulon 1B "U" bottom microtiter plates (ThermoFisher, MA). Hexane was evaporated at room temp (in the hood) and the plates were blocked with 200 μl of 1% BSA in PBS for 1 hour. Plates were washed with 3× PBS. Serial dilutions (500 nM to 3.9 nM for PS vs PC assay—FIG. 58A and 275 nM to 2.2 nM for other lipid binding assay—FIG. 59A) of biotinylated PPS1D1 was dissolved in blocking buffer and added to wells (100 μl/well) and incubated for 1 hr on shaker. Plates were washed with 5× PBS and binding was detected with streptavidin-HRP (1:2000 in blocking buffer) followed by 100 μl OPD (Sigma-Aldrich). The reaction was stopped with 100 μl 0.18M H2SO4 and absorbance was read at 490 nm using the spectrophotometer (Spectramax i3, Molecular Devices, CA).

Annexin V competition on lipid ELISA

Lipids (Avanti Polar Lipids) were dissolved in chloroform at 10 μg/ml and coated on to Immulon 1B "U" bottom microtiter plates (ThermoFisher, MA). Chloroform was evaporated at room temp (in the hood) and plates were blocked with 200 μl of 1% BSA for 1 hour. Plates were washed with 3× PBS. Biotinylated PPS1D1 dissolved in blocking buffer was added and incubated for 1 hour at room temp. Plates were washed with 3× PBS and 2× Annexin binding buffer. 100 nM Annexin V was added to the wells and incubated for 20 mins. Plates were washed with 3×PBS. Binding was detected with streptavidin-HRP (1:1000 in blocking buffer) followed by 100 μl OPD (Sigma-Aldrich, MO). The reaction was stopped with 100 μl 0.18M H2SO4 and absorbance was read at 490 nm using the spectrophotometer (Spectramax i3, Molecular Devices, CA).

Liposome binding assay

Liposome binding assays were performed using two different types of liposomes, one containing 100 mol % 1-palmitoyl-2-oleoyl-sn-glycero-3-phosphocholine (POPC) and, another containing 85 mol %-15 mol % 1,2-dioleoylsn-glycero-3-phospho-L-serine (DOPS). (See detailed experimental procedures below).

Membrane lipid array

Membrane lipid arrays were purchased from Echelon Biosciences, UT. Membranes were blocked in 3% BSA in TBST for 1 hour and then incubated with 2.5 μg/ml of biotin-PPS1D1 for 2 hours. Membranes were washed with TBST and incubated with Streptavidin-HRP antibody at 1:750 dilutions (BioLegend,CA). After washing, signal was detected with ECL western blotting substrate (Life technologies, CA) using Fluorchem 8900 (Alpha Innotech Imaging system).

Cell staining with Annexin V for PS expression

HCC4017, H460, HCC95, H1693,H1395 and HBEC30KT cells were dissociated from tissue culture plates with enzyme free cell dissociation buffer (Life technologies, CA). ~0.1×106 cells were suspended in binding buffer (0.01 M HEPES/NaOH (pH 7.4), 0.14 M NaCl, and 2.5 mM CaCl2) and were treated with FITC-Annexin V and PI. After 15 minute incubation at RT, cells were analyzed by BD Accuri™ C6 flow cytometer.

Cell viability assay

HCC4017, H460, HCC95, H1693, H1395 and HBEC30KT cells were grown in clear bottom 96 well plates. On second day, lung cancer cells were treated with PPS1, PPS1D1 and control PC462D1 in RPMI medium with 10% FBS containing 3% BSA. HBEC30KT was treated with PPS1, PPS1D1 and control PC462D1 in KSFM media with 3% BSA. On day 3, 20 μl of CellTiter 96® AQueous One Solution (Promega, Wis.) was added to each well and absorbance was measured at 490 nm.

Cell staining with Hoechst 33342 and Propidium iodide 10,000 cells of HCC4017, H460, HCC95, H1693,H1395 and HBEC30KT were plated on chamber slides (Lab-Tek, Thermo Fisher, MA). On second day, cells were treated with PPS (1 μM and 20 μM), control PC462D1 (20 μM) and 0.005% Benzalkonium chloride (BAC) in RPMI medium with 10% FBS containing 3% BSA (KSFM media with 3% BSA for HBEC30KT). Chamber slides were washed with PBS three times. Cells were then stained with Hoechst 33342 (10 μg/ml) for 30 min in dark. Chamber slides were washed with 3× PBS. Cells were then stained with propidium iodide (1 mg/ml) for 15 mins. Cells were washed with 3× PBS and imaged using Fluorescence Microscope (Olympus BX-53).

Magnetic bead binding assay

The assay was done using Dynabeads M-280 Streptavidin (Invitrogen). Nearly 9×106 beads were transferred, re-suspended in PBS with 0.1% BSA. Biotinylated PPS1D1 and control PC462D1 were added to each vial and incubated for 30 minutes at RT. The beads were washed 3× PBS and 1 million H460 cells were added to each tube and incubated for 30 minutes at RT with gentle shaking. The bead bound cells were isolated by placing the vial on the magnet and after removing supernatant, cells were counted with hemocytometer.

Animal studies

All animals were housed in a pathogen-free facility with continuous access to food and water. Mice were purchased from the core breeding facility at UT Southwestern. Six to eight-week-old female NOD/SCID mice were injected with 2.5×106 H460 cells subcutaneously. Tumor volume was followed by twice weekly measurements with Vernier calipers. Animals were randomized and treatment was initiated with mean tumor volume of each group was 100 mm3. Four different groups used were: (I) control PC462D1, (II)

PPS1D1, (III) docetaxel, and (IV) combination of PPS1D1+ docetaxel. Mice (n=8/group) were treated with PPS1D1 or PC462D1 in saline by ip injection at a dose of 0.25 mg/mouse, 3 times per week on a M-W-F schedule. Docetaxel from the UT Southwestern Clinical pharmacy was diluted in saline and delivered 2x/week ip at 5 mg/kg. Animals were sacrificed after 4 weeks of therapy. Tumor tissue was snap frozen, sectioned and stained with antibodies specific for phospho-Histone H3 (Millipore, #06-570) and cleaved caspase 3 (Cell Signaling, #9664). Reactivity was developed with appropriate fluorescently conjugated secondary antibodies (Jackson ImmunoResearch) and mounted with Prolong Gold with DAPI (Invitrogen), coverslipped and evaluated by fluorescence microscopy.

FIG. 59 depicts PPS1D1 binding studies on large panel of lipids. (A) ELISA binding assay of PPS1D1-FITC with Phosphatidylethanolamine (PE), Sphingomyelin (SM), Phosphatidic Acid (PA), Phosphatidylinositol (PI) and Phosphatidylglycerol (PG). Only PA, PI and PG showed binding to PPS1D1-FITC (Error bars represent standard deviation) (B) Lipid dot blot showing binding of biotinylated-PPS1D1 with membrane phospholipids PS, PA, PG and PI, but not to PC, DAG, PE and SM. (C) Quantification of lipid-blot assay figure shown in (B). (D) Net charges of PA, PE, PC, PS, PG, PI and DAG lipids at neutral pH (Adapted from, Lehninger Principles of Biochemistry, 5th Edition. Chapter 10, pg:351).

FIG. 60 depicts PPS1D1 binding and activity evaluation on panel of lung cancer cells. (A) PS expression levels of lung cancer cell lines HCC4017, H460, HCC95, H1693, H1395 and normal HBEC30KT by binding with FITC-Annexin V. Lung cancer cells exhibited high PS levels while HBEC30KT has lower levels of PS (Error bars represent standard deviation). (B) Standard MTS cell viability data for the treatment of PPS1D1 and control PC462D1 on same lung cancer cells lines and HBEC30KT cells shown in (A). PPS1D1 at 20 µM caused strong cell cytotoxicity on cancer cells, but not on HBEC30KT. (C) Treatment of same lung cancer cells lines and HBEC30KT shown in (A) with Propidium iodide (PI) and Hoechst 33342 dyes. PI stained nuclei of all the cancer cell lines at 20 µM of PPS1D1, but not HBEC30KT cells. A known cell membrane damaging agent, BAC treatment caused PI stain on all the cells lines tested.

FIG. 61 depicts comprehensive in vitro activity validation of PPS1D1 on H460 lung cancer cell line. (A) Magnetic bead pulls down of H460 with PPS1D1, but not with control compound PC462D1 (Error bars represent standard deviation). (B) Standard MTS cell viability assay of H460 and normal HBEC30KT cells treated with PPS1D1, PPS1 and PC462D1. Only PPS1D1 induce the cell cytotoxicity on HCC4017, while no effect on normal HBEC30KT cells. (C) Flow cytometry studies of PPS1D1-FITC binding to H460 cells in the presence of Propidium iodide (PI). H460 cell population significantly moved to double positive region when PPS1D1-FITC concentration increases. (D) Quantification of FITC and PI double stained region.

FIG. 62 depicts that in vivo treatment of PPS1D1 on mice bearing H460 xenografts suppresses tumor growth. (A) Mice bearing subcutaneous H460 xenografts were treated with PPS1D1 (D1, n=8, 0.25 mg/mouse, 3 times per week on a M-W-F schedule), PC462D1 (Control, n=8, 0.25 mg/mouse, 3 times per week on a M-W-F schedule), docetaxel (n=8, 5 mg/kg, 2x/week), or the combination of PPS1D1 and docetaxel (n=8, combo). Mean+/−SEM tumor volume is displayed. PPS1D1 displayed tumor burden effects as a single agent as well as in combination with docetaxel. (B, C) Tumor tissue harvested after 4 weeks of therapy was evaluated for cell proliferation (B, phopshohistone H3) and apoptosis (C, cleaved caspase-3) by immunofluorescence. DAPI was used as a counterstain and to normalize quantification of reactivity. *p<0.05; p<0.01; *p<0.005. The PPS1D1 and docetaxel combination therapy strongly reduce cell proliferation and induce apoptosis.

FIG. 63 depicts characterization of PPS1: (A) Chemical structure of PPS1, (B) Analytical HPLC of PPS1, (C) MALDI-TOF spectrum of PPS1.

FIG. 64 depicts characterization of PPS1D1: (A) Chemical structure of PPS1D1, (B) Analytical HPLC of PPS1D1, (C) MALDI-TOF spectrum of PPS1D1.

FIG. 65 depicts characterization of biotinylated PPS1D1: (A) Chemical structure of biotinylated PPS1D1, (B) Analytical HPLC of biotinylated PPS1D1, (C) MALDI-TOF spectrum of biotinylated PPS1D1.

FIG. 66 depicts characterization of FITC-PPS1D1: (A) Chemical structure of FITC-PPS1D1, (B) Analytical HPLC of FITC-PPS1D1, (C) MALDI-TOF spectrum of FITC-PPS1D1.

FIG. 67 depicts characterization of PC462: (A) Chemical structure of PC462, (B) Analytical HPLC of PC462, (C) MALDI-TOF spectrum of PC462.

FIG. 68 depicts characterization of PC462D1: (A) Chemical structure of PC462D1, (B) Analytical HPLC of PC462D1, (C) MALDI-TOF spectrum of PC462D1.

FIG. 69 depicts characterization of PPS1: (A) Chemical structure of PPS1 (cleaved with cyanogen bromide) synthesized on Tentagel MB-NH2 beads, (B) MALDI-TOF spectrum of PPS1 after cleavage from Tentagel MB-NH2 beads.

FIG. 70 depicts characterization of PC462: (A) Chemical structure of PC462 (cleaved with cyanogen bromide) synthesized on Tentagel MB-NH2 beads, (B) MALDI-TOF spectrum of PC462 after cleavage from Tentagel MB-NH2 beads.

FIG. 71 depicts unlabeled Annexin V did not compete with FITC-PPS1D1 binding on an ELISA-like binding assay.

FIG. 72 depicts unlabeled Annexin V did not compete with FITC-PPS1 binding to liposomes made with 85% PC-15% PS.

FIG. 73 depicts unlabeled PPS1 did not compete with FITC-Annexin V binding to liposomes made with 85% PC-15% PS.

FIG. 74 depicts liposomes (85% PC-15% PS) incorporated with fluorophore NBD and then competed with Annexin V at 10, 50 and 100 nM. None of these conditions were able to remove liposomes from beads.

FIG. 75 depicts ELISA binding assay of PPS1D1-FITC and PPS1D1-Glu-FITC [replacing one of the positively charged lysine residues (3rd residue from C-terminal) of PPS1D1] with phosphotidylserine (PS) indicates that PPS1D1-Glu-FITC loses its binding ability when positive charges are converted to negative charges.

FIG. 76 depicts MTS assay results of PPS1D1 and control PC462D1 on HCC4017 cell line evaluated at 6, 12 and 24 hours.

Experimental procedure 1: Synthesis of PPS1. NovaSyn TGR resin (EMD Millipore, MA) 150 mg were swelled in dimethylformamide (DMF, Acros Organics, NJ) for 30 min at room temperature in a 5 ml reaction vessel (intavis AG, Germany). The reaction vessels were drained and treated with 2 M Fmoc-Met-OH amino acid (with coupling agents HBTU, HOBt and DIPEA) in anhydrous DMF (Sigma-Aldrich, MO). Then the reaction vessel was placed on a shaker for overnight, drained and washed with DMF (5 ml×10 times). Fmoc group was removed by treating the beads with 20% piperidine (Sigma-Aldrich, MO) for 10 minutes twice on the shaker. After washing the reaction vessel, subsequent amino acids Fmoc-D-Lys(Boc)-OH and Fmoc-Lys(Boc)-OH were added (for 2 h reaction time) with each time removing Fmoc group as described above. Then the 5-mer peptoid region was synthesized using microwave assisted peptoid synthesis protocol. Reaction vessels were treated with 2 M Bromoacetic acid in anhydrous DMF (1 ml) and 2M DIC in anhydrous DMF (1 ml), gently shaken for 30 seconds and microwaved (1000 W) for 15 seconds with the power set at 10%. The beads were shaken again for about 15 seconds and microwaved another round as described above. The reaction vessel was drained and washed with DMF (2 ml×10 times). Then the reaction vessel was treated with 1 M solution of the primary amine (2 ml) and microwaved two times for 15 seconds after gentle shaking. The primary amines used were Boc-Diaminobutane, 4-methoxybenzylamine, (R)-Methylbenzylamine, Piperonylamine and (R)-Methylbenzylamine. At the end of synthesis the beads were washed with Dichloromethane (DCM) (2 ml×10 times), and the compound was cleaved with 2.5 ml of cleavage cocktail containing 95% Triflouoroacetic acid (TFA), 2.5% water and 2.5% Triisopropylsialine(TIS) on the shaker for 2 hours and compound was purified using HPLC. Synthesis was confirmed using MALDI-TOF MS (Voyager DePro, AB Systems, MA).

Experimental procedure 2: Synthesis of PPS1D1. PPS1D1 was synthesized on NovaSyn TGR resin (EMD Millipore, MA). First, Fmoc-Lys(Fmoc)-OH was coupled overnight as the central linker, and both Fmoc groups were removed simultaneously allowing two copies of the sequence to be built on two amine groups of this central Lys. First three amino acids, Fmoc-Met-OH, Fmoc-D-Lys(Boc)-OH and Fmoc-Lys(Boc)-OH were loaded to the resin after Fmoc removal each time. Then 5-mer peptoid region containing Boc-Diaminobutane, 4-methoxybenzylamine, (R)-Methylbenzylamine, Piperonylamine and (R)-Methylbenzylamine was completed using microwave assisted peptoid synthesis protocol. At the end of synthesis the beads were washed with Dichloromethane (DCM) (2 ml×10 times), and the compound was cleaved with 2.5 ml of cleavage cocktail containing 95% Triflouoroacetic acid (TFA), 2.5% water and 2.5% Triisopropylsialine(TIS) on the shaker for 2 hours and compound was purified using HPLC. Synthesis was confirmed using MALDI-TOF MS (Voyager DePro, AB Systems, MA).

Experimental procedure 3: Synthesis of biotinylated PPS1D1. This synthesis was carried out on NovaSyn TGR resin (EMD Millipore, MA). Fmoc-Cys(Trt)-OH (HOBt, HBTU,DIPEA) was loaded as first amino acid on to the resin and the rest of the PPS1D1 synthesis was conducted as described previously. At the end 95% TFA, 2.5% water and 2.5% TIS mixture was used to cleave the compound from resin and to remove the side chain protection. Then the TFA was evaporated and resulting solid compound was dissolved in 1:1 water:Acetonitrile (ACN) mixture. This solution was subjected to HPLC purification using the solvent conditions starting from 100:0 water:ACN to 50:50 water:ACN. The purified compound was lyophilized to obtain the dry product. Biotin-5-maleimide (Thermofisher, MA) dissolved in DMSO was coupled to this compound (1 M:1 M ratio) in buffer solution at pH 7. The coupled Biotinylated PPS1D1 compound was purified with HPLC. Synthesis was confirmed using MALDI-TOF MS (Voyager DePro, AB Systems, MA).

Experimental procedure 4: Synthesis of FITC-PPS1D1. This synthesis was carried out on NovaSyn TGR resin (EMD Millipore, MA). Fmoc-Cys(Trt)-OH (HOBt, HBTU, DIPEA) was loaded as first amino acid on to the resin and the rest of the PPS1D1 synthesis was conducted as described previously. At the end 95% TFA, 2.5% water and 2.5% TIS mixture was used to cleave the compound from resin and to remove the side chain protection. Then the TFA was evaporated and resulting solid compound was dissolved in 1:1 water:Acetonitrile (ACN) mixture. This solution was subjected to HPLC purification using the solvent conditions starting from 100:0 water:ACN to 50:50 water:ACN. The purified compound was lyophilized to obtain the dry product. Fluorescein-5-maleimide (Thermofisher, MA) dissolved in DMSO was coupled to this compound (1 M:1 M ratio) in buffer solution at pH 7. The coupled FITC-PPS1D1 compound was purified with HPLC.

Experimental procedure 5: Synthesis of control compound PC462. PC462 was synthesized on NovaSyn TGR resin (EMD Millipore, MA).First amino acid Fmoc-Met-OH was coupled overnight, the next two amino acids Fmoc-D-Lys(Boc)-OH and Fmoc-Gly-OH were loaded to the resin with removing Fmoc group each time. Then the 5-mer peptoid region containing Allyamine and 2-Methoxyethylamine was synthesized using microwave assisted peptoid synthesis protocol as described previously. At the end of synthesis the beads were washed with Dichloromethane (DCM) (2 ml×10 times), and peptoid was cleaved with 2.5 ml of cleavage cocktail containing 95% Triflouoroacetic acid (TFA), 2.5% water and 2.5% Triisopropylsialine(TIS) on the shaker for 2 hours and compound was purified using HPLC. Synthesis was confirmed using MALDI-TOF MS (Voyager DePro, AB Systems).

Experimental procedure 6: Synthesis of control compound PC462D1. PC462D1 was synthesized on NovaSyn TGR resin (EMD Millipore, MA). First, Fmoc-Lys(Fmoc)-OH was coupled overnight as the central linker, and both Fmoc groups were removed simultaneously allowing two copies of the sequence to be built on two amine groups of this central Lys. Then first three amino acids Fmoc-Met-OH, Fmoc-D-Lys(Boc)-OH and Fmoc-Gly-OH were loaded to the resin with removing Fmoc group each time. Then the 5-mer peptoid region containing Allyamine and 2-Methoxyethylamine was synthesized using microwave assisted peptoid synthesis protocol as described previously. At the end of synthesis the beads were washed with Dichloromethane (DCM) (2 ml×10 times), and peptoid was cleaved with 2.5 ml of cleavage cocktail containing 95% Triflouoroacetic acid (TFA), 2.5% water and 2.5% Triisopropylsialine(TIS) on the shaker for 2 hours and compound was purified using HPLC. Synthesis was confirmed using MALDI-TOF MS (Voyager DePro, AB Systems).

Experimental procedure 7: Synthesis of PPS1 on Tentagel. This synthesis was carried out on Tentagel MB-NH2 beads(Rapp Polymere, Germany).First amino acid Fmoc-Met-OH was coupled overnight and the rest of the PPS1 synthesis was conducted as described previously. At the end cyanogen bromide cleavage was performed. Small amounts of beads were removed from reaction vessels before storage and washed with DCM (2 ml×3 times). 30 mg/ml CNBr solution (1 ml) was prepared in 5:4:1 Acetonitrile:Acetic acid:water. 50 µl from this solution was added to the beads and kept on the shaker overnight. CNBr solution was allowed to evaporate and 1:1 mixture of acetonitrile and water was added to the beads and resulting solution was used to confirm mass of the compound.

Experimental procedure 8: Synthesis of PC462 on Tentagel. This synthesis was carried out on Tentagel MB-NH2 beads (Rapp Polymere, Germany).First amino acid Fmoc-Met-OH was coupled overnight and the rest of the PC462 synthesis was conducted as described previously. At the end cyanogen bromide cleavage was performed. Small amounts of beads were removed from reaction vessels before storage and washed with DCM (2 ml×3 times). 30 mg/ml CNBr solution (1 ml) was prepared in 5:4:1 Acetonitrile:Acetic acid:water. 50 µl from this solution was added to the beads and kept on the shaker overnight. CNBr solution was allowed to evaporate and 1:1 mixture of acetonitrile and water was added to the beads and resulting solution was used to confirm mass of the compound.

Experimental procedure 9: Magnetic bead pull down assay with PPS1. This assay was performed with Dynabeads M-280 Streptavidin (Life technologies, CA). First the beads were re-suspended in the original vial by vortexing. From this 14 µl of beads (approximately 9×106 beads) were transferred to a microcentrifuge tube and 500 µl of PBS with 0.1% BSA was added. The microcentrifuge tube containing the beads was placed on the magnet for 2 minutes and the supernatant was removed by aspiration. The beads were washed three times with 500 µl of PBS with 0.1% BSA. Then biotinylated PPS1D1 or PC462 were added to each vial and the reaction was incubated for 30 minutes at room temperature with gentle shaking. Then the beads were washed 3 times with 500 µl of PBS with 0.1% BSA. H460 cells (1×106 cells in 1 ml of RPMI with 1% BSA) were added to each vial and incubated for 30 minutes at room temperature with gentle shaking. The supernatant was removed and numbers of bead bound cells were calculated using hemocytometer.

Experimental procedure 10: MTS viability assay on H460 cells. 5,000 of H460 cells and HBEC30KT cells were grown in each well of a white clear bottom 96 well plates (Corning Inc, NY) on day 1 of the experiment. On day 2, four experimental sets were designed to treat the wells with graded concentrations of PPS1, PPS1D1 and control compound PC462D1 prepared in RPMI medium containing 5% FBS with 3% BSA for H460 cells treatment and PPS1D1 on Keratinocyte-SFM with 3% BSA media for HBEC30KT treatment. Eight graded concentrations ranging from 0.01 µM-50 µM were used for all compounds and each concentration was done in triplicates. 6 wells were left untreated as controls. On day 4, media was removed from each well and treatment was repeated as described previously. On day 5, 20 µl of CellTiter 96® AQueous One Solution Cell Proliferation Assay (Promega, Wis.) was added to each well and absorbance was measured at 490 nm using a plate reader 2 hours after treatment.

Experimental procedure 11: Competition on liposomes.

Liposome preparation. 1-palmitoyl-2-oleoyl-sn-glycero-3-phosphocholine (POPC) and 1,2-dioleoyl-sn-glycero-3-phospho-L-serine (DOPS) were purchased from Avanti Polar Lipids (Alabaster, AL). POPC and DOPS were mixed in an 85:15 molar ratio for PS containing liposomes. For PC containing liposomes POPC alone was used. Dried lipids were re-suspended in Tris buffer solution (10 mM, pH 7.4) to 1 mg/ml. This stock was fully mixing and exposed to more than 5 freeze-thaw cycles. A mini-extruder from Avanti Polar Lipids and Whatman Nucleopore Track-Etch 1.0 µm filters from GE Healthcare were used to produce liposomes. To produce 7-nitro-2-1,3-benzoxadiazol-4-yl (NBD) labeled liposomes 1 mol % was added to lipid mixes.

Unlabeled Annexin V vs FITC-PPS1 competition. 0.1 mM liposomes (85 mol % POPC, 15 mol % DOPS) were incubated with incubated with 50 nM Annexin V in Binding Buffer (0.01 M HEPES/NaOH (pH 7.4), 0.14 M NaCl, and 2.5 mM CaCl2) with 3% BSA for 1hour. FITC PPS1 was added and the solution was incubated for 1 hour at room temperature. The binding of FITC-PPS1 to liposomes was analyzed by BD Accuri™ C6 flow cytometer (Becton-Dickinson, NJ). All data were analyzed using BDAccuriC6 software.

Unlabeled PPS1 vs FITC-Annexin V competition. 0.1 mM liposomes (85 mol % POPC, 15 mol % DOPS) were incubated PPS1 in Binding buffer with 3% BSA for 1 hour. 50 nM FITC Annexin V was added to the solution and the solution was incubated for 1 hour at room temperature. The binding of FITC-Annexin V to liposomes was analyzed by BD Accuri™ C6 flow cytometer (Becton-Dickinson, NJ). All data were analyzed using BDAccuriC6 software.

Experimental procedure 12: On-bead competition assay. PPS1 and PC462 were synthesized on Tentagel beads. Organic solvent was removed and the beads were washed with 3 times with PBS. The beads were then incubated with PBS containing 3% BSA for 1 hour at room temperature. These beads were then incubated with 0.1 mM liposomes (84 mol % POPC, 15 mol % DOPS and 1 mol % NBD) for 2 hours at room temperature. Beads containing liposomes were the washed with binding buffer 3 times. 50 nM Annexin V was added to the beads and incubated for 2 hours at room temperature. Beads were then washed with binding buffer and imaged using fluorescence Microscope (Olympus BX-53).

Example 22

List of 12 amino acids used in the library
1. Lysine
2. Leucine
3. Valine
4. Phenylalanine
5. Asparagine
6. Glutamine
7. Aspartic acid
8. Glutamic acid
9. Histidine
10. Serine
11. Threonine
12. Glycine FIG. 77 depicts Edman sequencing graphs of PPS1 structure elucidation.

Genetic data profiles of HCC4017 & HBEC30KT. FIG. 78 depicts the PowerPlex 1.2 STR Fingerprinting results for HBEC30-KT and HCC4017 showing identity at 7/9 markers. The remaining two markers DS13S317 and vWA show loss of heterozygosity (red lines) in the tumor derived cell line (HCC4017).

Synthesis and characterization of control compound PC462 NovaSyn TGR resin (EMD Millipore, MA) 150 mg were swelled in dimethylformamide (DMF, Acros Organics, NJ) for 30 min at room temperature in a 5 ml reaction vessel (intavis AG, Germany). The reaction vessels were drained and treated with 2M Fmoc-Met-OH amino acid (with coupling agents HBTU, HOBt and DIPEA) in anhydrous DMF (Sigma-Aldrich, MO). Then the reaction vessel was placed on a shaker overnight, drained and washed with DMF (5 ml×10 times). Fmoc group was removed by treating the beads with 20% piperidine (Sigma-Aldrich, MO) for 10 minutes twice on the shaker. After washing the reaction vessel, subsequent amino acids Fmoc-D-Lys(Boc)-OH and Fmoc-Gly-OH were added (for 2 h reaction time) after removing Fmoc group as described above. Then the 5-mer peptoid region was synthesized using microwave assisted peptoid synthesis protocol. Reaction vessels were treated with 2M Bromoacetic acid in anhydrous DMF (1 ml) and 2M DIC in anhydrous DMF (1 ml), gently shaken for 30 seconds and microwaved (1000 W) for 15 seconds with the power set at 10%. The beads were shaken again for about 15 seconds and microwaved another round as described above. The reaction vessel was then drained and washed with DMF (2 ml×10 times). Then the reaction vessel was treated with 1M solution of the primary amine (2 ml) and microwaved two times for 15 seconds after gentle shaking. The primary amines used were Allyamine and 2-Methoxyethylamine. At the end of synthesis the beads were washed with Dichloromethane (DCM) (2 ml×10 times), and the compound was cleaved with 2.5 ml of cleavage cocktail containing 95% Triflouoroacetic acid (TFA), 2.5% water and 2.5% Triisopropylsialine(TIS) on the shaker for 2 hours and compound was purified using HPLC. Synthesis was confirmed using MALDI-TOF MS (Voyager DePro, AB Systems, MA).

FIG. 79 depicts the Chemical structure of PC462.
FIG. 80 depicts the MALDI-TOF spectrum of PC462.
FIG. 81 depicts the Analytical HPLC of PC462.

Synthesis and characterization of control compound PC462D1 PC462D1 was synthesized on NovaSyn TGR resin (EMD Millipore, MA).First, Fmoc-Lys(Fmoc)-OH was coupled overnight as the central linker, and both Fmoc groups were removed simultaneously allowing two copies of the sequence to be built on two amine groups of this central Lys. Then first three amino acids Fmoc-Met-OH, Fmoc-D-Lys(Boc)-OH and Fmoc-Gly-OH were loaded to the resin with removing Fmoc group each time. Then the 5-mer peptoid region containing Allyamine and 2-Methoxyethylamine was synthesized using microwave assisted peptoid synthesis protocol as described previously. At the end of synthesis the beads were washed with Dichloromethane (DCM) (2 ml×10 times), and peptoid was cleaved with 2.5 ml of cleavage cocktail containing 95% Triflouoroacetic acid (TFA), 2.5% water and 2.5% Triisopropylsialine(TIS) on the shaker for 2 hours and compound was purified using HPLC. Synthesis was confirmed using MALDI-TOF MS (Voyager DePro, AB Systems).

FIG. 82 depicts the Chemical structure of PC462D1.
FIG. 83 depicts the MALDI-TOF spectrum of PC462D1.
FIG. 84 depicts the Analytical HPLC of PC462D1.

Synthesis and characterization of PPS1 PPS1 was synthesized on: (I) TentaGel beads (Rapp polymere, Germany) for on-bead cell binding assay, and (II) NovaSyn TGR resin (EMD Millipore, MA) for all the other assays. First three amino acids, Fmoc-Met-OH, Fmoc-D-Lys(Boc)-OH and Fmoc-Lys(Boc)-OH were loaded to the resin after Fmoc removal each time. Then 5-mer peptoid region containing Boc-Diaminobutane, 4-methoxybenzylamine, (R)-Methylbenzylamine, Piperonylamine and (R)-Methylbenzylamine was completed using microwave assisted peptoid synthesis protocol. At the end of synthesis the beads were washed with Dichloromethane (DCM) (2 ml×10 times), and the compound was cleaved with 2.5 ml of cleavage cocktail containing 95% Triflouoroacetic acid (TFA), 2.5% water and 2.5% Triisopropylsialine(TIS) on the shaker for 2 hours and compound was purified using HPLC. Synthesis was confirmed using MALDI-TOF MS (Voyager DePro, AB Systems, MA).

FIG. 85 depicts the Chemical structure of PPS1.
FIG. 86 depicts the MALDI-TOF spectrum of PPS1.
FIG. 87 depicts the Analytical HPLC of PPS1.

Synthesis and characterization of PPS1D1 PPS1D1 was synthesized on NovaSyn TGR resin (EMD Millipore, MA). First, Fmoc-Lys(Fmoc)-OH was coupled overnight as the central linker, and both Fmoc groups were removed simultaneously allowing two copies of the sequence to be built on two amine groups of this central Lys. First three amino acids, Fmoc-Met-OH, Fmoc-D-Lys(Boc)-OH and Fmoc-Lys(Boc)-OH were loaded to the resin after Fmoc removal each time. Then 5-mer peptoid region containing Boc-Diaminobutane, 4-methoxybenzylamine, (R)-Methylbenzylamine, Piperonylamine and (R)-Methylbenzylamine was completed using microwave assisted peptoid synthesis protocol. At the end of synthesis the beads were washed with Dichloromethane (DCM) (2 ml×10 times), and the compound was cleaved with 2.5 ml of cleavage cocktail containing 95% Triflouoroacetic acid (TFA), 2.5% water and 2.5% Triisopropylsialine (TIS) on the shaker for 2 hours and compound was purified using HPLC. Synthesis was confirmed using MALDI-TOF MS (Voyager DePro, AB Systems, MA).

FIG. 88 depicts the Chemical structure of PPS1D1.
FIG. 89 depicts the MALDI-TOF spectrum of PPS1D1.
FIG. 90 Analytical HPLC of PPS1D1.

Synthesis and characterization of FITC-PPS1 This synthesis was carried out on NovaSyn TGR resin (EMD Millipore, MA). Fmoc-Cys(Trt)-OH (HOBt, HBTU,DIPEA) was loaded as first amino acid on to the resin and the rest of the PPS1 synthesis was conducted as described previously. At the end 95% TFA, 2.5% water and 2.5% TIS mixture was used to cleave the compound from resin and to remove the side chain protection. Then the TFA was evaporated and resulting solid compound was dissolved in 1:1 water:Acetonitrile (ACN) mixture. This solution was subjected to HPLC purification using the solvent conditions starting from 100:0 water:ACN to 50:50 water:ACN. The purified compound was lyophilized to obtain the dry product. Fluorescein-5-maleimide (Thermofisher, MA) dissolved in DMSO was coupled to this compound (1M:1 M ratio) in buffer solution at pH 7. The coupled FITC-PPS1D1 compound was purified with HPLC. Synthesis was confirmed using MALDI-TOF MS (Voyager DePro, AB Systems, MA).

FIG. 91 depicts the Chemical structure of FITC-PPS1.
FIG. 92: depicts the MALDI-TOF spectrum of FITC-PPS1.
FIG. 93 depicts the Analytical HPLC of FITC-PPS1.

Synthesis and characterization of biotinylated PPS1 This synthesis was carried out on NovaSyn TGR resin (EMD Millipore, MA). Fmoc-Cys(Trt)-OH (HOBt, HBTU,DIPEA) was loaded as first amino acid on to the resin and the rest of the PPS1 synthesis was conducted as described previously. At the end 95% TFA, 2.5% water and 2.5% TIS mixture was used to cleave the compound from resin and to remove the side chain protection. Then the TFA was evaporated and resulting solid compound was dissolved in 1:1 water:Acetonitrile (ACN) mixture. This solution was subjected to HPLC purification using the solvent conditions starting from 100:0 water:ACN to 50:50 water:ACN. The purified compound was lyophilized to obtain the dry product. Biotin-5-maleimide (Thermofisher, MA) dissolved in DMSO was coupled to this compound (1M:1 M ratio) in buffer solution at pH 7. The coupled Biotinylated PPS1 compound was purified with HPLC. Synthesis was confirmed using MALDITOF MS (Voyager DePro, AB Systems, MA).

FIG. 94 depicts the Chemical structure of biotinylated PPS1.
FIG. 95: depicts the MALDI-TOF spectrum of biotinylated PPS1.

FIG. 96: depicts the Analytical HPLC of biotinylated PPS1.

Synthesis and characterization of PPS1-(Eu3+)-DTPA PPS1-(Eu3+)-DTPA was synthesized on NovaSyn TGR resin (EMD Millipore, MA). The PPS1 synthesis was conducted as described previously. The beads with compound PPS1 having secondary amine at the terminal were then coupled with 0.2M Fmoc-amino-ethyloxy-ethyloxyacetyl (Fmoc-AEEAc-OH) using coupling reagent HBTU (0.2M) and HOBt (0.2 M) in presence of DIPEA (0.4M) in DMF (2 mL) at room temperature for overnight. After washing with DMF (2 mL×10 times), Fmoc group was removed by 20% piperidine solution in DMF [2 times×(2 mL×10 min)]. The resulting free terminal amine was then coupled to DTPA using same peptide coupling reaction conditions. The beads were then treated with 95% TFA, 2.5% triisopropylsilane, and 2.5% water mixture for 4 h. This solution was subjected to HPLC purification using the solvent conditions starting from 100:0 water:ACN to 50:50 water:ACN. The purified compound was lyophilized to obtain the dry product. The metal complexation was then performed overnight with a 0.2 M EuCl3 solution at pH 6.3. Synthesis was confirmed using MALDI-TOF MS (Voyager DePro, AB Systems, MA).

FIG. 97 depicts the Chemical structure of PPS1-(Eu3+)-DTPA.

FIG. 98 depicts the MALDI-TOF spectrum of PPS1-(Eu3+)-DTPA.

FIG. 99 depicts the Analytical HPLC of PPS1-(Eu3+)-DTPA.

Synthesis and characterization of scramble PC2 on tentagel beads This synthesis was carried out on TentaGel beads (Rapp polymere, Germany) for on-bead cell binding assay. First, amino acid Fmoc-Met-OH was coupled overnight and Fmoc group was removed. Then the 4-mer peptoid region containing 4-Methoxybenzylamine, (R)-Methylbenzylamine, Boc-Diaminobutane and Piperonylamine was synthesized using microwave assisted peptoid synthesis protocol as described previously. Then amino acid Fmoc-DLys(Boc)-OH was coupled overnight followed by Fmoc-Lys(Boc)-OH after Fmoc removal. In the end, peptoid (R)-Methylbenzylamine was added through microwave assisted synthesis described previously. At the end of synthesis, the beads were washed with Dichloromethane (DCM) (2 ml×3 times), and treated with 2.5 ml of 95% Trifluoroacetic acid (TFA), 2.5% water and 2.5% Triisopropylsilane (TIS) on the shaker for 2 hours to remove the side chain protection. Reaction vessel was drained, washed with DMF (2 ml×3 times) and stored in anhydrous DMF at 400 C. Synthesis was confirmed using MALDI-TOF MS (Voyager DePro, AB Systems) after cyanogen bromide cleavage.

FIG. 100 depicts the Chemical structure of PC2.

FIG. 101 depicts the MALDI-TOF spectrum of PC2.

Synthesis and characterization of scramble PC2D1 for MTS PC2D1 was synthesized on NovaSyn TGR resin (EMD Millipore, MA). First, Fmoc-Lys (Fmoc)-OH was coupled overnight as the central linker, and both Fmoc groups were removed simultaneously allowing two copies of the sequence to be built on two amine groups of this central Lysine. Then first amino acid Fmoc-Met-OH was loaded to the resin after removing Fmoc group. Then the 4-mer peptoid region containing 4-Methoxybenzylamine, (R)-Methylbenzylamine, Boc-Diaminobutane and Piperonylamine was synthesized using microwave assisted peptoid synthesis protocol as described previously. Then amino acid Fmoc-DLys(Boc)-OH was coupled overnight followed by Fmoc-Lys(Boc)-OH after Fmoc removal. In the end, peptoid (R)-Methylbenzylamine was added through microwave assisted synthesis described previously. At the end of synthesis the beads were washed with Dichloromethane (DCM) (2 ml×10 times), and peptoid was cleaved with 2.5 ml of cleavage cocktail containing 95% Trifluoroacetic acid (TFA), 2.5% water and 2.5% Triisopropylsilane (TIS) on the shaker for 2 hours and compound was purified using HPLC. Synthesis was confirmed using MALDI-TOF MS (Voyager DePro, AB Systems).

FIG. 102 depicts the Chemical structure of PC2D1.

FIG. 103 depicts the MALDI-TOF spectrum of PC2D1.

FIG. 104 depicts the Analytical HPLC of PC2D1.

Compound synthesis. All the amino acids were purchased from EMD Millipore, MA and all the primary amines from Sigma-Aldrich, MO. O-Benzotriazole-N,N,N',N'-tetramethyl-uronium-hexafluoro-phosphate (HBTU) and N-Hydroxybenzotriazole H2O (HOBt) were purchased from AnaSpec, CA. Applied Biosystems Voyager DePro MALDI mass spectrometer was used in positive reflector mode to acquire MALDI-TOF mass spectra. Alpha-Cyano-4-hydroxycinnamic acid (Sigma Aldrich, MO) was used as matrix. HPLC purification was performed in a Waters 1525 Binary HPLC pump connected to Waters 2487 Dual λ Absorbance Detector using Protein & Peptide C18 300A°, 22×250 mm, 10 micron column from Grace Davison Discovery Sciences. Compound separation was carried out at room temperature using Acetonitrile (ACN; Honeywell, N.J.) and water containing 0.1% Trifluoroacetic acid (TFA; Sigma Aldrich, MO).

Library synthesis. The basic structure of the library consists of three amino acids followed by 5-mer diversified peptoid region. TentaGel macrobeads 2 g (140-170 μm; substitution: 0.48 mmol/g resin; Rapp Polymere, Germany) were swelled in extra pure dimethylformamide (DMF, Acros Organics, NJ) for 30 min at room temperature in a 5 ml reaction vessels (intavis AG, Germany). The reaction vessels were drained and treated with premixed 0.4M Fmoc-Met-OH amino acid (Sigma-Aldrich, MO) and 0.4M HBTU in anhydrous DMF containing 0.8M N-methyl morphaline (NMM, 12 ml, Sigma-Aldrich, MO). Then the reaction vessels were placed on a shaker for overnight, after which they were drained and washed with DMF (5 ml×10 times). Fmoc group was removed by treating the beads with 20% piperidine (Sigma-Aldrich, MO) for 10 minutes twice on the shaker. After washing the resins, subsequent amino acid Fmoc-D-Lys(Boc)OH was added (for 2 h reaction time) and Fmoc group was removed as described previously. The rest of the synthesis was achieved using the split-pool synthesis protocol. The beads were equally distributed into 12 reaction columns and each of the following amino acids was added to each one of them: Fmoc-Gly-OH, Fmoc-Leu-OH, Fmoc-Val-OH, Fmoc-Phe-OH, Fmoc-Asn-OH, Fmoc-Glu(Trt)-OH, Fmoc-Gln(Ot-Bu)-OH, Fmoc-Asp(Ot-Bu)-OH, Fmoc-His(Trt)-OH, Fmoc-Ser(t-Bu)-OH, Fmoc-Thr(tBu)-OH, Fmoc-Lys(Boc)-OH. The beads from all 12 reaction columns were pooled together, Fmoc group was removed and the beads were equally divided into 8 reaction columns for microwave (1000 W) assisted peptoid synthesis steps. Each of the reaction vessels were treated with 2M Bromoacetic acid in anhydrous DMF (1 ml) and 2M DIC in anhydrous DMF (1 ml), gently shaken for 30 seconds and microwaved (1000 W) for 15 seconds with the power set at 10%. The beads were shaken again for about 15 seconds and microwaved another round as described above. The reaction vessels were drained and washed with DMF (2 ml×10 times). Then each of the reaction vessels was treated with 1M solution of the primary amines (2 ml) and microwaved two times for 15 seconds after gentle shaking. The beads were washed, pooled and divided equally into 8 reaction columns and subjected to addition of next peptoid residue. This procedure was repeated until 5-mer peptoid region was completed. At the end of synthesis, the beads were washed with Dichloromethane (DCM) (2 ml×3 times), and treated with 2.5 ml of 95% Triflouoroacetic acid (TFA), 2.5% water and 2.5% Triisopropylsialine (TIS) on the shaker for 2 hours to remove the side chain protection and were neutralized with 10% diisopropylethylamine in DMF. Reaction vessel was drained, washed with DMF (2 ml×3 times) and stored in anhydrous DMF at 40 C.

On bead two color binding assay for combinatorial library screen using HCC4017 cells and HBEC30KT cells. Nearly 100,000 peptoid library beads were washed two times in RPMI medium (Sigma-Aldrich, MO) with 5% fetal bovine serum (FBS) and equilibrated in the same medium containing 2% Bovine Serum Albumin (BSA, Sigma-Aldrich, MO) for 1 hour in three polypropylene tubes. HCC4017 and HBEC30KT cells were removed from culture plates with GIBCO enzyme free cell dissociation buffer (Invitrogen, NY) 2 ml per plate (5 minutes for HCC4017 and 20 minutes for HBEC30KT) at 370 C. HCC4017 cells were washed and suspended in RPMI medium with 5% FBS. HBEC30KT cells were washed and suspended in KSFM medium (Life technologies, CA). Cells were counted and distributed in three 1.5 ml microcentrifuge tubes (total of six tubes for both cell lines) with 1×106 cells in 1ml of media per each tube. Then the cell labeling procedure was conducted as follows: to prepare 10 nM labeling solution (typical working concentration is 2-15 nM), pre-mix 1 µl each of Qtracker reagent (Invitrogen) A and B in a 1.5 ml microcentrifuged tubes (prepared three tubes for each color) and incubated for 5 minutes at room temperature. 0.2 ml of respective medium was added to each tube and vortexed for 30 seconds. 1×106 cells were added to each tube (three HCC4017 and three HBEC30KT) containing the labeling solution and incubated at 37° C. for 60 minutes. HCC4017 cells were labeled with Qtracker 655 (red color) and HBEC30KT cells labeled with Qtracker 565 (green color). Cells were twice washed with RPMI medium with 5% FBS and re-suspended in RPMI media with 5% FBS and 1% BSA (3 mL for each type). Labeled cells were visualized with DAPI filter of BX-51 fluorescence microscope (Olympus, Pa.) with a color camera. Both cell types were mixed thoroughly and pipetted up and down several times to break the clumps. 2 ml of cell suspension mixture was added to each of the beads containing (approximately 33,000 beads) three polypropylene tubes and incubated at room temperature with gentle shaking for 30 minutes. (Final cell density for each cell type was 0.5×106 and the total cell density was 1×106). During incubation, cell binding to the beads were checked time to time at about 10 minutes intervals to make sure not to over equilibrate, which could increase non-specific binding of cells to the beads. The beads were gently washed two times with RPMI medium and visualized under the fluorescent microscope using DAPI filter.

Isolation and preparation of beads for sequencing Single positive bead containing fluorescently tagged cells (red color) was identified using a fluorescent microscope under 2.5× objective magnification and removed manually with a 20 µl pipette with medium size pipette tips. Care was taken to avoid picking up of the beads with both red and green cells. Selected beads were washed three times with 1% SDS and boiled in the same solution for 45 minutes to strip off bound cells and proteins. Finally the beads were washed three times with water. Single bead placed on Edman sequencing cartridges was used for sequencing.

Cyanogen Bromide (CNBr) cleavage of beads. Small amounts of beads were removed from reaction vessels before storage and washed with DCM (2 ml×3 times). 30 mg/ml CNBr solution (1 ml) was prepared in 5:4:1 Acetonitrile:Acetic acid:water. 50 µl from this solution was added to the beads and kept on the shaker overnight. CNBr solution was allowed to evaporate and 1:1 mixture of acetonitrile and water was added to the beads and resulting solution was used to confirm mass of the compound.

On bead cell binding assay for qualitative binding confirmation of HCC4017 cells to PPS1 compound. 200 µl of TentaGel beads containing PPS1 compound were transferred into each of three 1.5 microcentrifuge tubes. The beads were washed 2 times in RPMI medium with 5% FBS and equilibrated in same medium containing 2% BSA for 1 hour. HCC4017 and HBEC30KT cells were removed from culture plates, counted and 0.4×106 cells from each cell types were distributed in 1.5 ml microcentrifuge tube and subjected to labeling procedure as described in library screening. At the end of the labeling procedure cells were suspended in 0.5 ml of RPMI medium containing 5% FBS or KSFM media with supplements and pipetted several times to break cell clumps. Red and green cells were separately added to two tubes and 1:1 mixture to third tube. Cell density for each cell type was kept as 0.4×106 cells in each tube. The beads were incubated at room temperature with gentle shaking for 20 minutes. During incubation cell binding to the beads were checked time to time at about 5 minutes intervals and it was observed that HCC4017 cells demonstrated significant binding within 10 minutes. Finally, the beads were gently washed and visualized under the fluorescent microscope equipped with the DAPI filter.

Magnetic bead binding assay. This assay was performed with Dynabeads M-280 Streptavidin (Life technologies, CA). First the beads were re-suspended in the original vial by vortexing. From this 14 µl of beads (approximately 9×106 beads) were transferred to a microcentrifuge tube and 500 µl of PBS with 0.1% BSA was added. The microcentrifuge tube containing the beads was placed on the magnet for 2 minutes and the supernatant was removed by aspiration. The beads were washed three times with 500 µl of PBS with 0.1% BSA. Then biotinylated PPS1 or PC462 was added to each vial and the reaction was incubated for 30 minutes at room temperature with gentle shaking. Then the beads were washed 3 times with 500 µl of PBS with 0.1% BSA. HCC4017, HBEC30KT and HBEC3KT cells (0.5× 106 cells in 1 ml of RPMI with 1% BSA) were added to each vial and incubated for 30 minutes at room temperature with gentle shaking. The bead bound cells were isolated by placing the vial on the magnet and after removing supernatant, cells were counted with hemocytometer.

ELISA-like binding assay. 5,000 of HCC4017 cells were grown in each well of a white clear bottom 96 well plate (Corning Inc, NY) 24 hours prior to the experiment. Each well was blocked with 100 µl of 5% BSA in Phosphate Buffered Saline (PBS; Life technologies, NY) for 15 minutes at room temperature. Then the BSA was removed from wells and each well was treated with 50 µl of graded concentrations of FITC-PPS1/PPS1-(Eu3+)-DTPA compound prepared in 1% BSA containing PBS and incubated for 45 minutes at room temperature. Wells were washed with PBS and fluorescence was measured at 520 nm (for FITC) and 610 nm [for (Eu3+)-DTPA] using the plate readers (Fluostar Optima, BMG Laboratories, NC and Spectra max i3, Molecular Devices, CA).

MTS viability assay on HCC4017 cells 5,000 of HCC4017 and HBEC30KT cells were grown in each well of a white clear bottom 96 well plates (Corning Inc, NY) on day 1 of the experiment. On day 2, wells were treated with graded concentrations of PPS1, PPS1D1, PPS1-Cys, control PC462D1 and PC462 in RPMI medium with 5% FBS containing 3% BSA. For HBEC30KT, Keratinocyte-SFM with 3% BSA media was used. Eight graded concentrations ranging from 0.01 µM-50 µM were used from both compounds and each concentration was done in triplicates. 6 wells were left untreated as controls. On day 4, media was removed from each well and treatment was repeated as described previously. On day 5, 20 µl of CellTiter 96® AQueous One Solution Cell Proliferation Assay (Promega, Wis.) was added to each well and absorbance was measured at 490 nm using a plate reader (Fluostar Optima, BMG Laboratories, NC and Spectra max i3, Molecular Devices, CA) 2 hours after treatment.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

Aggarwal, S., Harden, J. L., and Denmeade, S. R. (2006) Synthesis and screening of a random dimeric peptide library using the one-bead-one-dimer combinatorial approach, Bioconjugate chemistry 17, 335-340.

Aina, O. H., Liu, R., Sutcliffe, J. L., Marik, J., Pan, C. X., and Lam, K. S. (2007) From combinatorial chemistry to cancer-targeting peptides, Mol Pharm 4, 631-651.

Aina, O. H., Sroka, T. C., Chen, M. L., and Lam, K. S. (2002) Therapeutic cancer targeting peptides, Biopolymers 66, 184-199.

Alluri, P. G., Reddy, M. M., Bachhawat-Sikder, K., Olivos, H. J., and Kodadek, T. (2003) Isolation of protein ligands from large peptoid libraries, Journal of the American Chemical Society 125, 13995-14004.

Alluri, P., Liu, B., Yu, P., Xiao, X., and Kodadek, T. (2006) Isolation and characterization of coactivator-binding peptoids from a combinatorial library, Mol Biosyst 2, 568-579.

Andree H A, Reutelingsperger C P, Hauptmann R, Hemker H C, Hermens W T, Willems G M. Binding of vascular anticoagulant alpha (VAC alpha) to planar phospholipid bilayers. J Biol Chem. 1990; 265:4923-4928.

Astle, J. M., Udugamasooriya, D. G., Smallshaw, J. E., Kodadek, T. (2008) A VEGFR2 antagonist and other peptoids evade immune recognition, Int J Pept Res Ther. 14, 223-227.

Balasubramanian K, Mirnikjoo B, Schroit A J. Regulated externalization of phosphatidylserine at the cell surface: implications for apoptosis. J Biol chem. 2007; 282: 18357-18364.

Balasubramanian K, Schroit A J. Aminophospholipid asymmetry: A matter of life and death. Annu Rev Physiol. 2003; 65:701-734.

Beck A W, Luster T A, Miller A F, Holloway S E, Conner C R, Barnett C C, Thorpe P E, Fleming J B, Brekken R A. Combination of a monoclonal anti-phosphatidylserine antibody with gemcitabine strongly inhibits the growth and metastasis of orthotopic pancreatic tumors in mice. Int J cancer. 2006; 118:2639-2643.

Bitbol, M., Fellmann, P., Zachowski, A., and Devaux, P. F. (1987) Ion regulation of phosphatidylserine and phosphatidylethanolamine outside-inside translocation in human erythrocytes, Biochimica et biophysica acta 904, 268-282.

Brown, K. C. (2000) New approaches for cell-specific targeting: identification of cell-selective peptides from combinatorial libraries, Curr Opin Chem Biol 4, 16-21.

Bucana C D, Hoyer L C, Schroit A J, Kleinerman E, Fidler U. Ultrastructural studies of the interaction between liposomeactivated human blood monocytes and allogeneic tumor cells in vitro. Am J Pathol. 1983; 112:101-111.

Cancer research 2002, 62, 6132-6140.

Clin Cancer Res 2009, 15, 6871-6880.

Clin Cancer Res 2007, 13, 5211-5218.

Clin Cancer Res 2008, 14, 1377-1385.

Crump C J, am Ende C W, Ballard T E, Pozdnyakov N, Pettersson M, Chau D M, Bales K R, Li Y M, Johnson D S. Development of clickable active site-directed photoaffinity probes for gamma-secretase. Bioorg Med Chem Lett. 2012; 22:2997-3000.

Cullis P R, Verkleij A J. Modulation of Membrane-Structure by Ca2+ and Dibucaine as Detected by P-31 Nmr. Bioch Biophys Acta. 1979; 552:546-551.

Cuperlovic-Culf, M., Barnett, D. A., Culf, A. S., and Chute, I. (2010) Cell culture metabolomics: applications and future directions, Drug Discov Today 15, 610-621.

Current Protocols in Chemical Biology 4: 35-48, 2012.

Daleke D L. Regulation of transbilayer plasma membrane phospholipid asymmetry. J Lipid Res. 2003; 44:233-242.

De Leon-Rodriguez L M, Lubag A, Udugamasooriya D G, Proneth B, Brekken R A, Sun X, Kodadek T, Dean Sherry A. MRI detection of VEGFR2 in vivo using a low molecular weight peptoid-(Gd)8-dendron for targeting. J A Chem Soc. 2010; 132:12829-12831.

DeRose P, Thorpe P E, Gerber D E. Development of bavituximab, a vascular targeting agent with immunemodulating properties, for lung cancer treatment. Immunotherapy. 2011; 3:933-944.

Elayadi, A. N., Samli, K. N., Prudkin, L., Liu, Y. H., Bian, A., Xie, X. J., Wistuba, II, Roth, J. A., McGuire, M. J., and Brown, K. C. (2007) A peptide selected by biopanning identifies the integrin alphavbeta6 as a prognostic biomarker for nonsmall cell lung cancer, Cancer research 67, 5889-5895.

Fass, L. (2008) Imaging and cancer: a review, Mol Oncol 2, 115-152.

Figliozzi G M, Goldsmith R, Ng S C, Banville S C, Zuckermann R N. Synthesis of N-substituted glycine peptoid libraries. Methods Enzymol. 1996; 267:437-447.

Fowler S A, Blackwell H E. Structure-function relationships in peptoids: recent advances toward deciphering the structural requirements for biological function. Org Biomol Chem. 2009; 7:1508-1524.

Fuller N, Benatti C R, Rand R P. Curvature and bending constants for phosphatidylserine-containing membranes. Biophys J. 2003; 85:1667-1674.

Gaspar D, Veiga A S, Castanho M R B. From antimicrobial to anticancer peptides. A review. Front Microbiol. 2013; 4.

Gibbs J B. Mechanism-based target identification and drug discovery in cancer research. Science. 2000; 287:1969-1973.

Gocke A R, Udugamasooriya D G, Archer C T, Lee J, Kodadek T. Isolation of antagonists of antigen-specific autoimmune T cell proliferation. Chem Biol. 2009; 16:1133-1139.

Grimberg, H., Levin, G., Shirvan, A., Cohen, A., Yogev-Falach, M., Reshef, A., and Ziv, I. (2009) Monitoring of tumor response to chemotherapy in vivo by a novel small-molecule detector of apoptosis, Apoptosis 14, 257-267.

Hamon Y, Broccardo C, Chambenoit O, Luciani M F, Toti F, Chaslin S, Freyssinet J M, Devaux P F, McNeish J, Marguet D, Chimini G. ABC1 promotes engulfment of apoptotic cells and transbilayer redistribution of phosphatidylserine. Nature cell biology. 2000; 2:399-406.

Hanahan D, Weinberg R A. Hallmarks of cancer: the next generation. Cell. 2011; 144:646-674.

He J, Luster T A, Thorpe P E. Radiation-enhanced vascular targeting of human lung cancers in mice with a monoclonal antibody that binds anionic phospholipids. Cancer Res. 2007; 13:5211-5218.

He J, Yin Y, Luster T A, Watkins L, Thorpe P E. Antiphosphatidylserine antibody combined with irradiation damages tumor blood vessels and induces tumor immunity in a rat model of glioblastoma. Clin Cancer Res. 2009; 15:6871-6880.

Hemmila, I., and Laitala, V. (2005) Progress in lanthanides as luminescent probes, Journal of fluorescence 15, 529-542.

Hoskin D W, Ramamoorthy A. Studies on anticancer activities of antimicrobial peptides. BBA-Biomembranes. 2008; 1778:357-375.

Huang W, Seo J, Willingham S B, Czyzewski A M, Gonzalgo M L, Weissman I L, Barron A E. Learning from Host-Defense Peptides: Cationic, Amphipathic Peptoids with Potent Anticancer Activity. PloS one. 2014; 9.

Huang X, Bennett M, Thorpe P E. A monoclonal antibody that binds anionic phospholipids on tumor blood vessels enhances the antitumor effect of docetaxel on human breast tumors in mice. Cancer Res. 2005; 65:4408-4416.

JACS 130, 5744-5752, 2008.

Jennewein M, Lewis M A, Zhao D, Tsyganov E, Slavine N, He J, Watkins L, Kodibagkar V D, O'Kelly S, Kulkarni P, Antich P, Hermanne A, Rosch F, et al. Vascular imaging of solid tumors in rats with a radioactive arsenic-labeled antibody that binds exposed phosphatidylserine. Clin Cancer Res. 2008; 14:1377-1385.

Kwon Y U, Kodadek T. Quantitative evaluation of the relative cell permeability of peptoids and peptides. J Am Chem Soc. 2007; 129:1508-1509.

Lam, Kit 2006 Nat Chem.

Lam, K. S., Lebl, M., and Krchnak, V. (1997) The "One-Bead-One-Compound" Combinatorial Library Method, Chemical reviews 97, 411-448.

Lam, K. S., Salmon, S. E., Hersh, E. M., Hruby, V. J., Kazmierski, W. M., and Knapp, R. J. (1991) A new type of synthetic peptide library for identifying ligand-binding activity, Nature 354, 82-84.

Landon, L. A., and Deutscher, S. L. (2003) Combinatorial discovery of tumor targeting peptides using phage display, Journal of Cellular Biochemistry 90, 509-517.

Lee, J., Udugamasooriya, D. G., Lim, H. S., and Kodadek, T. (2010) Potent and selective photo-inactivation of proteins with peptoid-ruthenium conjugates, Nature Chemical Biology 6, 258-260.

Lee, R. T., and Lee, Y. C. (2001) A derivative of diethylenetriaminepentaacetic acid for europium labeling of proteins, Bioconjugate chemistry 12, 845-849.

Lehninger Principles of Biochemistry, 5th edition, pg 375.

Lim, H. S., Archer, C. T., and Kodadek, T. (2007) Identification of a peptoid inhibitor of the proteasome 19S regulatory particle, Journal of the American Chemical Society 129, 7750-7751.

Lynn, K. D., Udugamasooriya, D. G., Roland, C. L., Castrillon, D. H., Kodadek, T. J., and Brekken, R. A. (2010) GU81, a VEGFR2 antagonist peptoid, enhances the antitumor activity of doxorubicin in the murine MMTV-PyMT transgenic model of breast cancer, BMC cancer 10, 397.

Marconescu A, Thorpe P E. Coincident exposure of phosphatidylethanolamine and anionic phospholipids on the surface of irradiated cells. Biochim Biophys Acta. 2008; 1778:2217-2224.

Matharage J M, Minna J D, Brekken R A, Udugamasooriya D G. Unbiased Selection of Peptide-Peptoid Hybrids Specific for Lung Cancer Compared to Normal Lung Epithelial Cells. ACS Chem Biol. 2015; 10:2891-2899.

Meacham C E, Morrison S J. Tumour heterogeneity and cancer cell plasticity. Nature. 2013; 501:328-337.

Meers P, Mealy T. Calcium-dependent annexin V binding to phospholipids: stoichiometry, specificity, and the role of negative charge. Biochemistry. 1993; 32:11711-11721.

MRI (JACS, 2010).

Nilsson F, Tarli L, Viti F, Neri D. The use of phage display for the development of tumour targeting agents. Adv Drug Deliver Rev. 2000; 43:165-196.

Park C R, You D J, Kim D K, Moon M J, Lee C, Oh S H, Ahn C, Seong J Y, Hwang J I. CXCL14 enhances proliferation and migration of NCI-H460 human lung cancer cells overexpressing the glycoproteins containing heparan sulfate or sialic acid. J Cell Biochem. 2013; 114:1084-1096.

Park, C. R., You, D. J., Kim, D. K., Moon, M. J., Lee, C., Oh, S. H., Ahn, C., Seong, J. Y., and Hwang, J. I. (2013) CXCL14 enhances proliferation and migration of NCI-H460 human lung cancer cells overexpressing the glycoproteins containing heparan sulfate or sialic acid, Journal of cellular biochemistry 114, 1084-1096.

PET (Am J Nucl Med Mo/Imaging, 2011).

Plucinsky, M. C., Riley, W. M., Prorok, J. J., and Alhadeff, J. A. (1986) Total and lipid-associated serum sialic acid levels in cancer patients with different primary sites and differing degrees of metastatic involvement, Cancer 58, 2680-2685.

Poulsen S A. Direct screening of a dynamic combinatorial library using mass spectrometry. J Am Soc Mass Spectr. 2006; 17:1074-1080.

Ramstrom O, Lehn J M. Drug discovery by dynamic combinatorial libraries. Nat Rev Drug disco. 2002; 1:26-36.

Ran S, Downes A, Thorpe P E. Increased exposure of anionic phospholipids on the surface of tumor blood vessels. Cancer Res. 2002; 62:6132-6140.

Ran S, He J, Huang X, Soares M, Scothorn D, Thorpe P E. Antitumor effects of a monoclonal antibody that binds anionic phospholipids on the surface of tumor blood vessels in mice. Clin Cancer Res. 2005; 11:1551-1562.

Ran S, Thorpe P E. Phosphatidylserine is a marker of tumor vasculature and a potential target for cancer imaging and therapy. Int J Radiat Oncol Biol Phys. 2002; 54:1479-1484.

Reddy, M. M., and Kodadek, T. (2005) Protein "fingerprinting" in complex mixtures with peptide microarrays, Proc Natl Acad Sci USA 102, 12672-12677.

Riedl, S., Rinner, B., Asslaber, M., Schaider, H., Walzer, S., Novak, A., Lohner, K., and Zweytick, D. (2011) In search of a novel target—phosphatidylserine exposed by non-apoptotic tumor cells and metastases of malignancies with poor treatment efficacy, Biochimica et biophysica acta 1808, 2638-2645.

Riedl, S., Zweytick, D., and Lohner, K. (2011) Membrane-active host defense peptides—challenges and perspectives for the development of novel anticancer drugs, Chemistry and physics of lipids 164, 766-781.

Roland, C. L., Lynn, K. D., Toombs, J. E., Dineen, S. P., Udugamasooriya, D. G., and Brekken, R. A. (2009) Cytokine levels correlate with immune cell infiltration after anti-VEGF therapy in preclinical mouse models of breast cancer, PLoS One 4, e7669.

Rothman, J. E., and Lenard, J. (1977) Membrane asymmetry, Science 195, 743-753.

Sasisekharan, R., Shriver, Z., Venkataraman, G., and Narayanasami, U. (2002) Roles of heparan-sulphate glycosaminoglycans in cancer, Nature reviews. Cancer 2, 521-528.

Scott, J. K., and Smith, G. P. (1990) Searching for peptide ligands with an epitope library, Science 249, 386-390.

Shadidi, M., and Sioud, M. (2004) Selection of peptides for specific delivery of oligonucleotides into cancer cells, Methods Mol Biol 252, 569-580.

Shores, K. S., Udugamasooriya, D. G., Kodadek, T., and Knapp, D. R. (2008) Use of peptide analogue diversity library beads for increased depth of proteomic analysis: application to cerebrospinal fluid, J Proteome Res 7, 1922-1931.

Simon R J, Kania R S, Zuckermann R N, Huebner V D, Jewell D A, Banville S, Ng S, Wang L, Rosenberg S, Marlowe C K, et al. Peptoids: a modular approach to drug discovery. Proc Natl Acad Sci USA. 1992; 89:9367-9371.

Simpson, L. S., Burdine, L., Dutta, A. K., Feranchak, A. P., and Kodadek, T. (2009) Selective toxin sequestrants for the treatment of bacterial infections, J Am Chem Soc 131, 5760-5762.

Smith B A, Akers W J, Leevy W M, Lampkins A J, Xiao S, Wolter W, Suckow M A, Achilefu S, Smith B D. Optical imaging of mammary and prostate tumors in living animals using a synthetic near infrared zinc(II)-dipicolylamine probe for anionic cell surfaces. J Am Chem Soc. 2010; 132:67-69.

Soares et al. 12. Singh, A., and Settleman, J. (2010) EMT, cancer stem cells and drug resistance: an emerging axis of evil in the war on cancer, Oncogene 29, 4741-4751.

Stafford J H, Thorpe P E. Increased exposure of phosphatidylethanolamine on the surface of tumor vascular endothelium. Neoplasia. 2011; 13:299-308.

Stafford, J. H., Hao, G., Best, A. M., Sun, X., Thorpe P E., PLoS One, 2013,19;8(12):e84864.

Szakacs G, Paterson J K, Ludwig J A, Booth-Genthe C, Gottesman M. Targeting multidrug resistance in cancer. Nat Rev Drug Discov. 2006; 5:219-234.

Thapa, N., Kim, S., So, I. S., Lee, B. H., Kwon, I. C., Choi, K., and Kim, I. S. (2008) Discovery of a phosphatidylserine-recognizing peptide and its utility in molecular imaging of tumour apoptosis, J Cell Mol Med 12, 1649-1660.

Udugamasooriya, D. G., Dineen, S. P., Brekken, R. A., and Kodadek, T. (2008) A peptoid "antibody surrogate" that antagonizes VEGF receptor 2 activity, Journal of the American Chemical Society 130, 5744-5752.

Udugamasooriya, D. G., Ritchie, C., Brekken, R. A., and Kodadek, T. (2008) A peptoid antagonist of VEGF receptor 2 recognizes a 'hotspot' in the extracellular domain distinct from the hormone-binding site, Bioorganic & Medicinal Chemistry 16, 6338-6343.

Utsugi T, Schroit A J, Connor J, Bucana C D, Fidler I J. Elevated expression of phosphatidylserine in the outer membrane leaflet of human tumor cells and recognition by activated human blood monocytes. Cancer Res. 1991; 51:3062-3066.

van Engeland M, Nieland L J, Ramaekers F C, Schutte B, Reutelingsperger C P. Annexin V-affinity assay: a review on an apoptosis detection system based on phosphatidylserine exposure. Cytometry. 1998; 31:1-9.

Wolfs J L, Comfurius P, Bekers O, Zwaal R F, Balasubramanian K, Schroit A J, Lindhout T, Bevers E M. Direct inhibition of phospholipid scrambling activity in erythrocytes by potassium ions. Cell Mol Life Sci. 2009; 66:314-323.

Xiong C, Brewer K, Song S, Zhang R, Lu W, Wen X, Li C. www.impactjournals.com/oncotarget 13 Oncotarget Peptide-based imaging agents targeting phosphatidylserine for the detection of apoptosis. J Med Chem. 2011; 54:1825-1835.

Yoo B, Kirshenbaum K. Peptoid architectures: elaboration, actuation, and application. Curr Opin Chem Biol. 2008; 12:714-721.

Zhang, Y., Diao, T. Y., Gu, S. S., Wu, S. Y., Gebru, Y. A., Chen, X., Wang, J. Y., Ran, S., and Wong, M. S. (2014) Effects of angiotensin II type 1 receptor blocker on bones in mice with type 1 diabetes induced by streptozotocin, Journal of the renin-angiotensin-aldosterone system: JRAAS 15, 218-227.

Zhou, X., Chang, Y. C., Oyama, T., McGuire, M. J., and Brown, K. C. (2004) Cell-specific delivery of a chemotherapeutic to lung cancer cells, J Am Chem Soc 126, 15656-15657.

Zuckermann, R. N., and Kodadek, T. (2009) Peptoids as potential therapeutics, Curr Opin Mol Ther 11, 299-307.

Zuckermann, R. N., Kerr, J. M., Kent, S. B. H., Moos, W. H. (1992) Efficient method for the preparation of peptoids [oligo(N-substituted glycines)] by submonomer solid-phase synthesis, In J. Am. Chem. Soc., pp 10646-10647.

Zwaal R F, Comfurius P, Bevers E M. Surface exposure of phosphatidylserine in pathological cells. Cell Mol Life Sci. 2005; 62:971-988.

What is claimed is:

1. A composition of matter comprising a phosphatidylserine-targeting peptoid selected from the group consisting of 2P3H-PPS1 and 2-4-PPS1.

2. The composition of matter of claim 1 wherein the peptoid is 2P3H-PPS1.

3. The composition of matter of claim 1 wherein the peptoid is 2-4-PPS1.

4. A method of treating a cancer in a patient, said method comprising:
administering to a patient a composition of matter comprising a phosphatidylserine-targeting peptoid selected from the croup consisting of 2P3H-PPS1 and 2-4-PPS1, wherein the cancer comprises tumor cells expressing phosphatidylserine (PS) on their outer layers.

5. The method of claim 4, further comprising administering docetaxel to the patient.

6. The method of claim 4, wherein the peptoid is 2P3H-PPS1.

7. The method of claim 4, wherein the peptoid is 2-4-PPS1.

8. The method of claim 4, wherein the cancer comprises at least one of breast cancer, lung cancer, and prostate cancer.

9. The method of claim 4, wherein the cancer comprises lung cancer.

10. A method of detecting cancer in a patient, said method comprising:
   administering to a patient a composition of matter comprising a phosphatidylserine-targeting peptoid conjugated to a fluorescent label, wherein the phosphatidylserine-targeting peptoid is selected from the group consisting of 2P3H-PPS1 and 2-4-PPS1; and
   visualizing the location of the fluorescent label in the patient to detect the cancer, wherein the cancer comprises tumor cells expressing phosphatidylserine (PS) on their outer layers.

11. The method of claim 10 wherein the cancer comprises at least one of breast cancer, lung cancer, and prostate cancer.

* * * * *